United States Patent
Jeong et al.

(10) Patent No.: US 8,299,703 B2
(45) Date of Patent: Oct. 30, 2012

(54) BLUE LIGHT EMITTING COMPOUND AND ORGANIC LIGHT EMITTING DIODE DEVICE COMPRISING THE SAME

(75) Inventors: Hyuncheol Jeong, Gamdang-ri (KR); Chungun Park, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 36 days.

(21) Appl. No.: 12/630,589

(22) Filed: Dec. 3, 2009

(65) Prior Publication Data
US 2010/0140603 A1    Jun. 10, 2010

(30) Foreign Application Priority Data
Dec. 8, 2008   (KR) .................. 10-2008-0124243

(51) Int. Cl.
*H01J 1/62*       (2006.01)
(52) U.S. Cl. ........... 313/504; 428/690; 428/917; 257/40
(58) Field of Classification Search .................. 313/504; 428/690, 917
See application file for complete search history.

(56) References Cited

U.S. PATENT DOCUMENTS
2010/0051106 A1* 3/2010 Kim et al. .................. 136/263

FOREIGN PATENT DOCUMENTS
| | | | |
|---|---|---|---|
| CN | 101792422 A | | 8/2010 |
| JP | 2003146951 A | * | 5/2003 |
| JP | 2006248900 A | | 9/2006 |
| JP | 2007015933 A | * | 1/2007 |
| KR | 2009046731 A | * | 5/2009 |

* cited by examiner

*Primary Examiner* — Kiesha Bryant
*Assistant Examiner* — Mark Tornow

(74) *Attorney, Agent, or Firm* — Brinks Hofer Gilson & Lione

(57) ABSTRACT

A blue light emitting compound is provided. The blue light emitting compound has a structure of the following Chemical Formula 1:

[Chemical Formula 1]

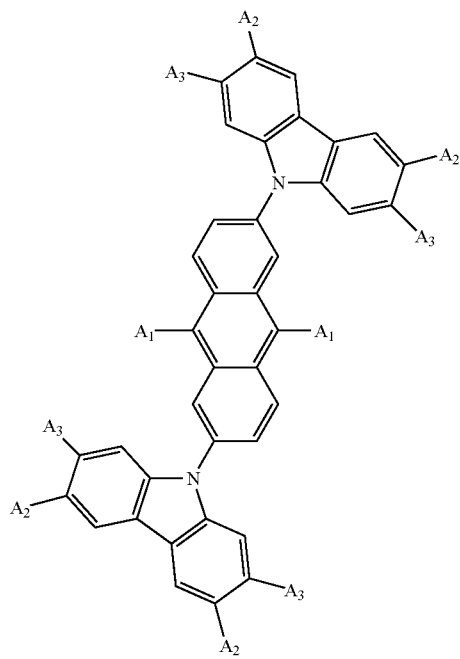

wherein $A_1$, $A_2$, and $A_3$ are each independently selected from the group consisting of hydrogen, a substituted or unsubstituted aromatic group, a hetero ring group, and an aliphatic group.

5 Claims, 1 Drawing Sheet

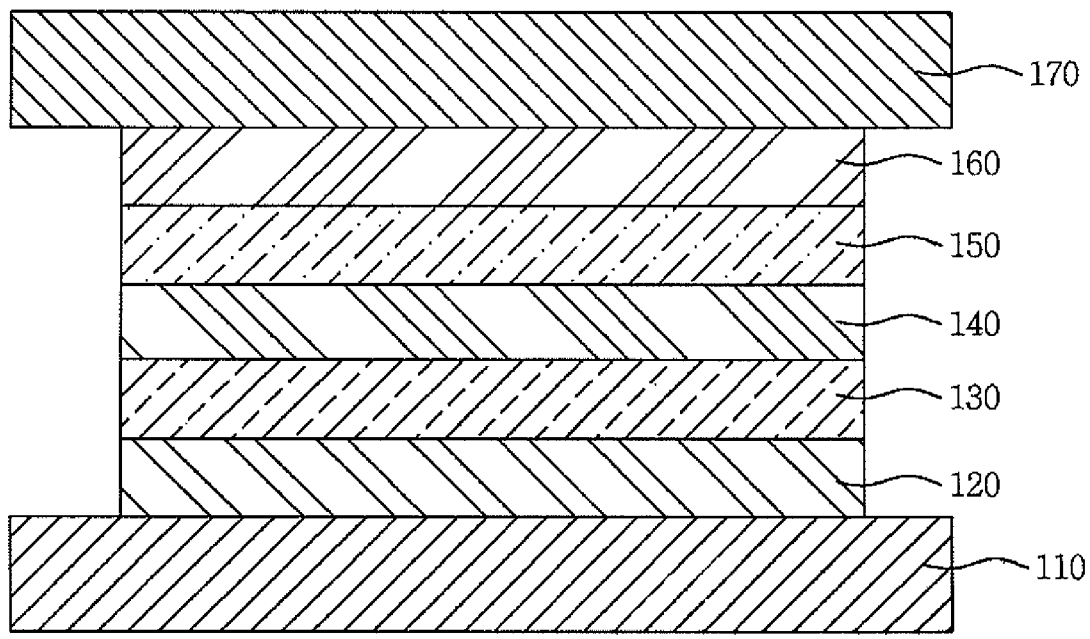

BLUE LIGHT EMITTING COMPOUND AND ORGANIC LIGHT EMITTING DIODE DEVICE COMPRISING THE SAME

This application claims the benefit of Korean Patent Application No. 10-2008-0124243 filed on Dec. 8, 2008, which is hereby incorporated by in its entirety reference.

BACKGROUND

1. Field

This document relates to an organic light emitting diode device, and more particularly, to an organic light emitting diode device comprising a blue light emitting compound.

2. Related Art

The importance of a flat panel display (FPD) has been emphasized following the development of multimedia technologies. In response to this trend, kinds of displays such as a liquid crystal display (LCD) device, a plasma display panel (PDP), a field emission display (FED), and an organic light emitting diode display device have been put to practical use.

Among them, the organic light emitting diode device is a self-emitting device which emits light in a manner that electric charges are injected into an organic layer between an electron injection electrode (cathode) and a hole injection electrode (anode), electrons and holes are paired, and then they become extinct to emit light.

Organic light emitting diode devices may have advantages in that the devices may be fabricated on flexible transparent substrates (e.g., plastic substrates) and may operate at a voltage (e.g., 10 V or below) lower than voltages required to operate plasma display panels (PDPs) and inorganic light emitting diode displays. Organic light emitting diode devices may also have other advantages such as relatively low power consumption and excellent color representation. Further, since organic light emitting diode devices may emit light of three colors (i.e., green, blue and red), organic light emitting diode devices may be considered next-generation full color display devices capable of producing images of various colors.

A blue organic light emitting diode device can be formed by sequentially stacking an anode, a hole injection layer, a hole transport layer, an emission layer, an electron transport layer, an electron injection layer, and a cathode. Although the emission layer employs a host-dopant system, conventionally used dopant materials exhibit relatively high driving voltage and low emission efficiency.

Accordingly, there is a demand for development of a dopant material having a new structure to obtain an organic light emitting diode device with high luminance and high efficiency.

SUMMARY

An aspect of this document is to provide a blue light emitting compound and an organic light emitting diode device comprising the same, which can exhibit high luminance and high efficiency.

A blue light emitting compound may have a structure of the following Chemical Formula 1:

[Chemical Formula 1]

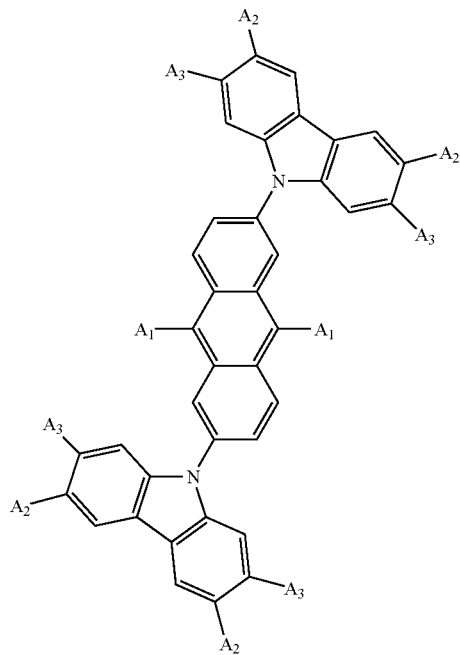

wherein $A_1$, $A_2$, and $A_3$ are each independently selected from the group consisting of hydrogen, a substituted or unsubstituted aromatic group, a hetero ring group, and an aliphatic group.

BRIEF DESCRIPTION OF THE DRAWINGS

The accompany drawings, which are included to provide a further understanding of the invention and are incorporated on and constitute a part of this specification illustrate embodiments of the invention and together with the description serve to explain the principles of the invention.

FIG. 1 is a view showing an organic light emitting diode device according to one exemplary embodiment of the present invention.

DETAILED DESCRIPTION

Reference will now be made in detail embodiments of the invention examples of which are illustrated in the accompanying drawings.

A blue light emitting compound according to one exemplary embodiment of the present invention may have a structure of the following Chemical Formula 1:

[Chemical Formula 1]

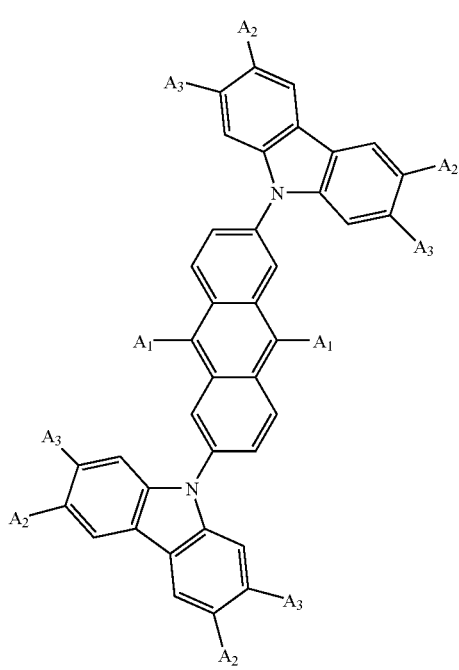

wherein $A_1$, $A_2$, and $A_3$ are each independently selected from the group consisting of hydrogen, a substituted or unsubstituted aromatic group, a hetero ring group, and an aliphatic group.

The substituted or unsubstituted $A_1$, $A_2$, and $A_3$ are each independently selected from the group consisting of phenyl, biphenyl, naphthyl, phenanthrenyl, terphenyl, pyridyl, bipyridyl, phenylpyridyl, pyridylphenyl, terpyridyl, quinolinyl, isoquinolinyl, phenoxalinyl, quinoxalinyl, methyl, ethyl, propyl, isopropyl, butyl, tert-butyl, trimethylsilyl, trifluoromethyl, cyano, fluoro, methoxy, and ethoxy.

If $A_1$, $A_2$, and $A_3$ are substituted, the substituents of $A_1$, $A_2$, and $A_3$ are selected from the group consisting of aryl, alkyl, alkoxy, halogen, cyano, and silyl groups.

If $A_1$, $A_2$, and $A_3$ are substituted, the substituents of $A_1$, $A_2$, and $A_3$ are each independently selected from the group consisting of methyl, ethyl, propyl, isopropyl, butyl, methoxy, ethoxy, butoxy, trimethylsilyl, fluorine, and chlorine.

$A_1$, $A_2$, and $A_3$ are represented by one of the following Chemical Formulae 2:

[Chemical Formulae 2]

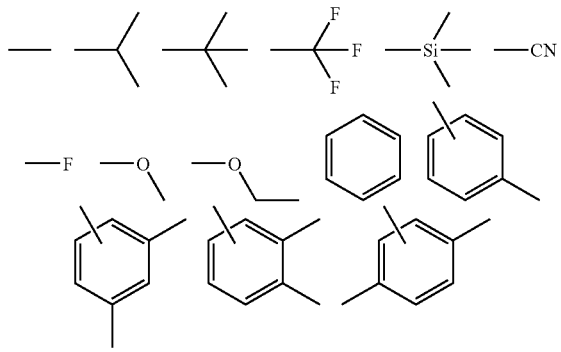

-continued

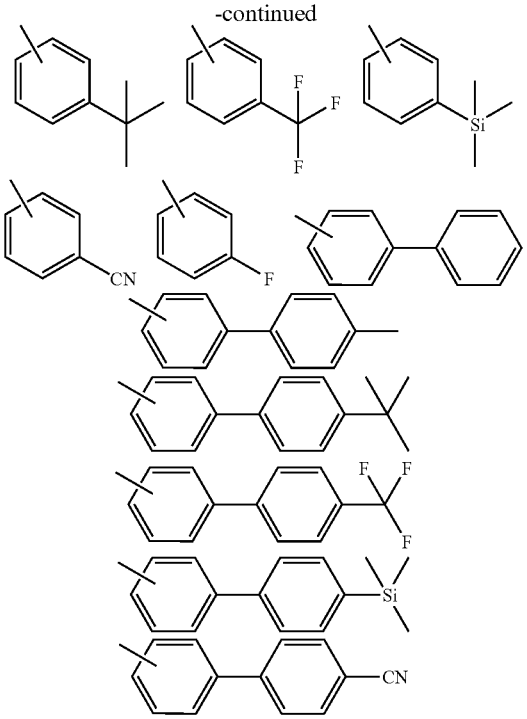

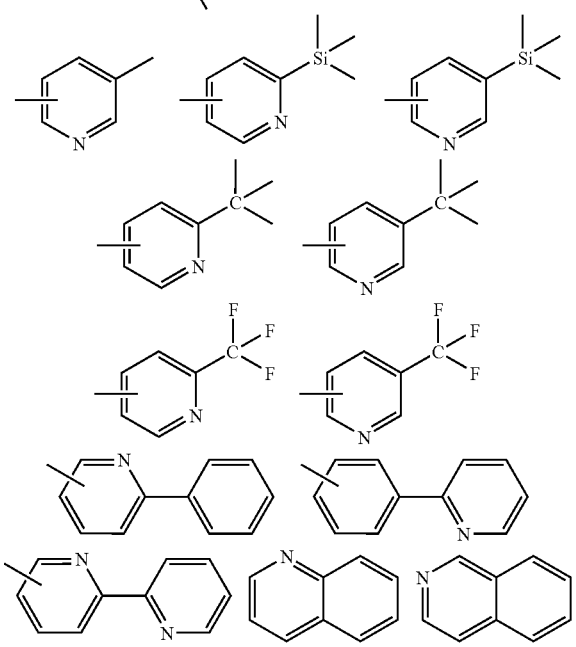

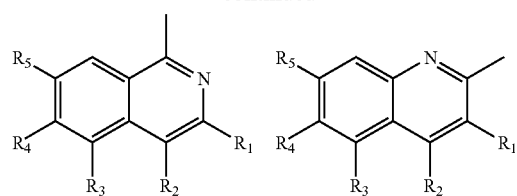
wherein $R_1$, $R_2$, $R_3$, and $R_4$ comprises at least one methyl group.
The blue light emitting compound is represented by one of the following Chemical Formulae 3:
[Chemical Formulae 3]
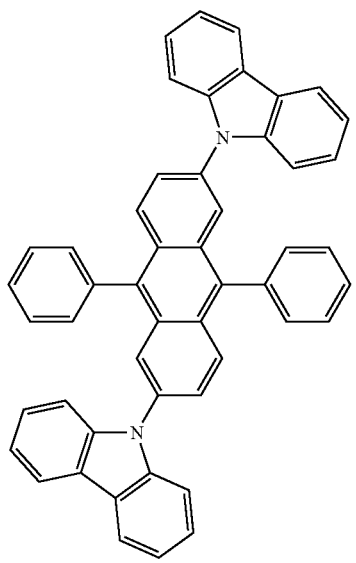
D-01
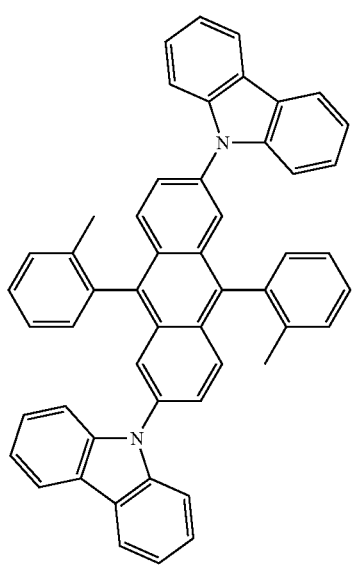
D-02
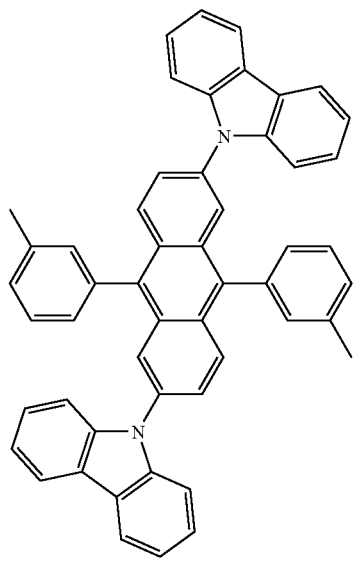
D-03
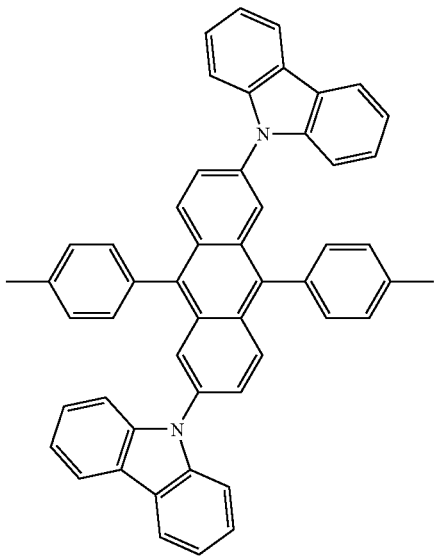
D-04
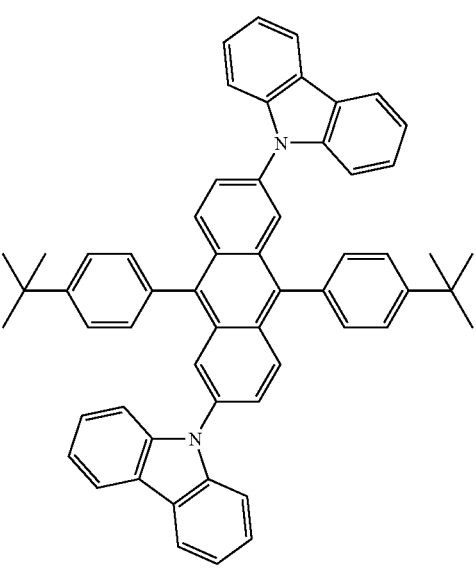
D-05

D-06
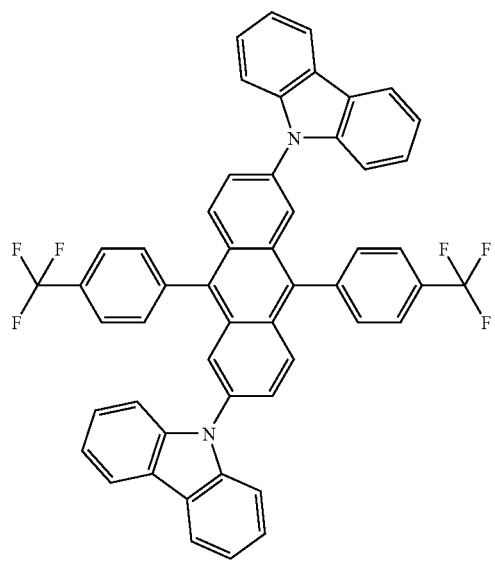
D-07
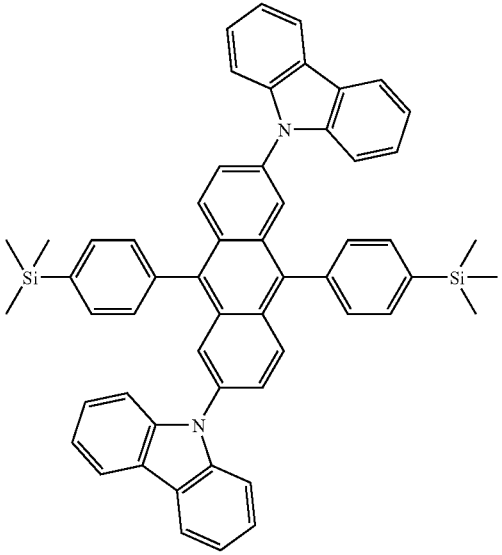
D-08
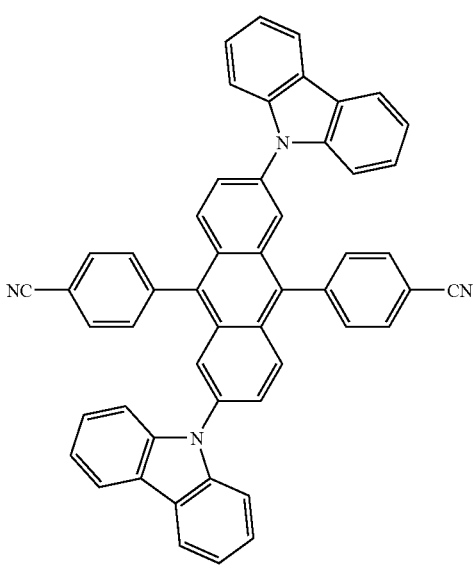
D-09
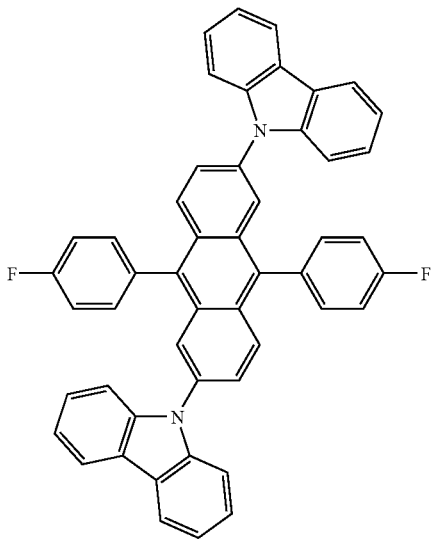
D-10
D-11
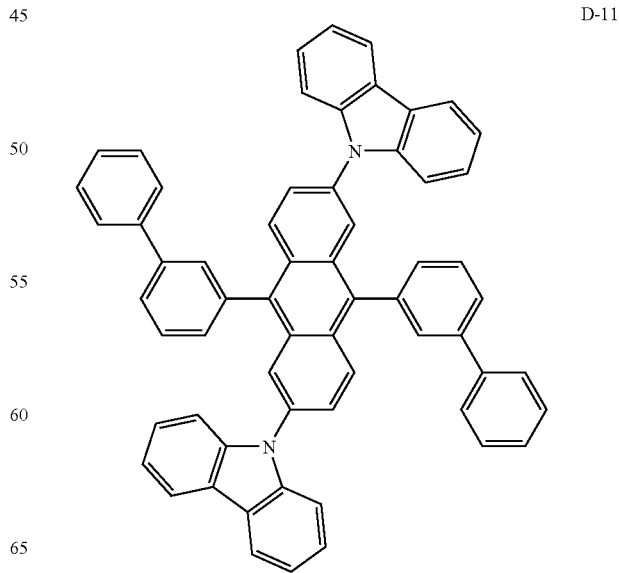

-continued
D-12
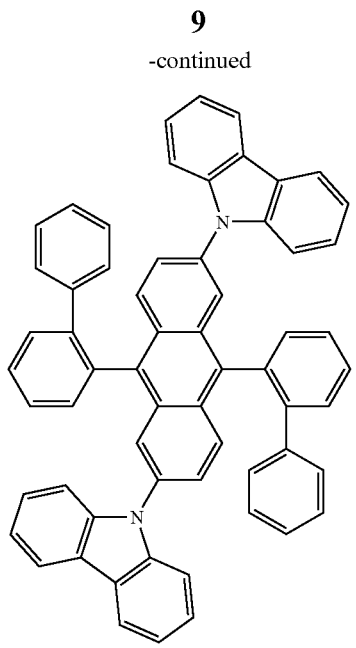
D-13
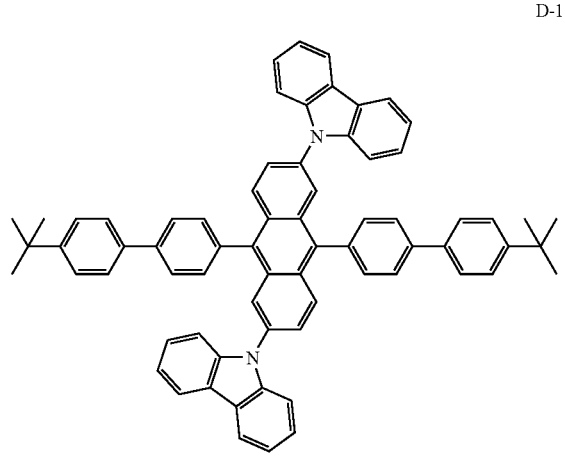
D-14
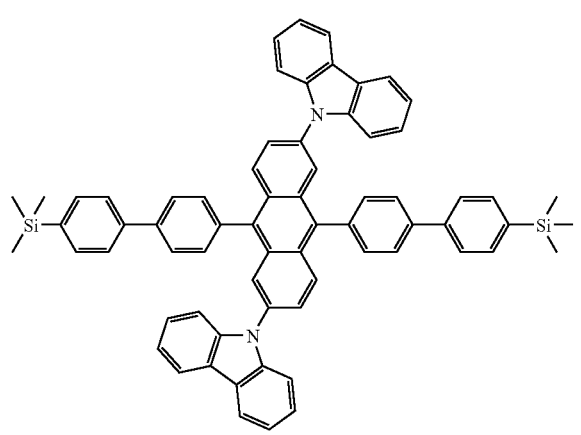
-continued
D-15
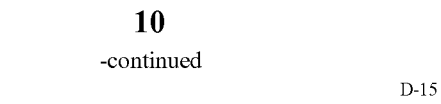
D-16
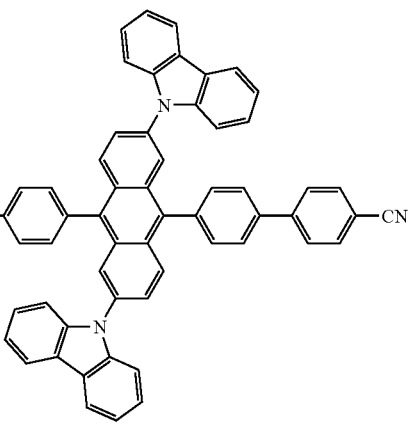
D-17
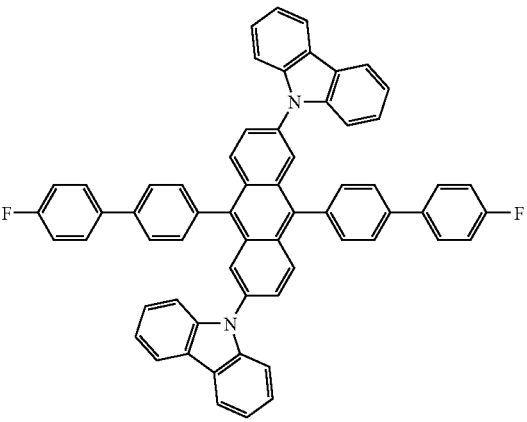

D-18
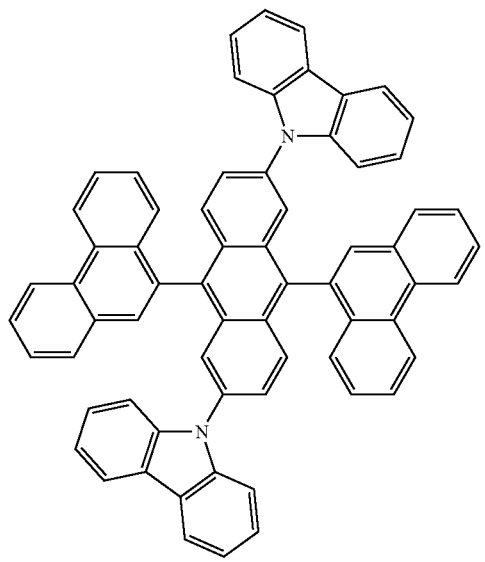
D-19
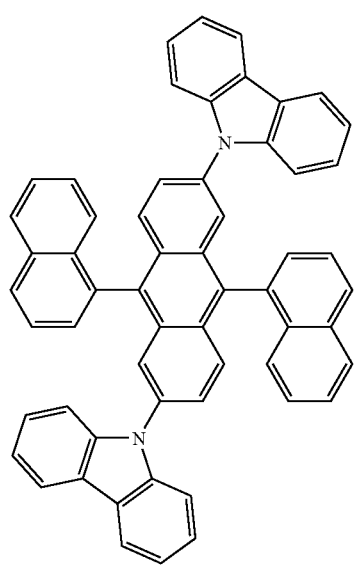
D-20
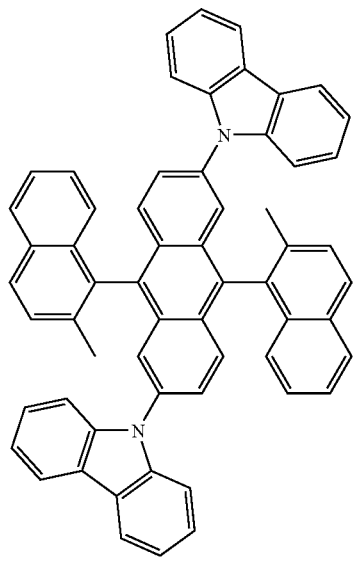
D-21
D-22
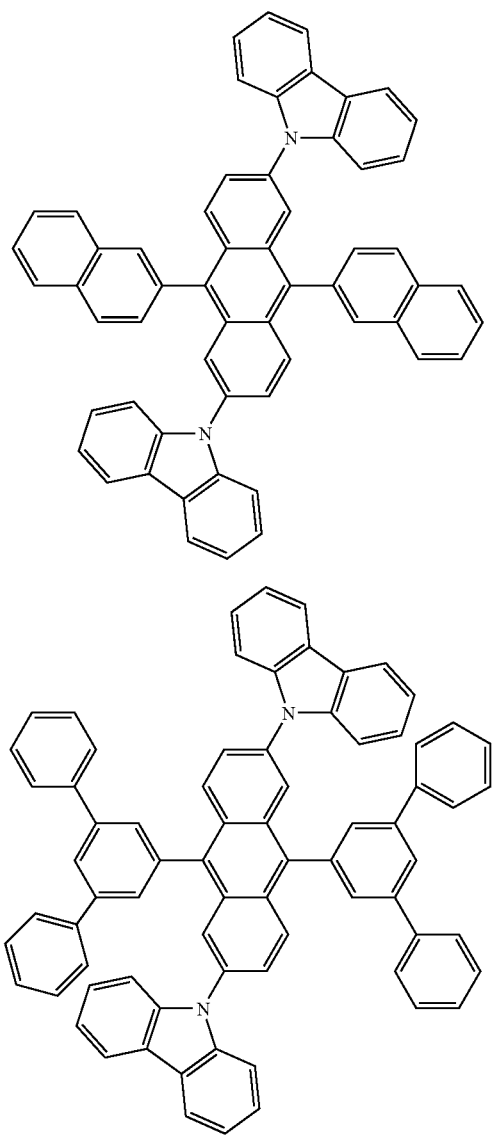

D-23
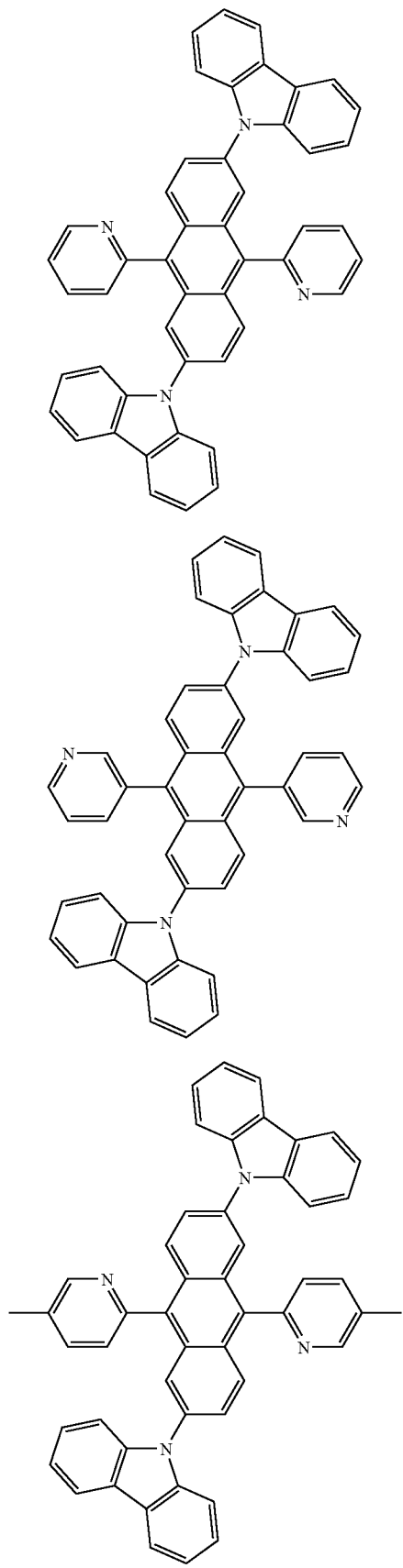
D-24
D-25
D-26
D-27

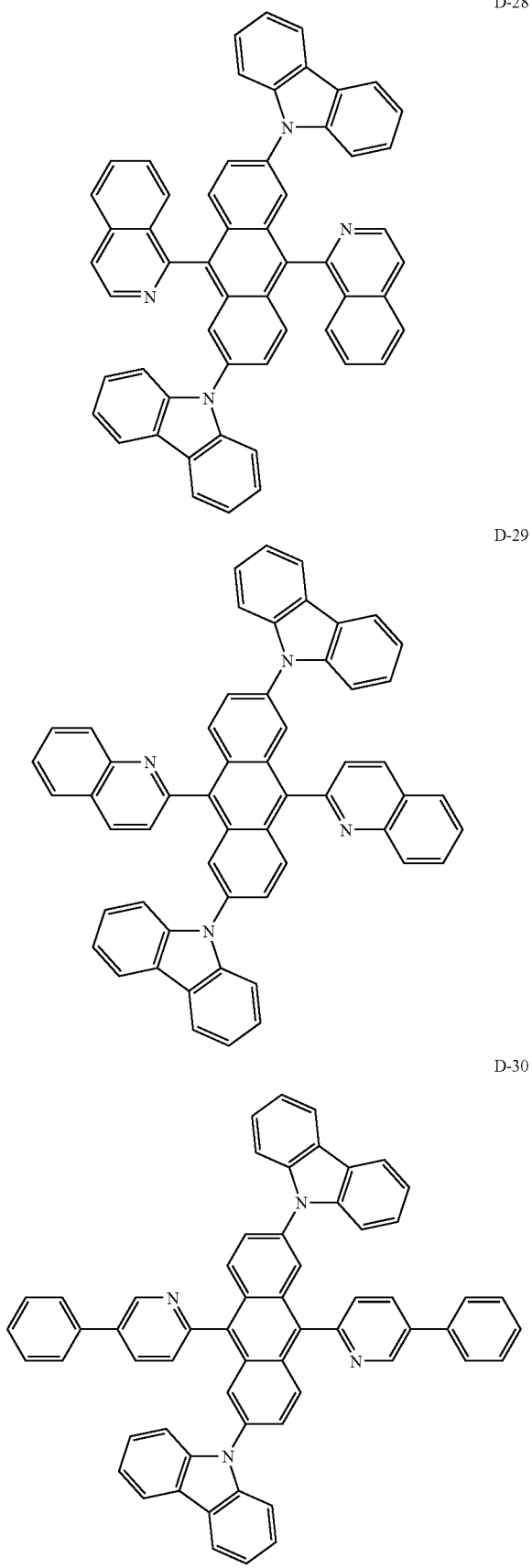
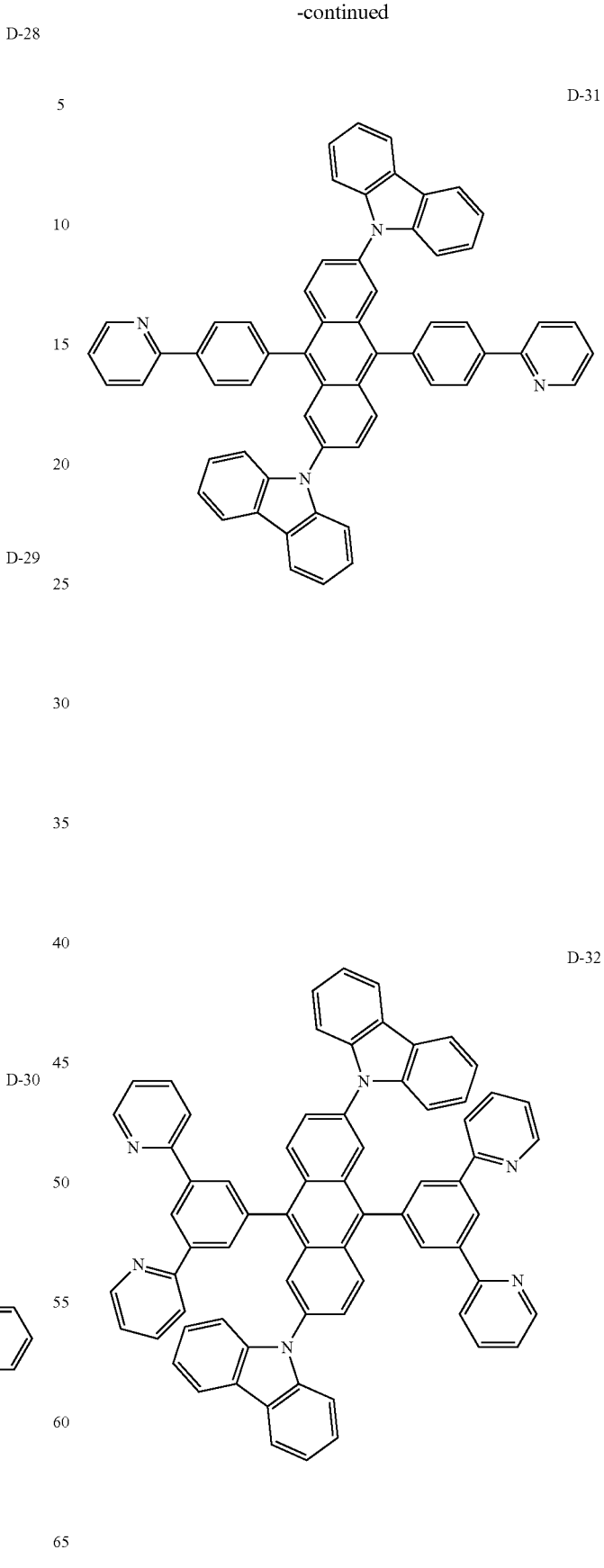

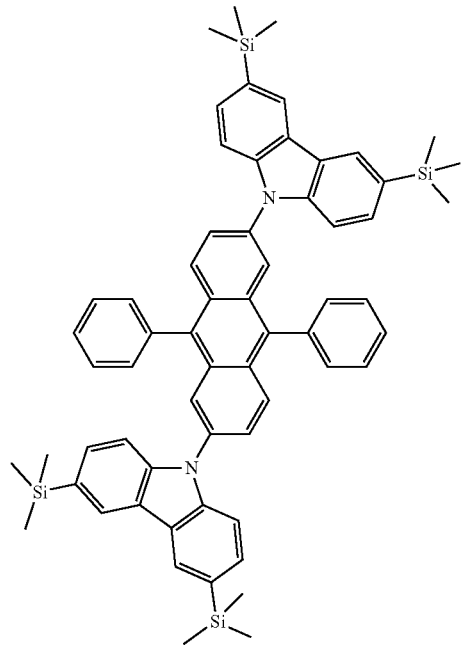
D-33
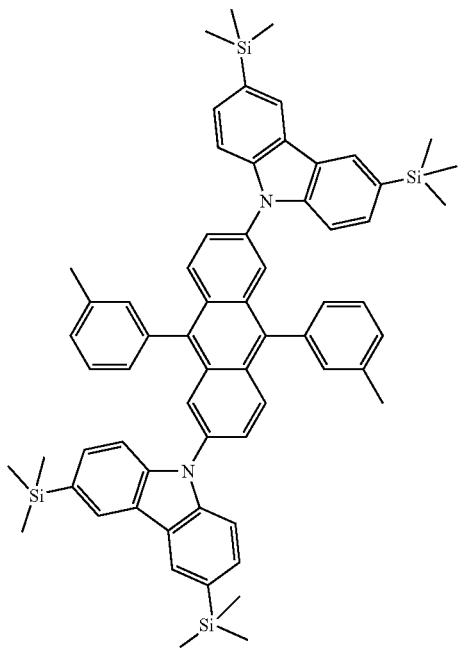
D-35
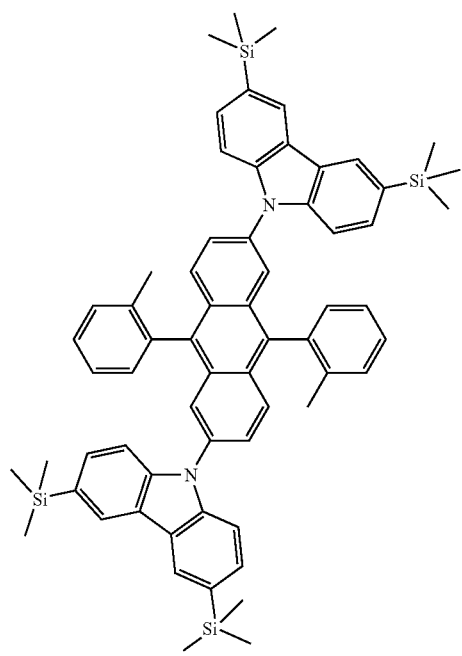
D-34
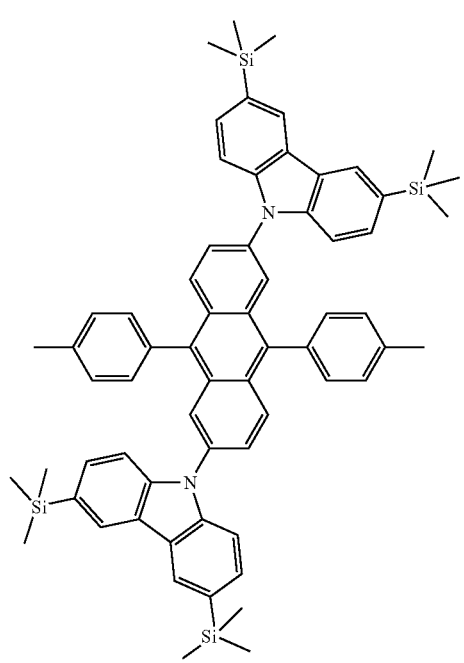
D-36

D-37
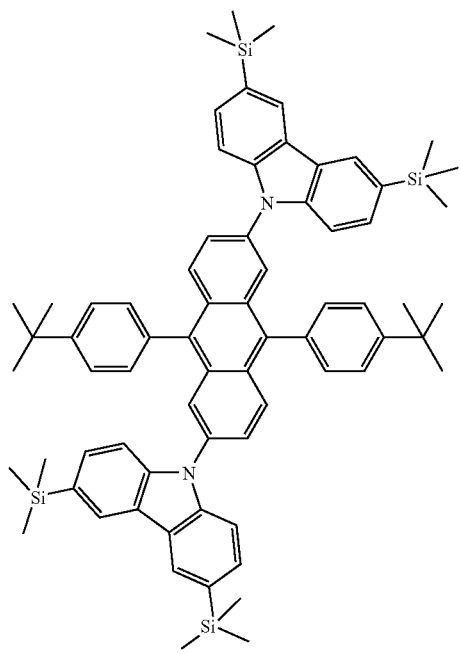
D-38
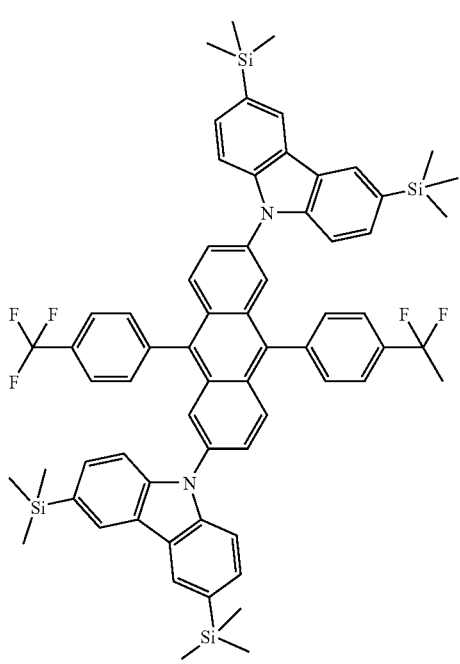
D-39
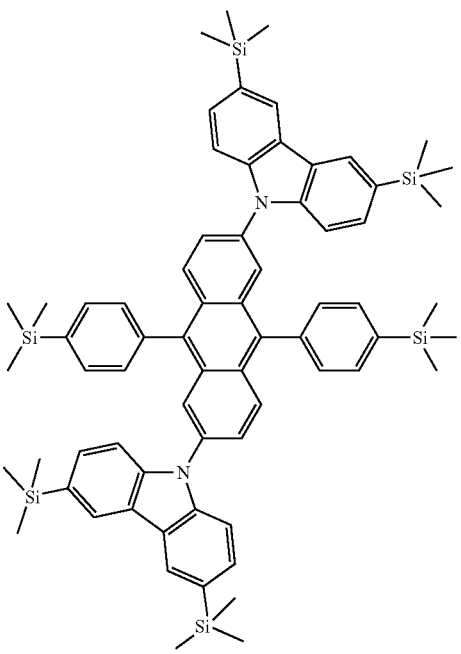
D-40
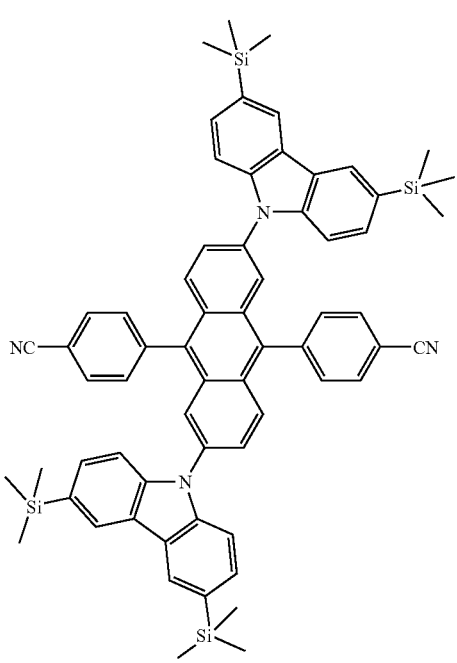

D-41
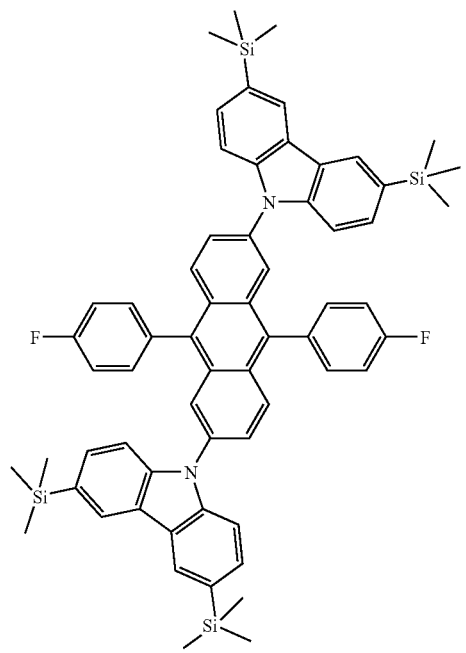
D-42
D-43
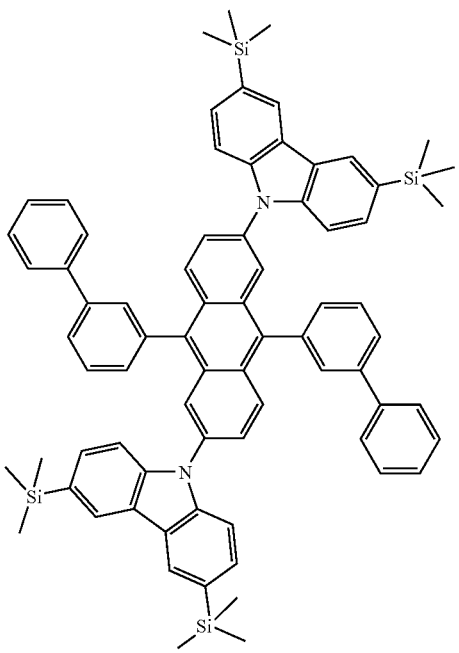
D-44

D-45
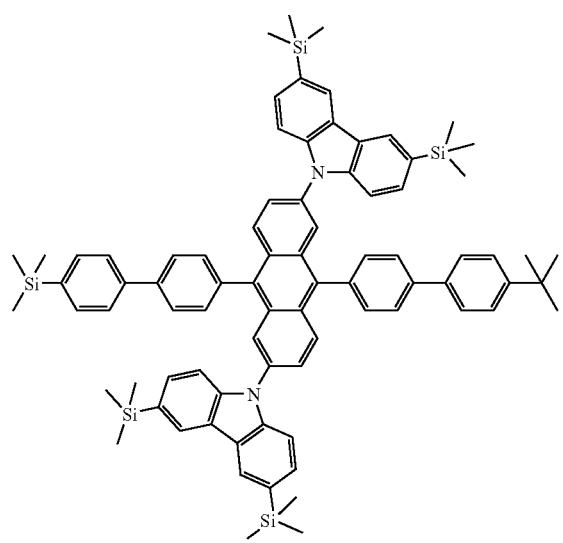
D-46
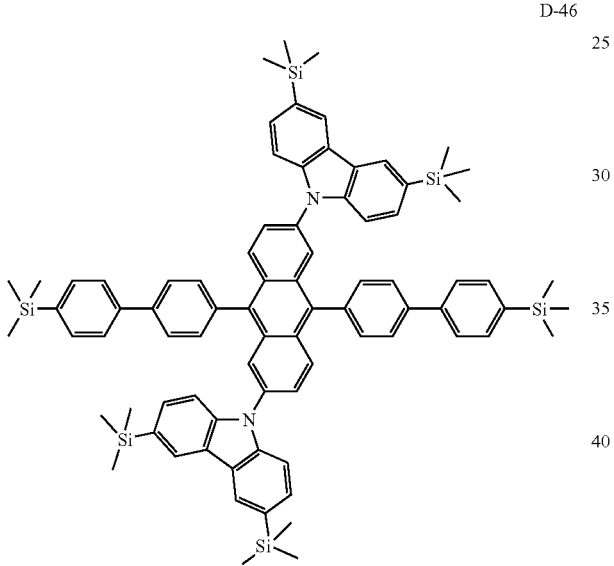
D-47
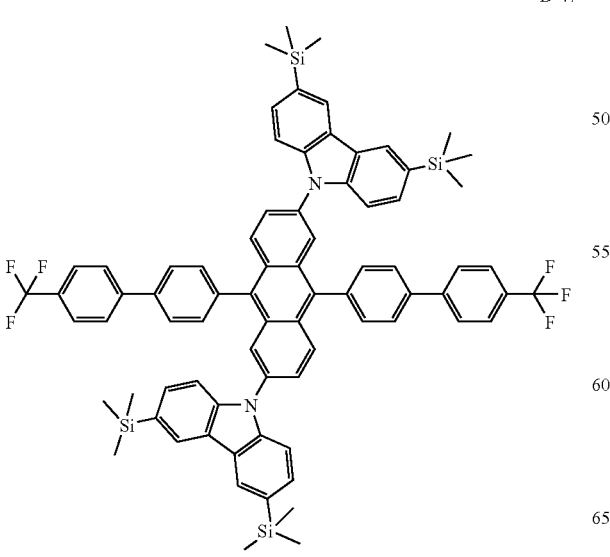
D-48
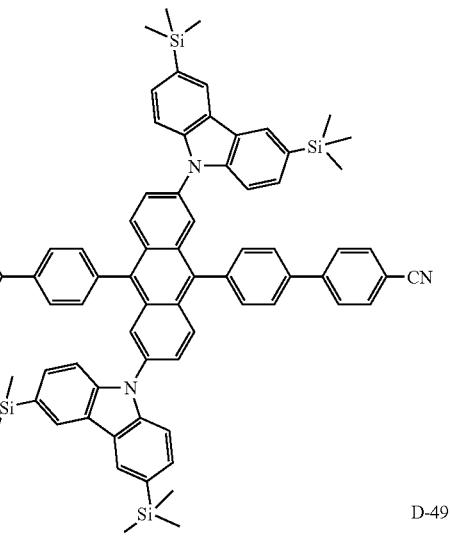
D-49
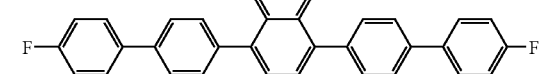
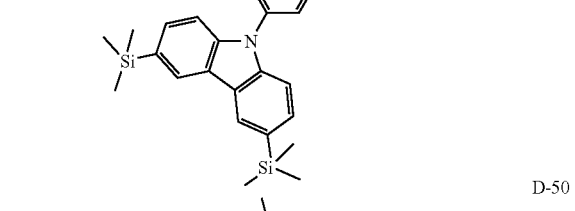
D-50
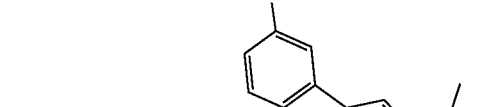
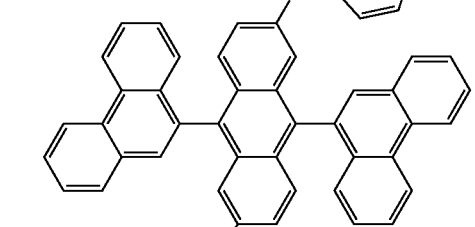
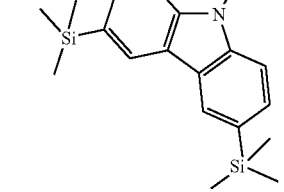

-continued
D-51
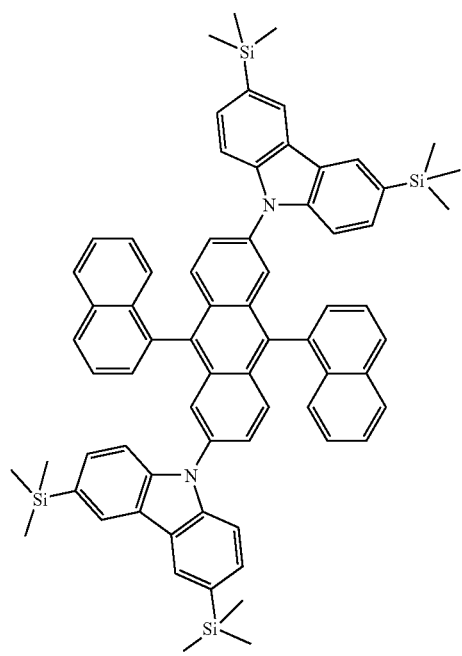
D-53
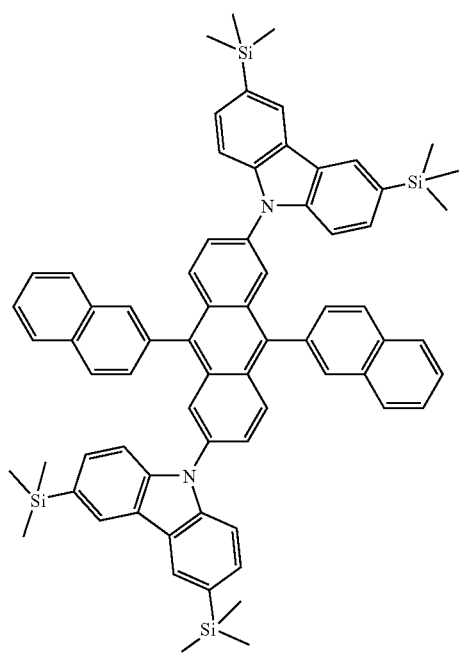
D-52
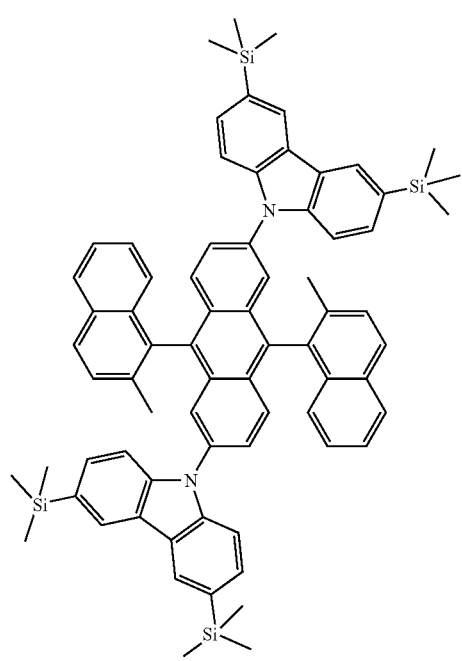
D-54
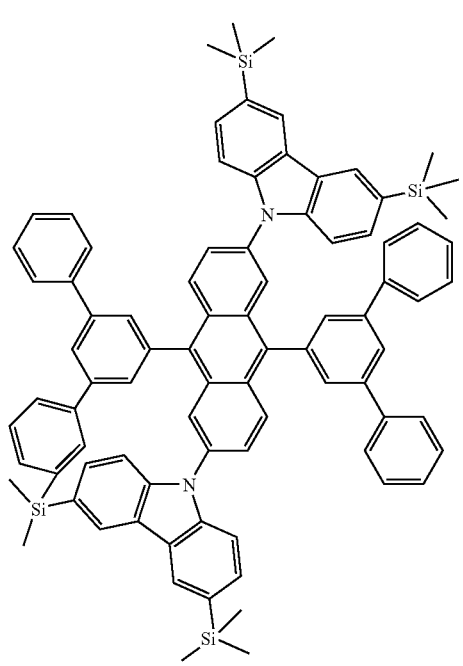

D-55
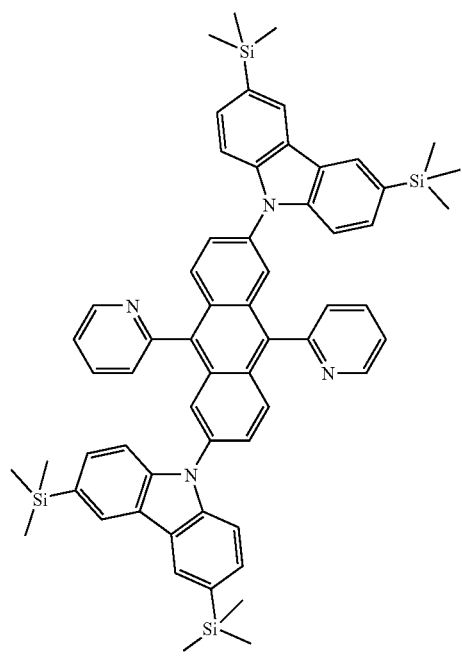
D-57
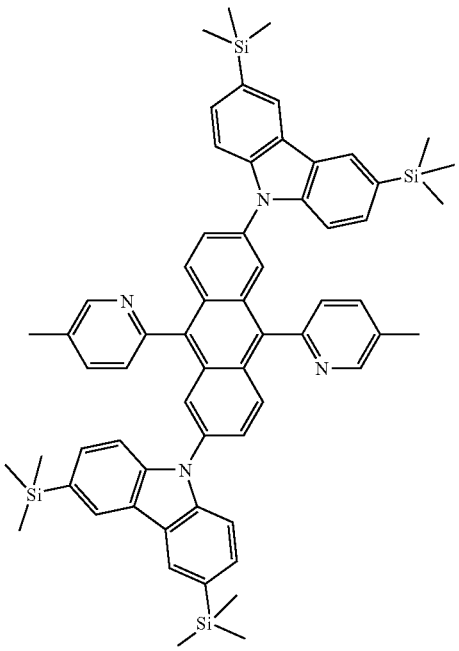
D-56
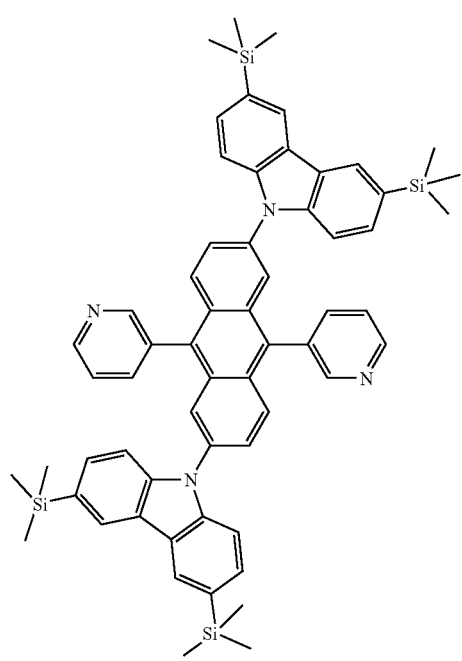
D-58
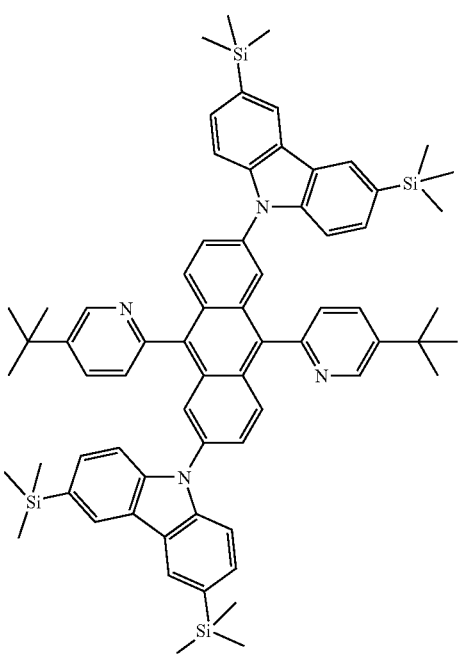

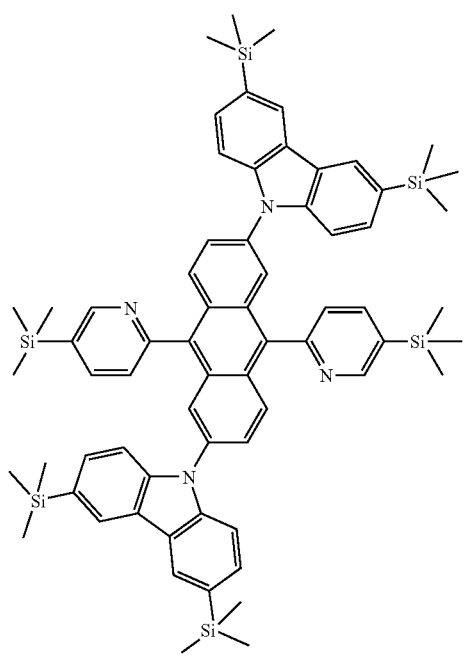
D-59
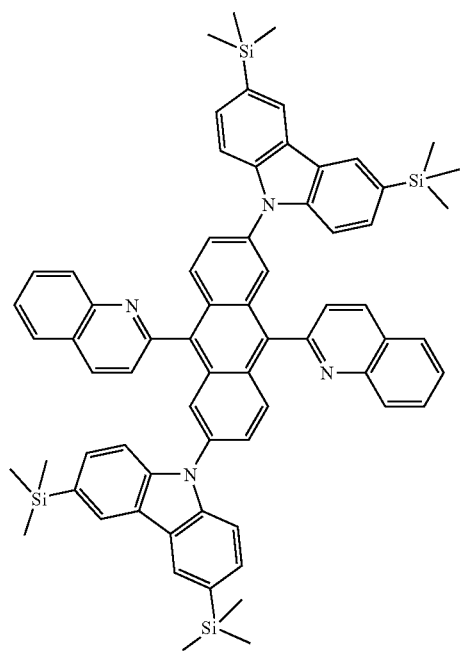
D-61
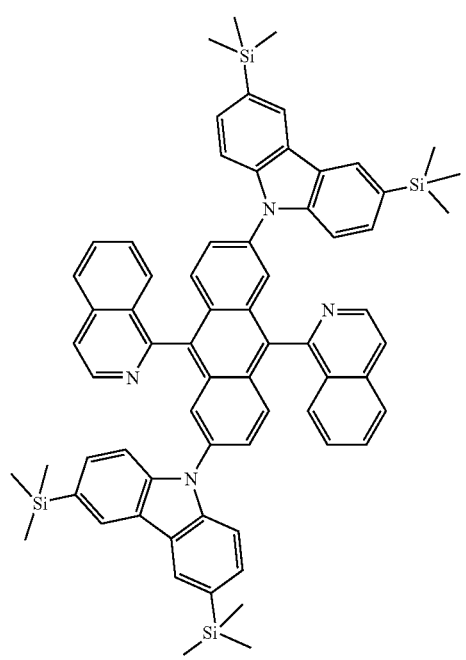
D-60
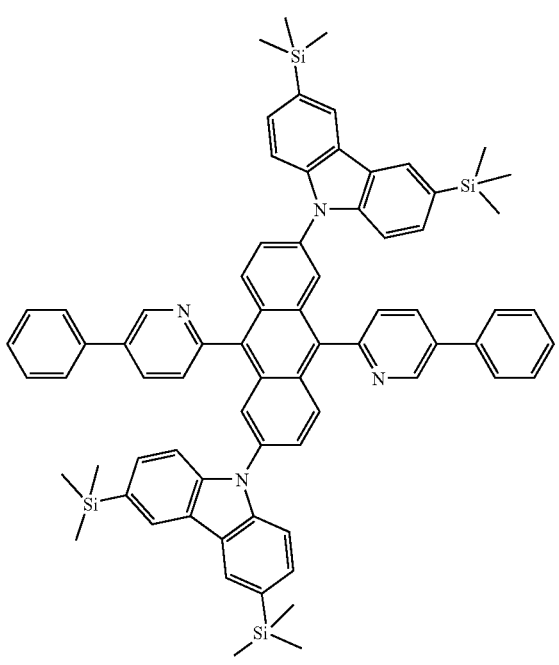
D-62

D-63
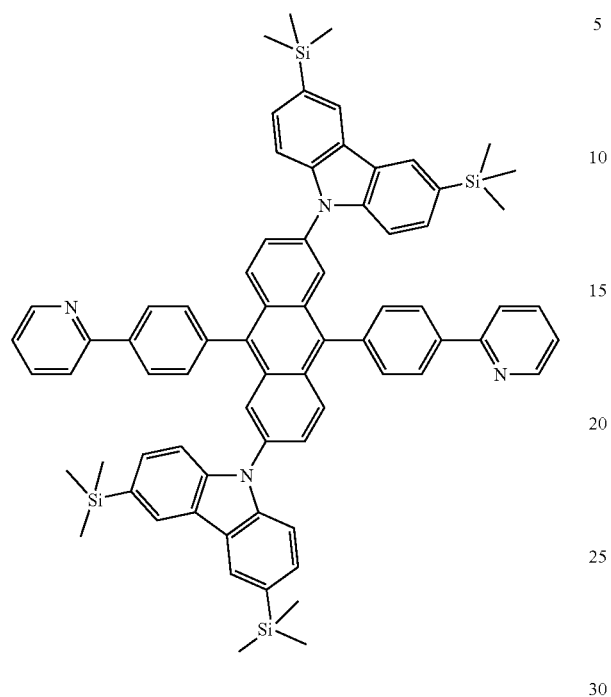
D-65
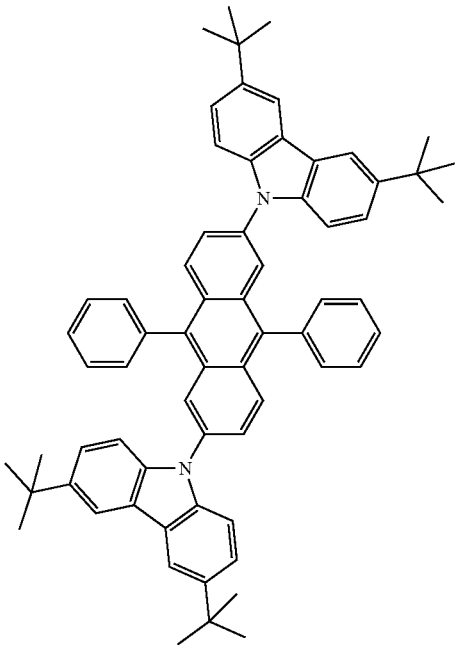
D-64
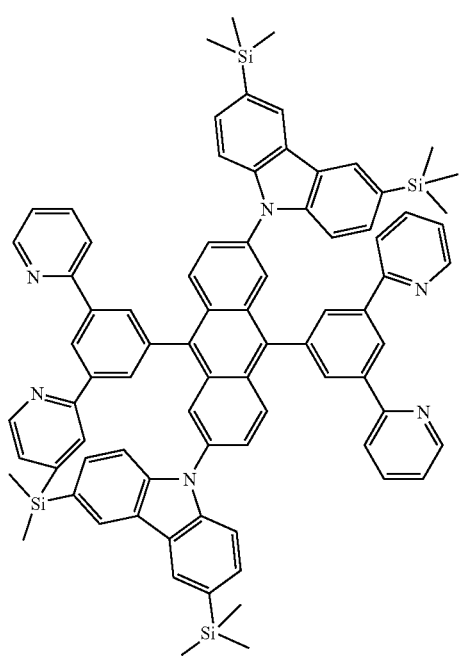
D-66
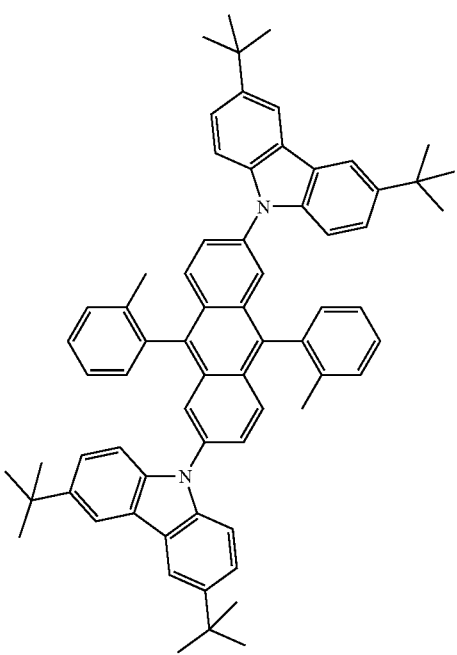

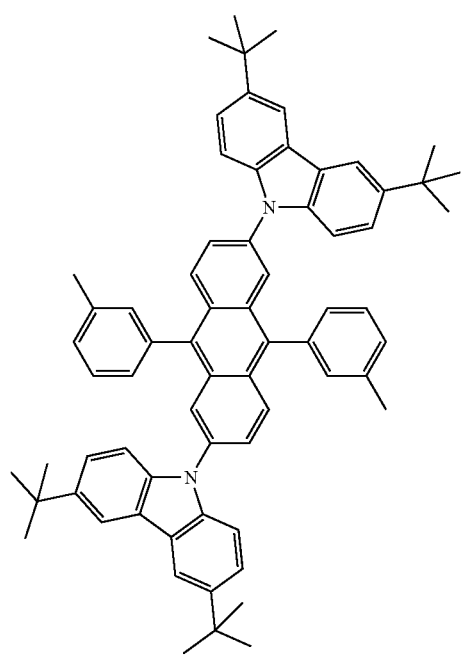
D-67
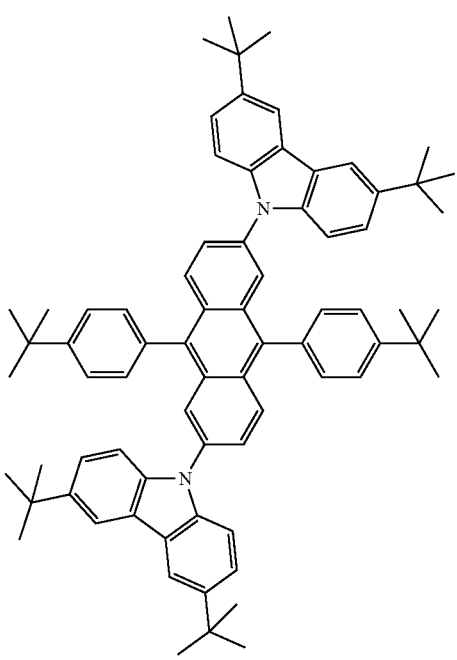
D-69
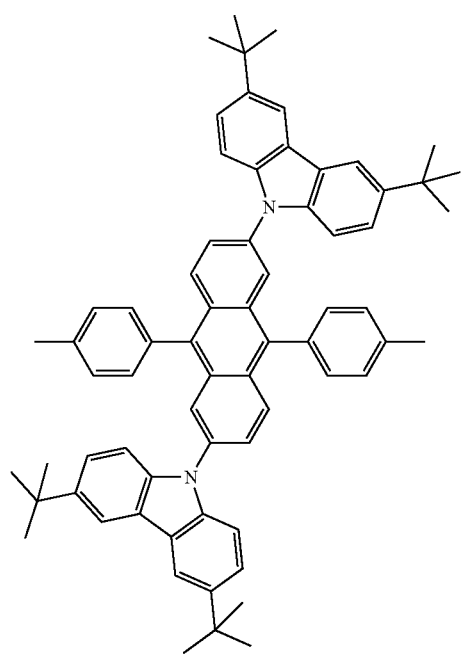
D-68
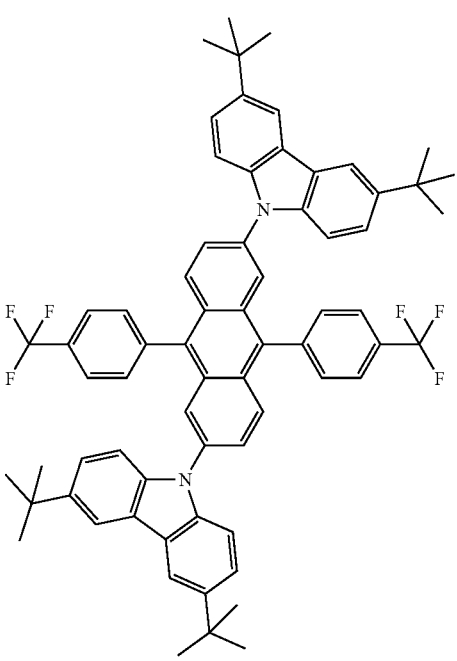
D-70

-continued
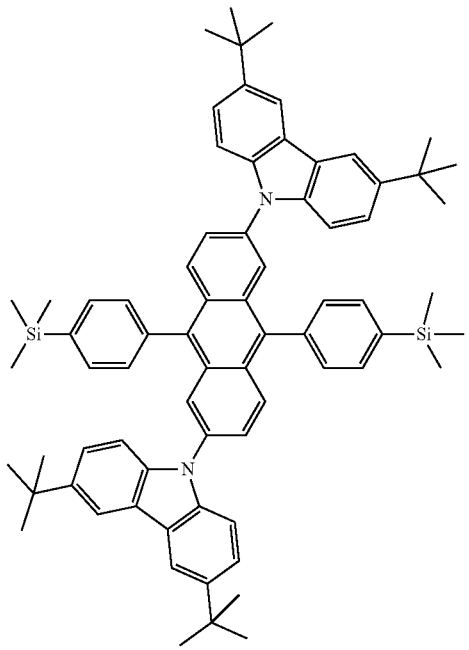
D-71
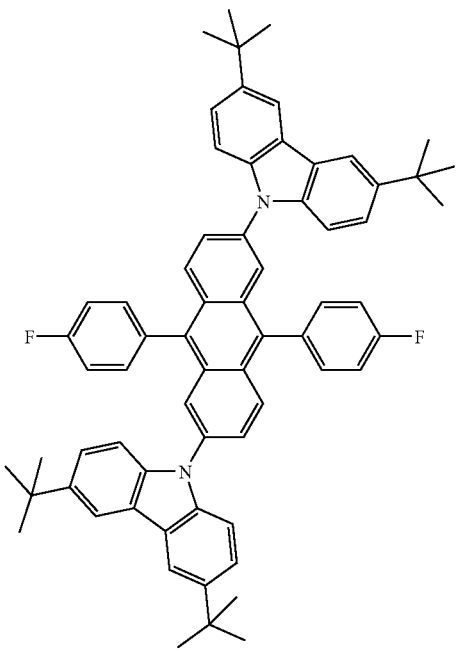
D-73
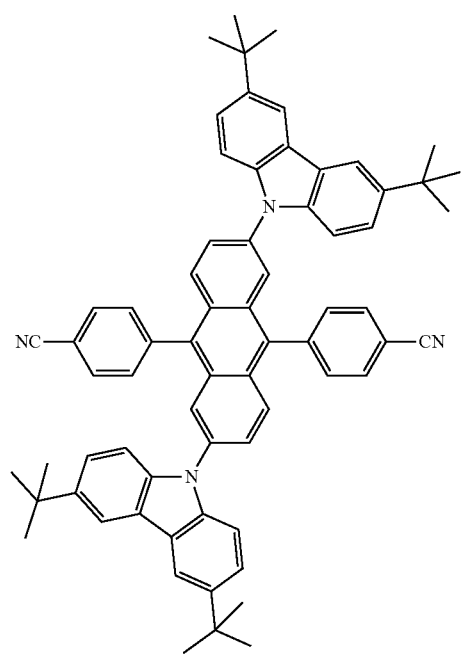
D-72
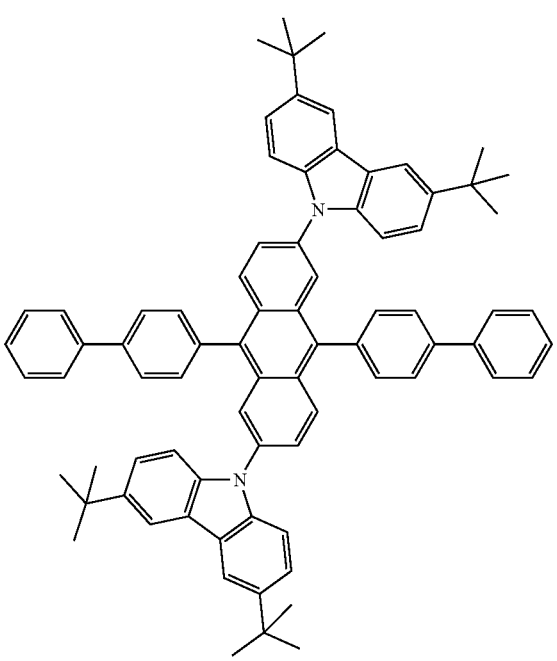
D-74

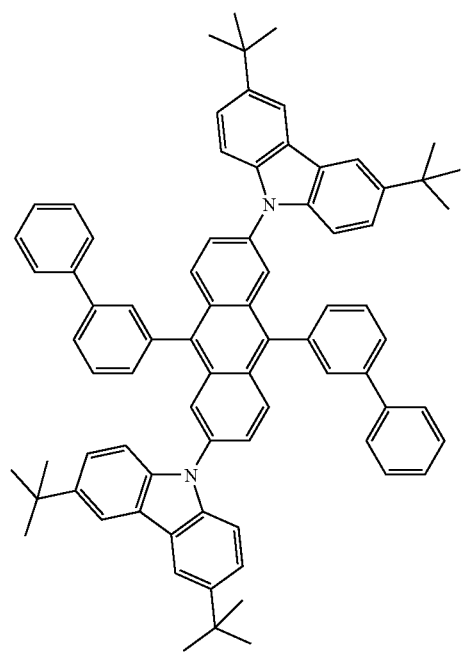
D-75
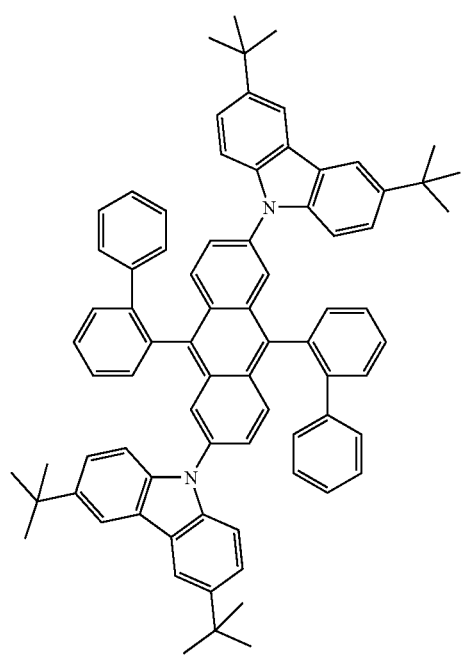
D-76
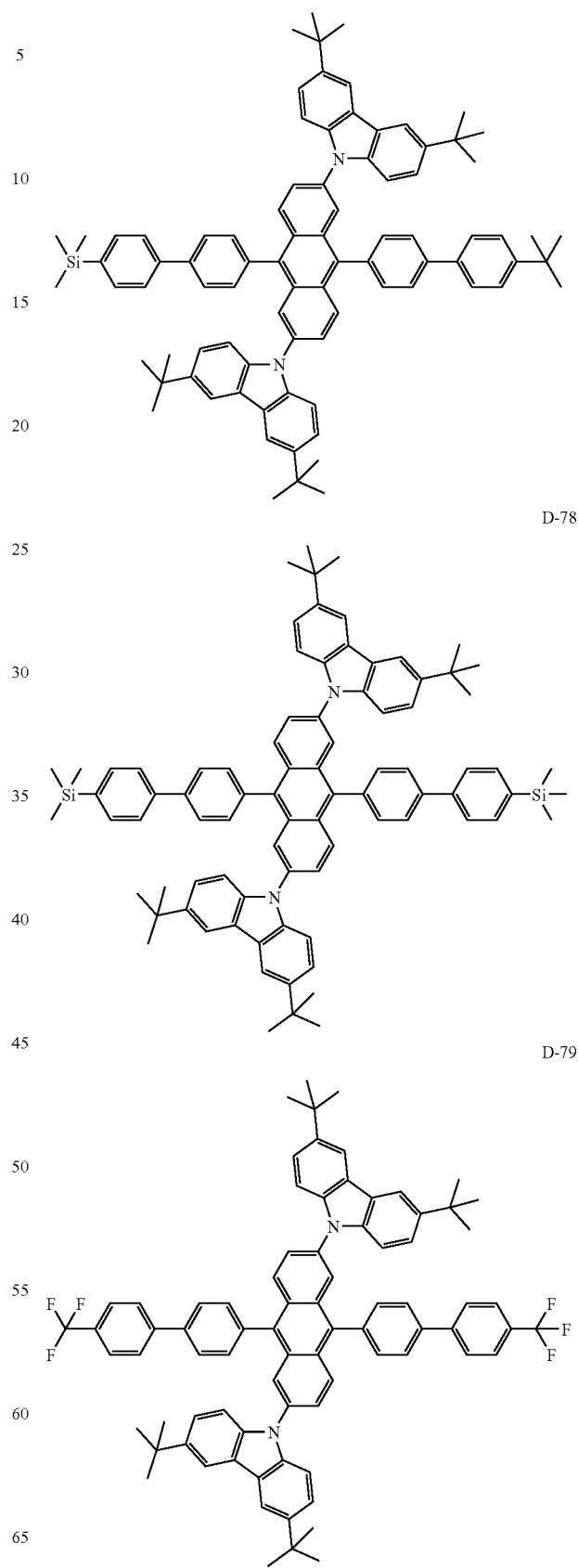
D-77
D-78
D-79

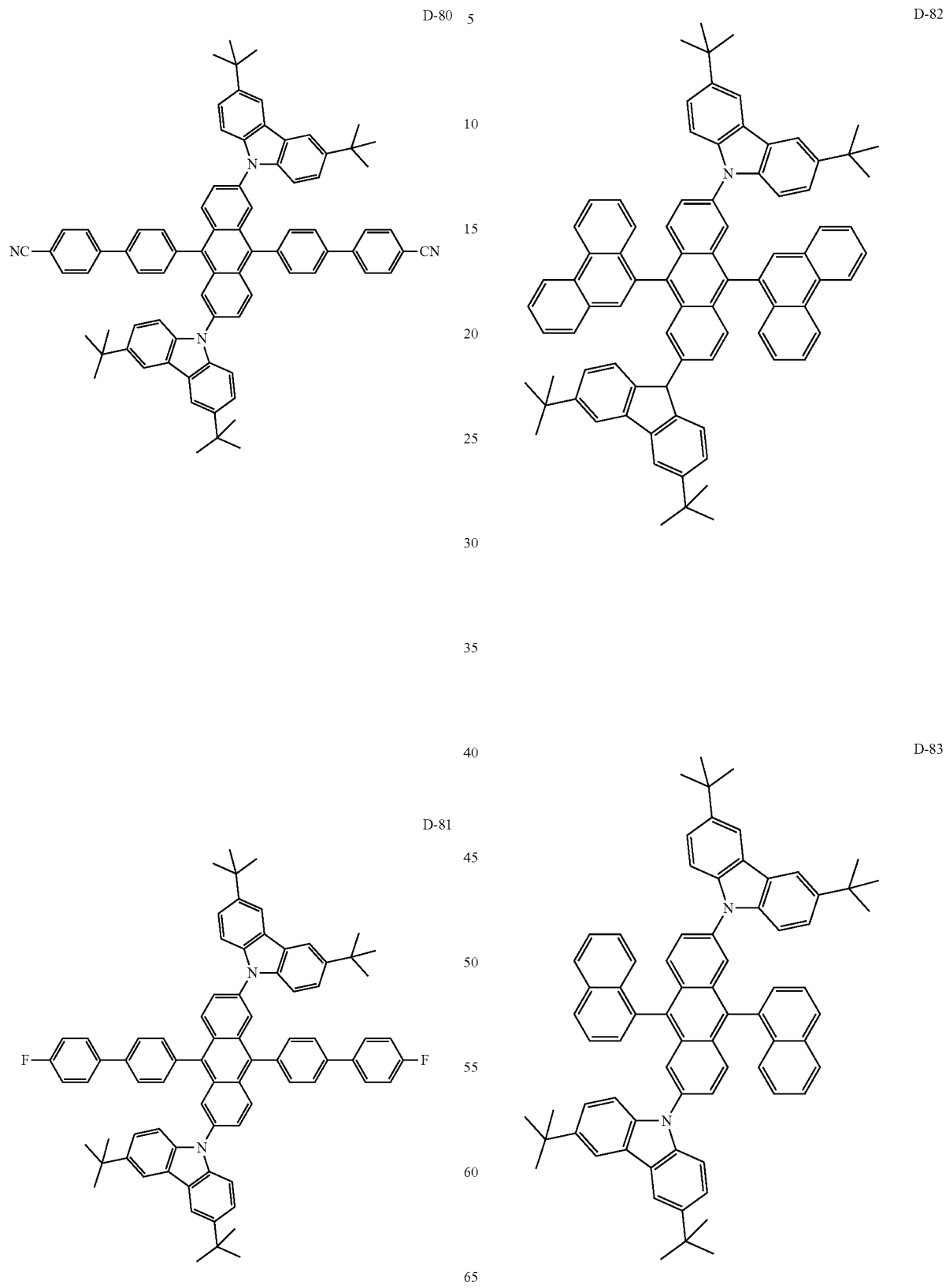

-continued
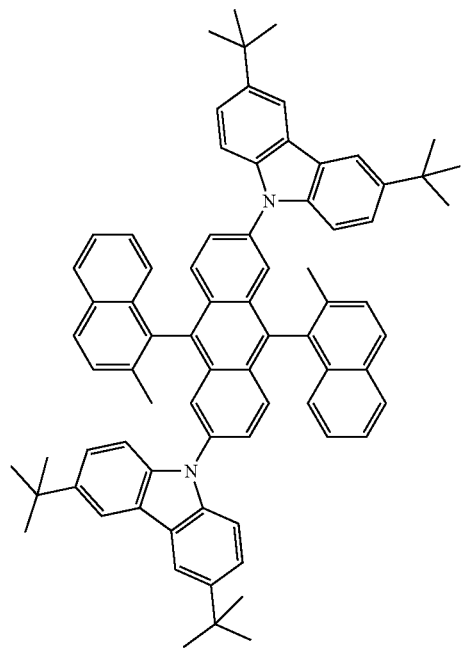
D-84
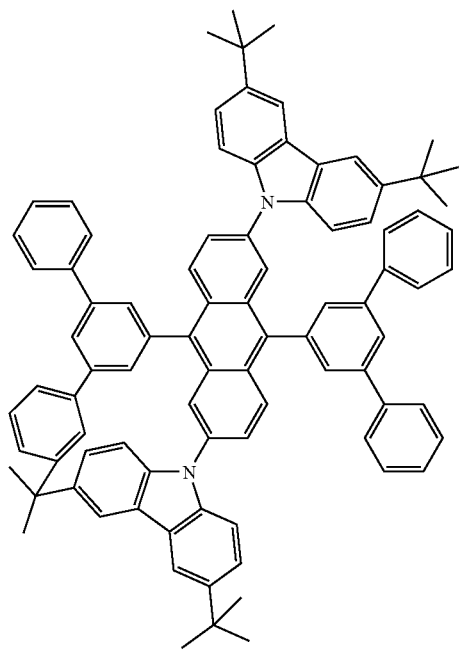
D-86
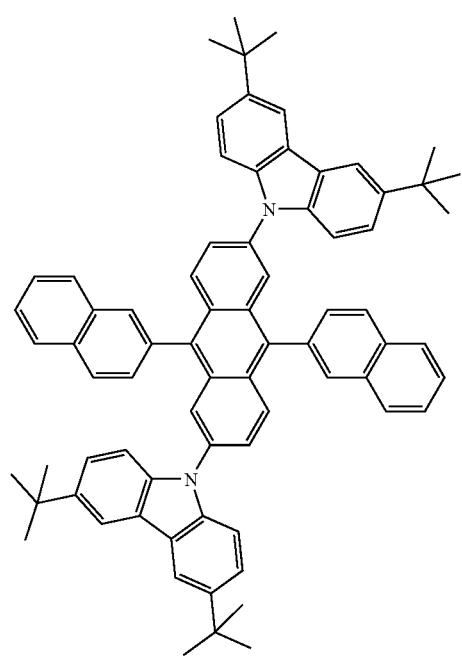
D-85
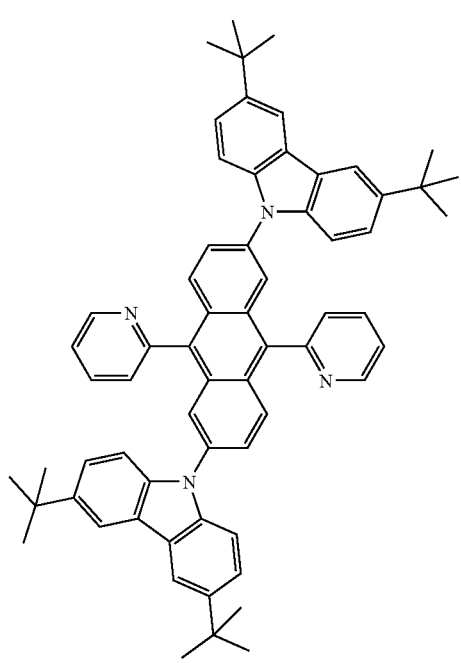
D-87

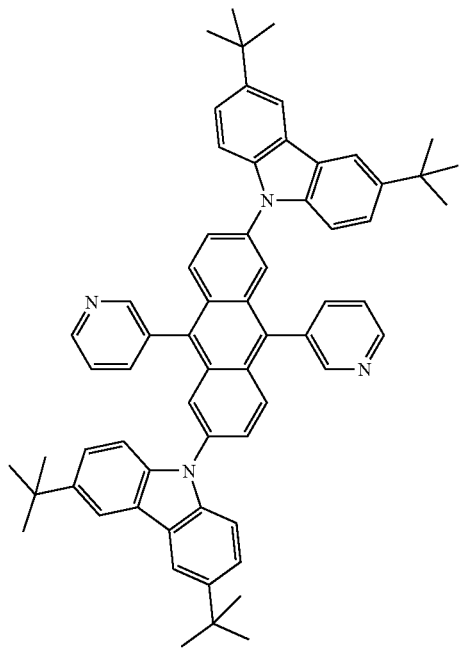
D-88
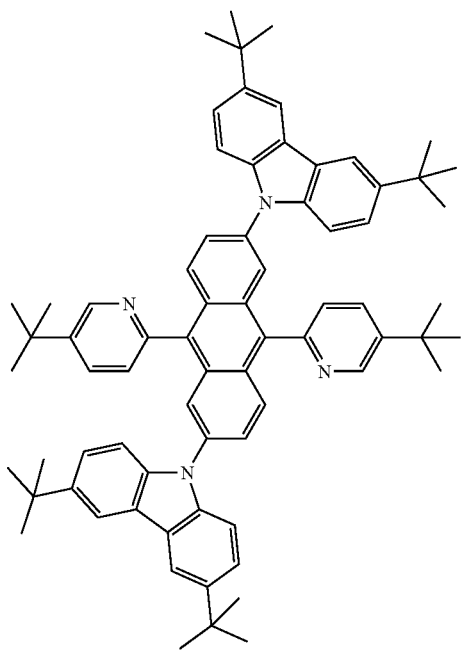
D-90
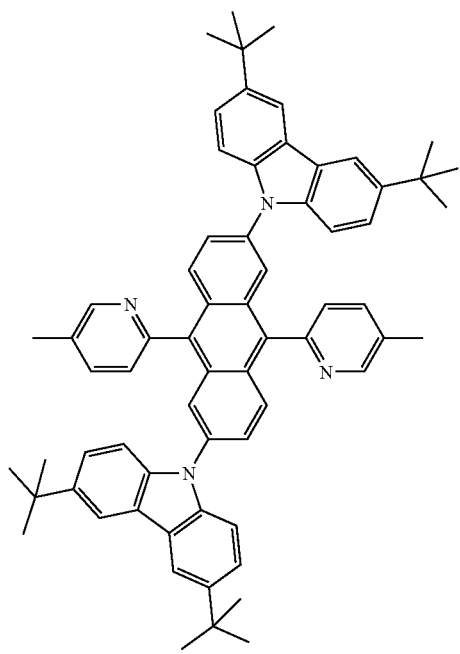
D-89
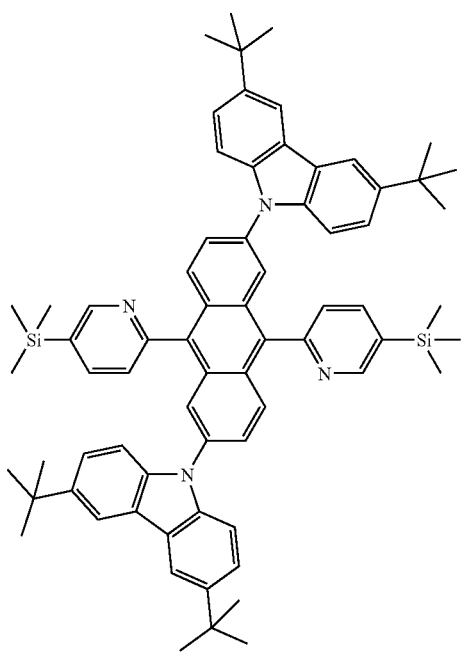
D-91

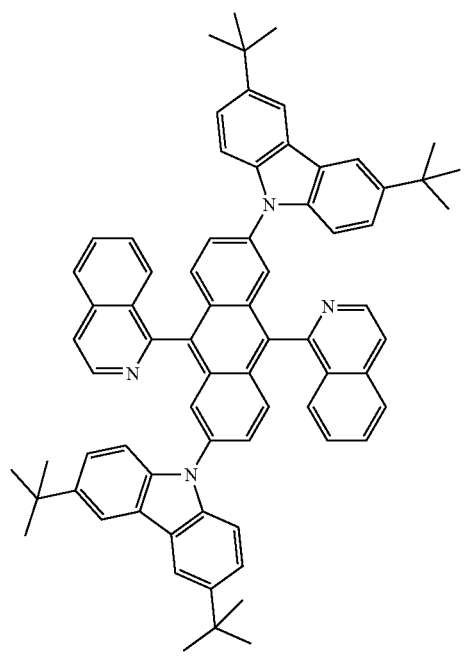
D-92
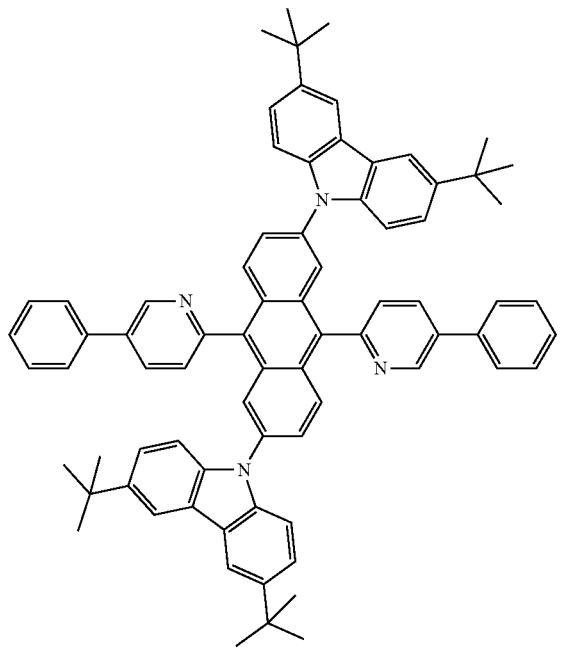
D-94
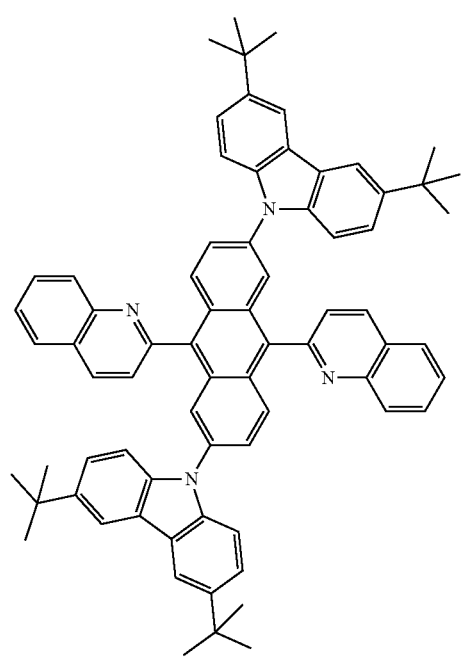
D-93
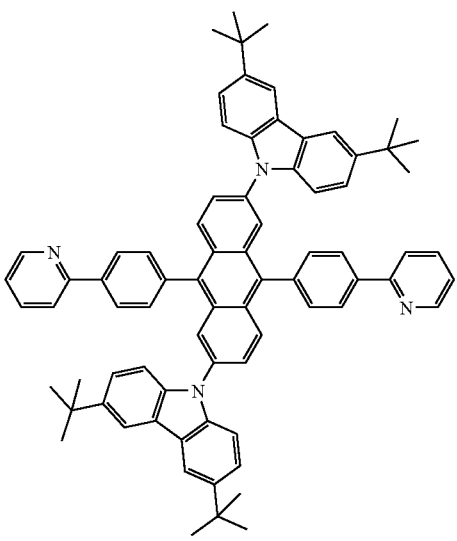
D-95

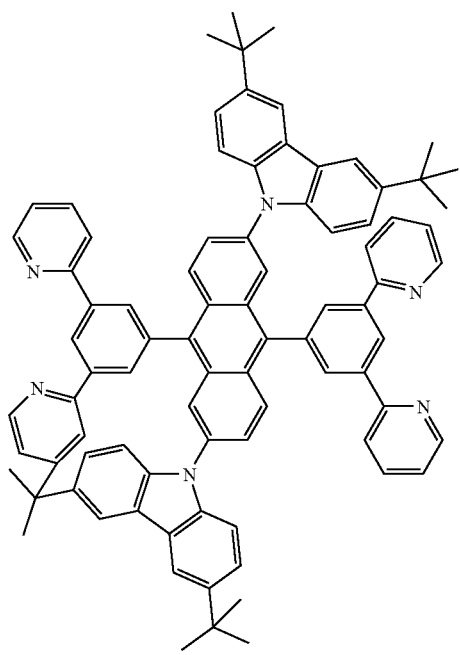
D-96
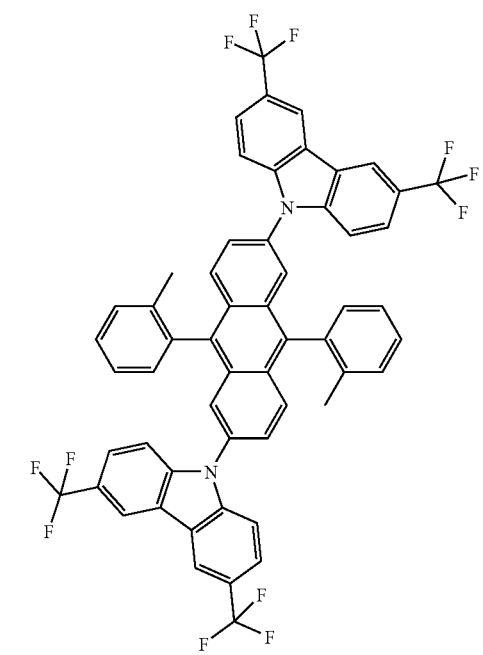
D-98
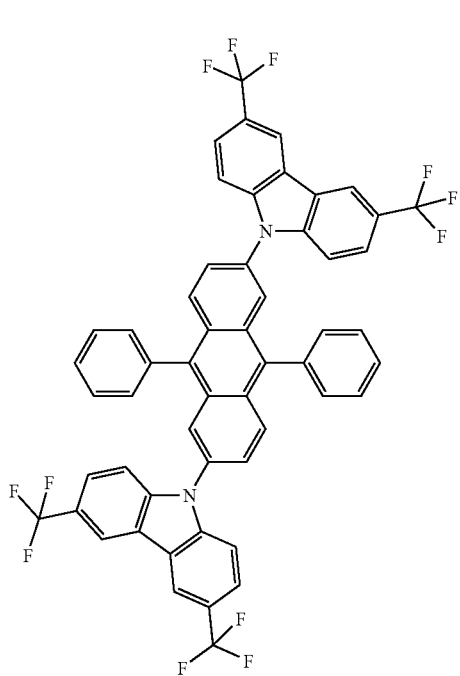
D-97
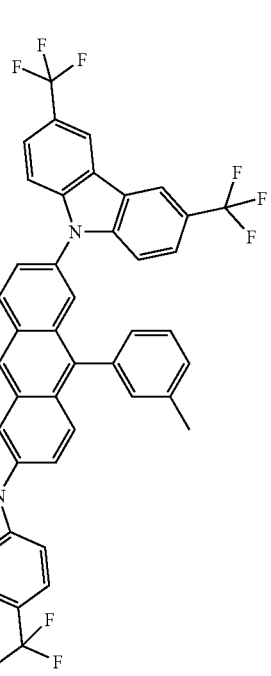
D-99

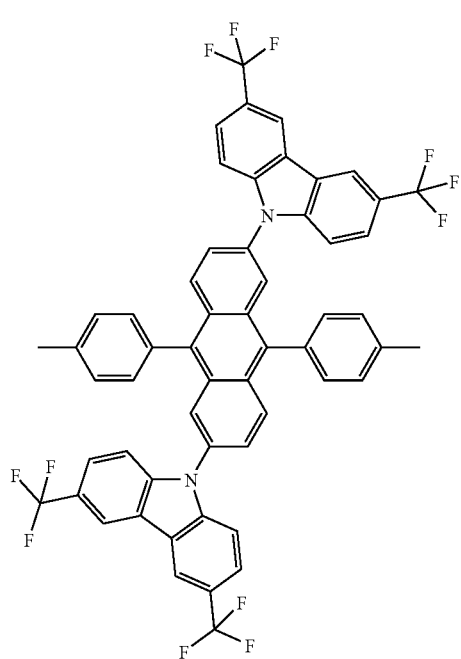
D-100
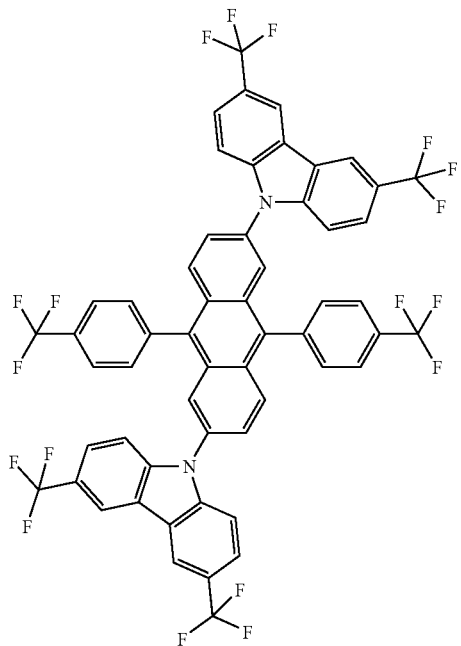
D-102
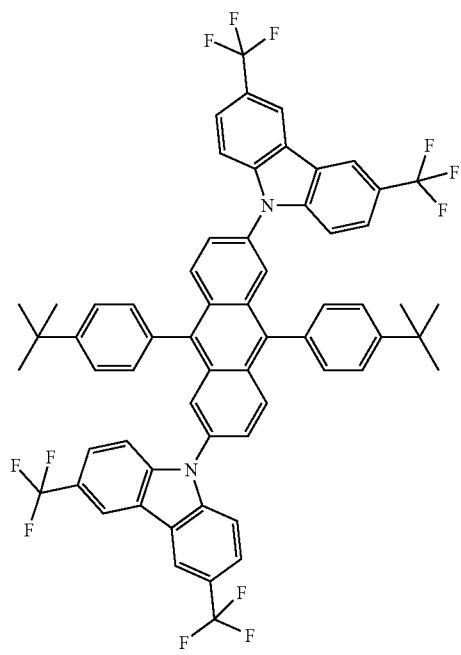
D-101
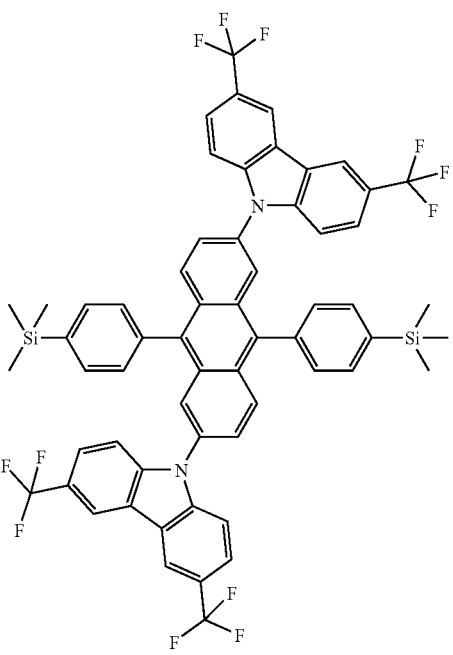
D-103

D-104
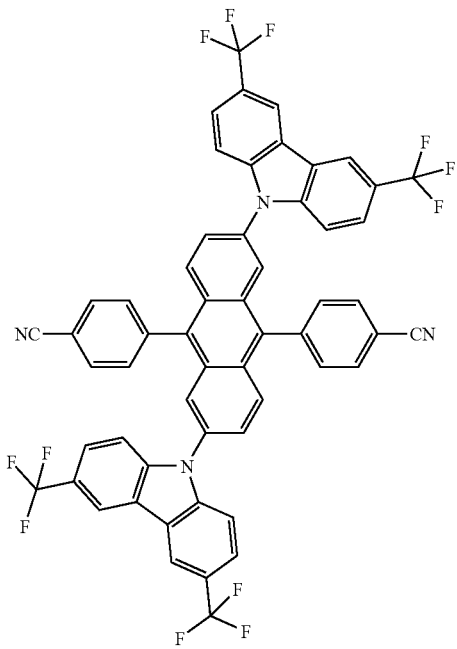
D-106
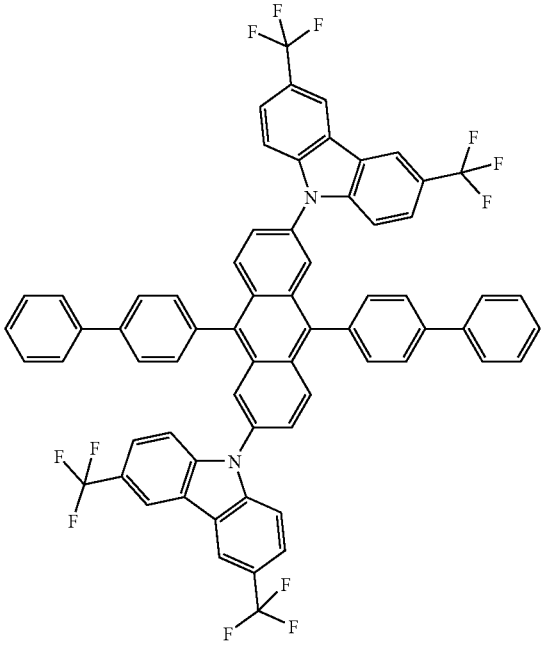
D-105
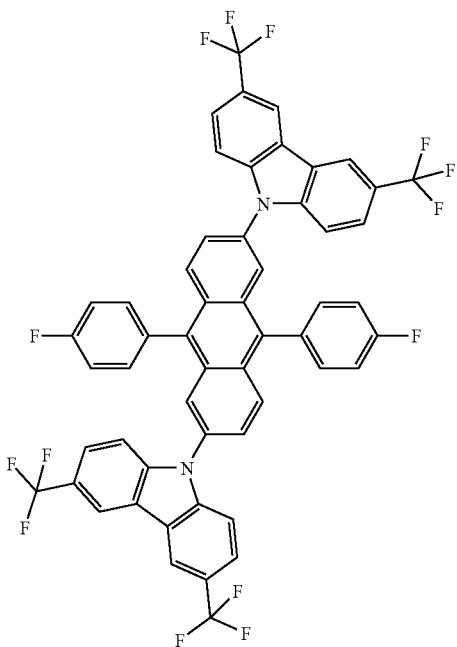
D-107
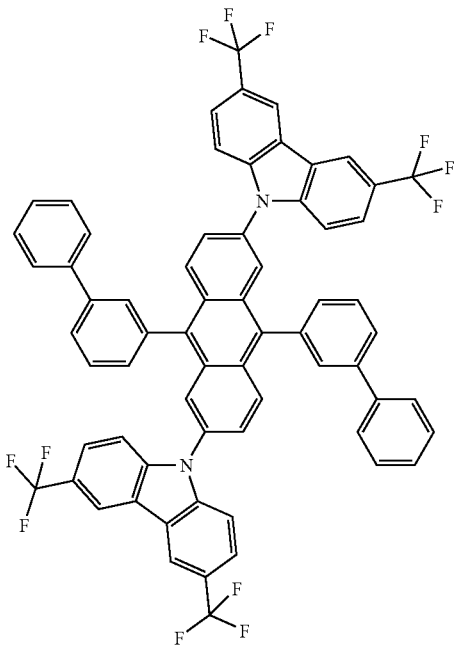

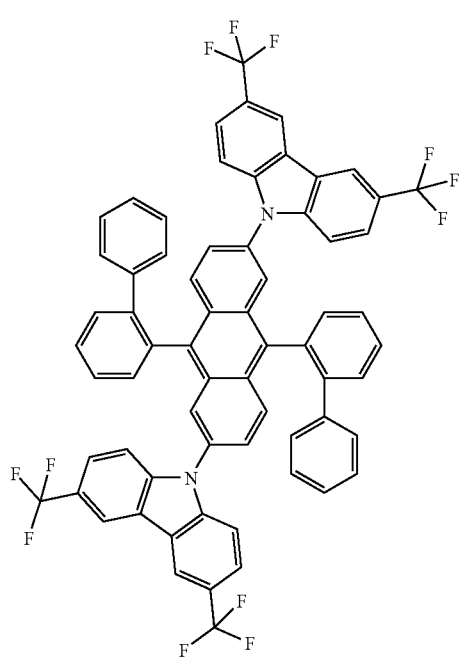
D-108
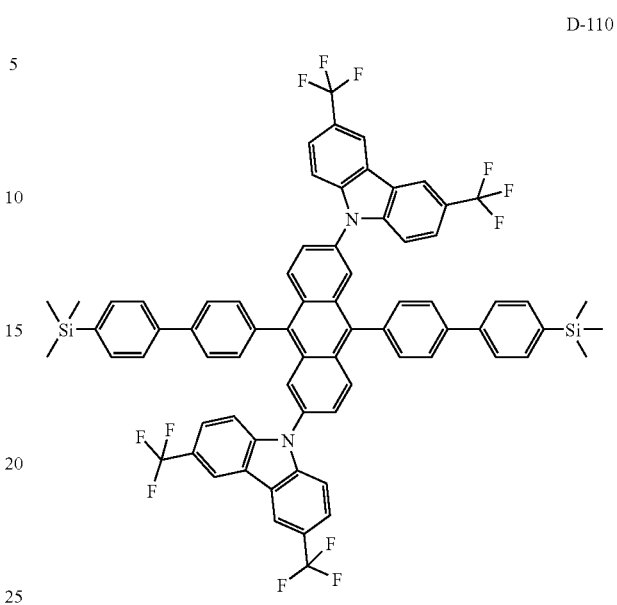
D-110
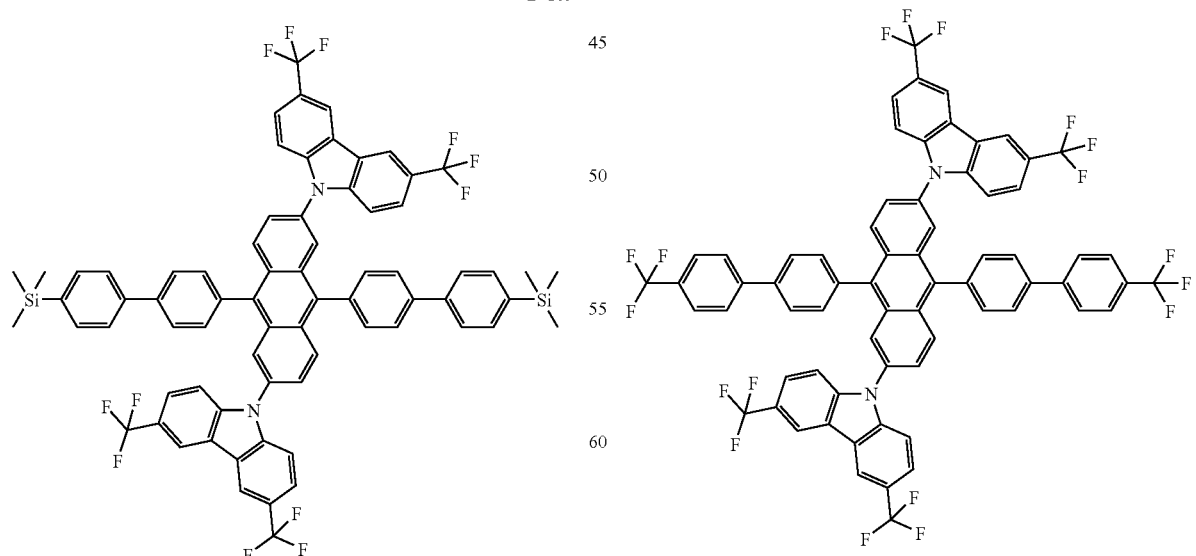
D-109
D-111

-continued
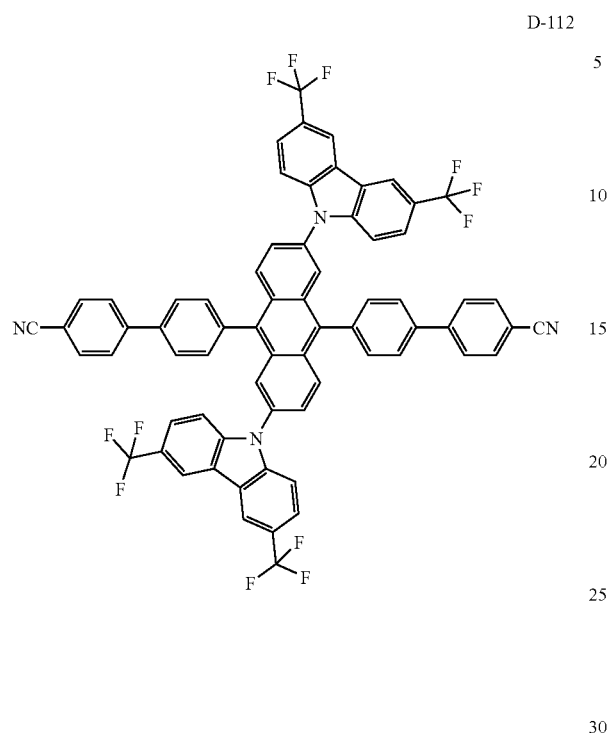
D-112
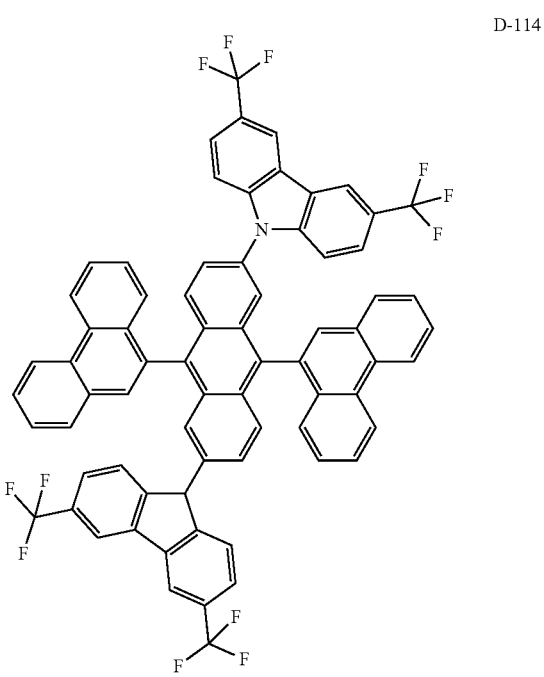
D-114
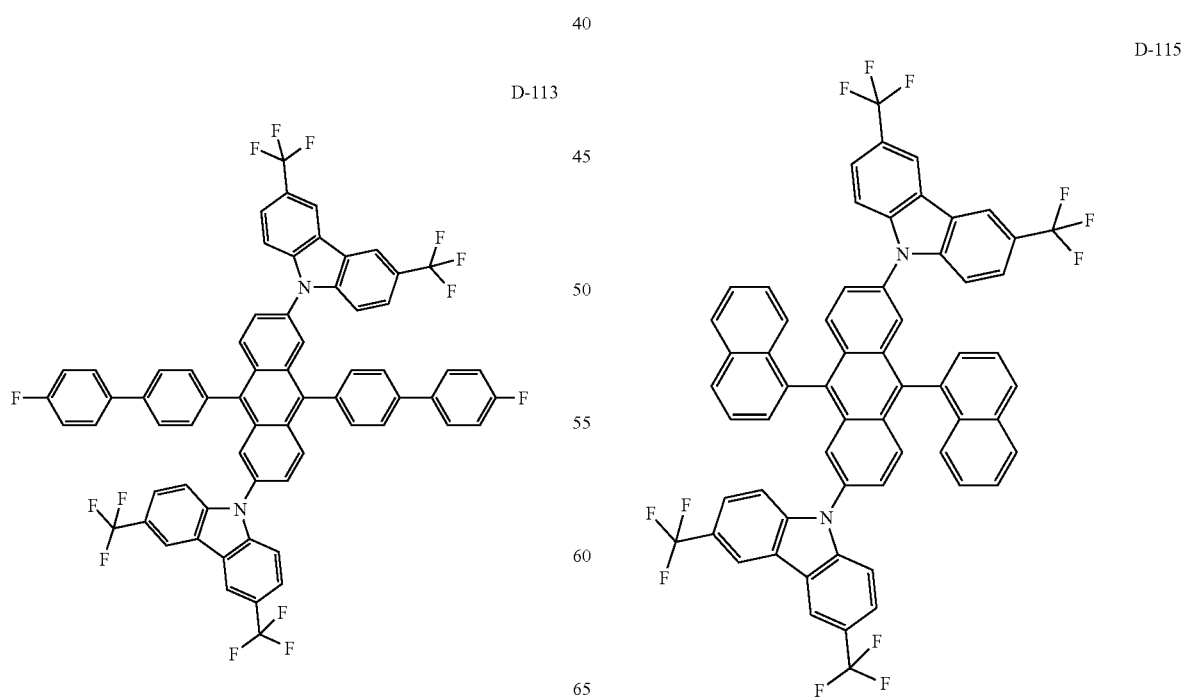
D-113
D-115

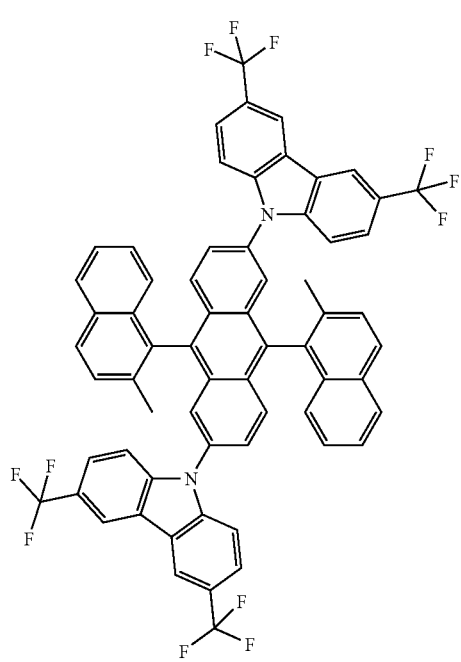
D-116
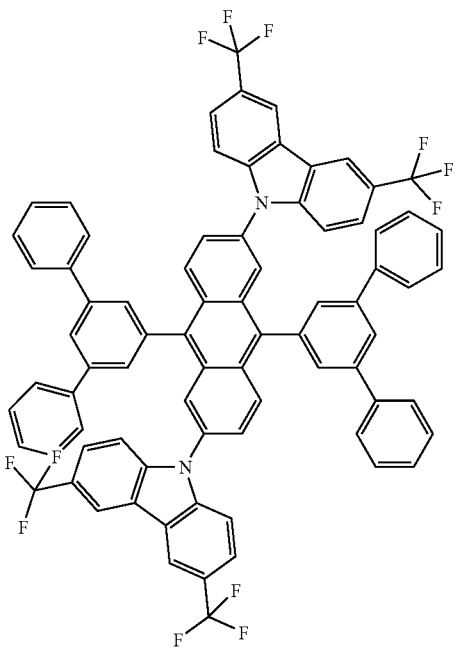
D-118
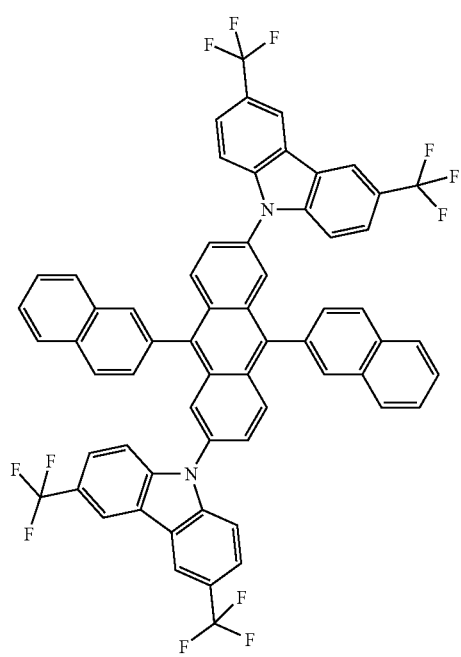
D-117
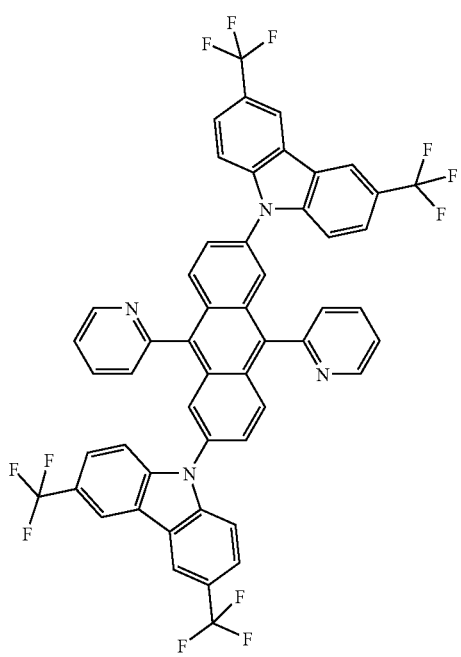
D-119

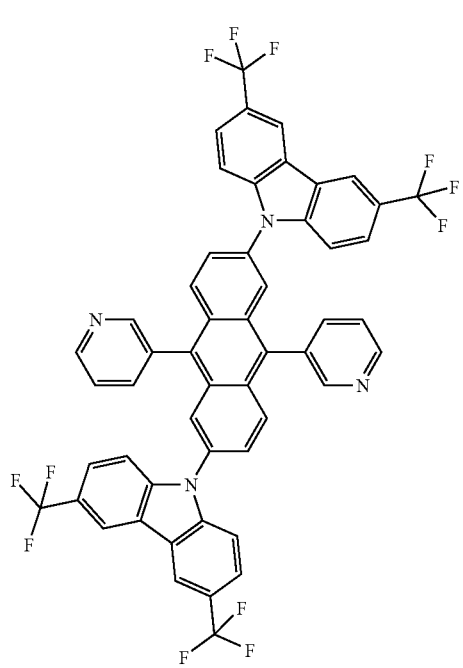
D-120
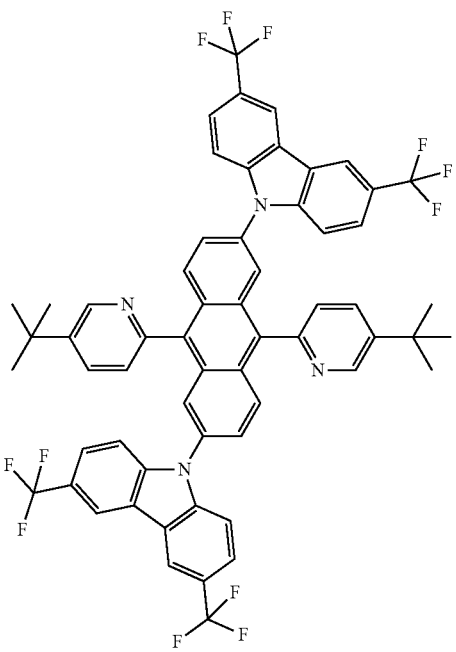
D-123
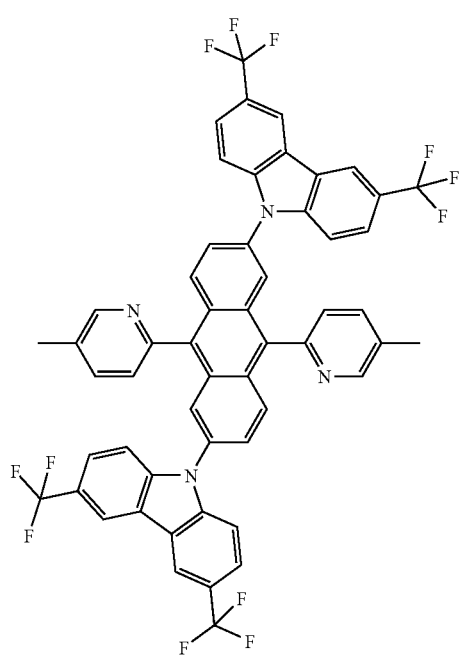
D-121
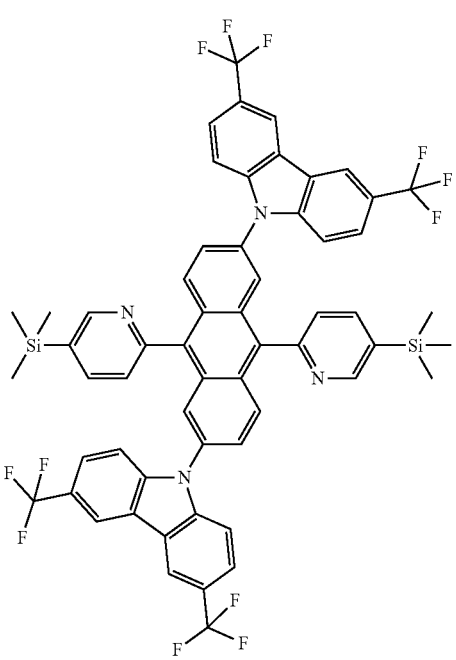
D-124

-continued
D-125
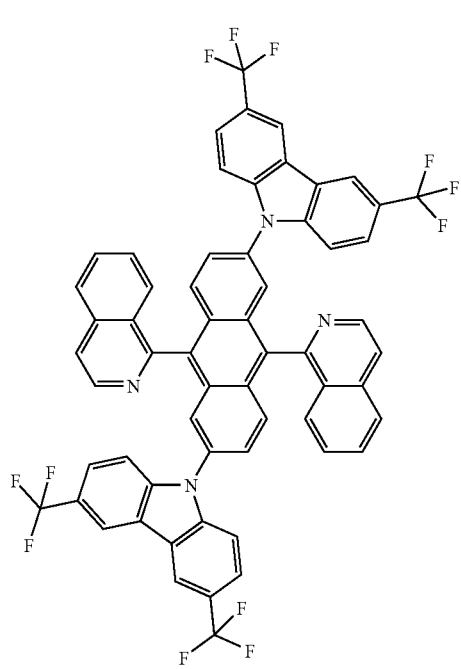
D-127
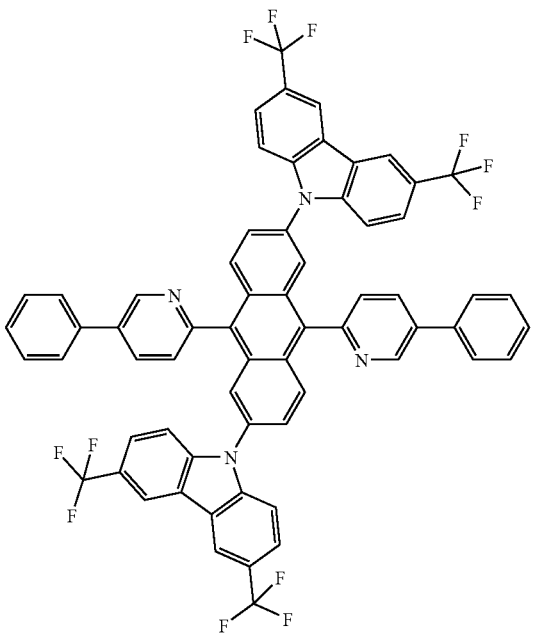
D-126
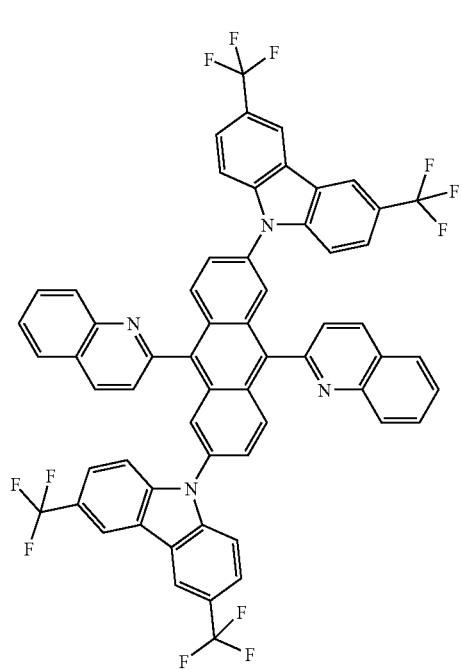
D-128
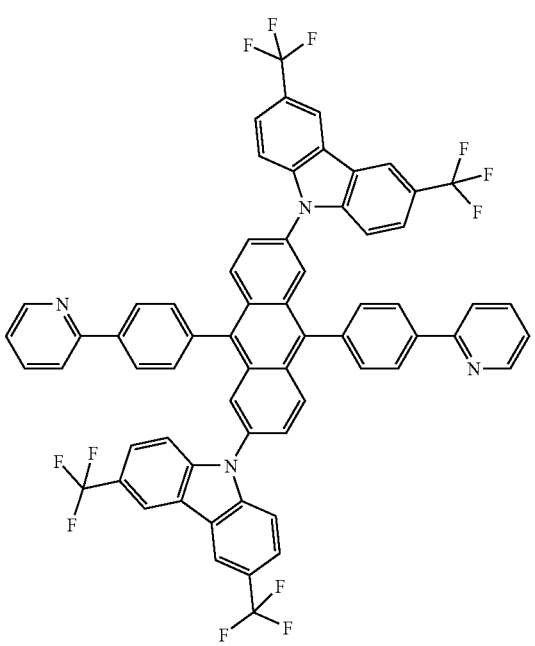

D-129
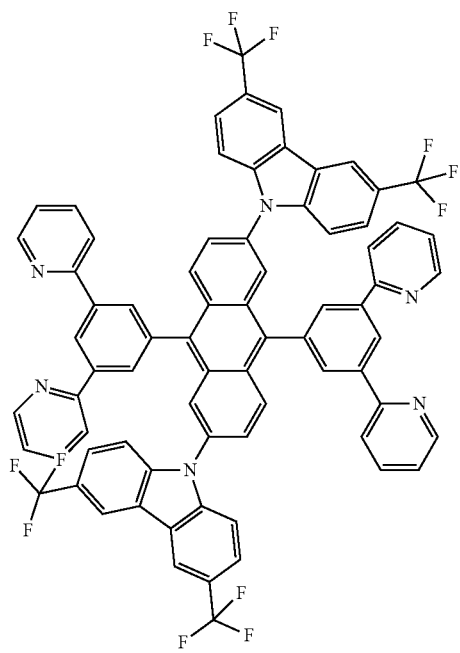
D-130
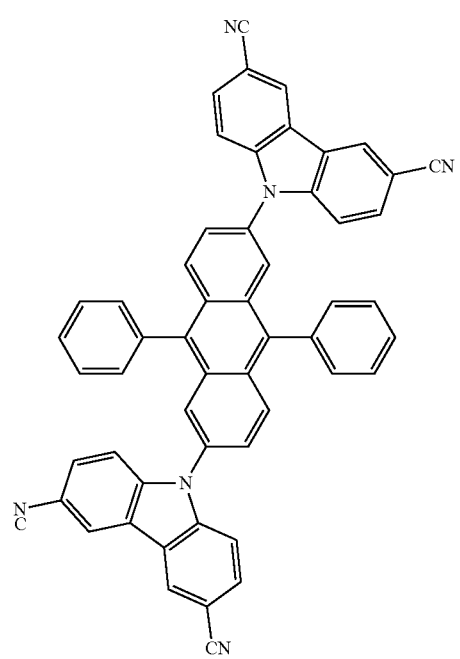
D-131
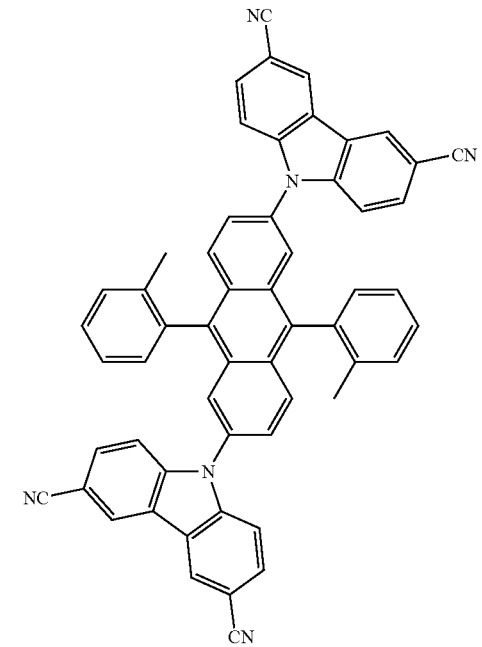
D-132

-continued
D-133
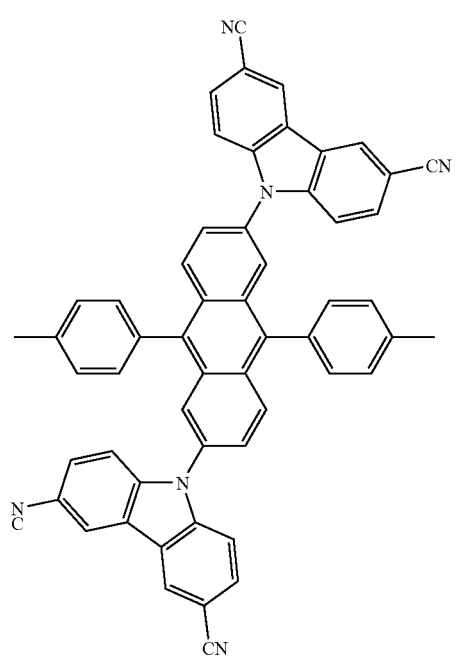
D-135
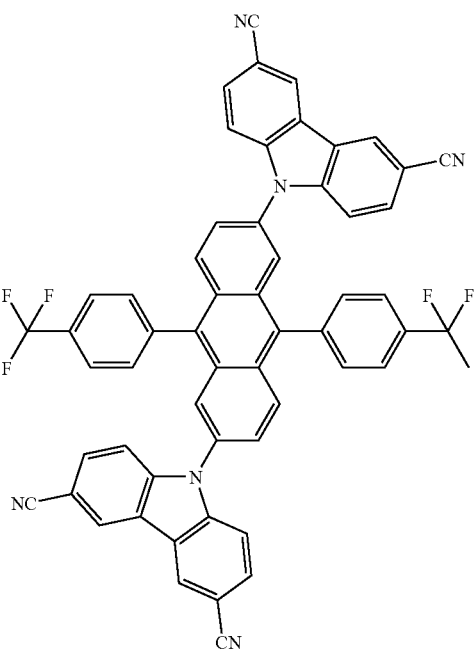
D-134
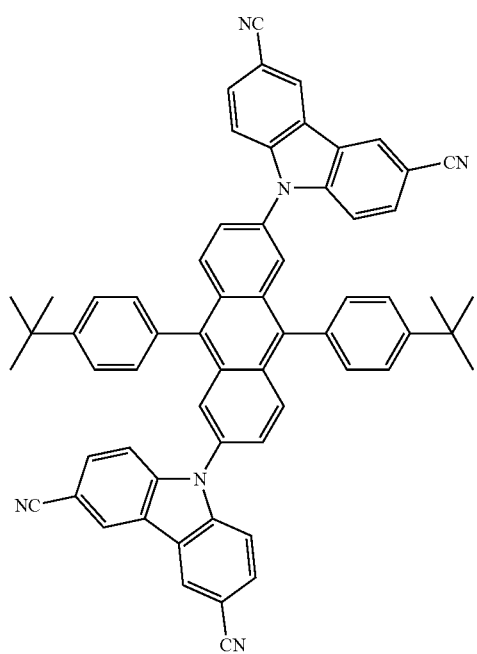
D-136
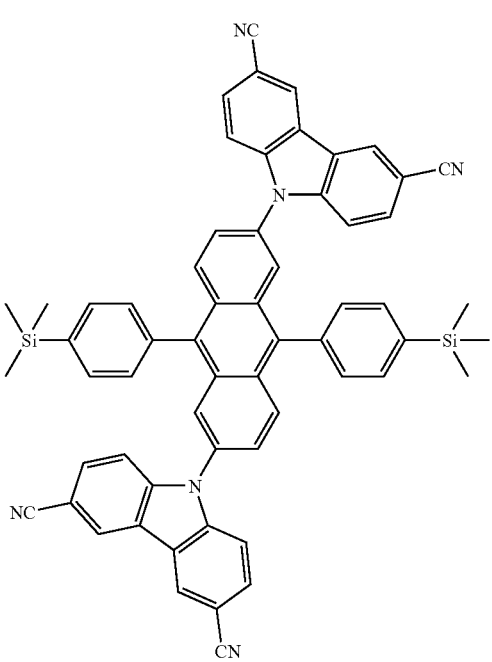

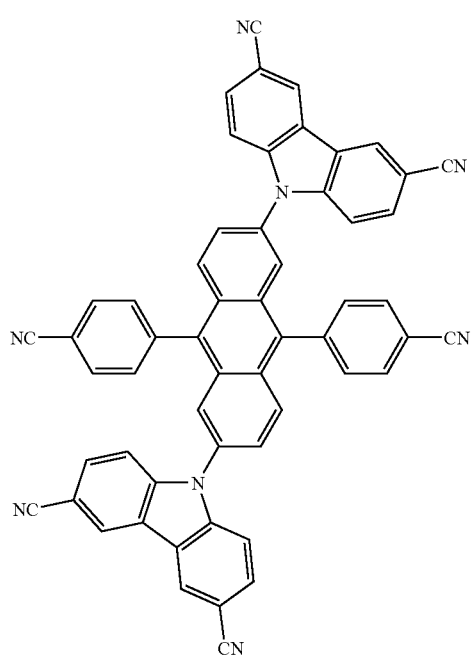
D-137
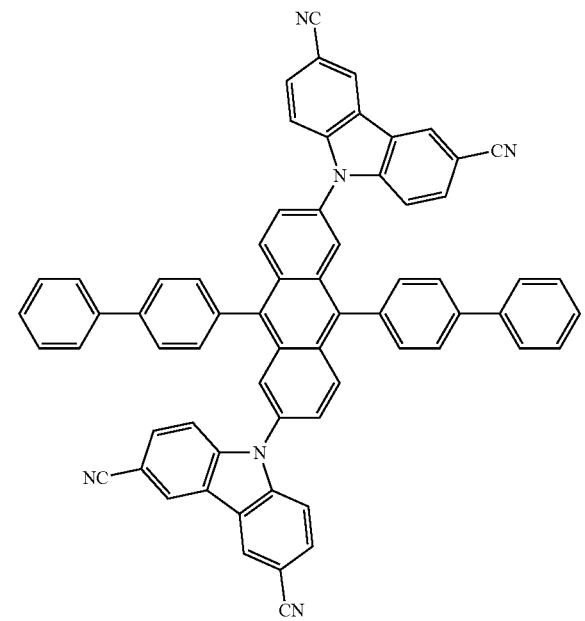
D-139
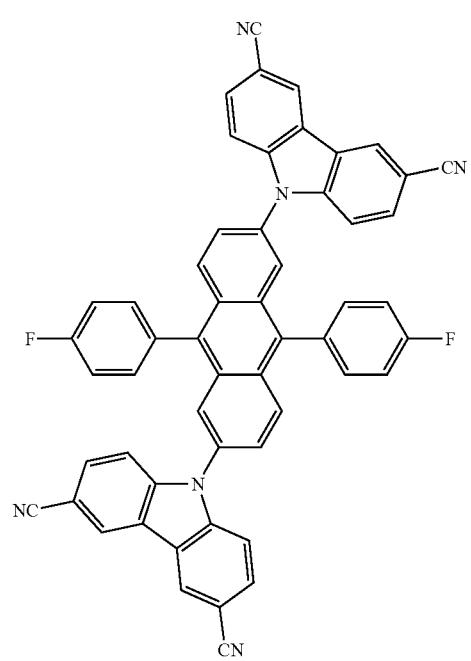
D-138
D-140

D-142
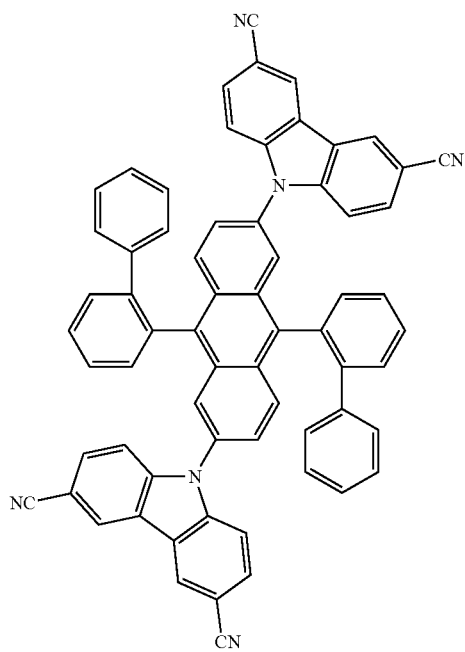
D-143
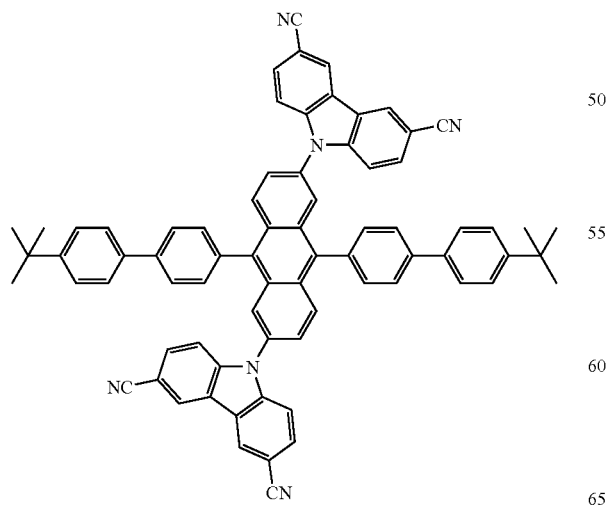
D-144
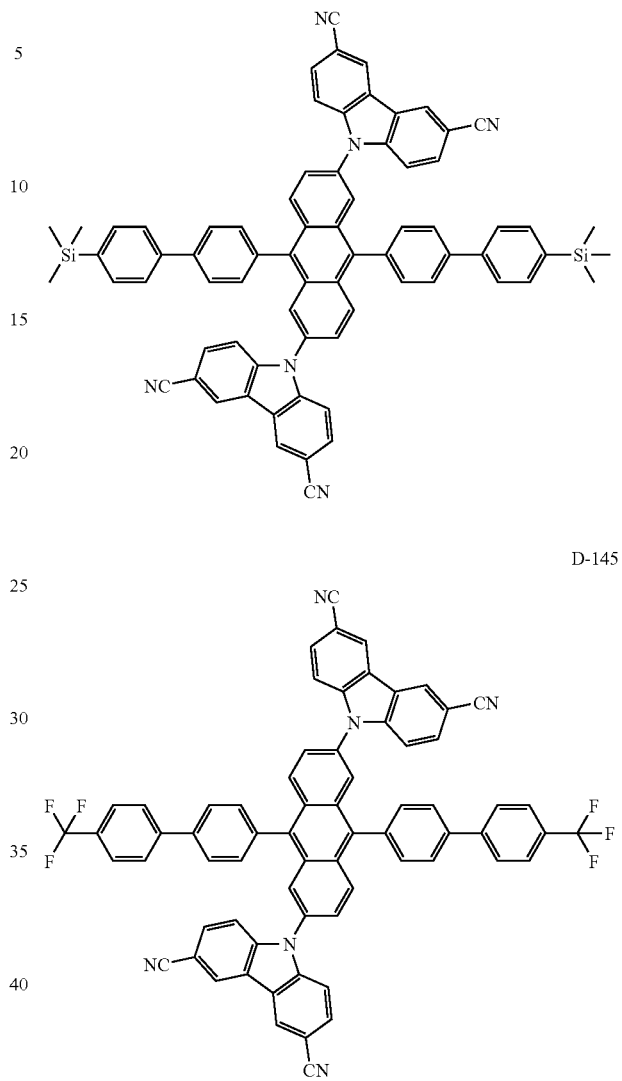
D-145
D-146

D-147
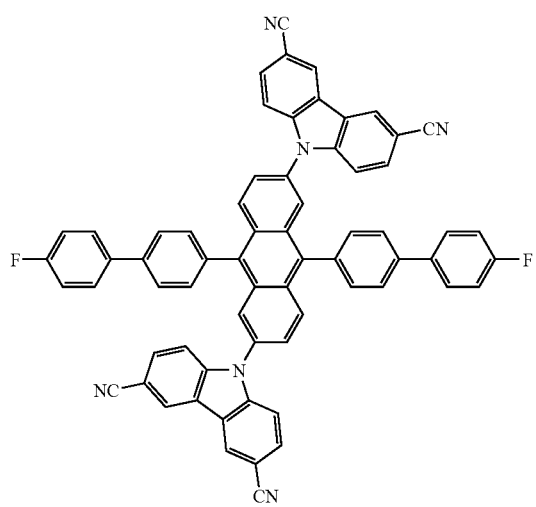
D-148
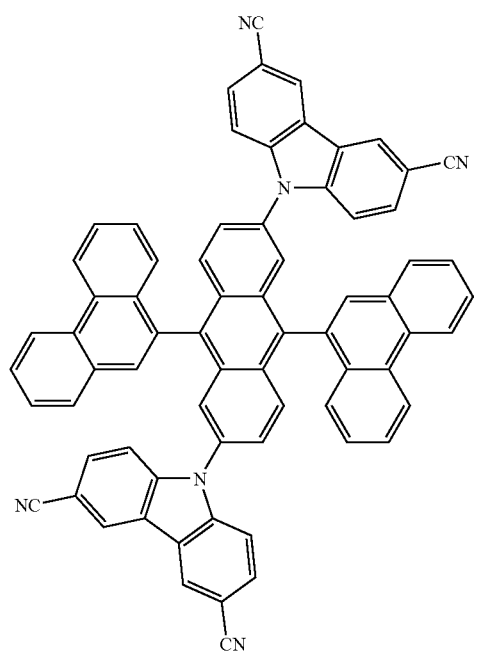
D-149
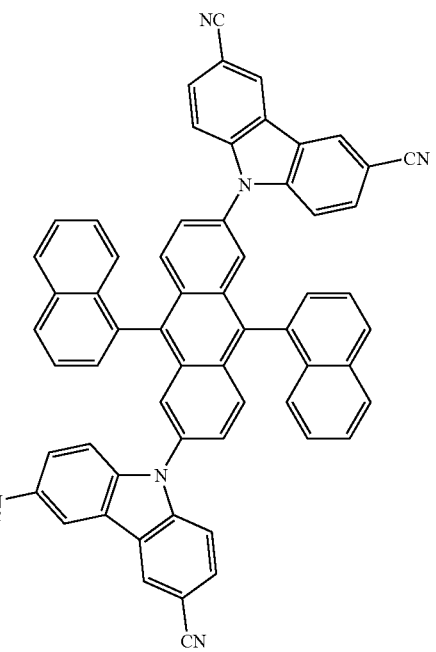
D-150
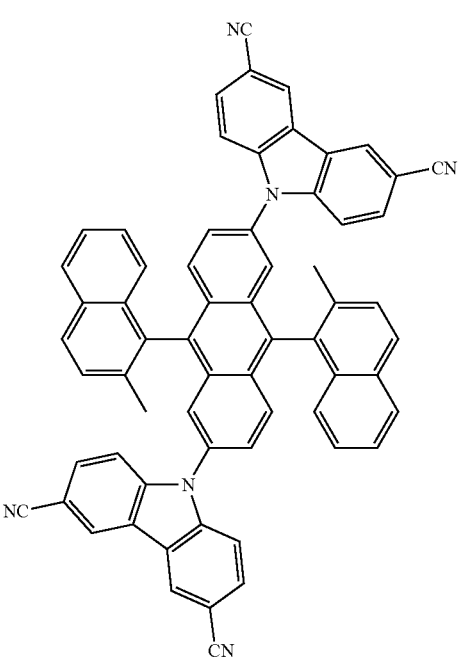

D-151
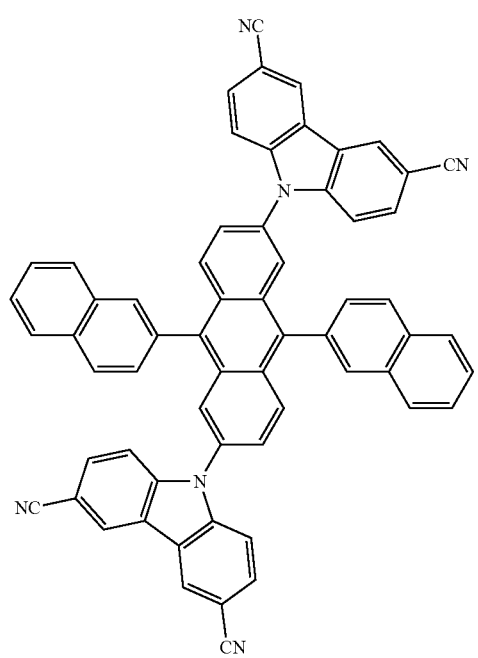
D-153
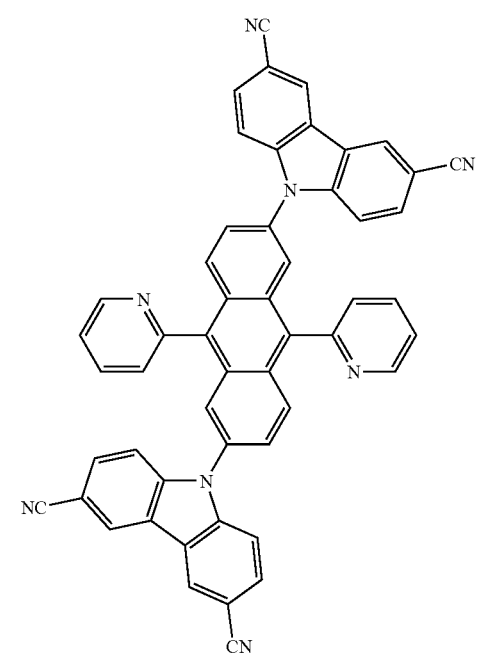
D-152
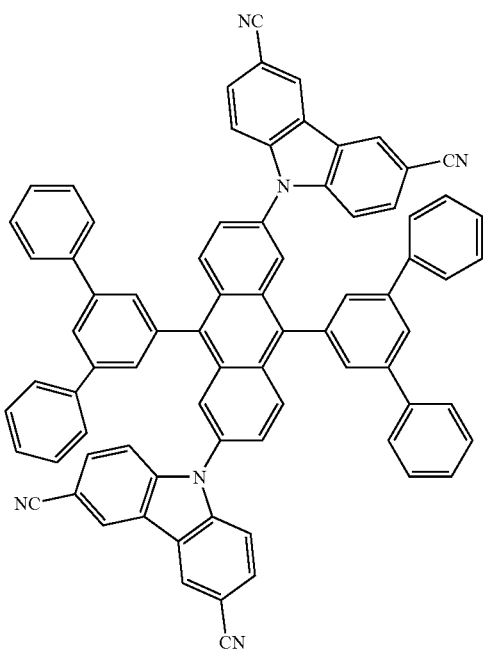
D-154
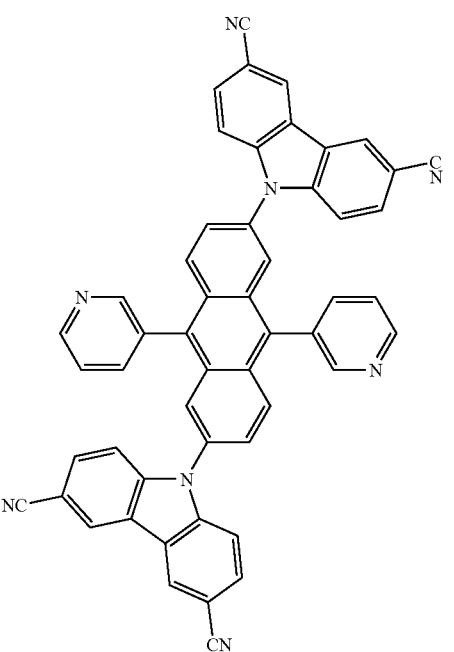

D-155
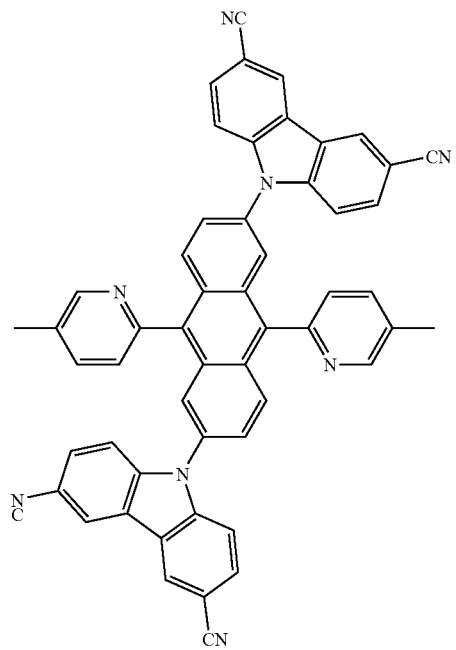
D-157
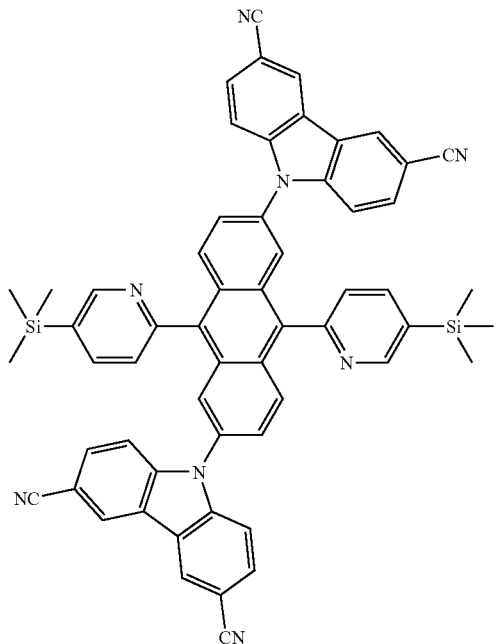
D-156
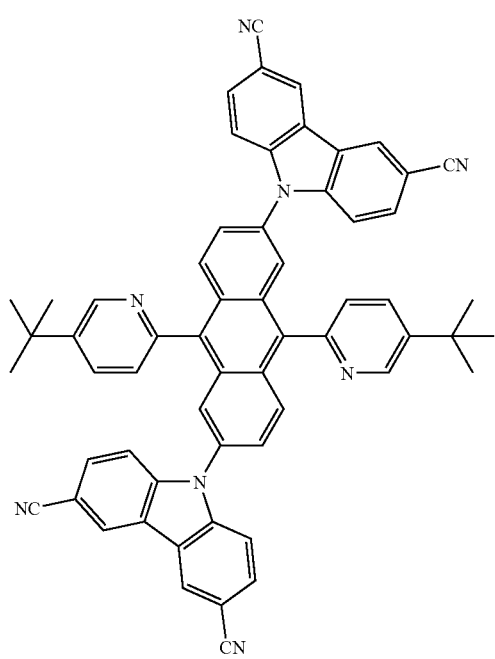
D-158
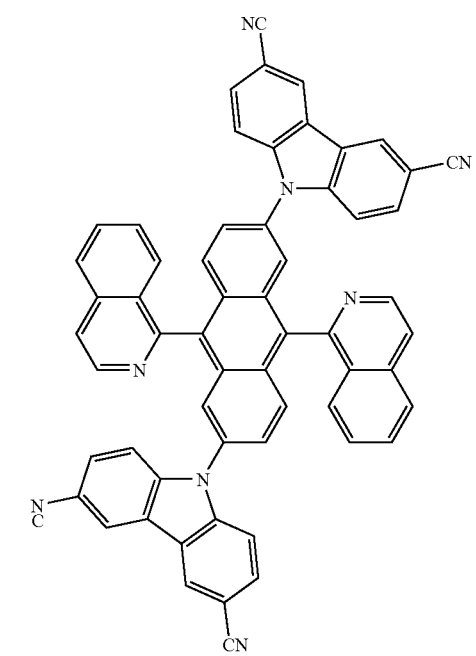

D-159
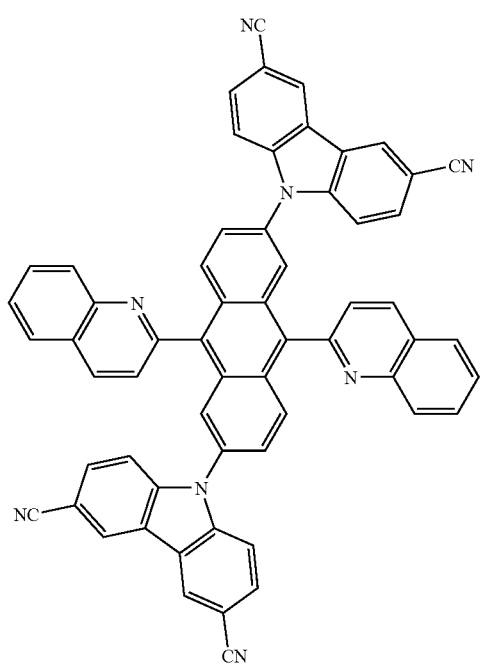
D-161
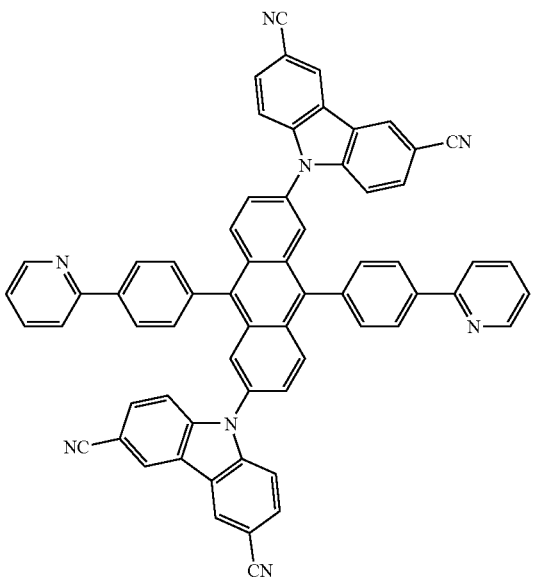
D-160
D-162

-continued
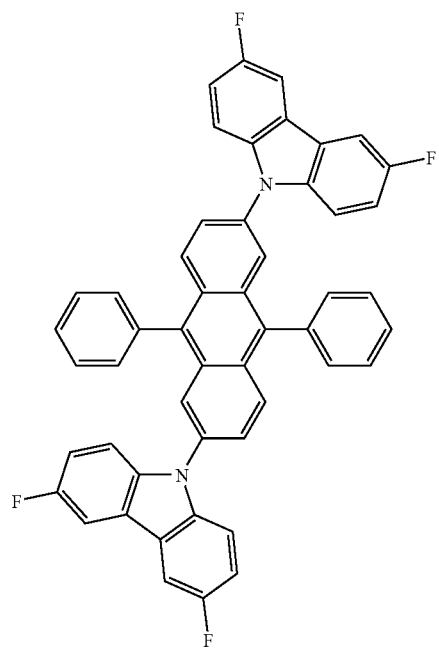
D-163
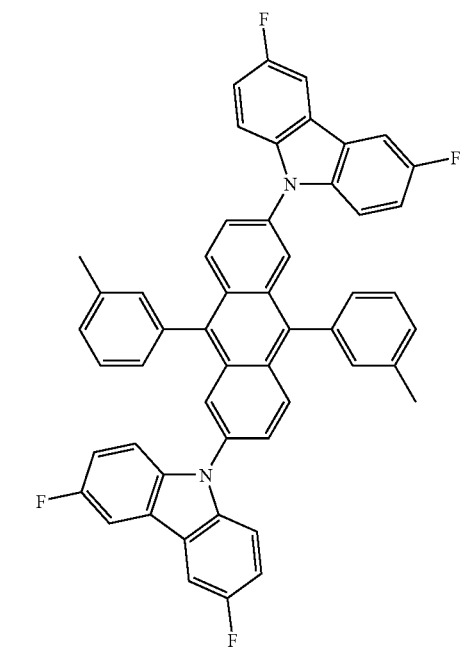
D-165
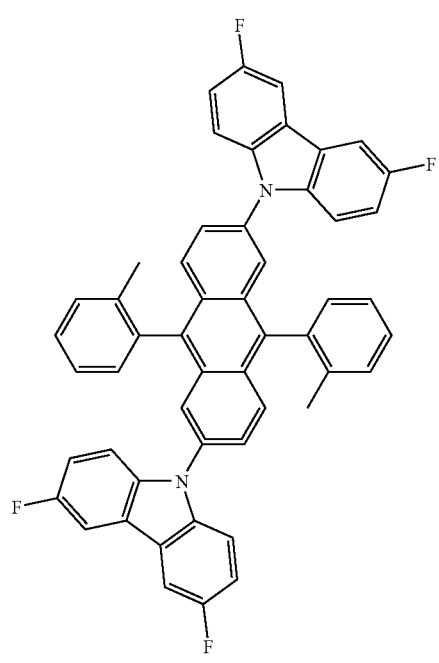
D-164
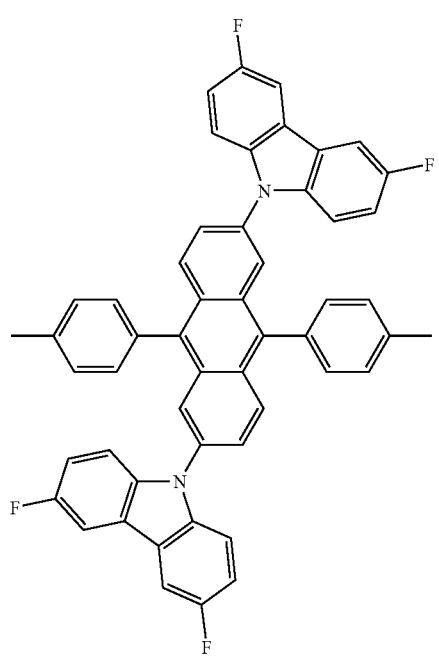
D-166

D-167
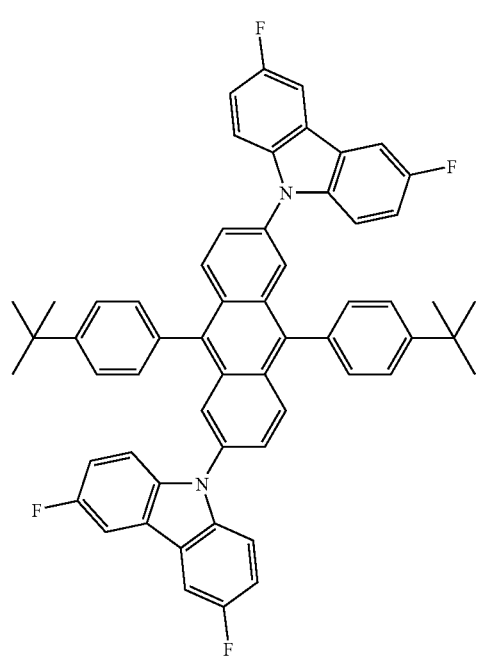
D-169
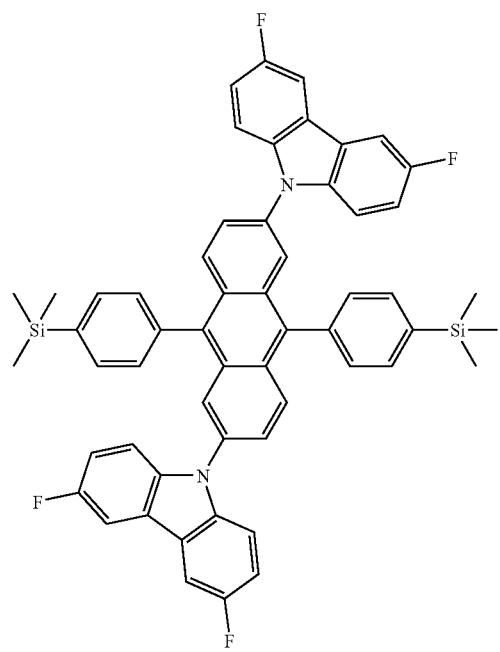
D-168
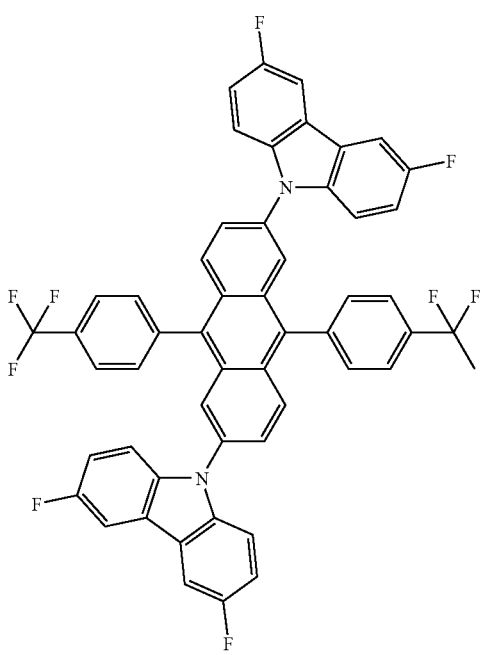
D-170
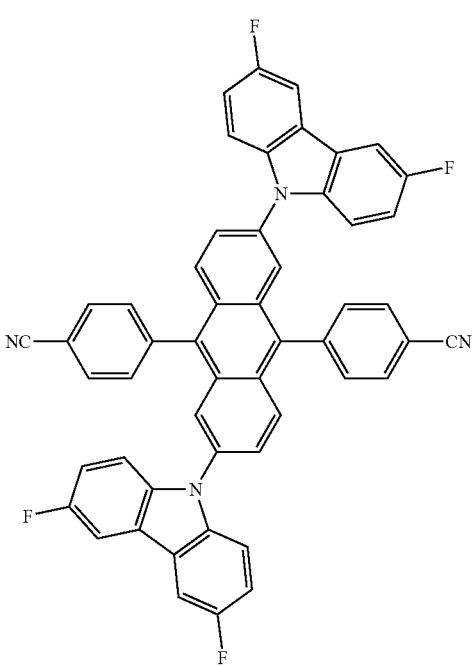

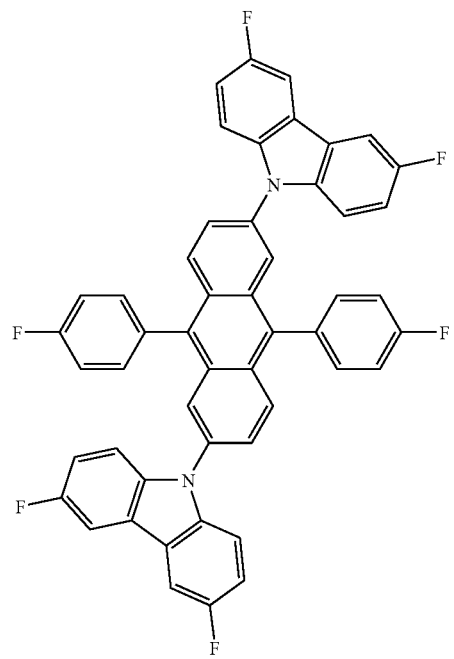
D-171
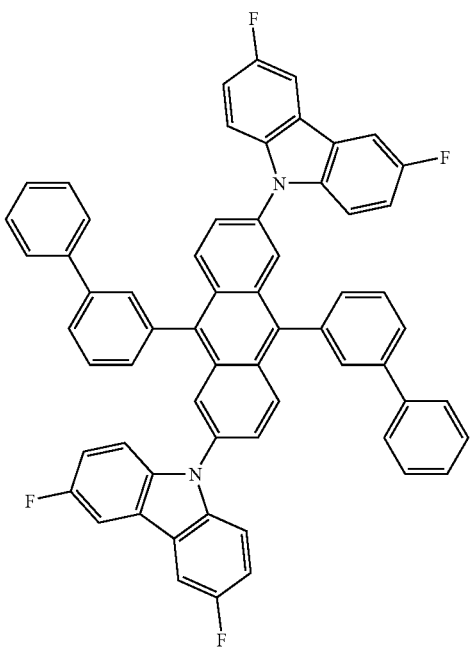
D-173
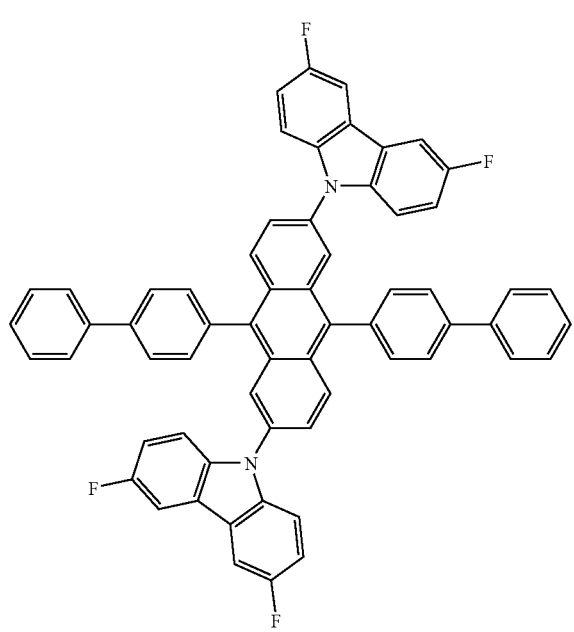
D-172
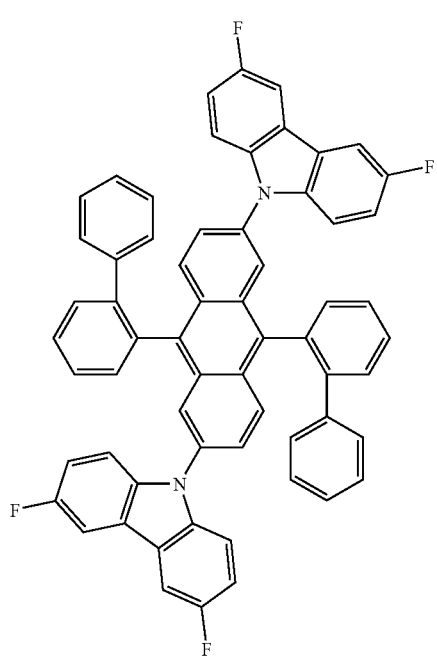
D-174

D-175

D-176

D-177

D-178

D-179

D-180

D-181
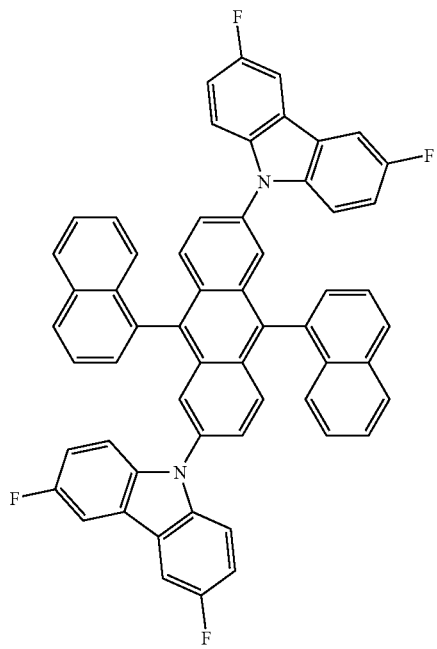
D-183
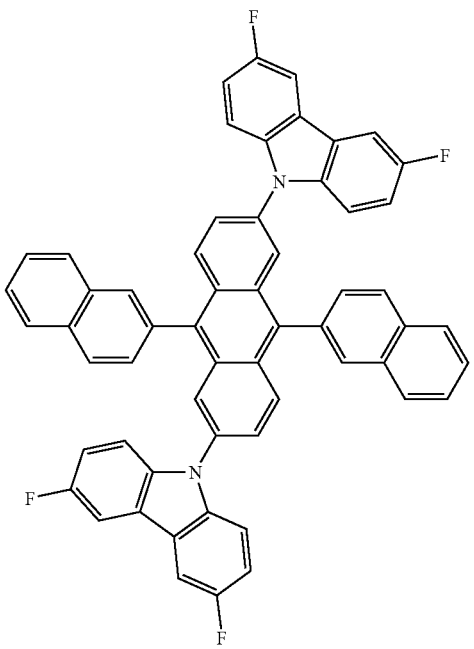
D-182
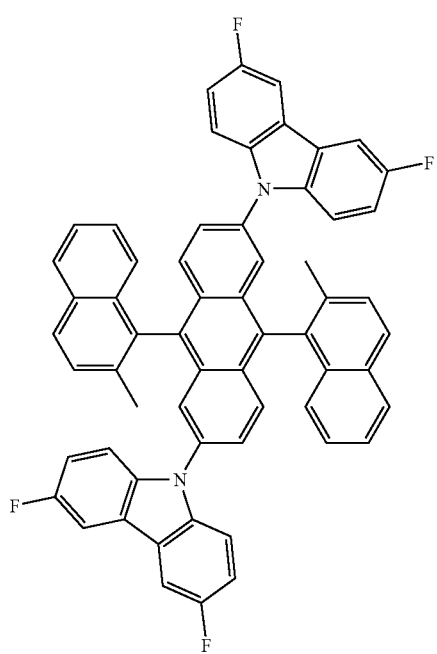
D-184

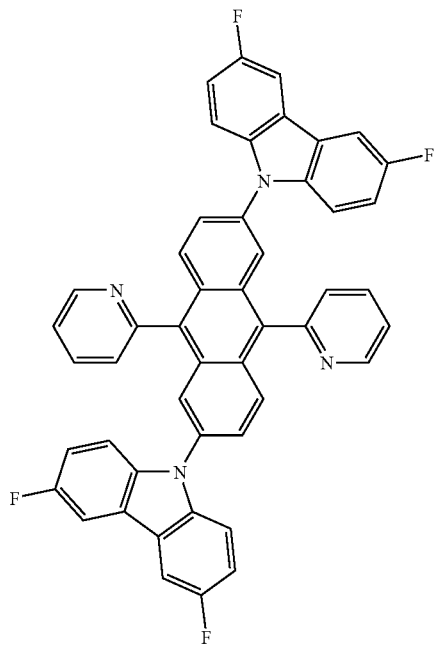
D-185
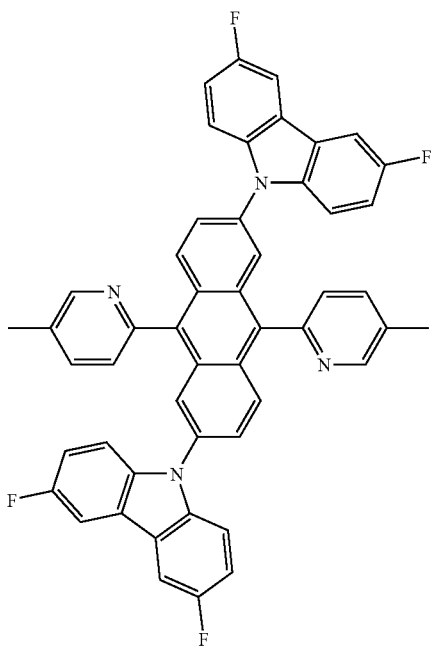
D-187
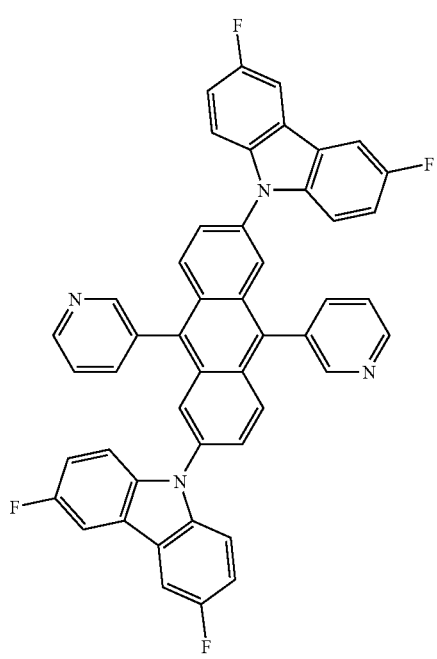
D-186
D-188

D-189
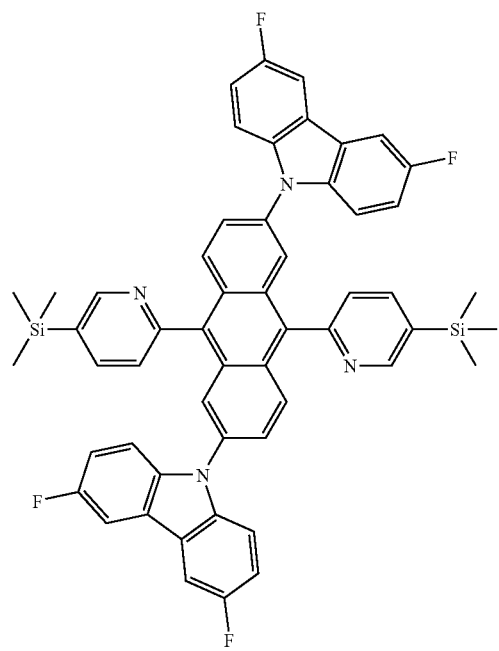
D-191
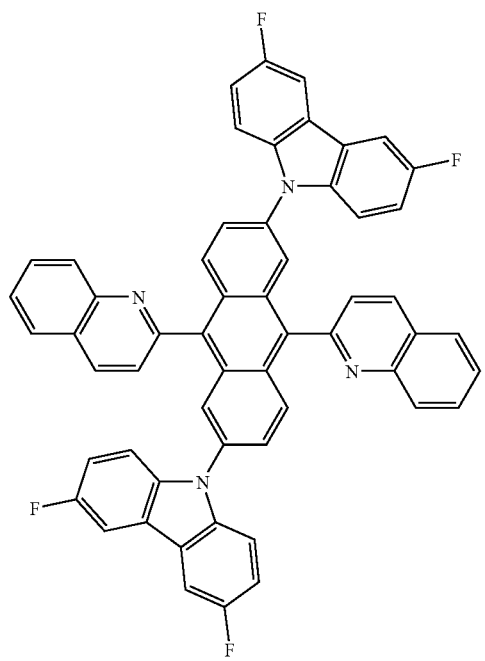
D-190
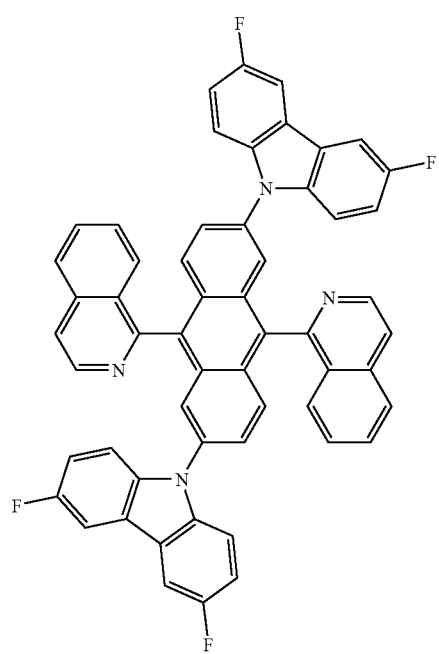
D-192
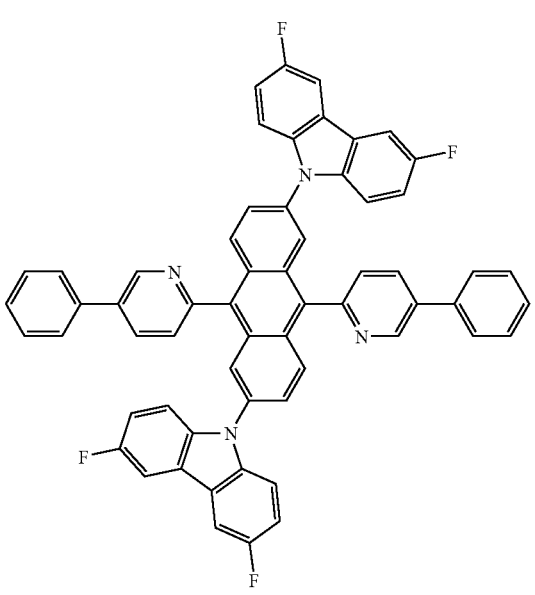

-continued

D-193

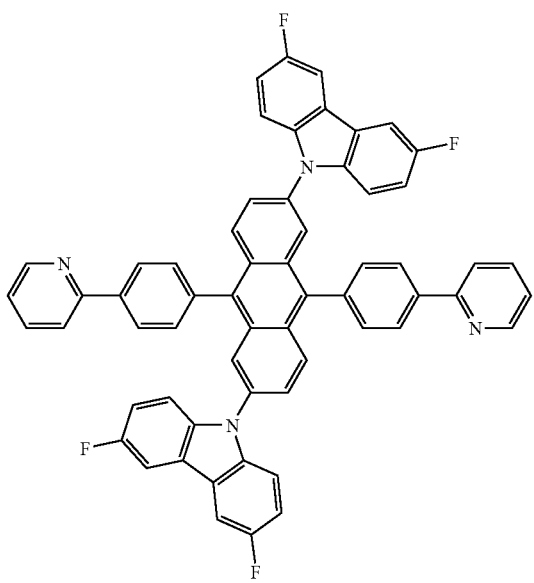

D-194

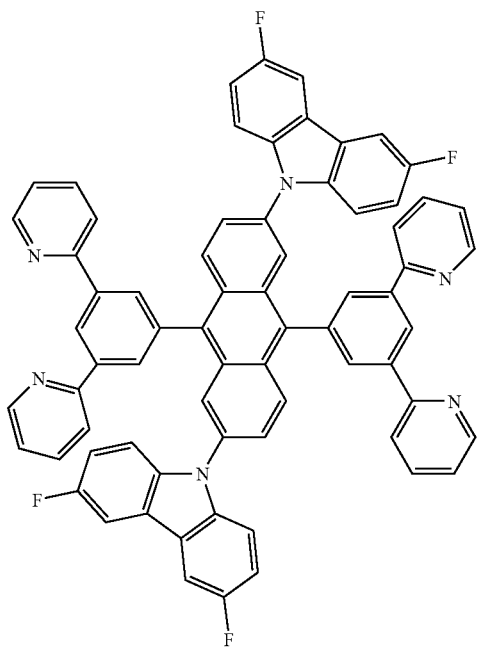

An organic light emitting diode device, which comprises an anode, a hole injection layer, a hole transport layer, an emission layer, an electron transport layer, an electron injection layer, and a cathode, according to one exemplary embodiment of the present invention, may comprise the blue light emitting compound as a dopant of the emission layer.

The doping concentration of the dopant may range from about 0.5 to about 10% by weight.

Hereinafter, exemplary embodiments of the present invention will be described below with reference to the accompanying drawings.

FIG. 1 is a view showing an organic light emitting diode device according to one exemplary embodiment of the present invention.

Referring to FIG. 1, the organic light emitting diode device according to one exemplary embodiment of the present invention comprises an anode 110, a hole injection layer 120, a hole transport layer 130, an emission layer 140, an electron transport layer 150, an electron injection layer 160, and a cathode 170.

The anode 110 is a hole injection electrode which is formed of one of ITO (Indium Tin Oxide), IZO (Indium Zinc Oxide), and ZnO (Zinc Oxide) having a high work function. If the anode 110 is a reflective electrode, the anode 110 may further comprise a reflective layer formed of one of aluminum (Al), silver (Ag) or nickel (Ni) under the layer formed of one of ITO, IZO, and ZnO.

The hole injection layer 120 functions to facilitate the injection of holes from the anode 110 to the emission layer 140. The hole injection layer 120 may be formed of at least one selected from the group consisting of copper phthalocyanine (CuPc), PEDOT (poly(3,4)-ethylenedioxythiophene), polyaniline (PANI) and NPD (N,N-dinaphthyl-N,N'-diphenyl benzidine), but is not limited thereto.

The thickness of the hole injection layer 120 may range from 1 to 150 nm. If the thickness of the hole injection layer 120 is 1 nm or greater, a reduction in a hole injection characteristic can be prevented. If the thickness of the hole injection layer 120 is 150 nm or less, an increase in driving voltage, which is applied in order to increase the movement of holes when the thickness of the hole injection layer 120 is too large, can be prevented.

The hole transport layer 130 functions to smoothly transport holes. The hole transport layer 130 may be formed of at least one selected from the group consisting of NPD (N,N-dinaphthyl-N,N'-diphenyl benzidine), TPD (N,N'-bis-(3-methylphenyl)-N,N'-bis-(phenyl)-benzidine, s-TAD and MTDATA (4,4',4''-Tris(N-3-methylphenyl-N-phenyl-amino)-triphenylamine), but is not limited thereto.

The hole transport layer 130 may also have a thickness of 1 to 150 nm. If the thickness of the hole transport layer 130 is 1 nm or more, a reduction in a hole transport characteristic can be prevented. If the thickness of the hole transport layer 130 is 150 nm or less, an increase in the driving voltage, which is applied in order to increase movement of holes when the thickness of the hole transport layer 130 is too large, can be prevented.

The emission layer 140 may be made of a material that emits red, green, or blue color light. This material may include a phosphorescence or fluorescent material. This exemplary embodiment will be described with respect to a material that emits green.

The emission layer 140 may comprise a host and a dopant. The host may be formed of one selected from the group consisting of spiro-DPVBi, DPVBi, spiro-6P, distilled benzene (DSB), distilled arylene (DSA), PFO-based polymer, and PPV-based polymer, but is not limited thereto.

The dopant may be a material represented by the following Chemical Formula 1:

[Chemical Formula 1]

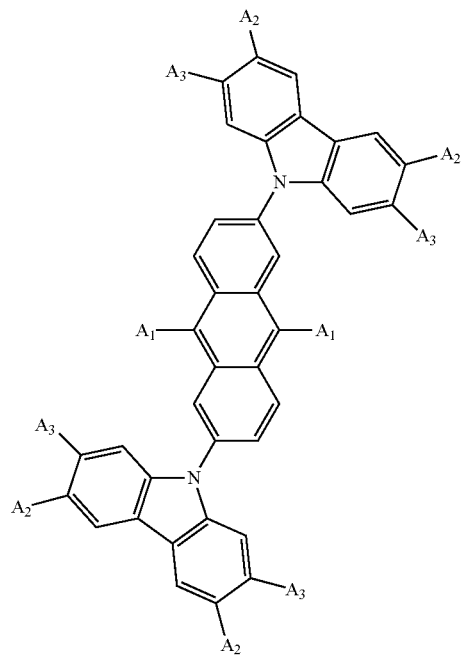

wherein $A_1$, $A_2$, and $A_3$ are each independently selected from the group consisting of hydrogen, a substituted or unsubstituted aromatic group, a hetero ring group, and an aliphatic group.

The substituted or unsubstituted $A_2$, $a_n d$ $A_3$ are each independently selected from the group consisting of phenyl, biphenyl, naphthyl, phenanthrenyl, terphenyl, pyridyl, bipyridyl, phenylpyridyl, pyridylphenyl, terpyridyl, quinolinyl, isoquinolinyl, phenoxalinyl, quinoxalinyl, methyl, ethyl, propyl, isopropyl, butyl, tert-butyl, trimethylsilyl, trifluoromethyl, cyano, fluoro, methoxy, and ethoxy.

If $A_1$, $A_2$, and $A_3$ are substituted, the substituents of $A_1$, $A_2$, and $A_3$ are selected from the group consisting of aryl, alkyl, alkoxy, halogen, cyano, and silyl groups.

If $A_1$, $A_2$, and $A_3$ are substituted, the substituents of $A_1$, $A_2$, and $A_3$ are each independently selected from the group consisting of methyl, ethyl, propyl, isopropyl, butyl, methoxy, ethoxy, butoxy, trimethylsilyl, fluorine, and chlorine.

$A_1$, $A_2$, and $A_3$ are represented by one of the following Chemical Formulae 2:

[Chemical Formulae 2]

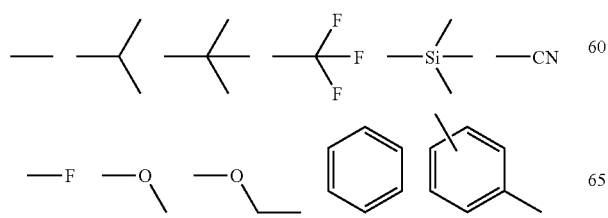

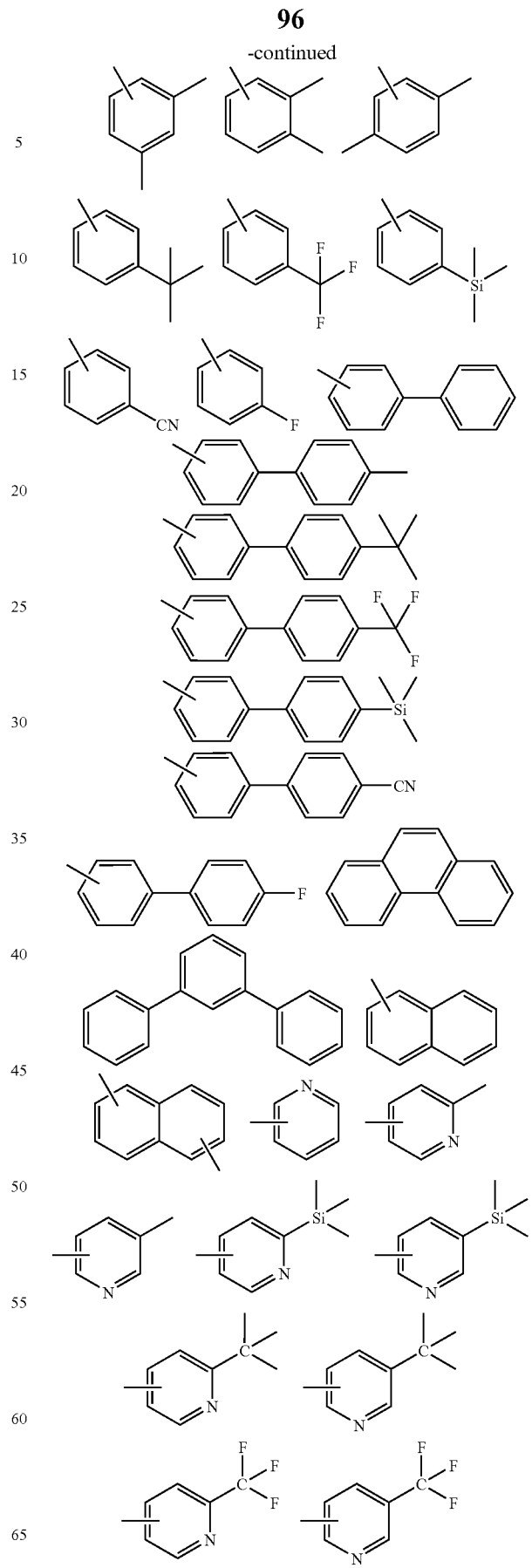

97
-continued
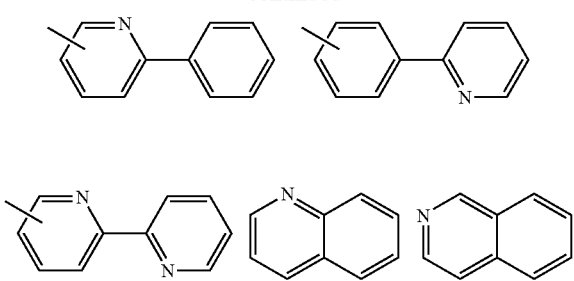
98
-continued
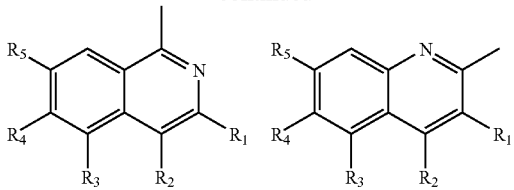
wherein $R_1$, $R_2$, $R_3$, and $R_4$ comprises at least one methyl group.
The blue light emitting compound is represented by one of the following Chemical Formulae 3:
[Chemical Formulae 3]
D-01
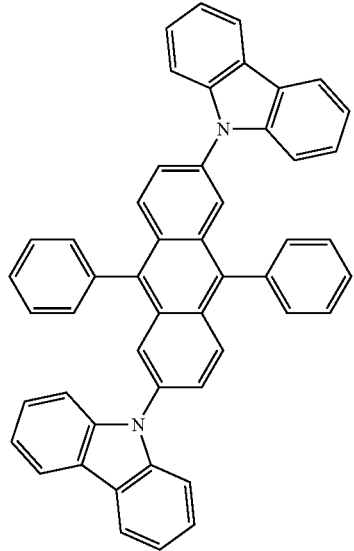
D-02
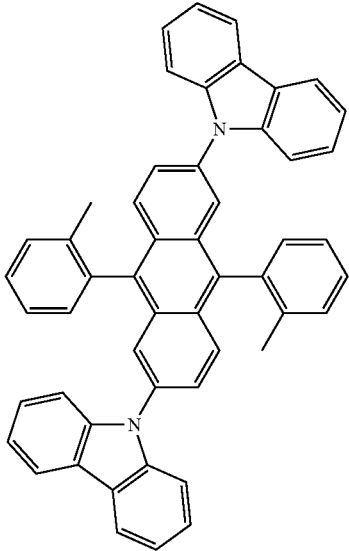
D-03
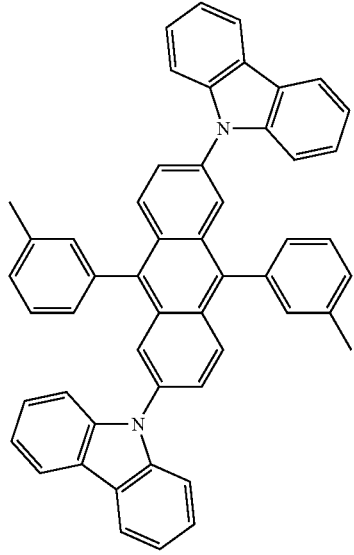
D-04
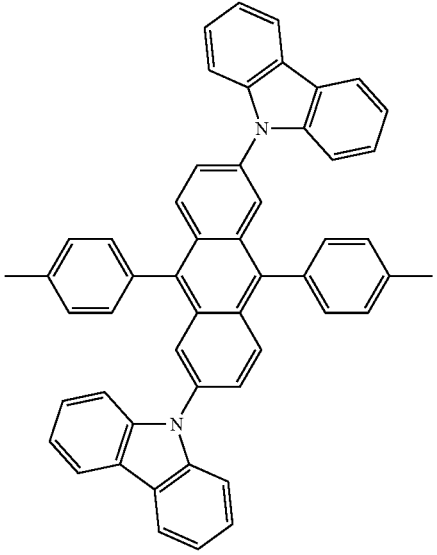

-continued
D-05
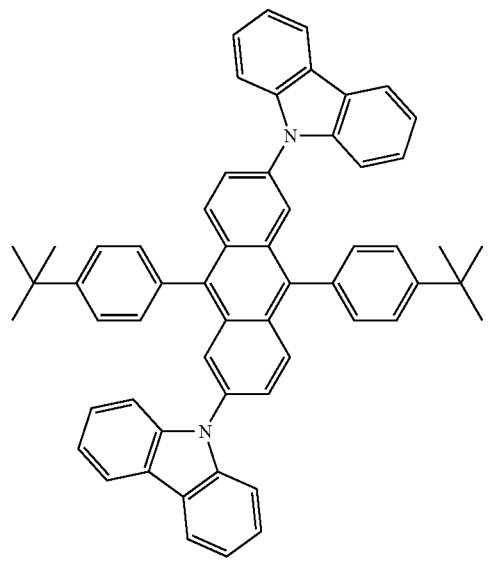
D-06
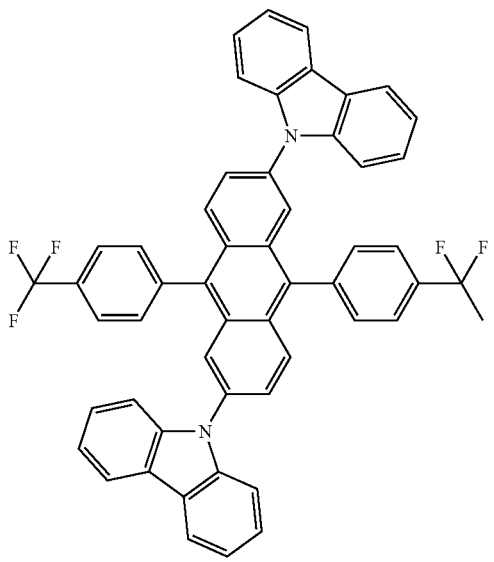
D-07
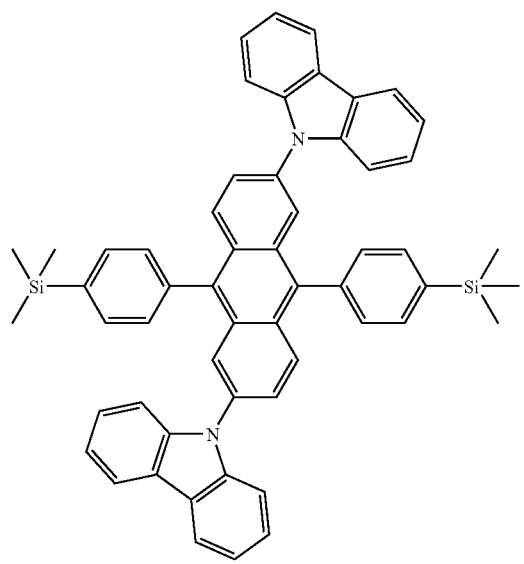
D-08
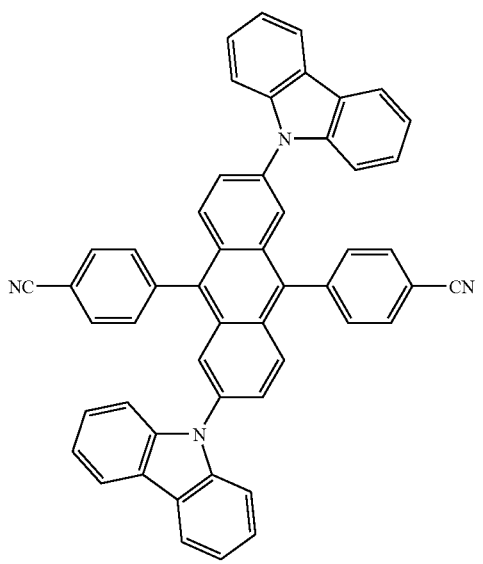
D-09
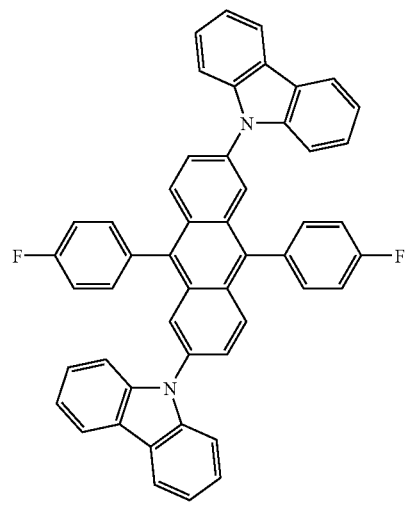
D-10
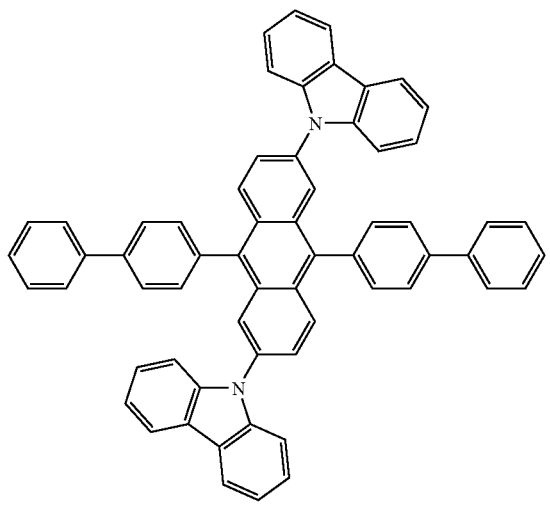

-continued
D-11
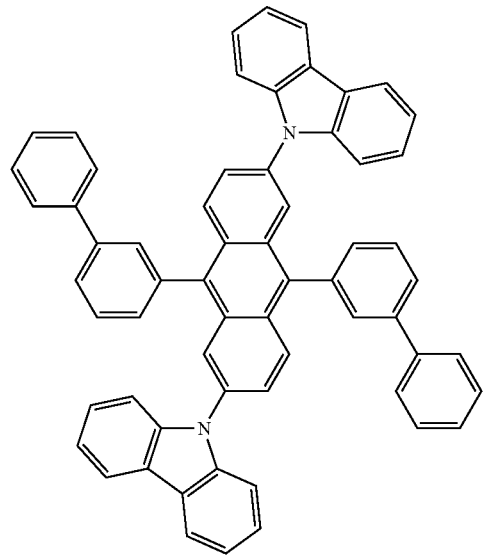
D-12
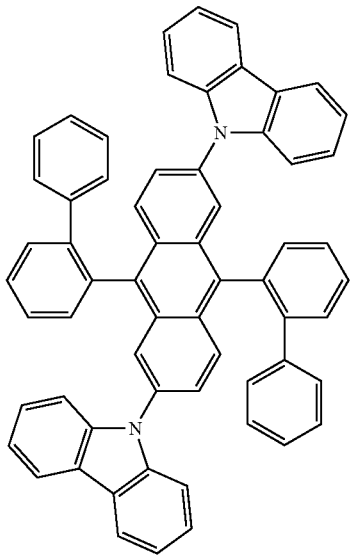
D-13
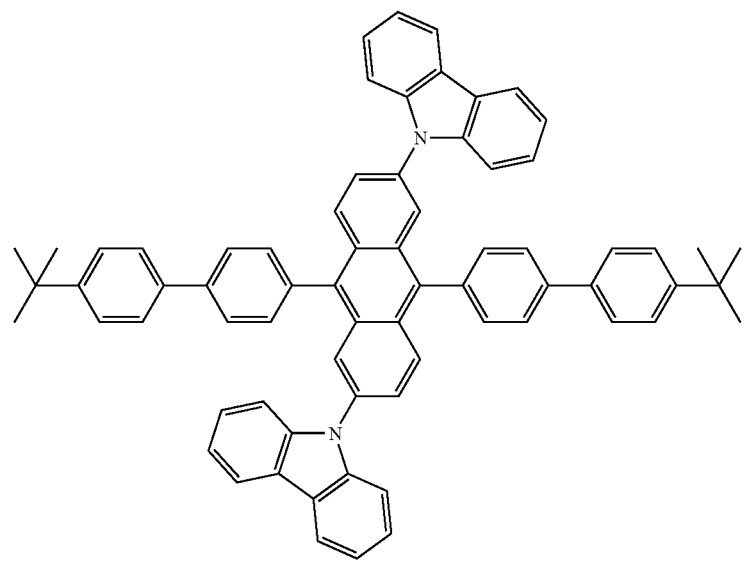
D-14
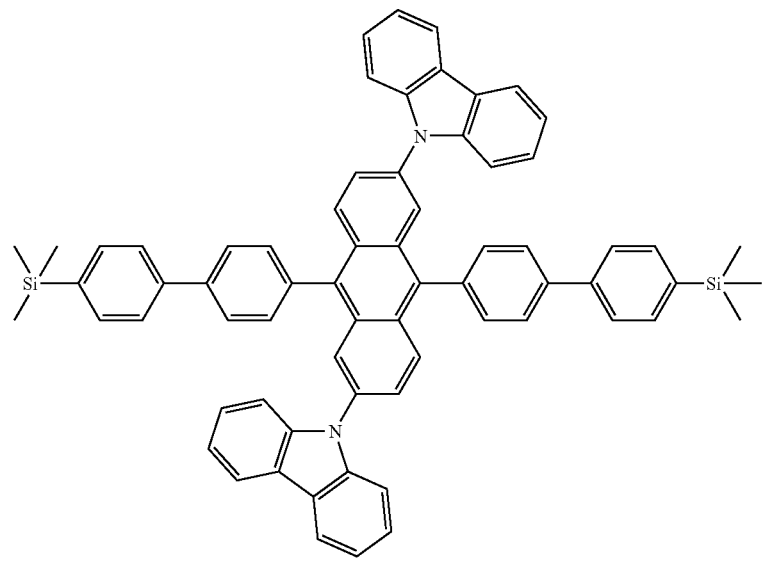

D-15
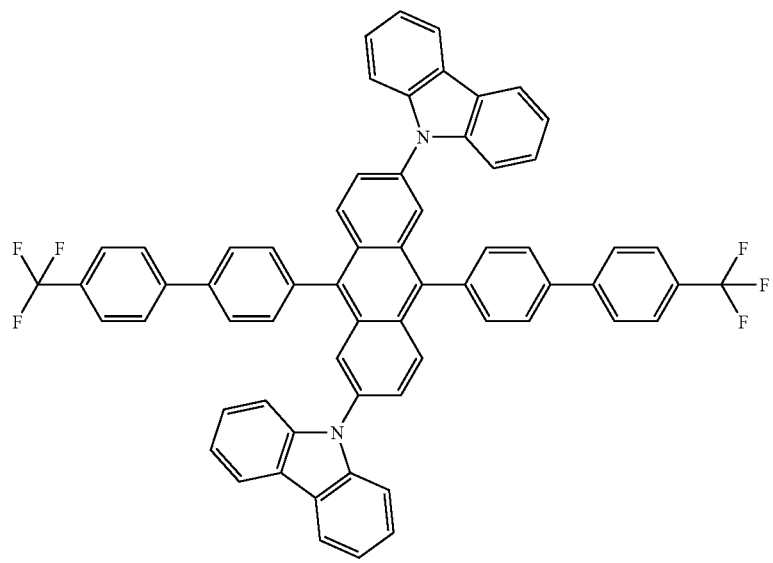
D-16
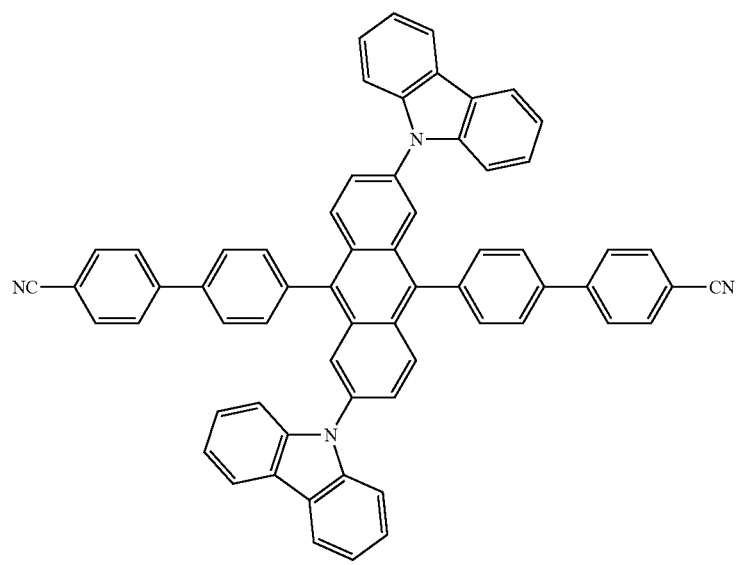
D-17
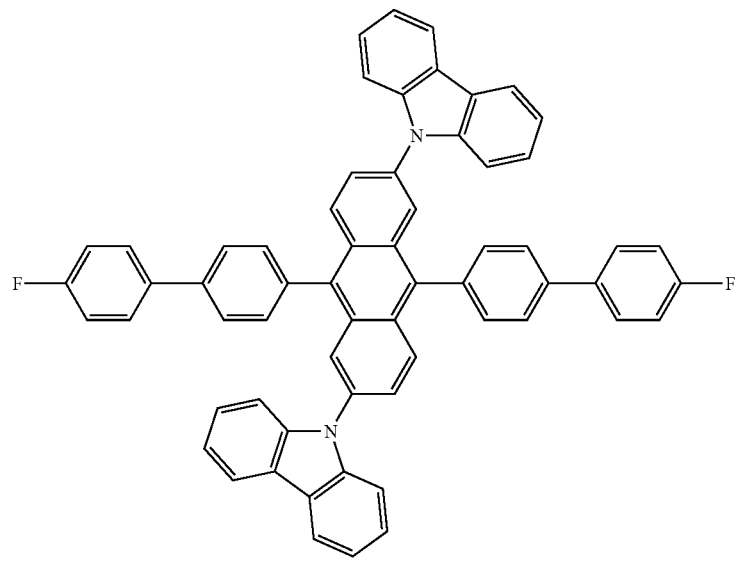

-continued
D-18
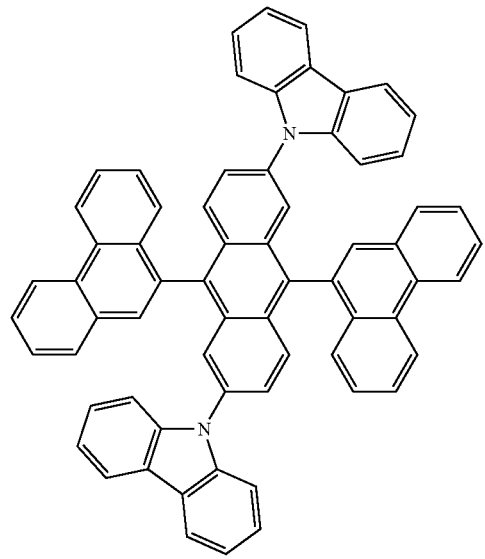
D-19
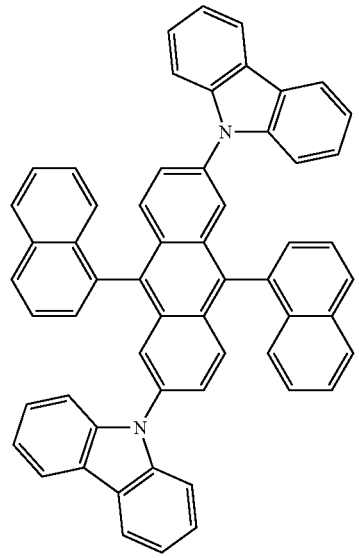
D-20
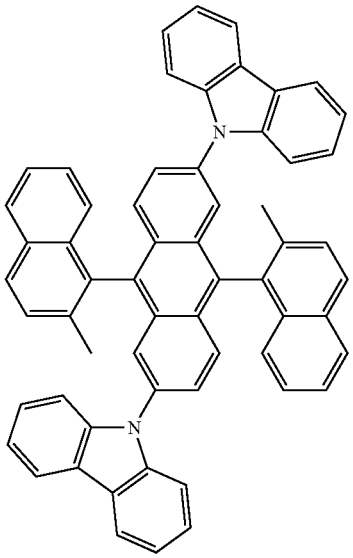
D-21
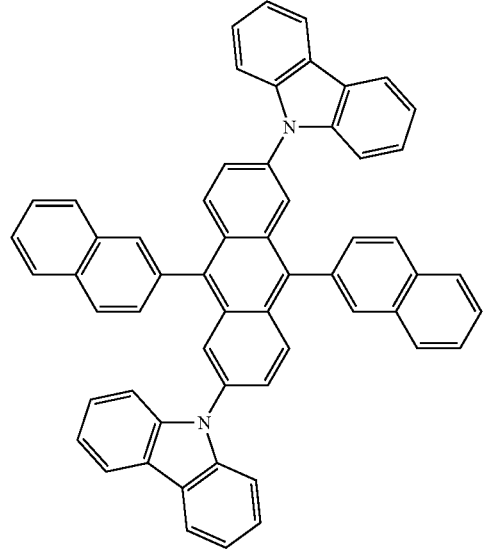
D-22
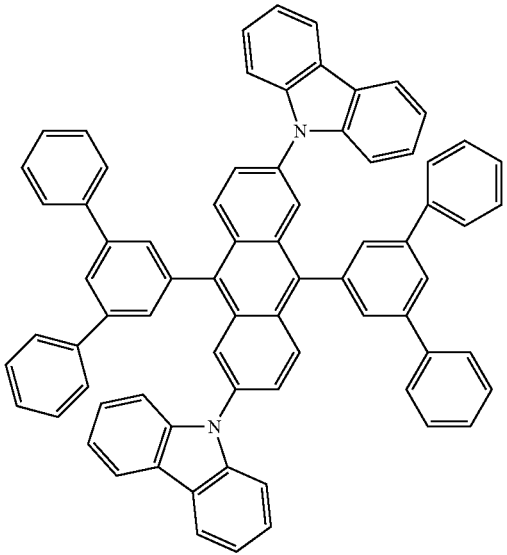

-continued
D-23
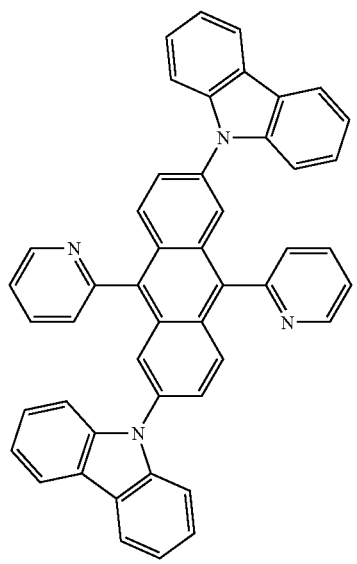
D-24
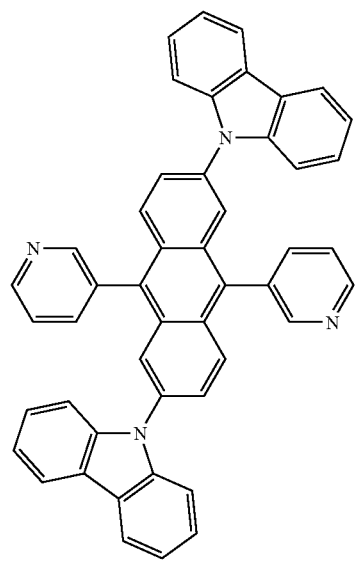
D-25
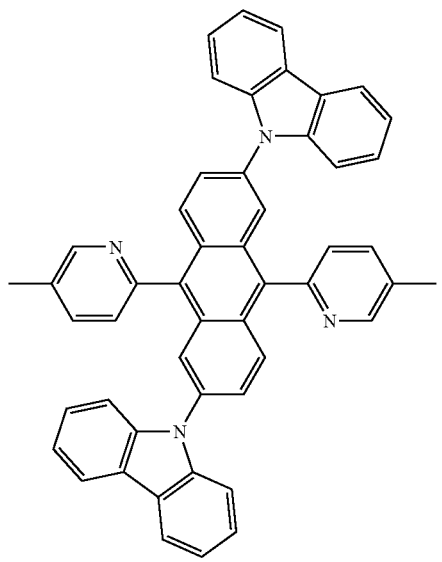
D-26
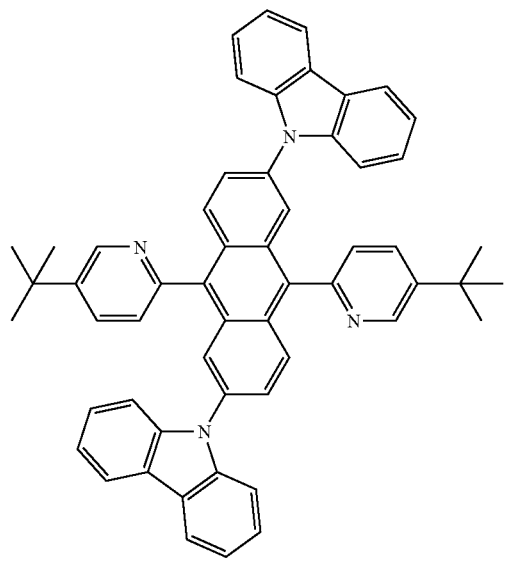
D-27
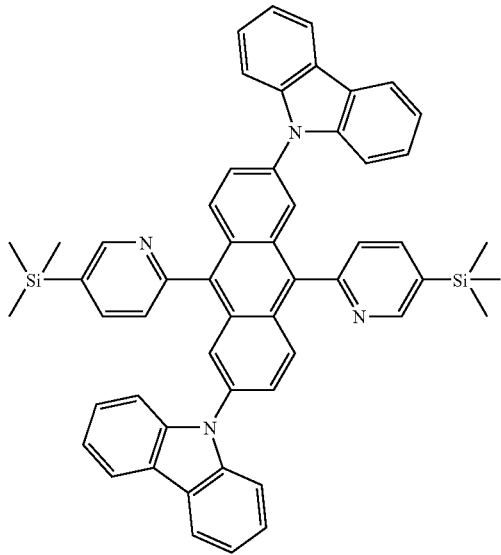
D-28
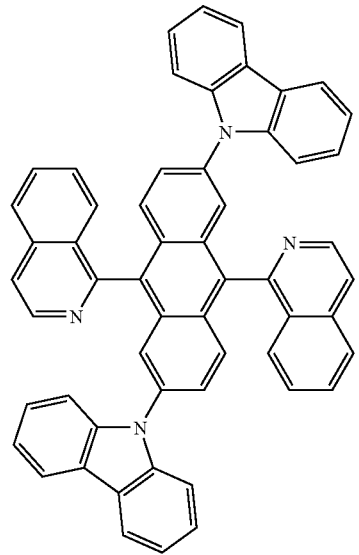

D-29
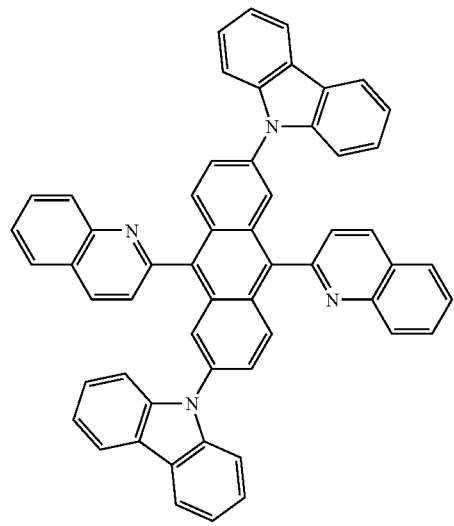
D-30
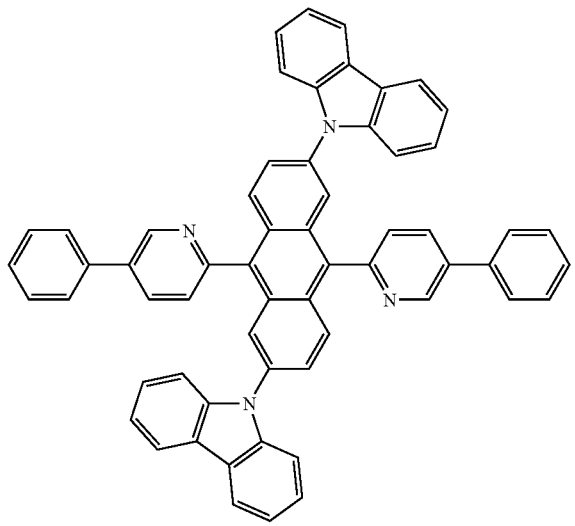
D-31
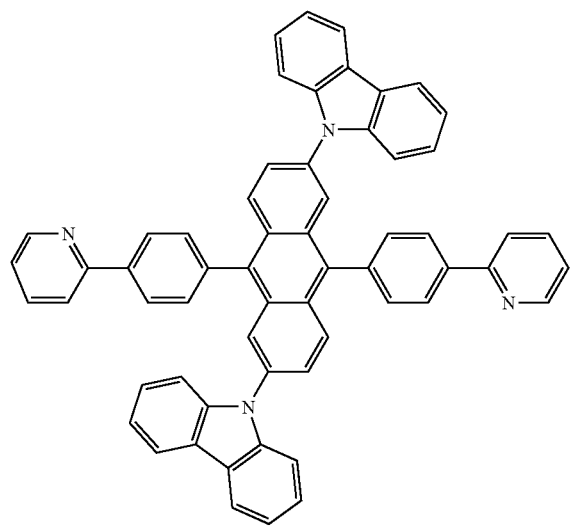
D-32
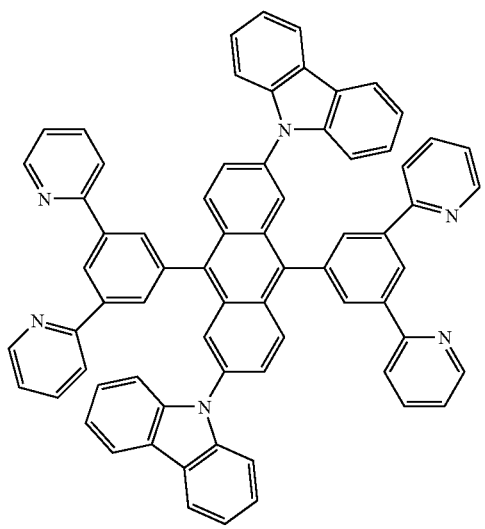

-continued
D-33
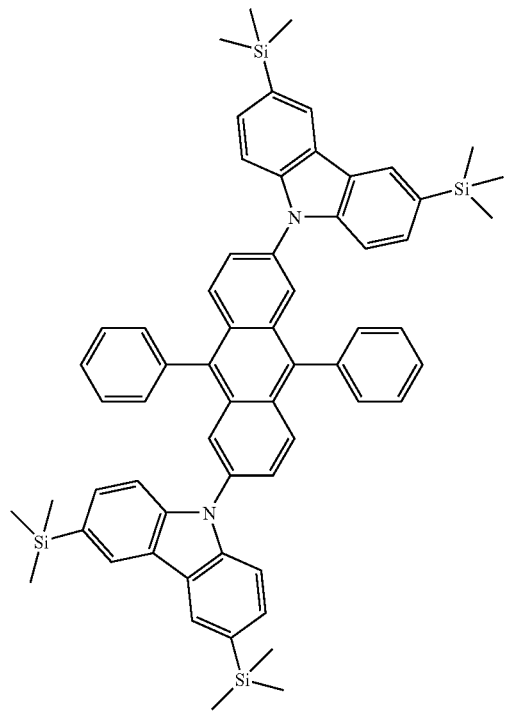
D-34
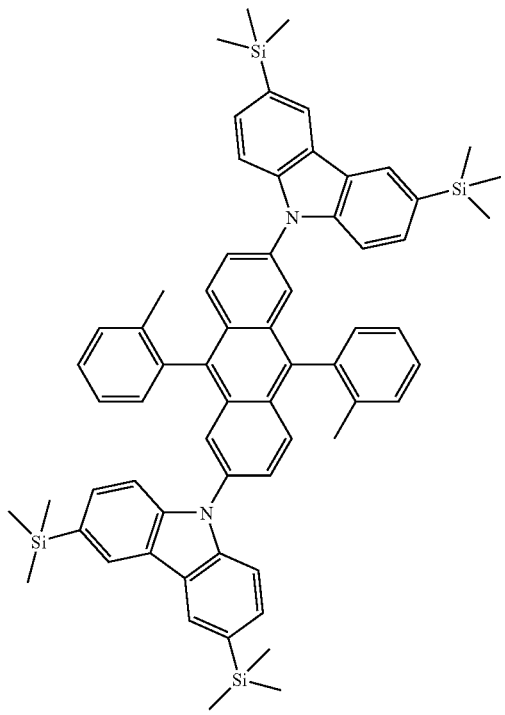
D-35
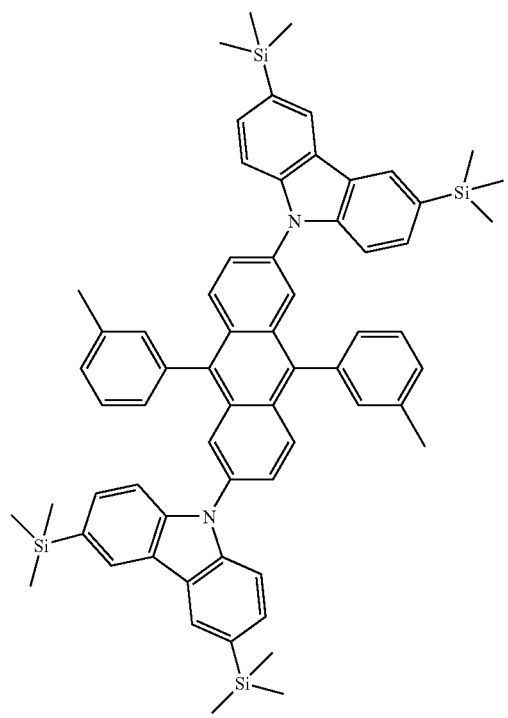
D-36
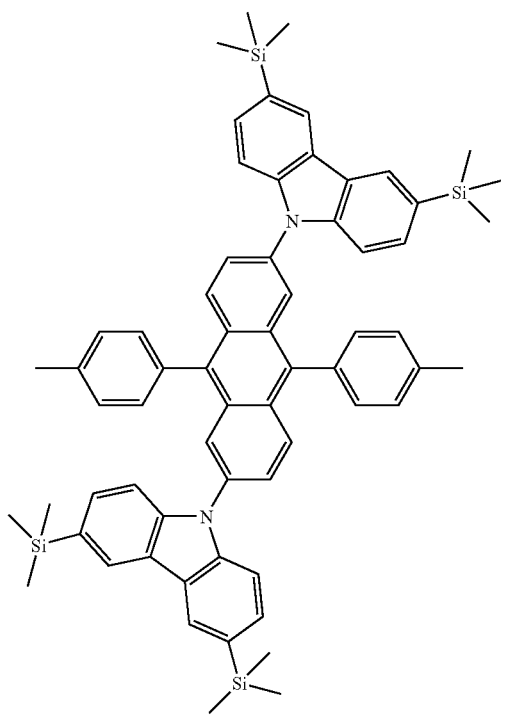

-continued
D-37
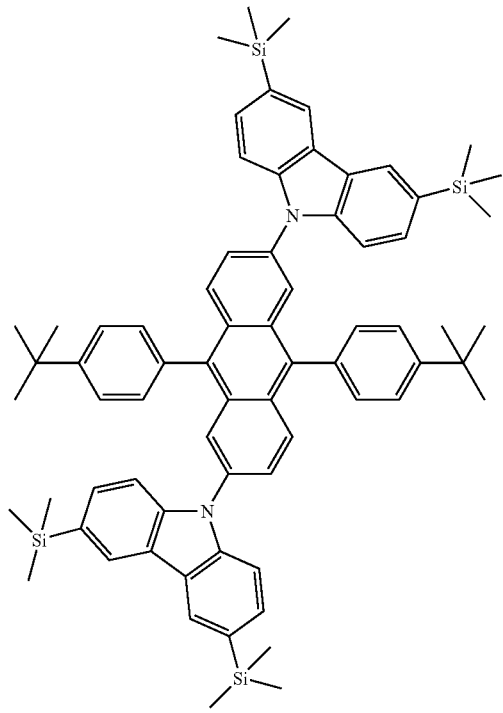
D-38
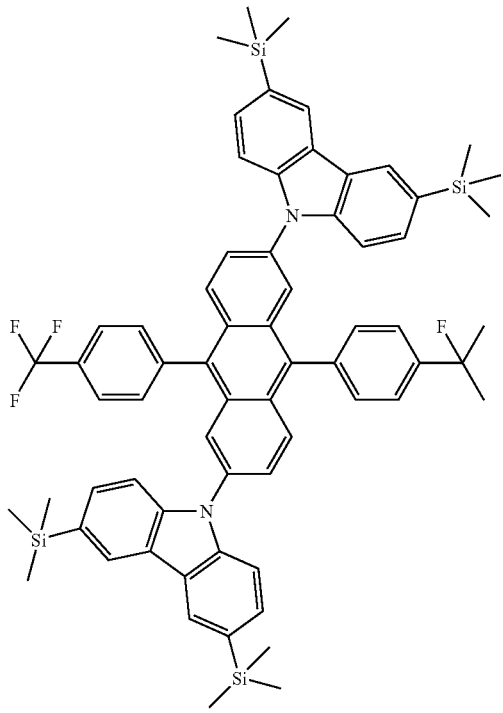
D-39
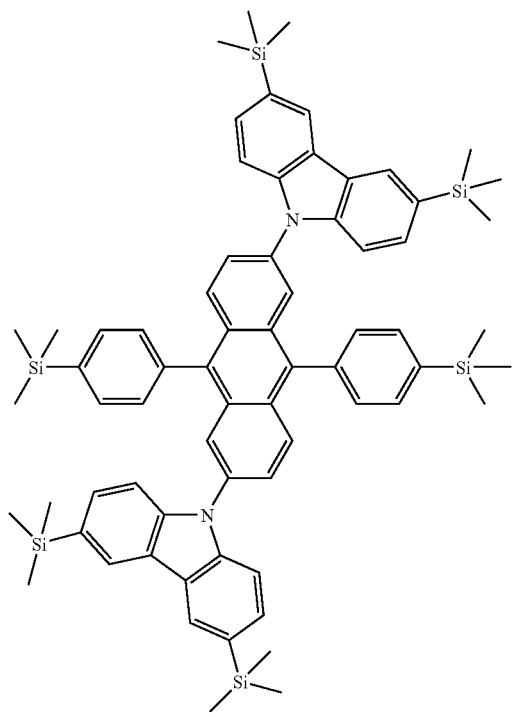
D-40
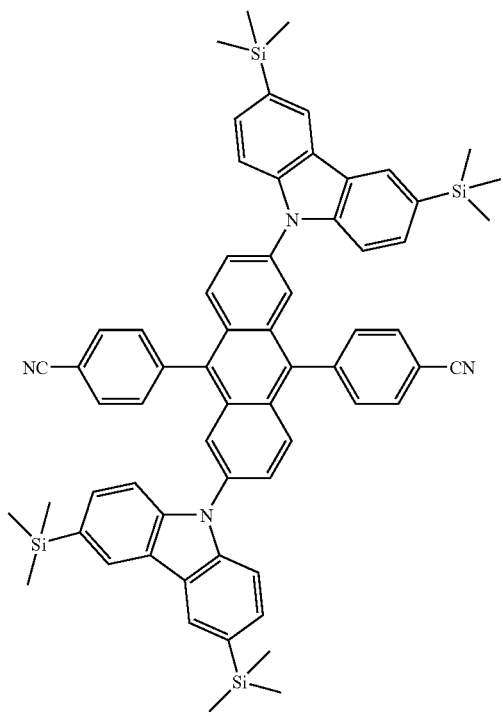

-continued
D-41
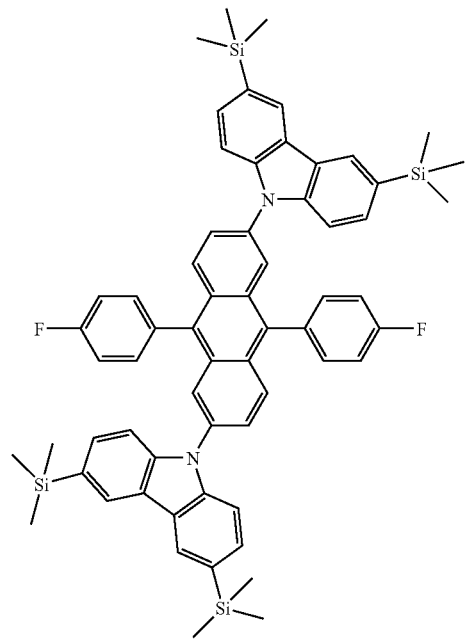
D-42
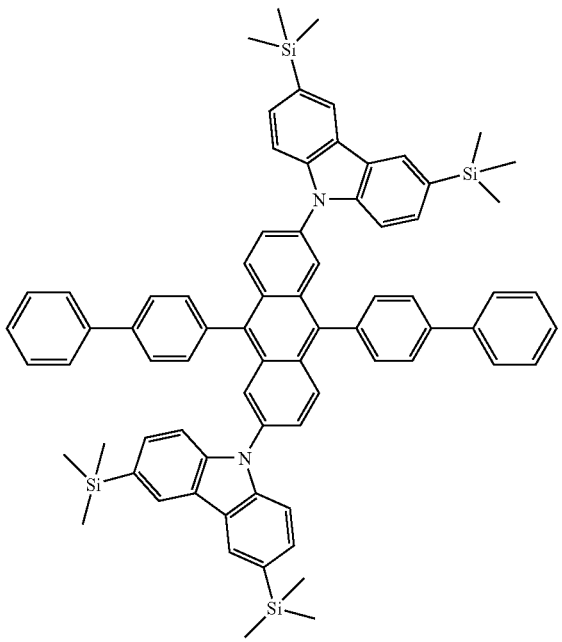
D-43
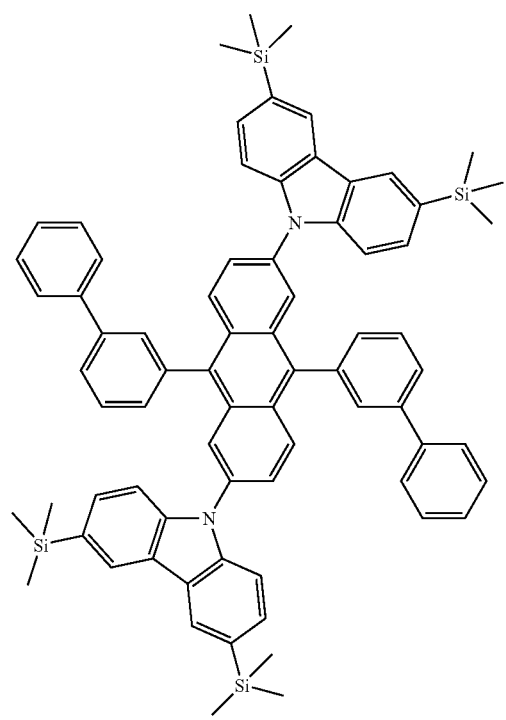
D-44
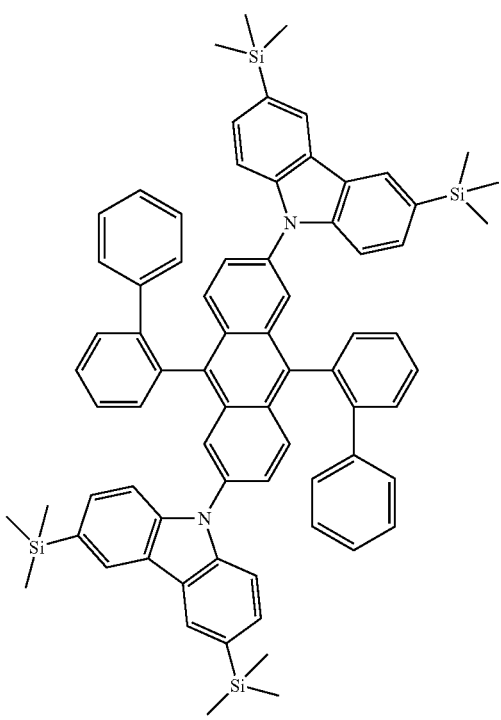

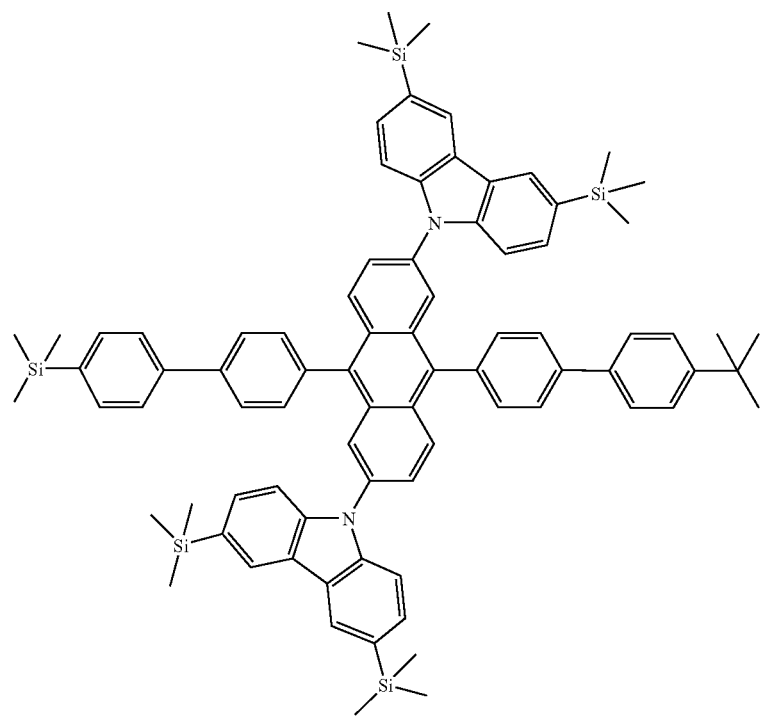
D-45
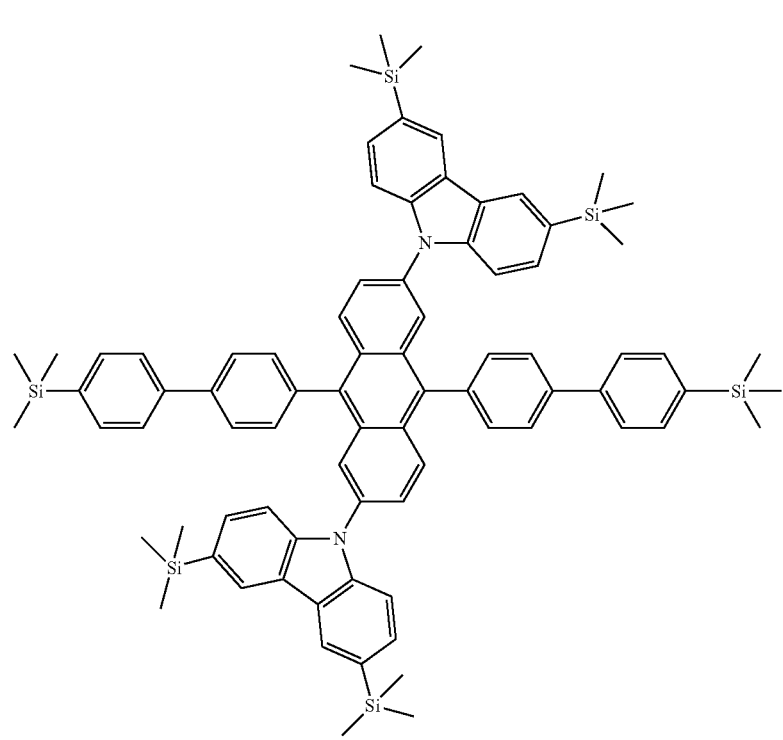
D-46

-continued
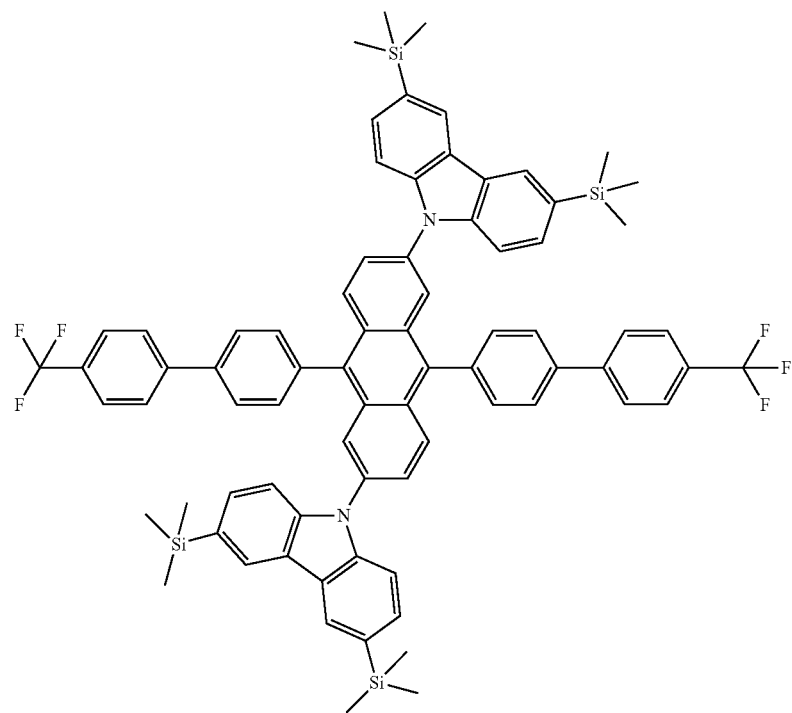
D-47
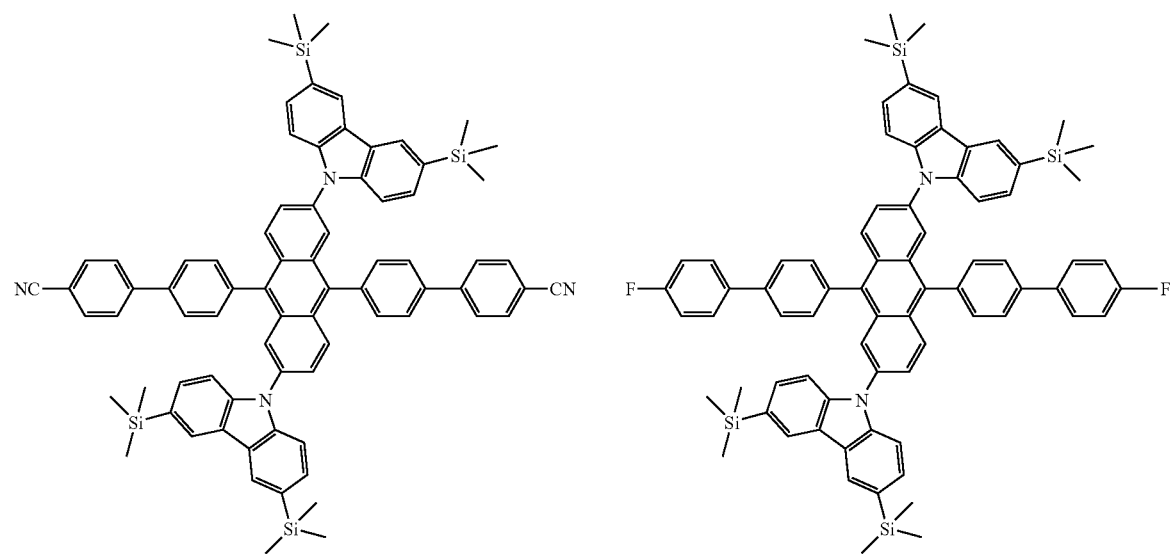
D-48
D-49

-continued
D-50
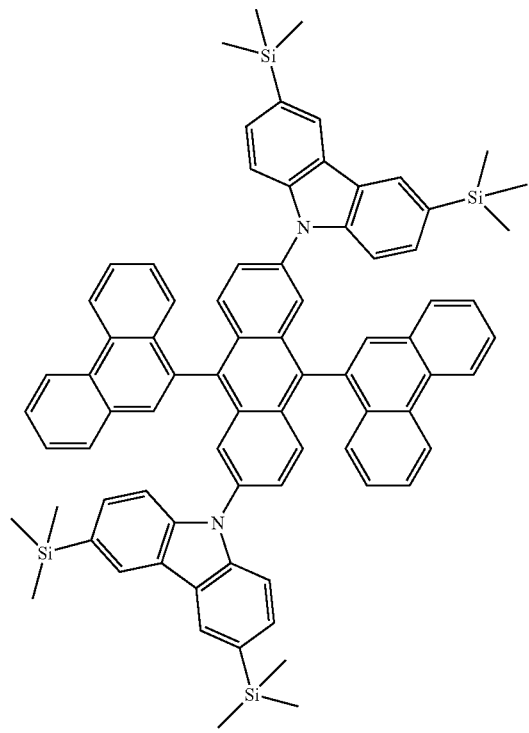
D-51
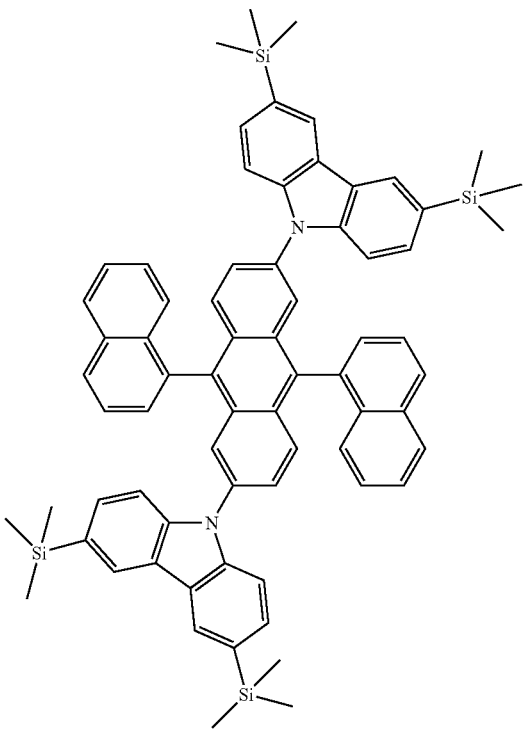
D-52
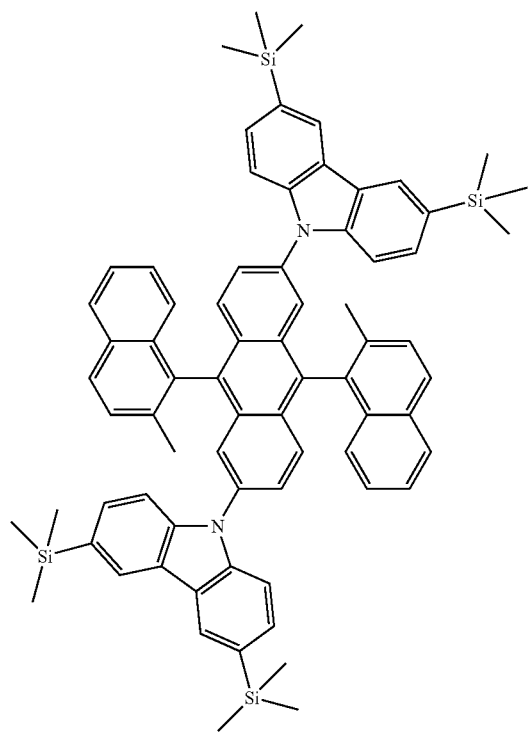
D-53
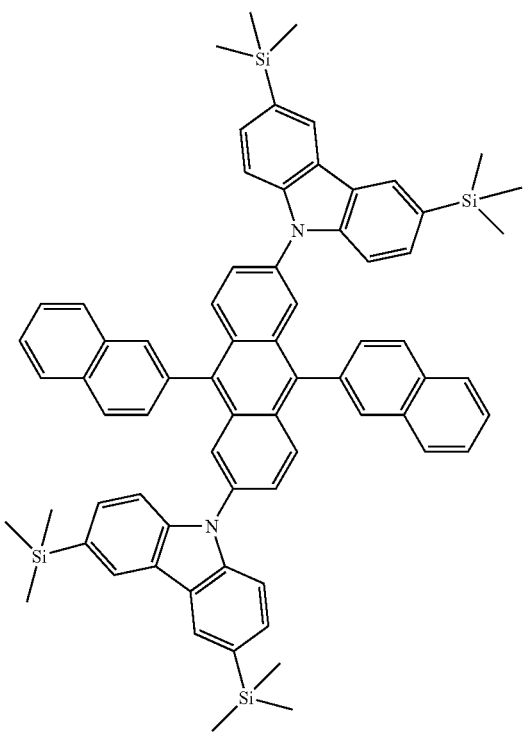

-continued
D-54
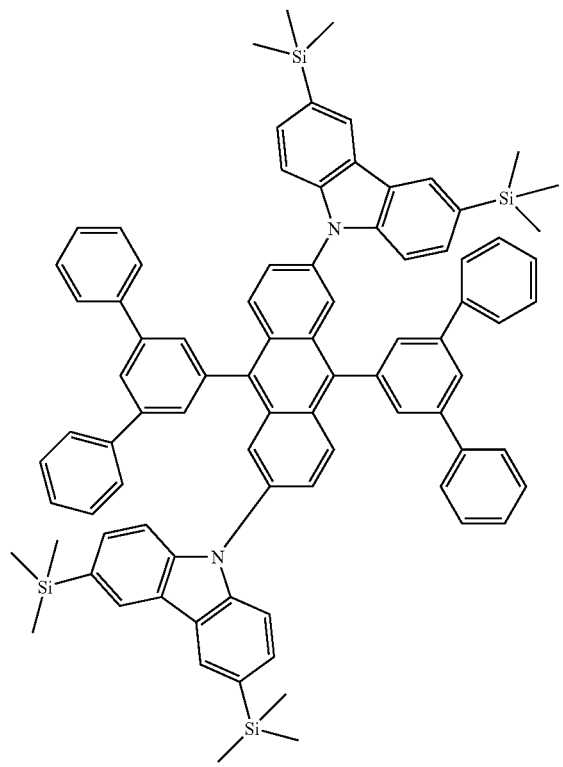
D-55
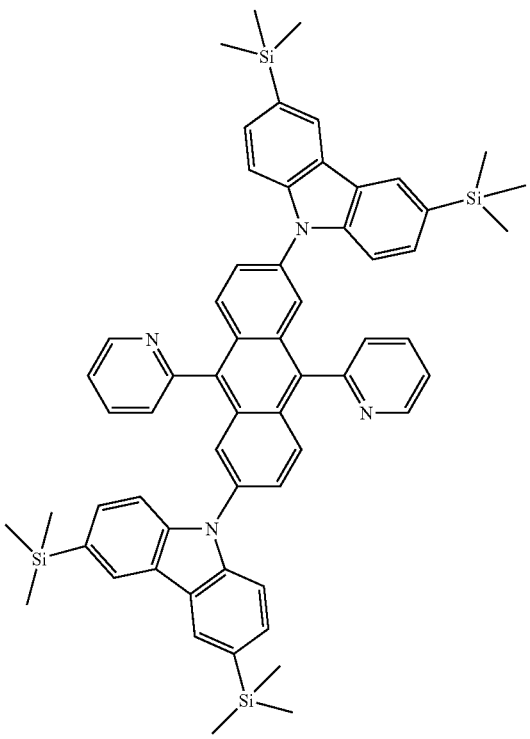
D-56
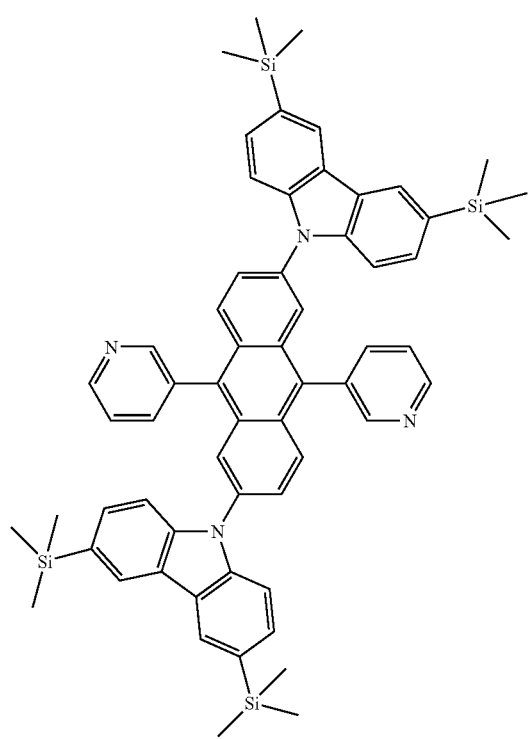
D-57
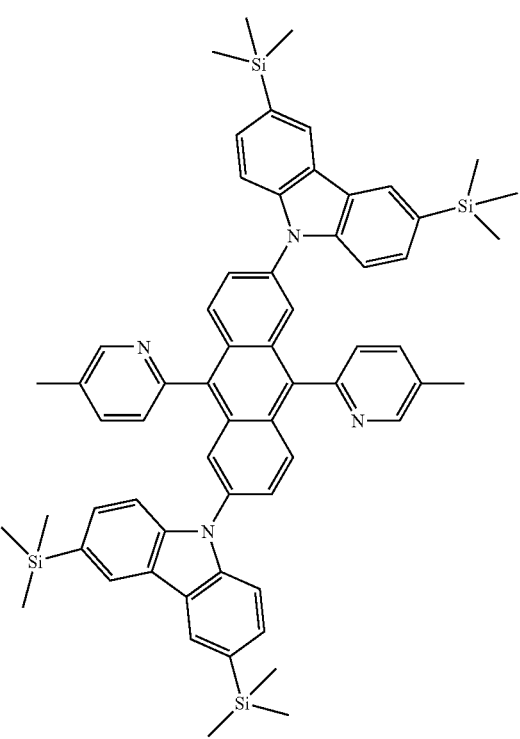

-continued
D-58
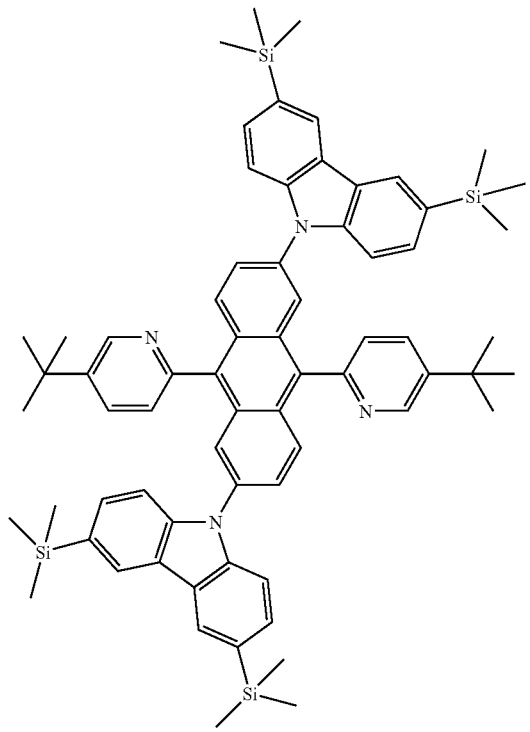
D-59
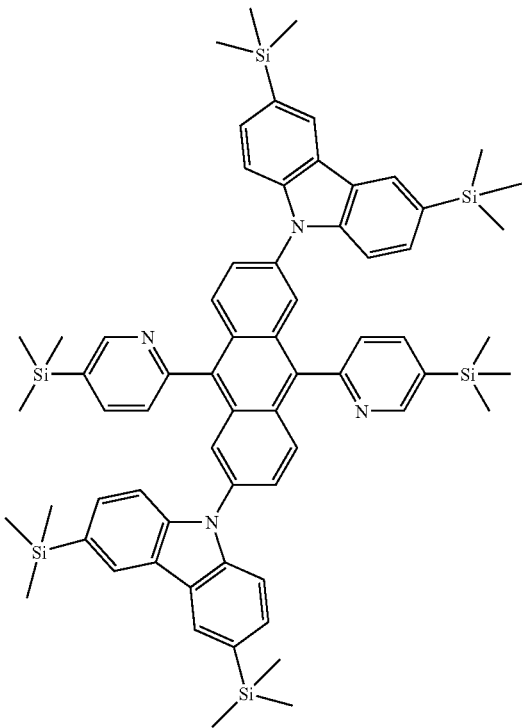
D-60
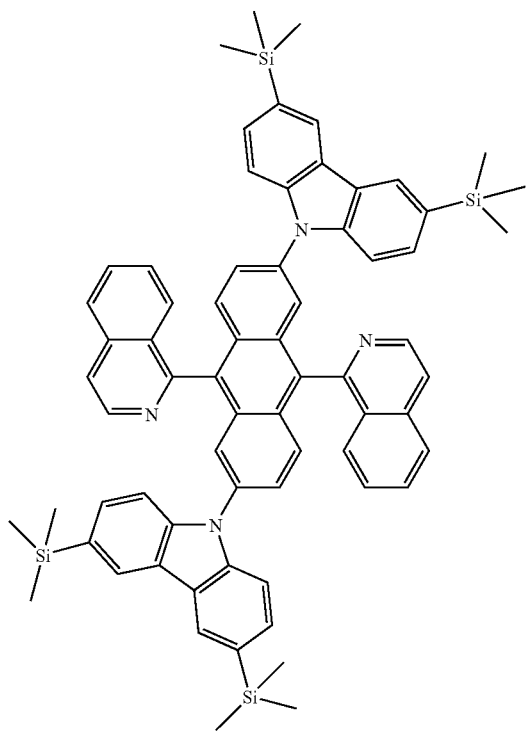
D-61
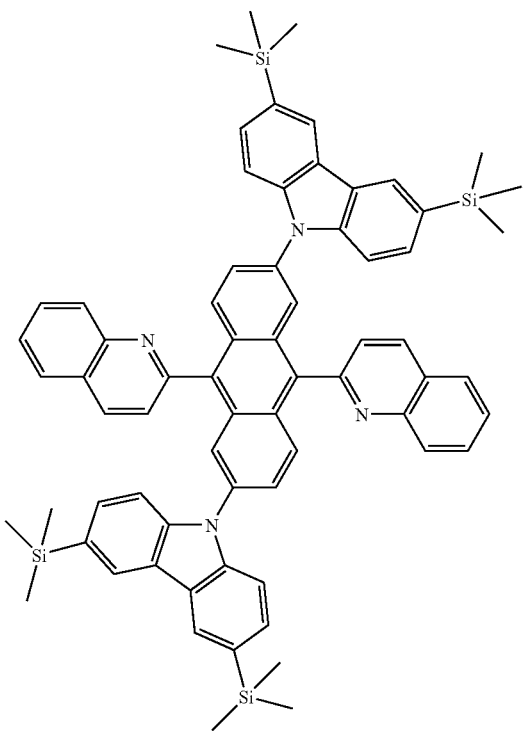

-continued
D-62
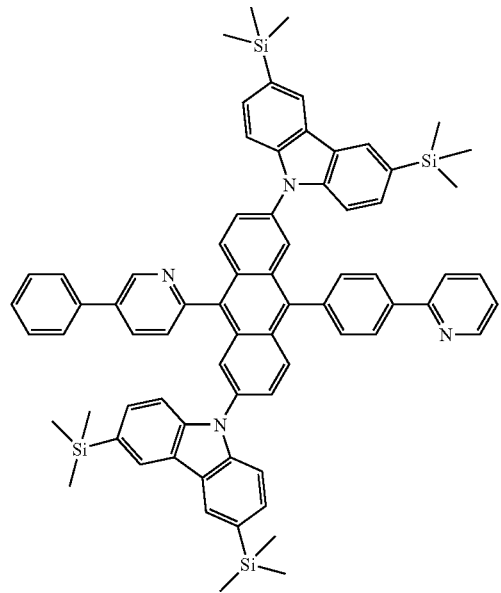
D-63
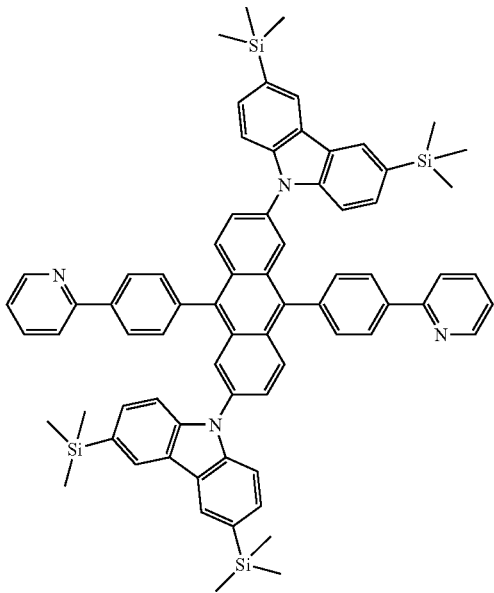
D-64
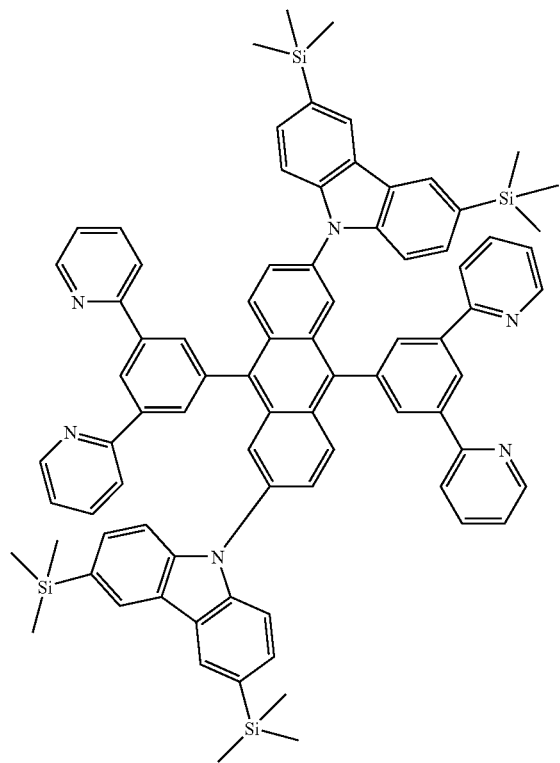
D-65
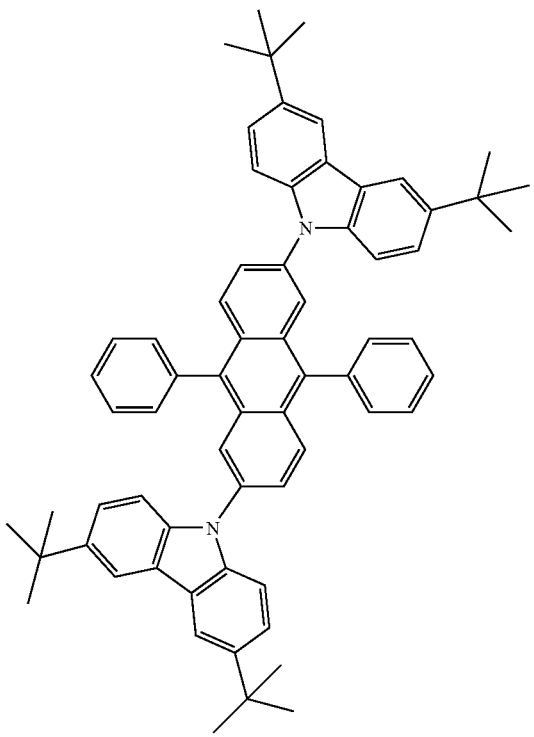

-continued
D-66
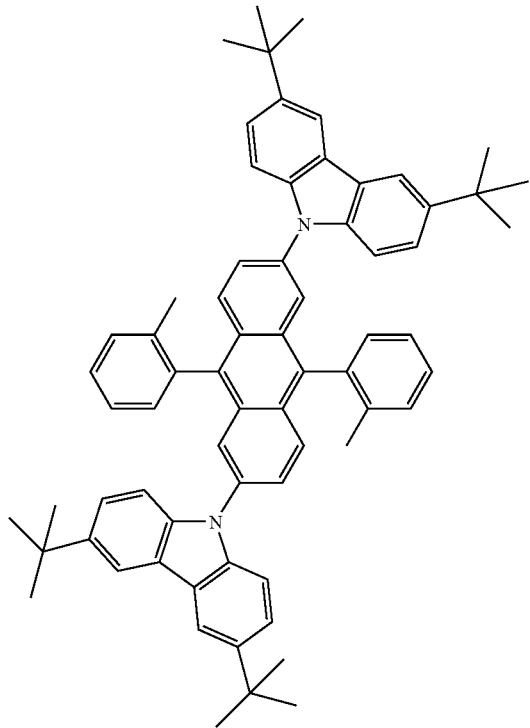
D-67
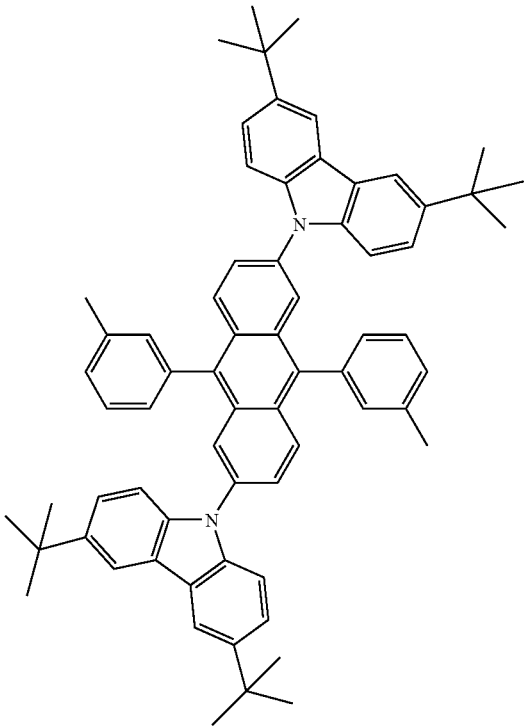
D-68
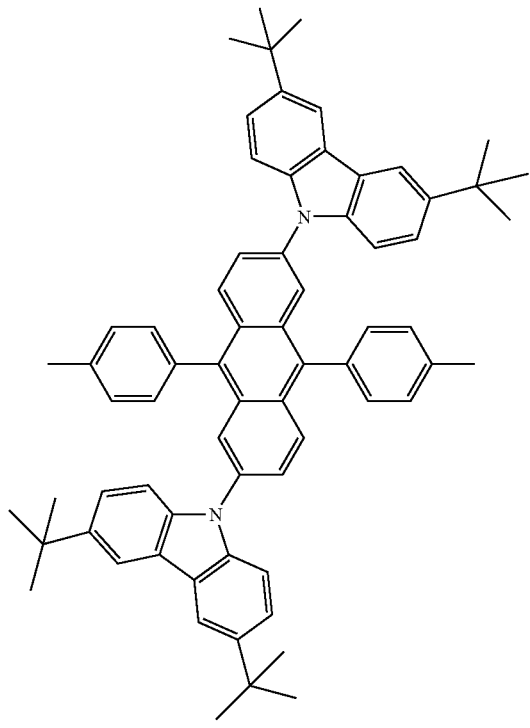
D-69
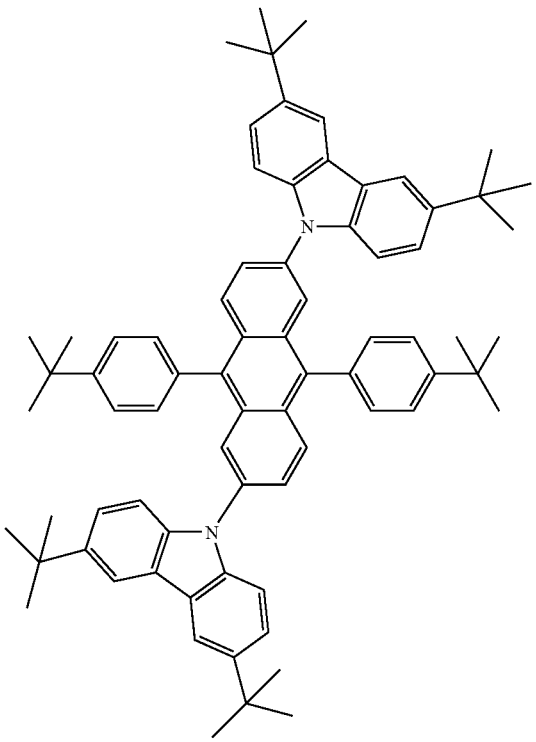

-continued
D-70
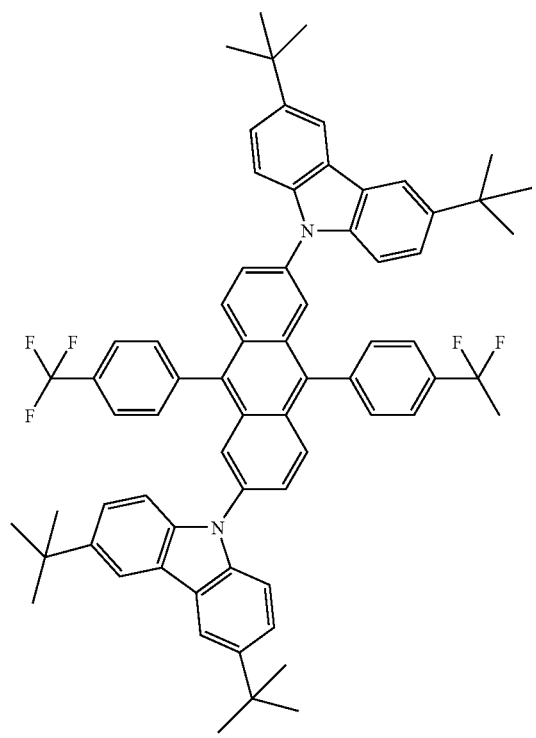
D-71
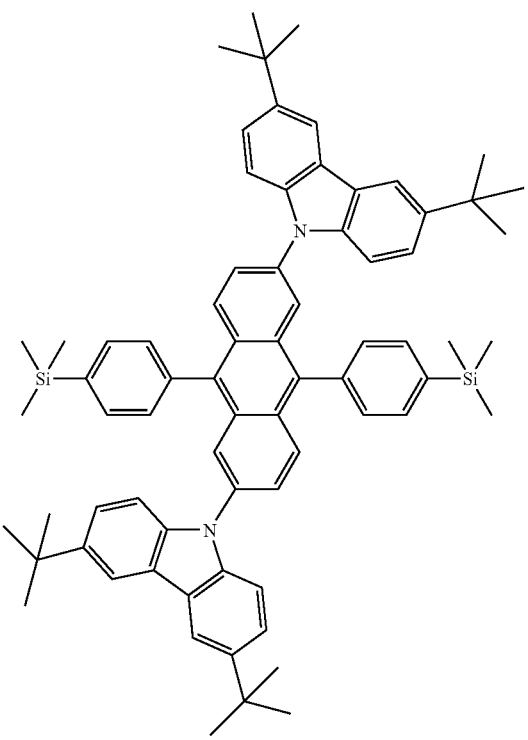
D-72
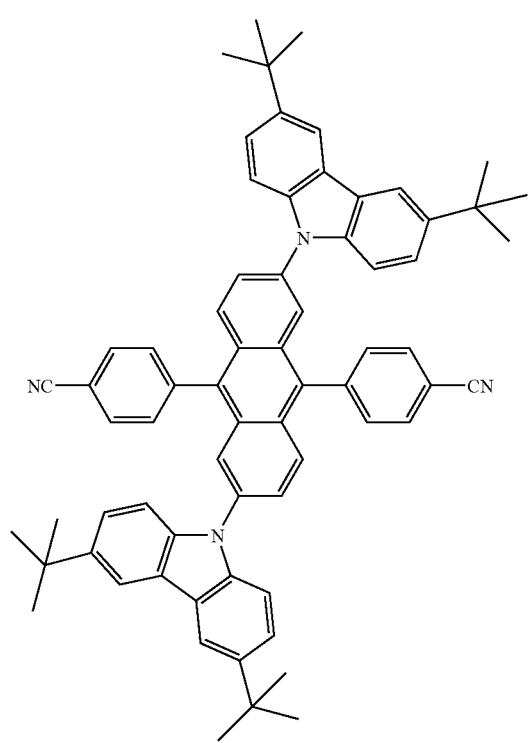
D-73
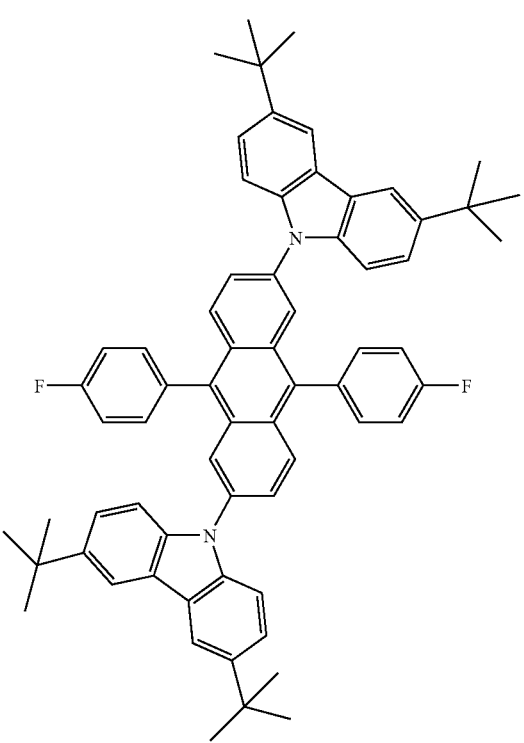

-continued
D-74
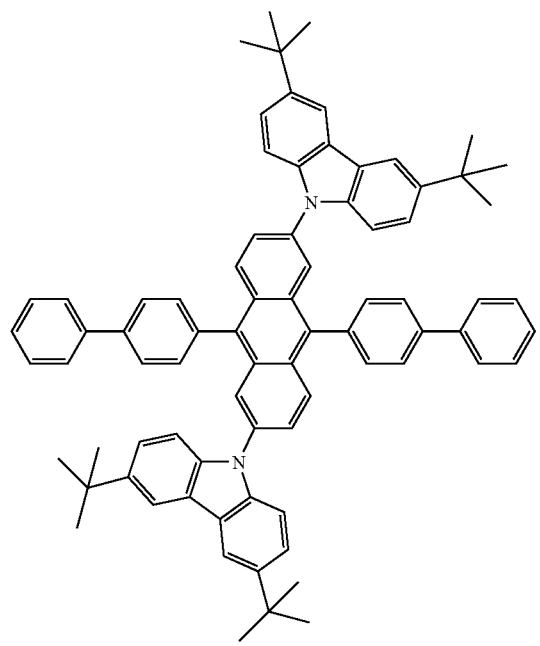
D-75
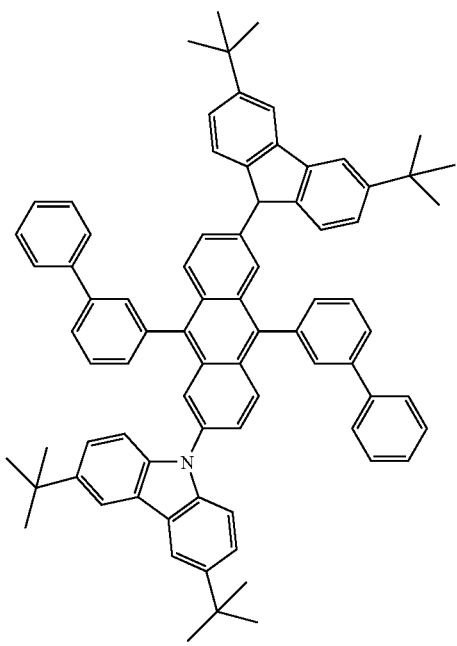
D-76
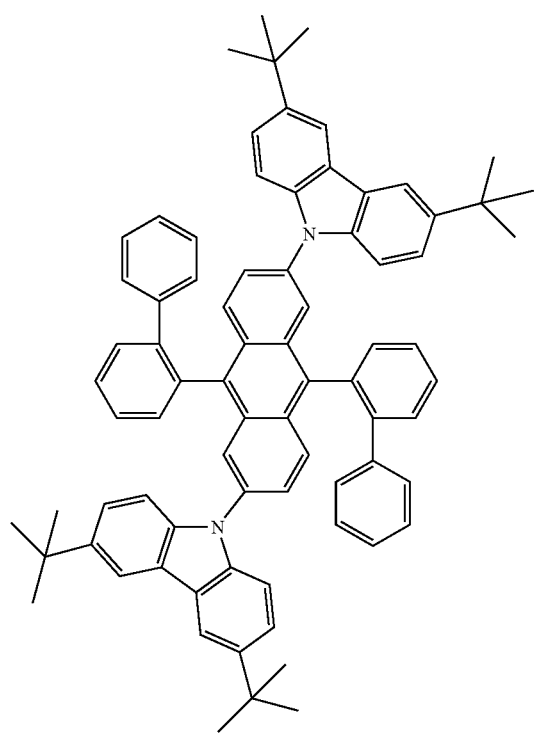

-continued
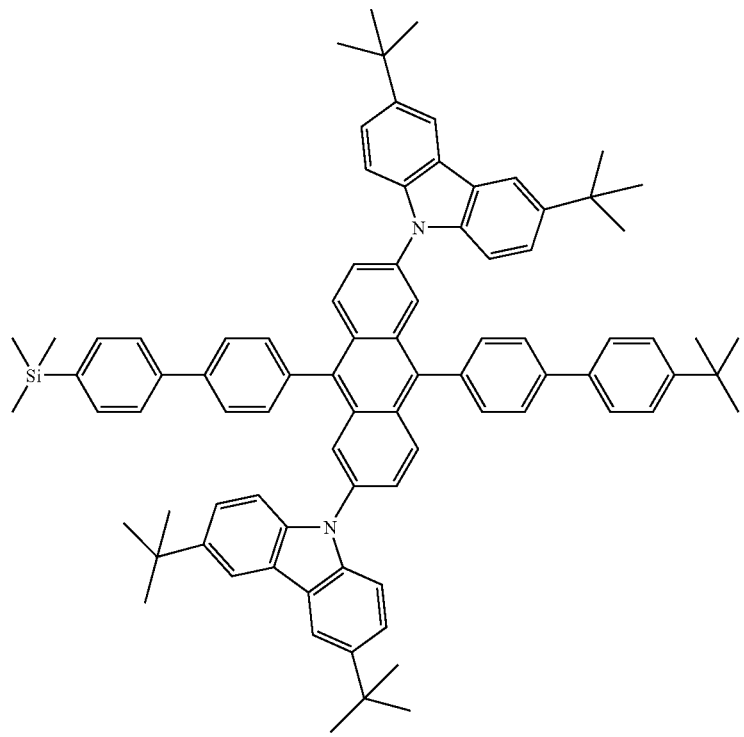
D-77
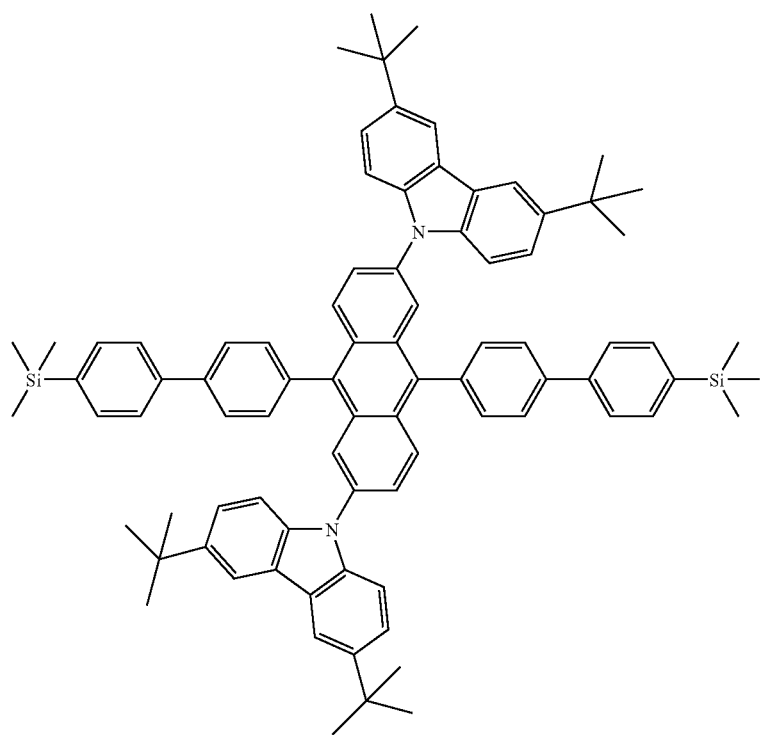
D-78

-continued
D-79
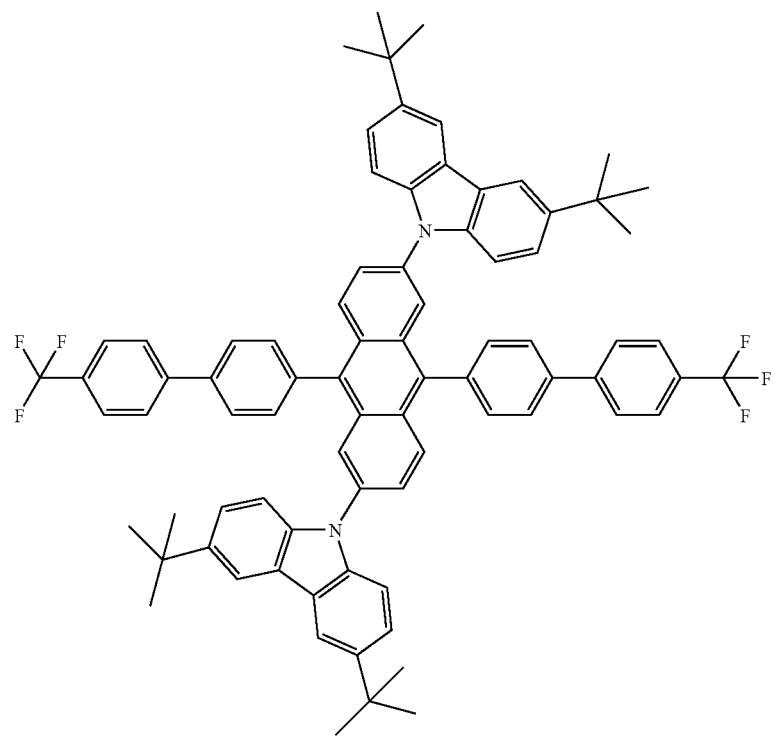
D-80

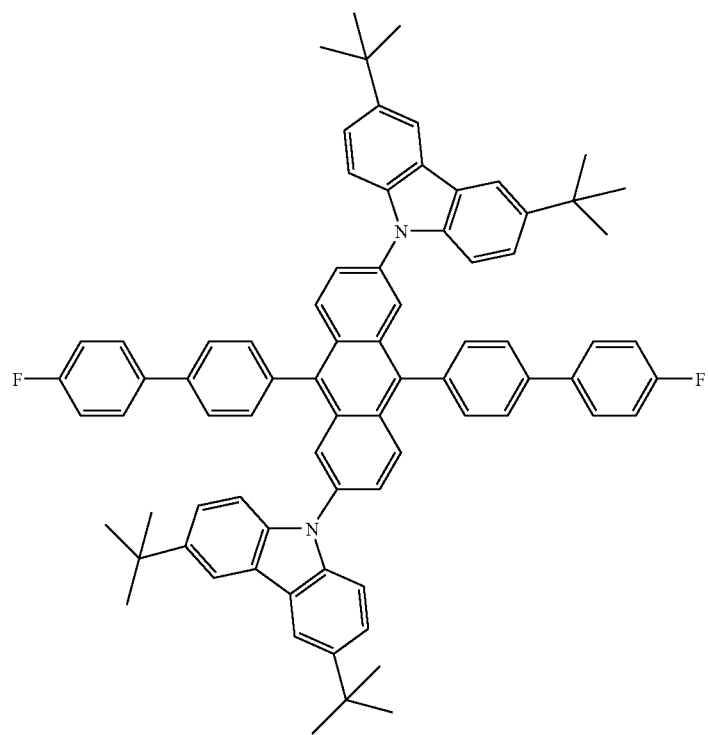
D-81
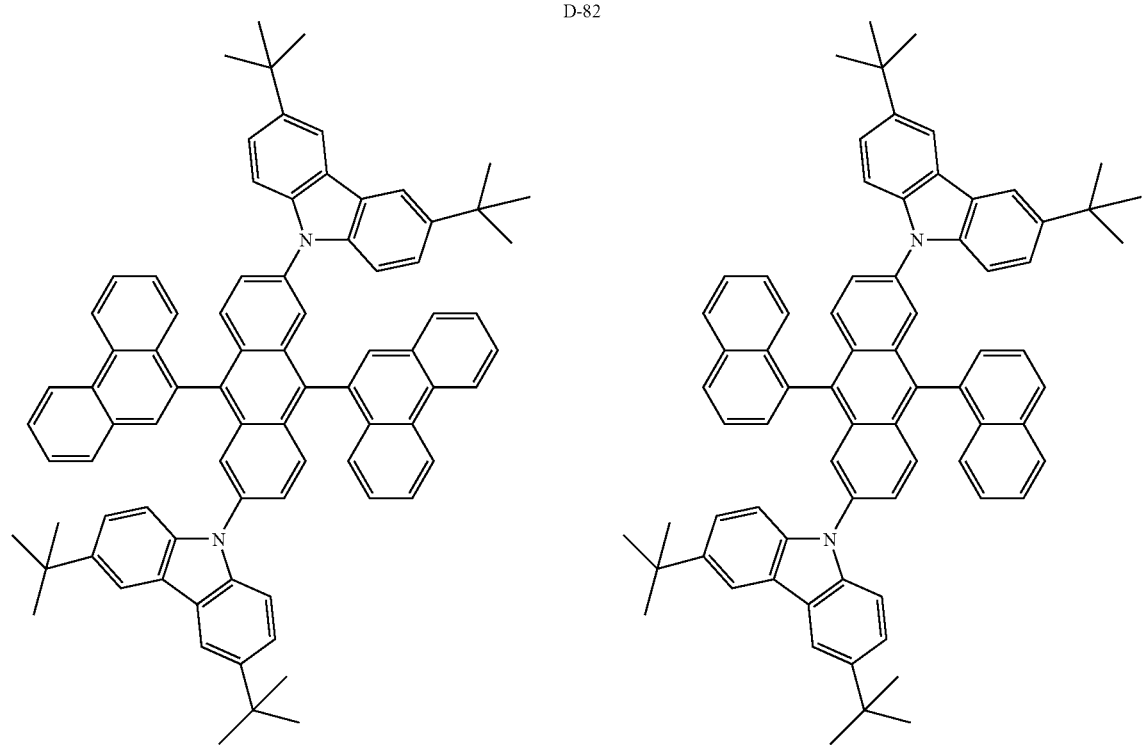
D-82
D-83

D-84
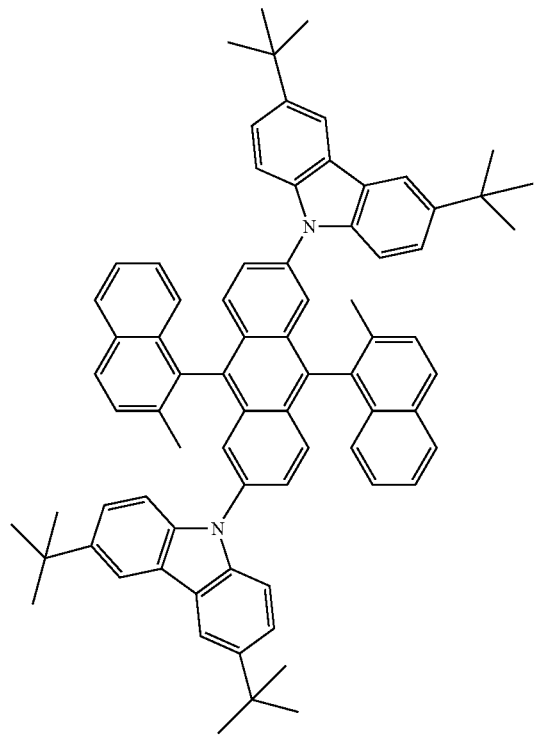
D-85
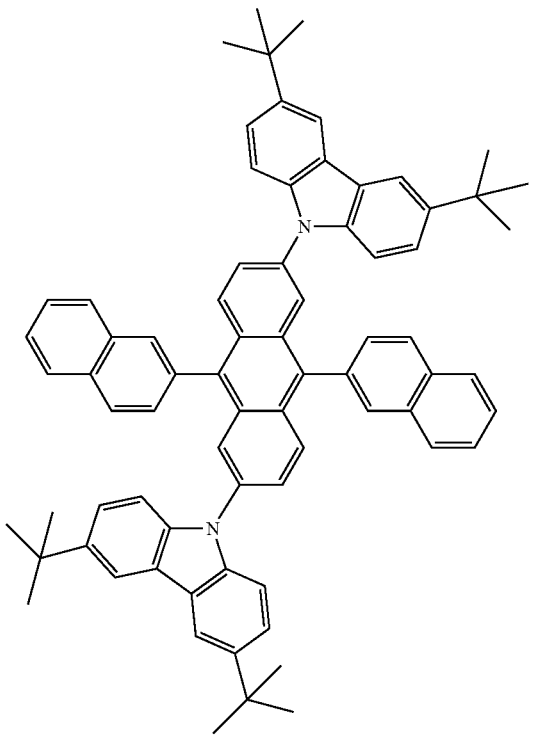
D-86
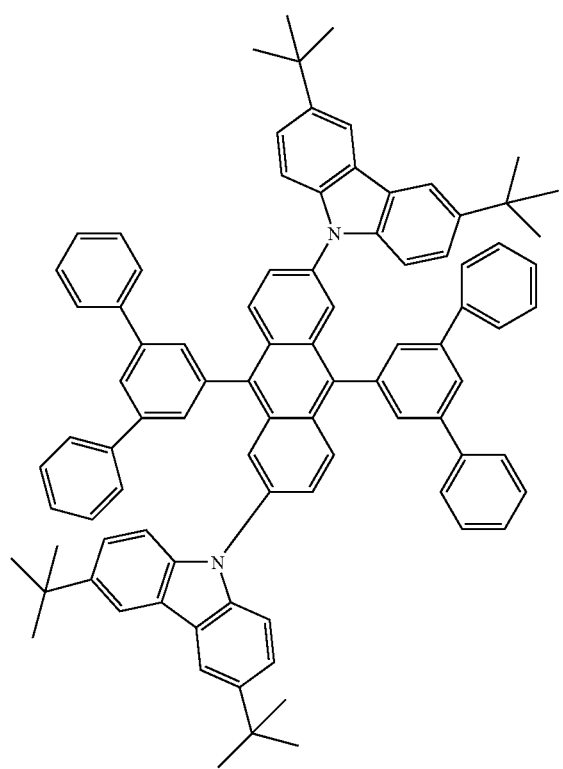
D-87
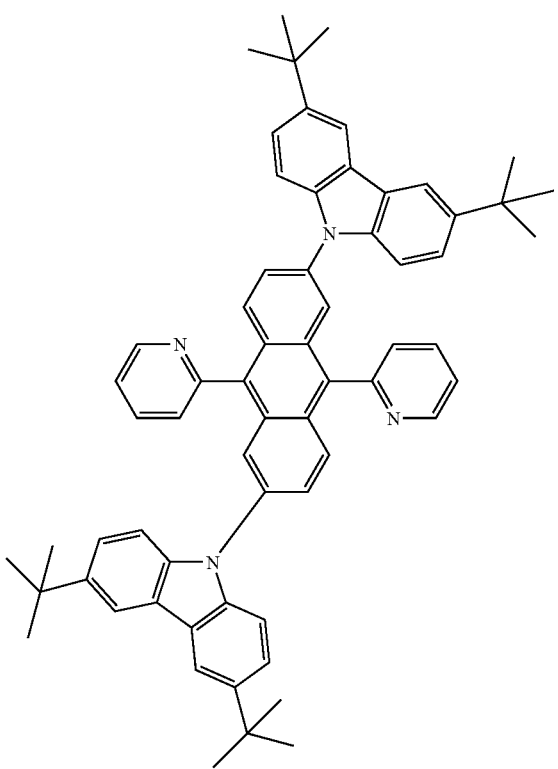

-continued
D-88
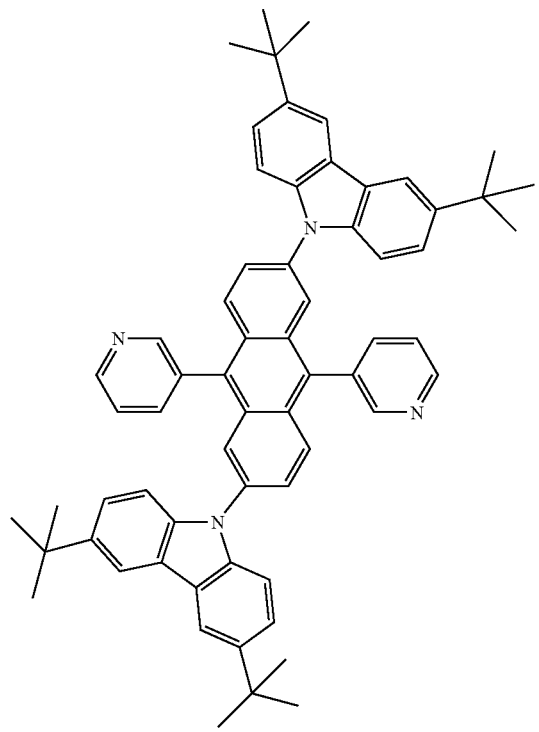
D-89
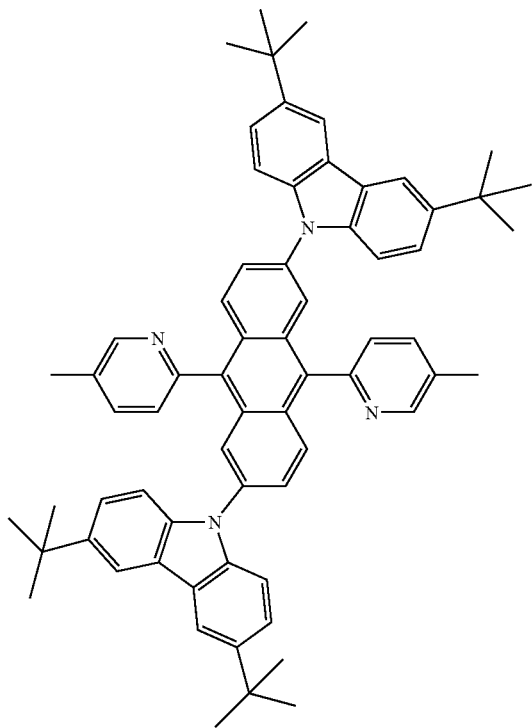
D-90
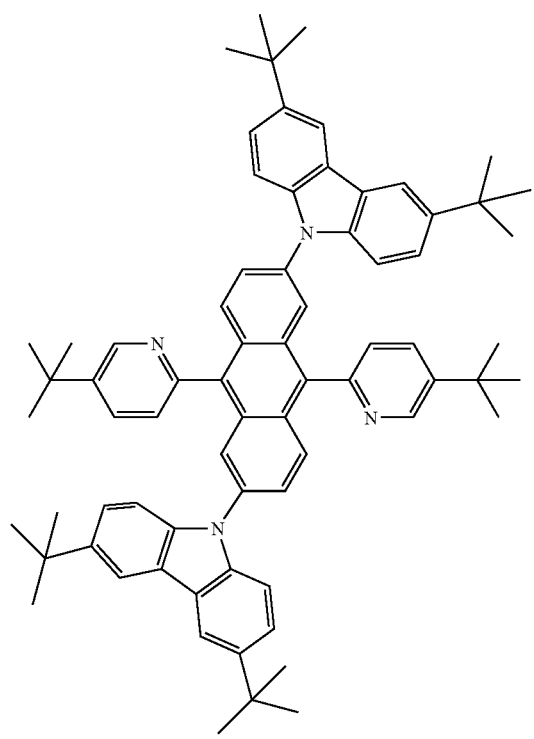
D-91
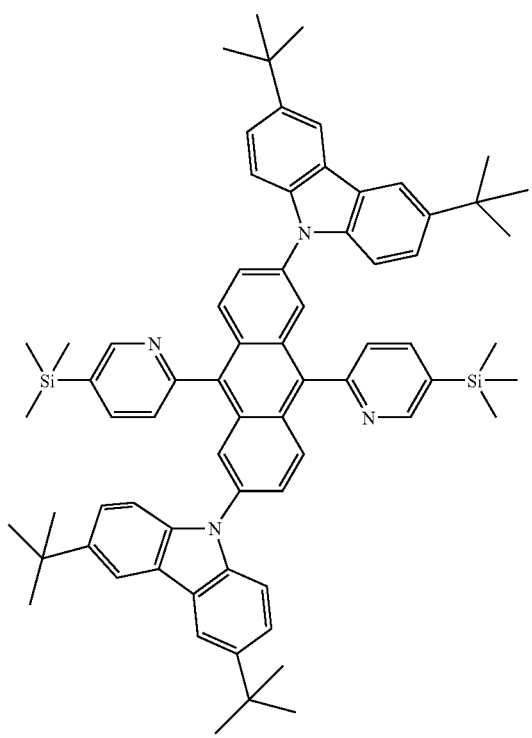

-continued
D-92
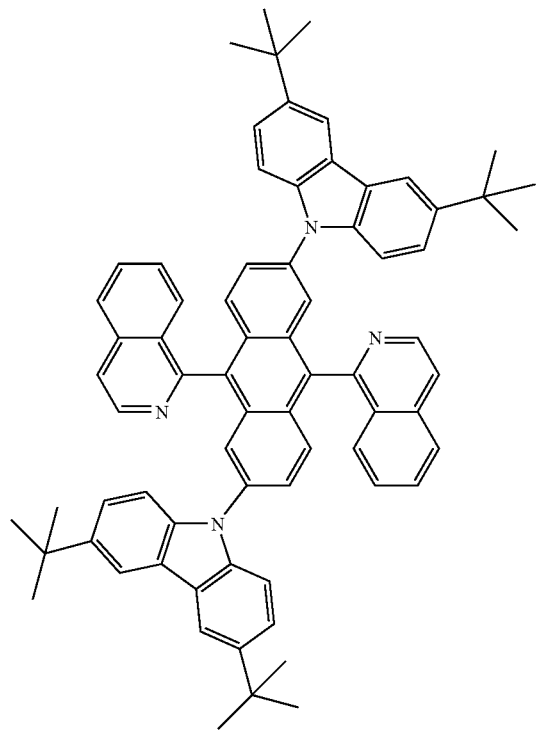
D-93
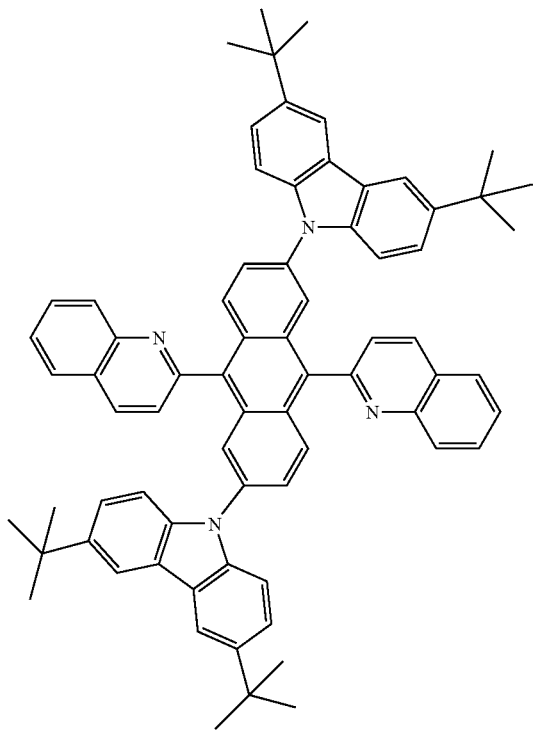
D-94
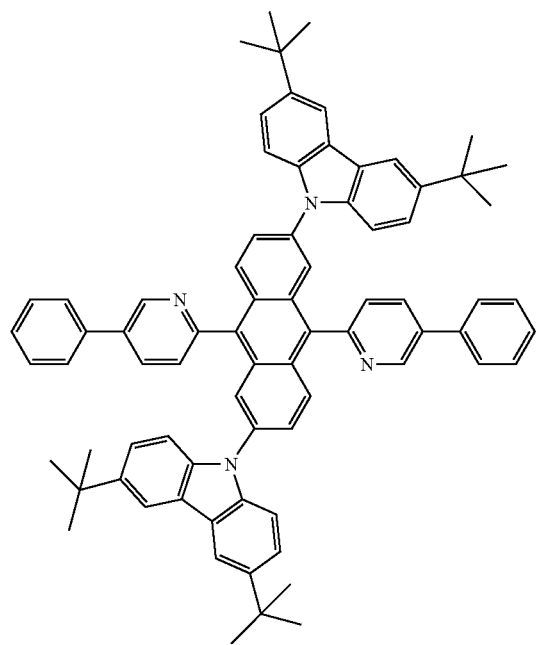
D-95
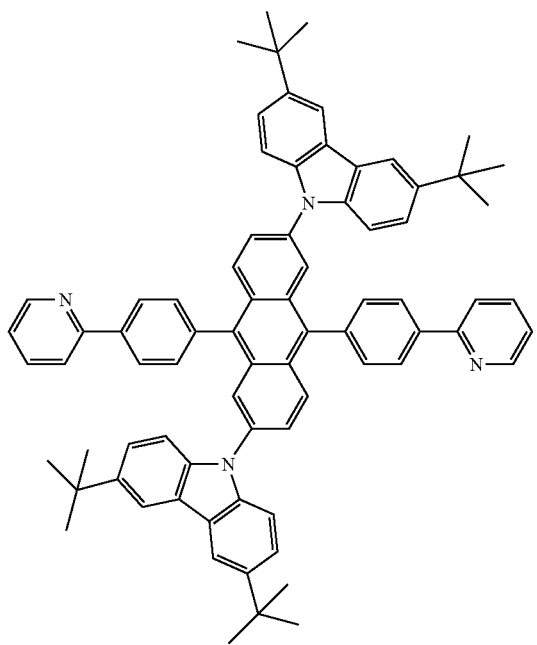

-continued
D-96
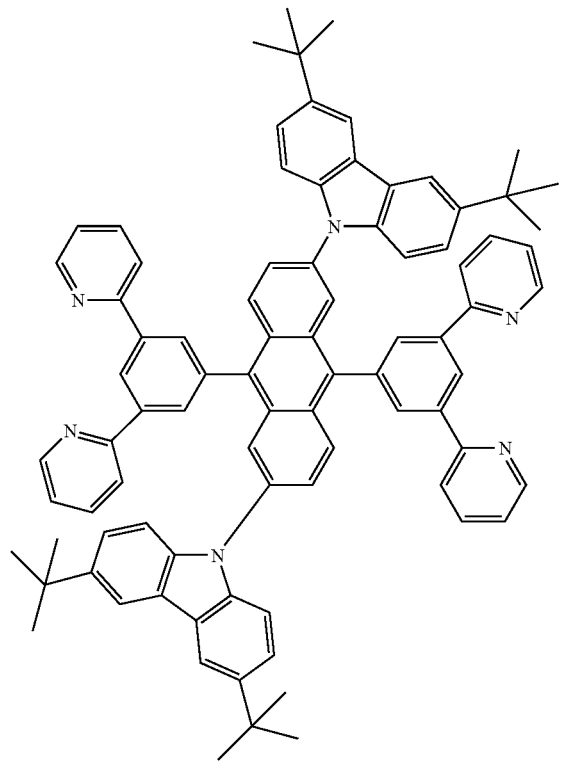
D-97
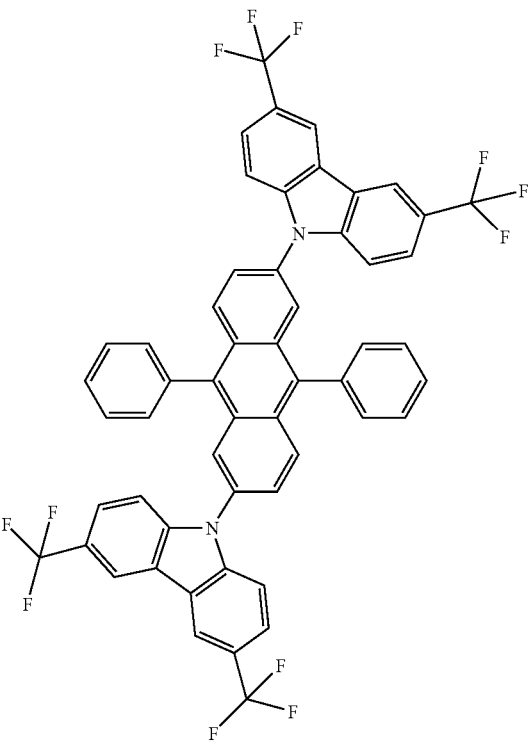
D-98
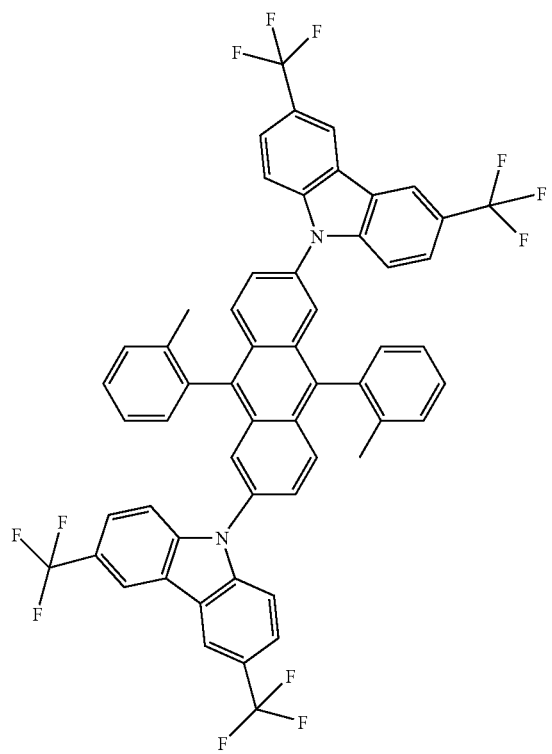
D-99
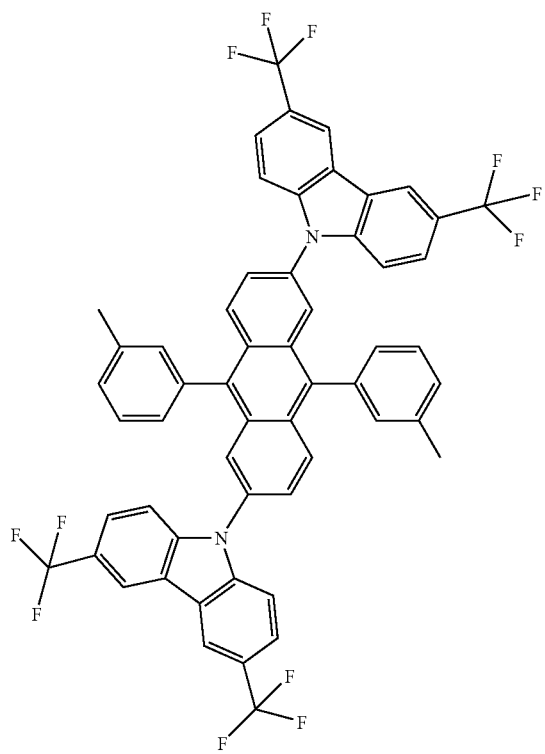

D-100
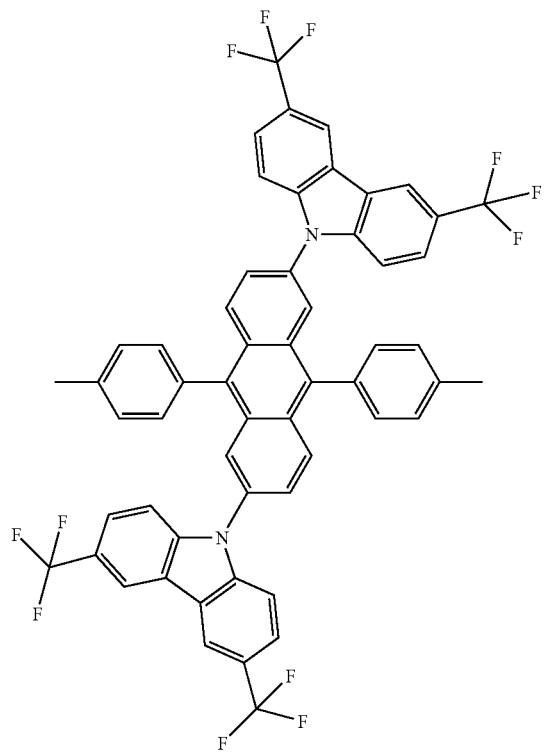
D-101
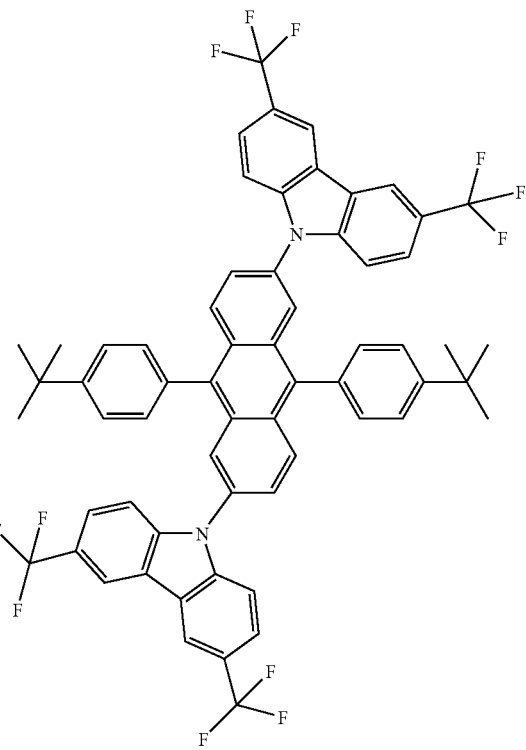
D-102
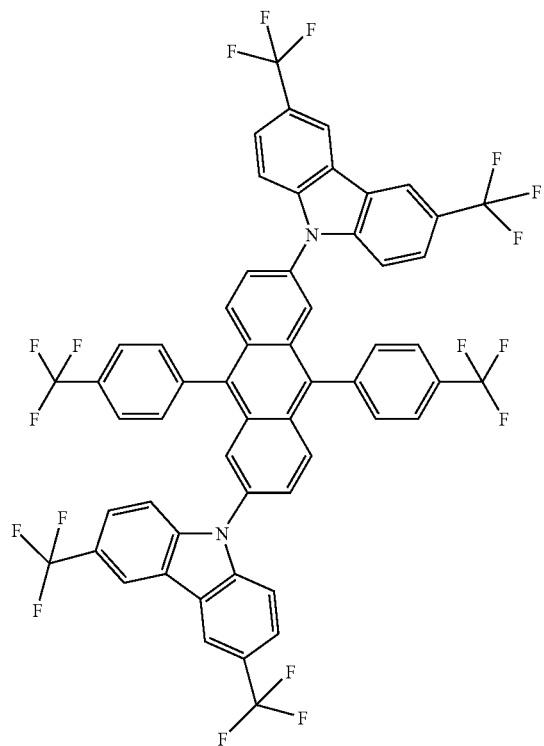
D-103
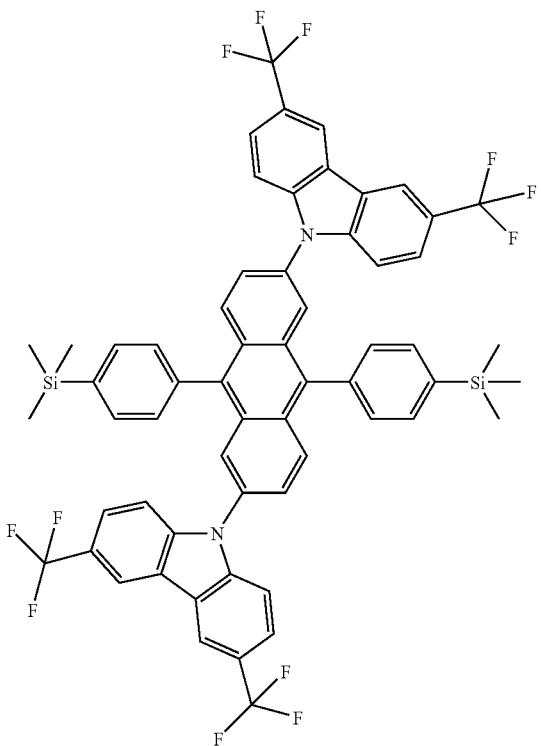

-continued
D-104
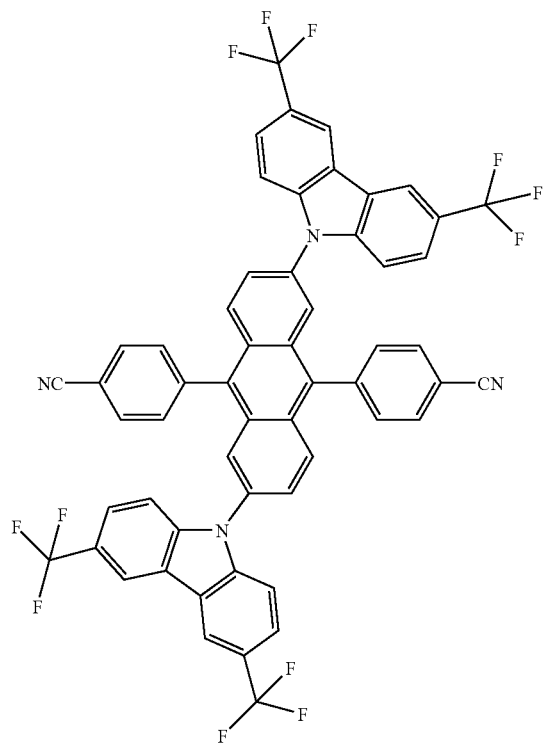
D-105
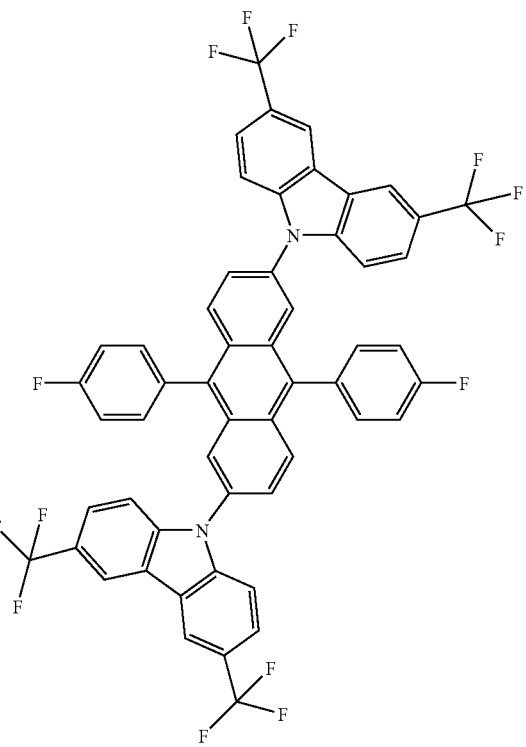
D-106
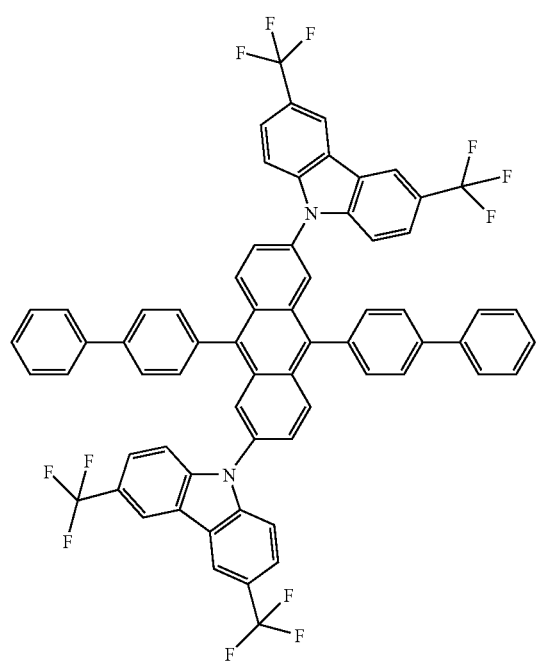
D-107
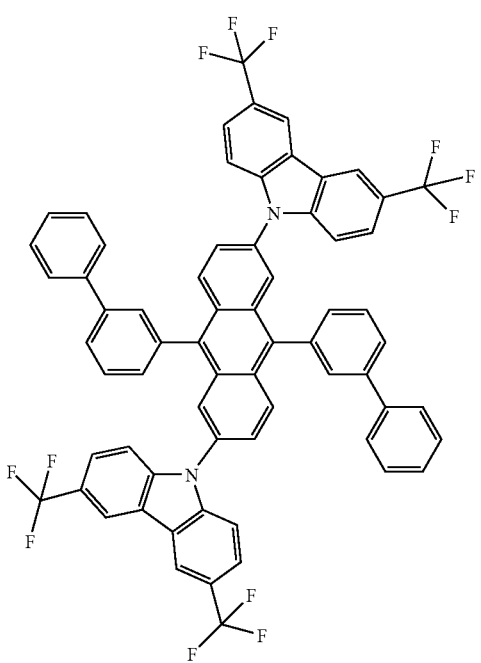

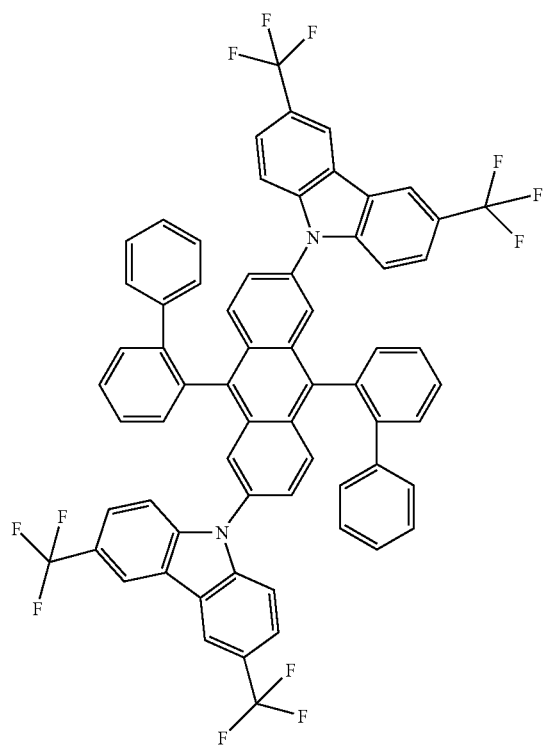
D-108
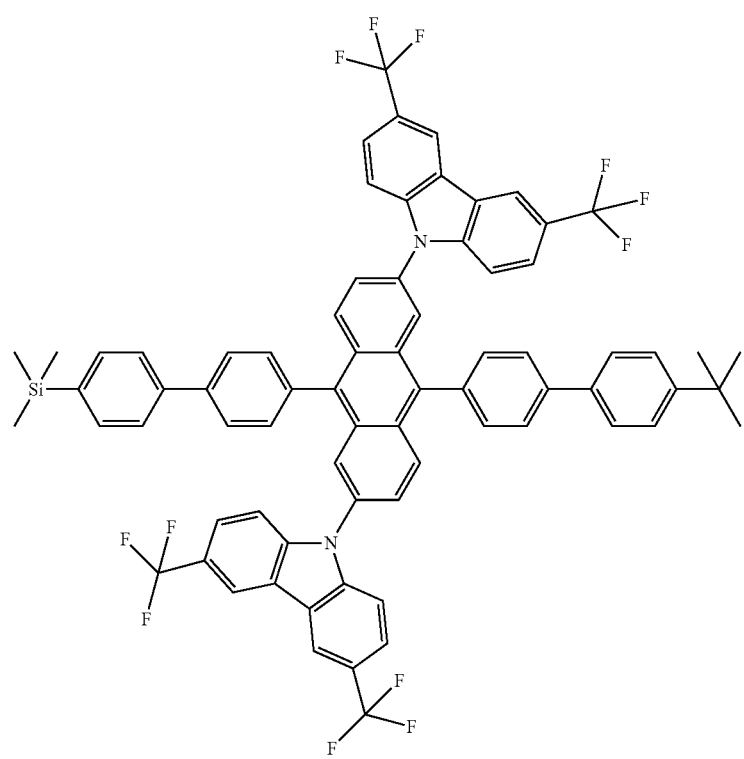

D-110
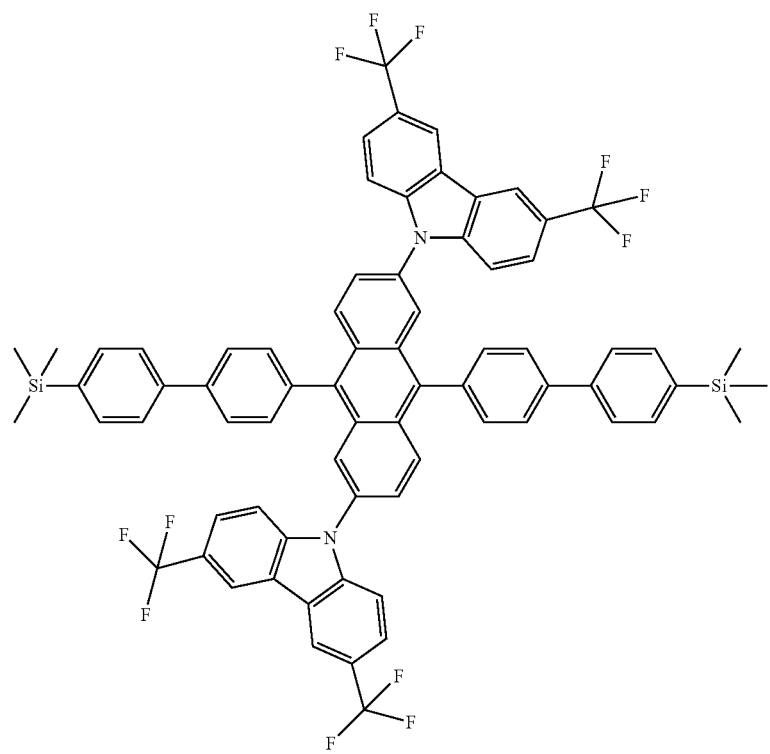
D-111
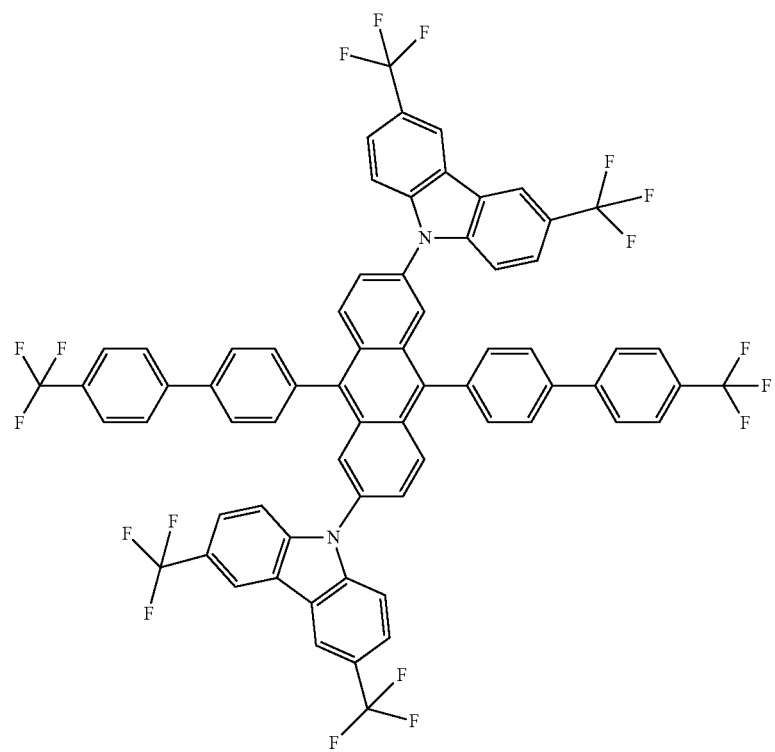

D-112
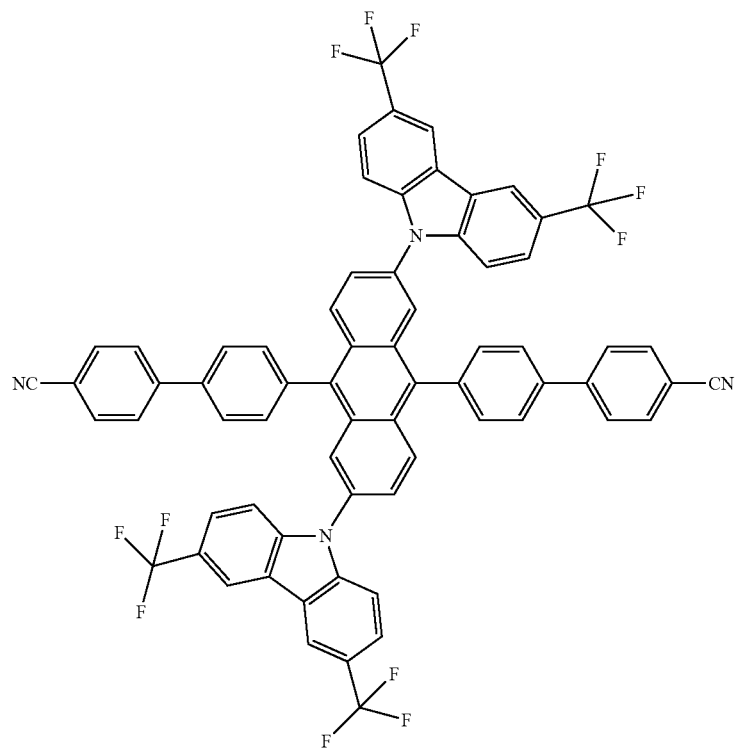
D-113
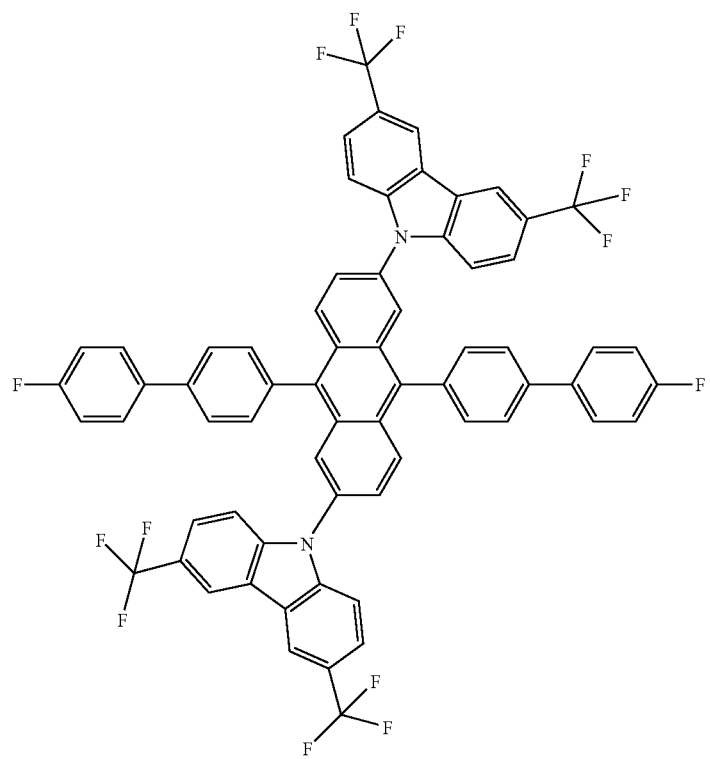

-continued
D-114
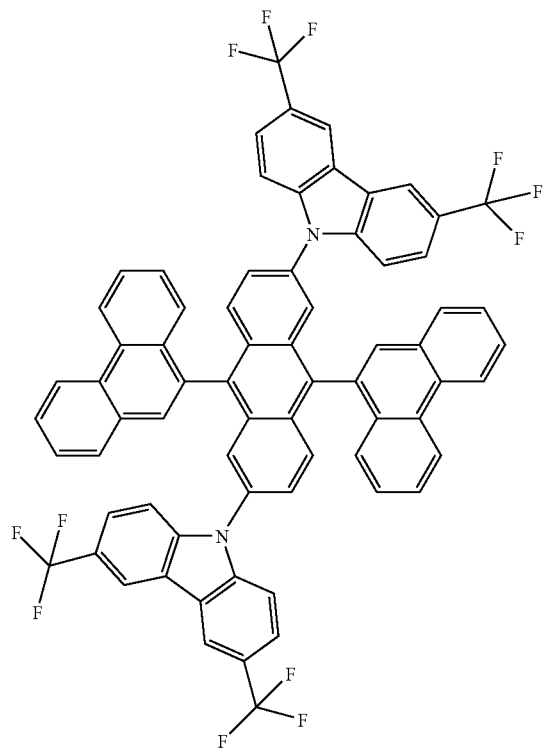
D-115
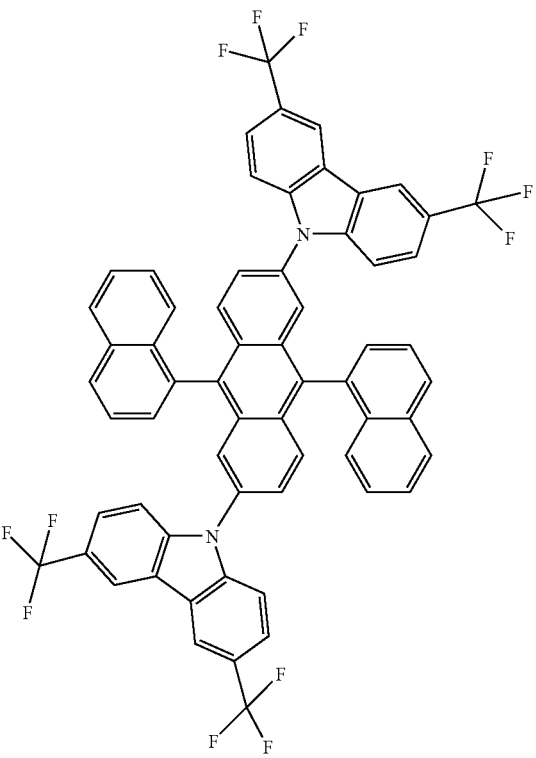
D-116
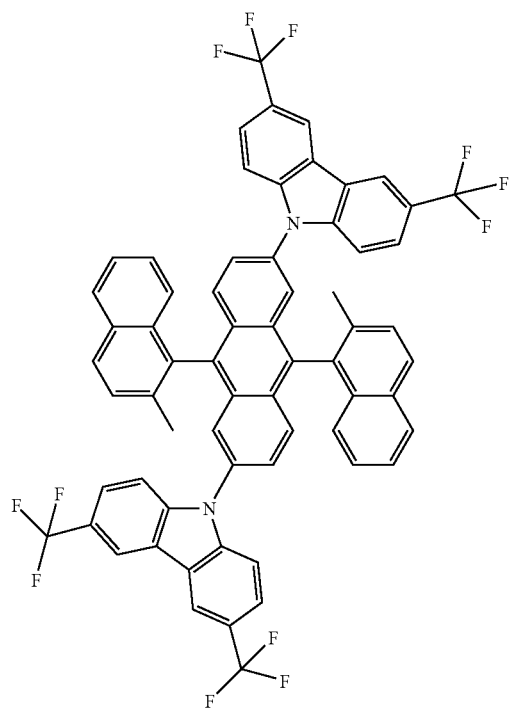
D-117
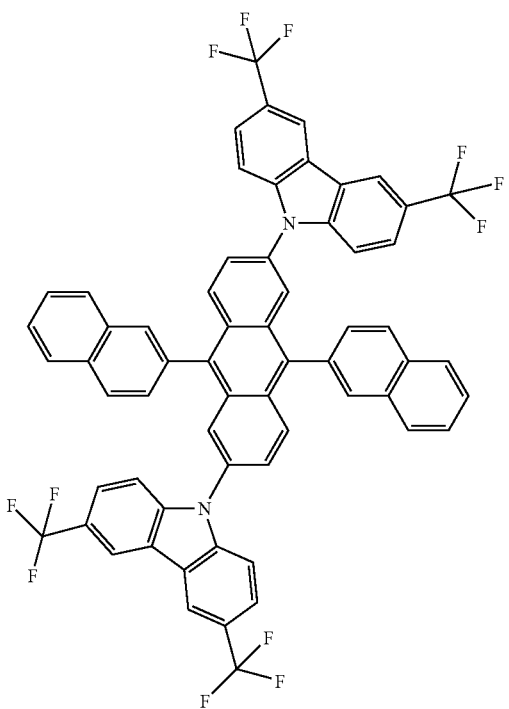

-continued
D-118
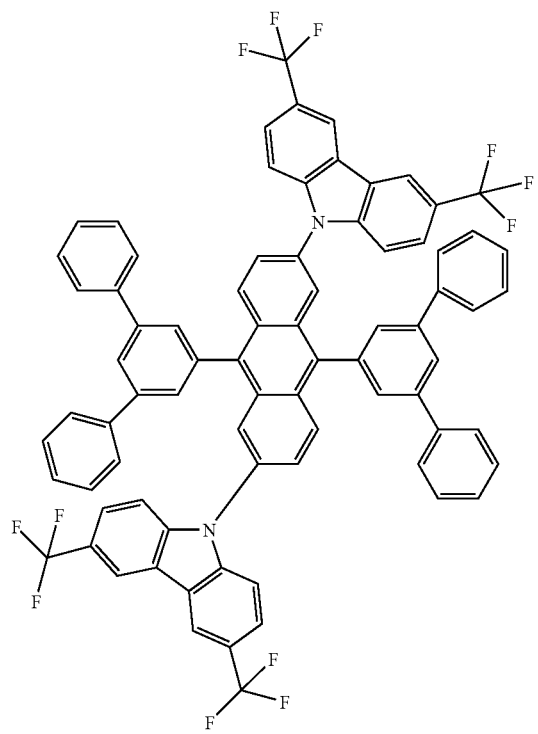
D-119
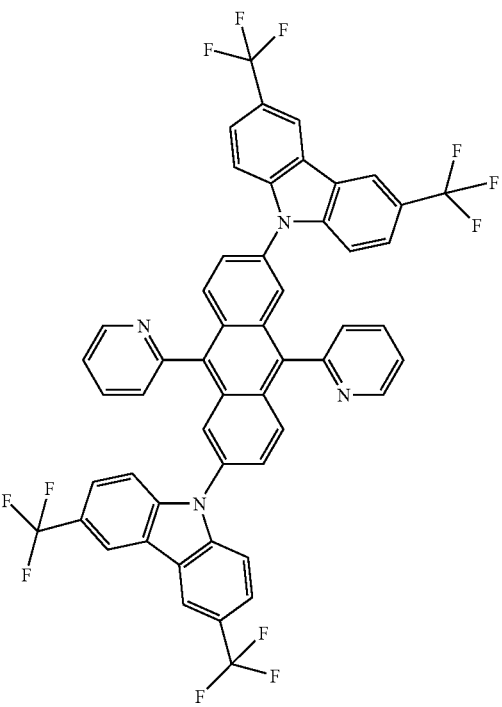
D-120
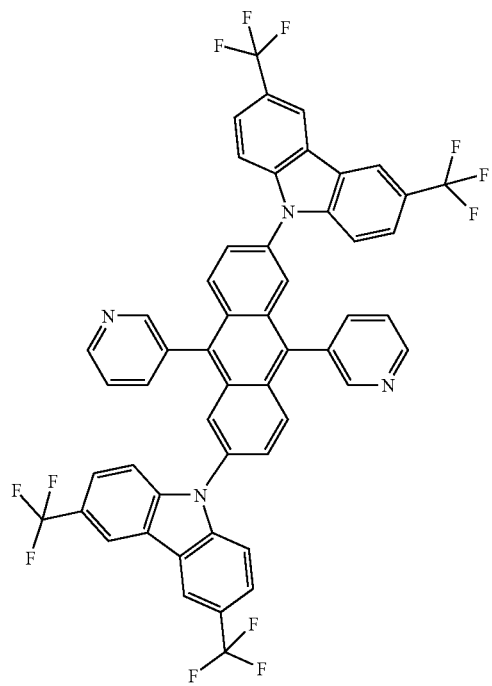
D-121
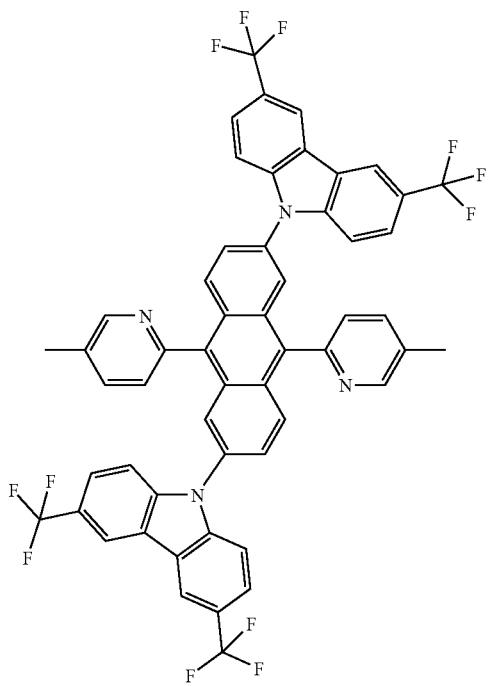

-continued
D-123
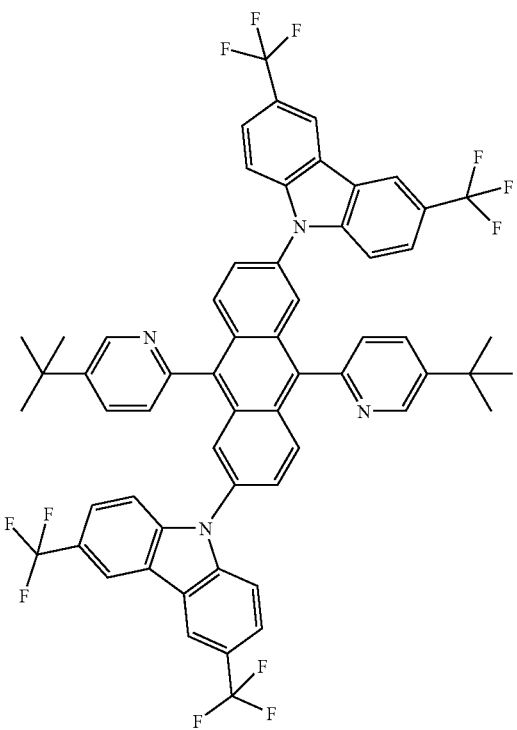
D-124
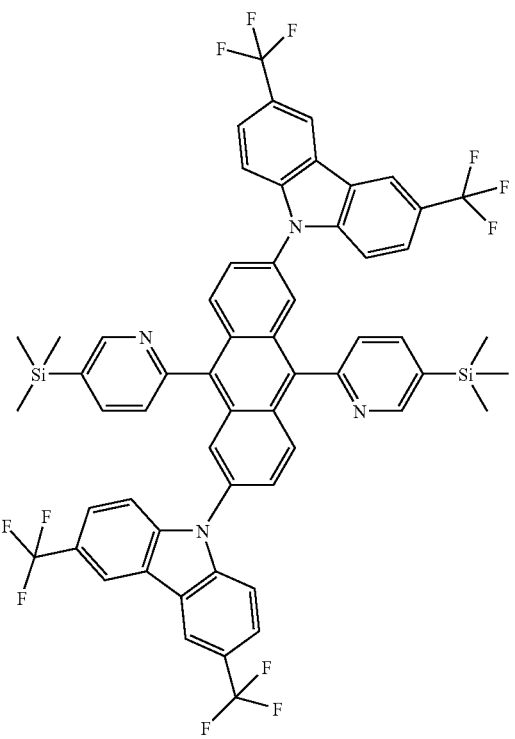
D-125
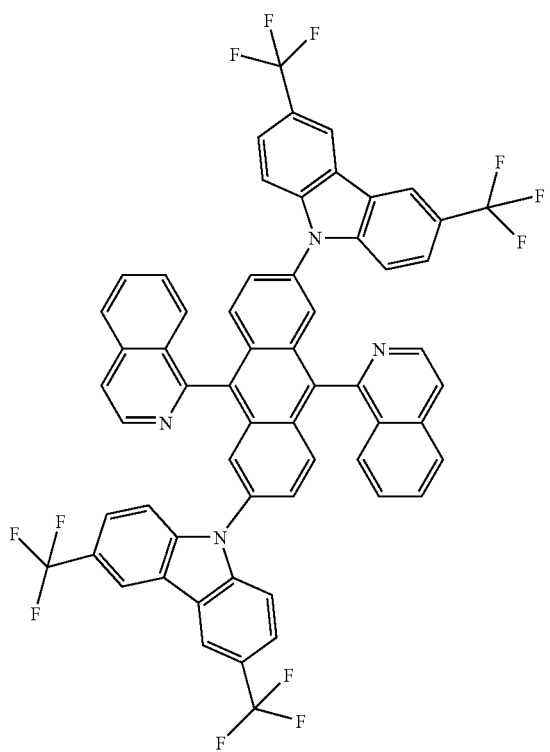
D-126
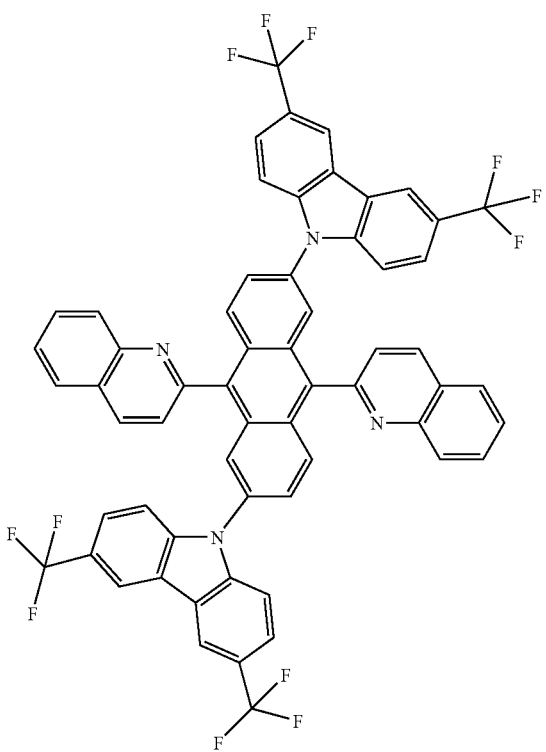

-continued
D-127
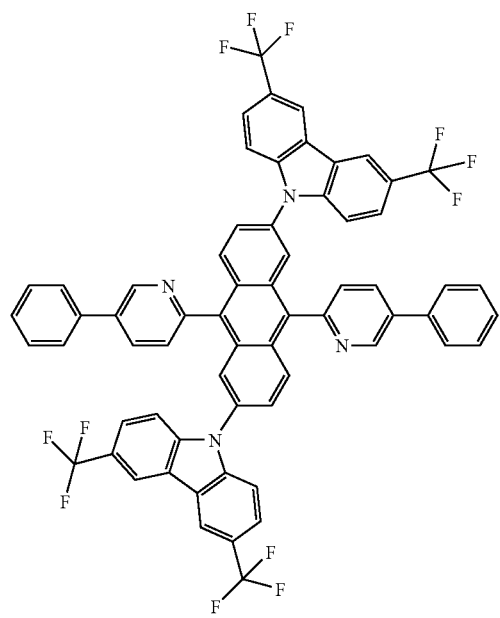
D-128
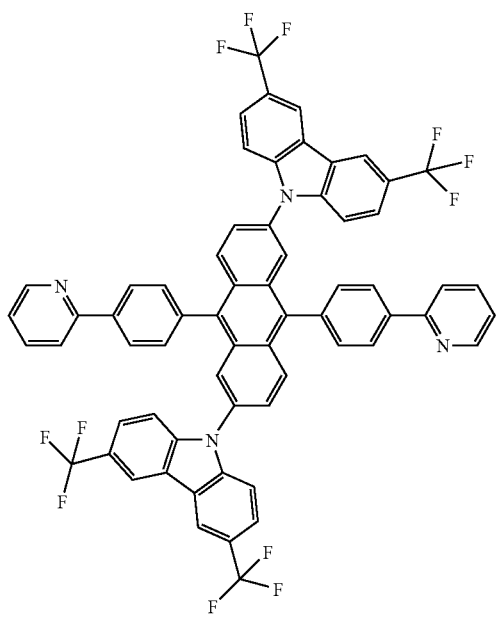
D-129
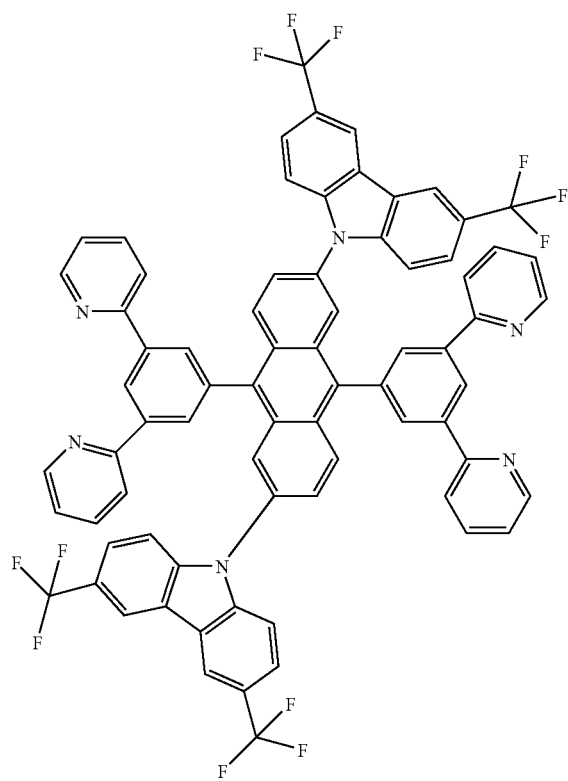
D-130
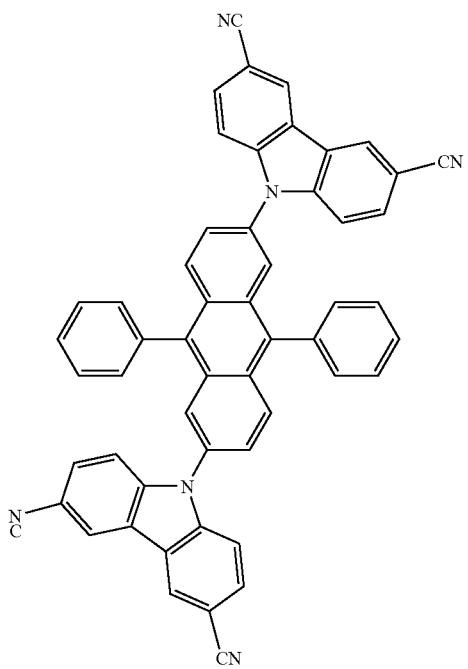

-continued
D-131
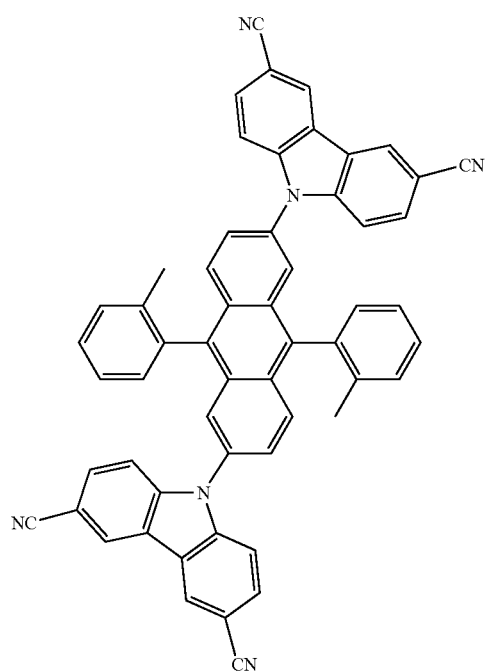
D-132
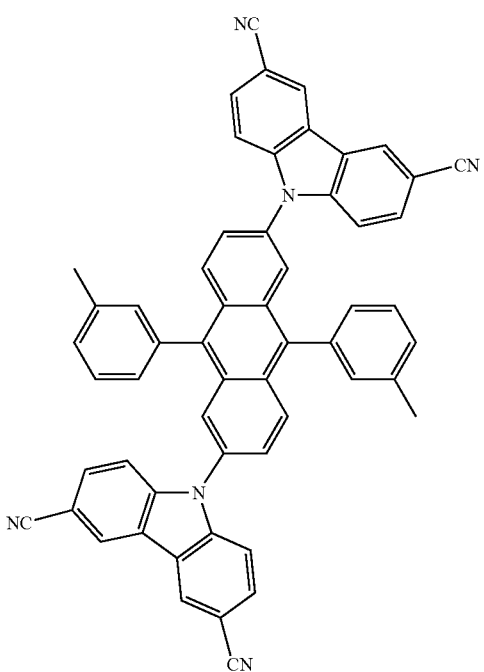
D-133
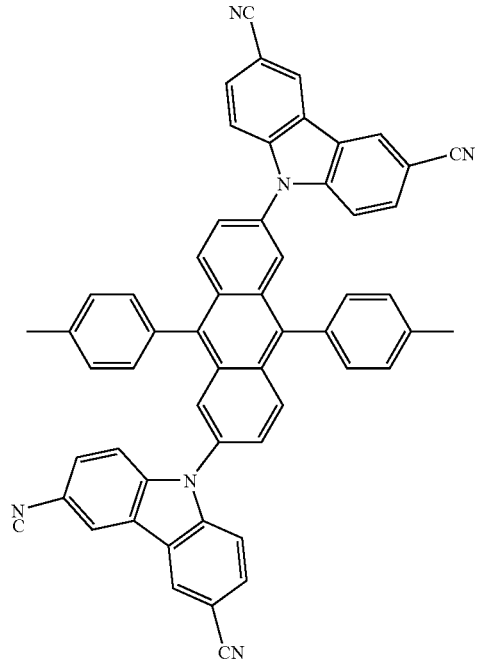
D-134
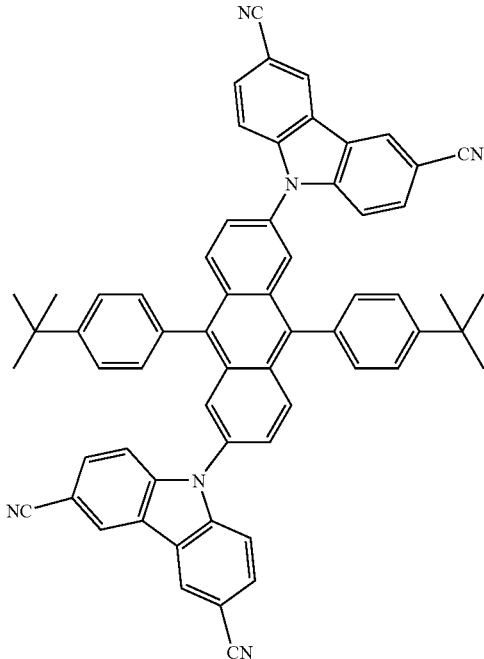

-continued
D-135
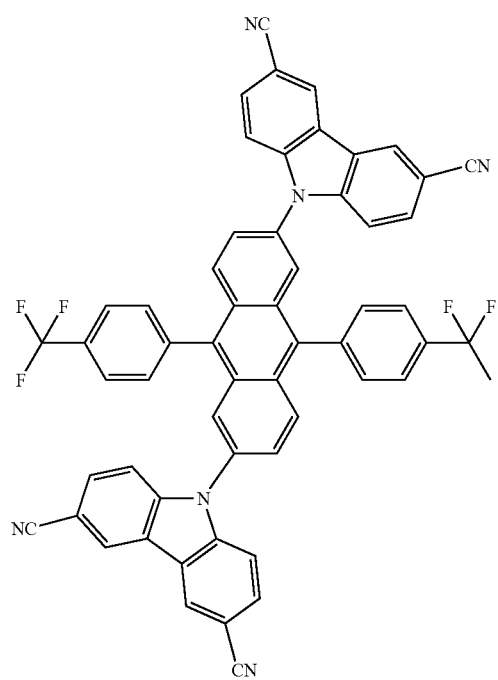
D-136
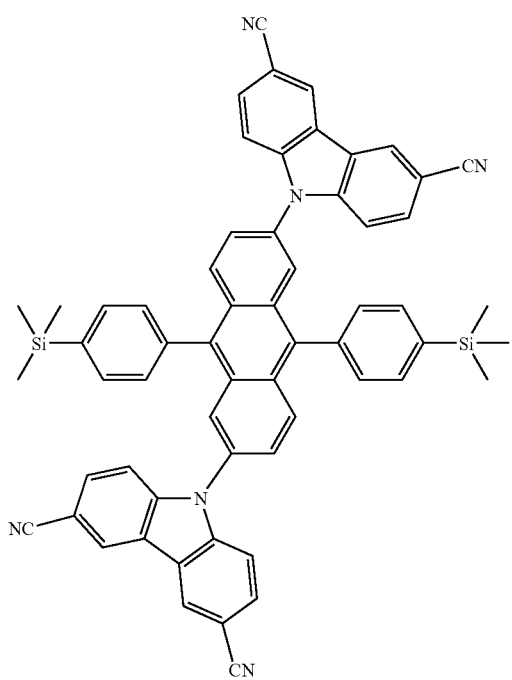
D-137
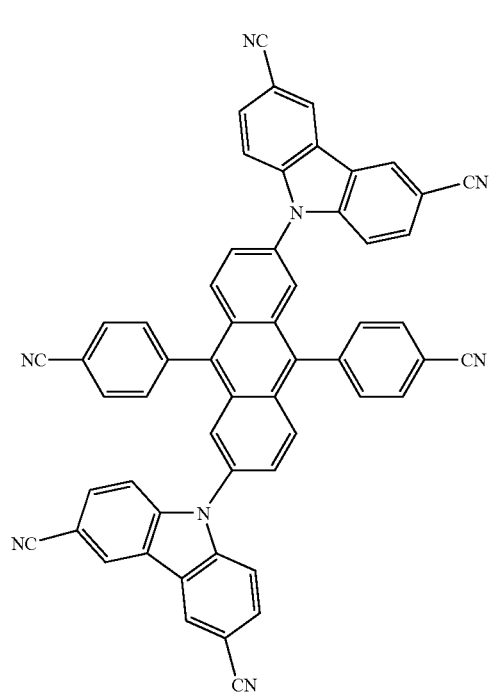
D-138
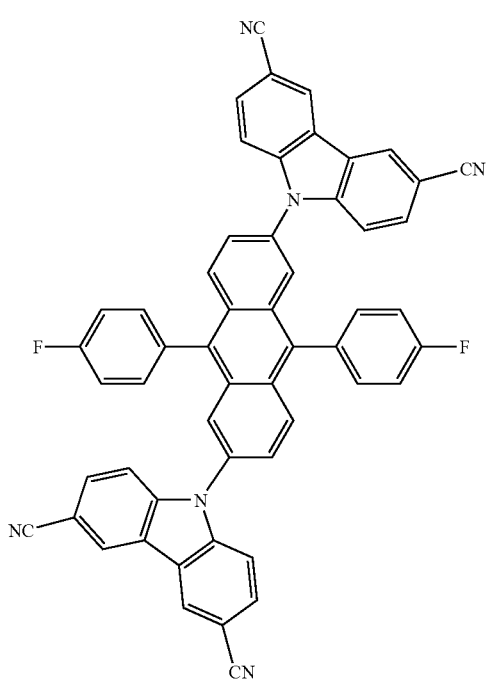

-continued
D-139
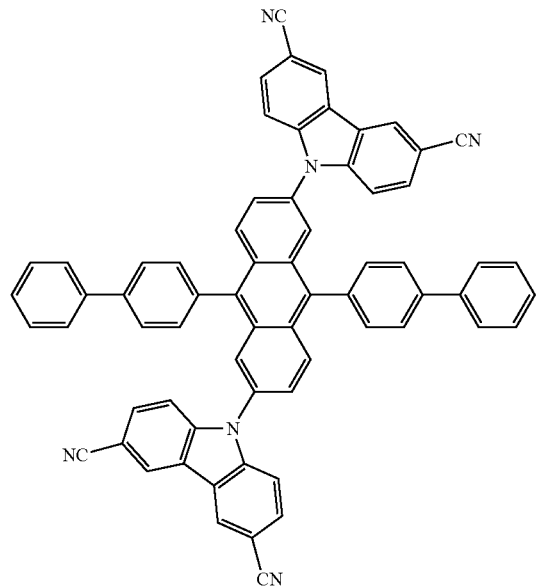
D-140
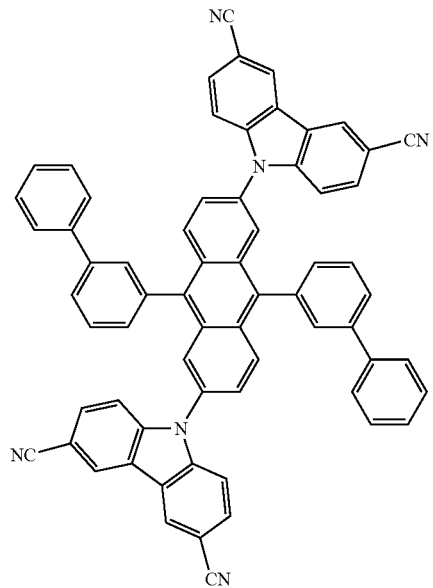
D-142
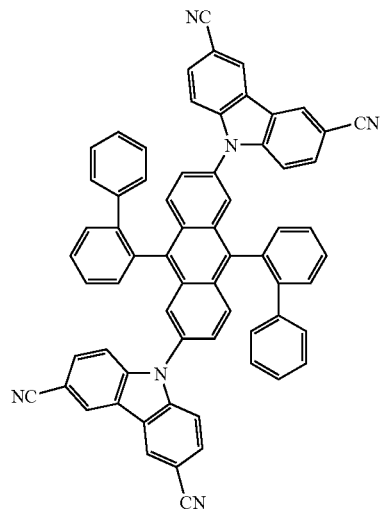
D-143
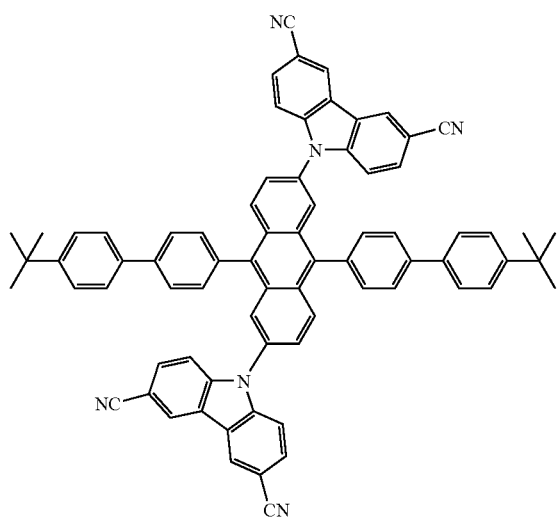

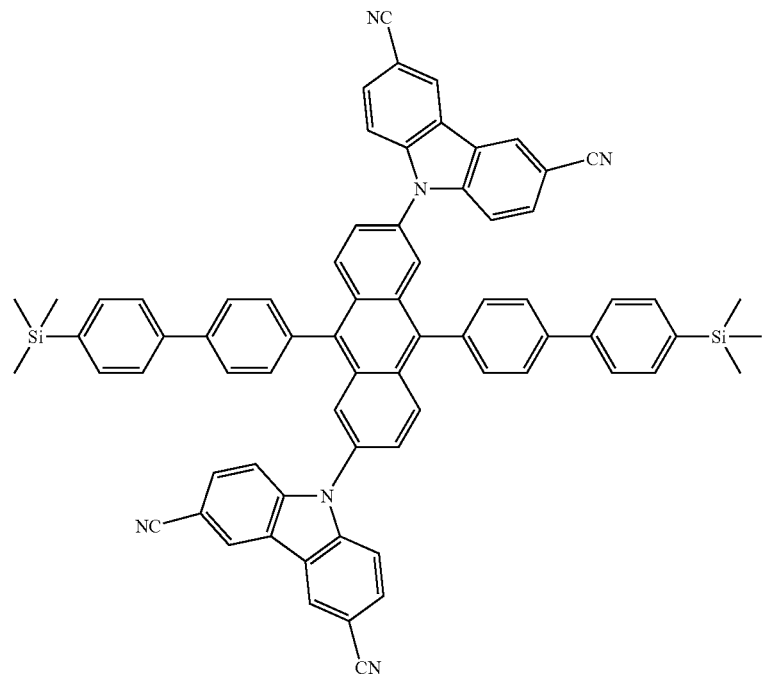
D-144
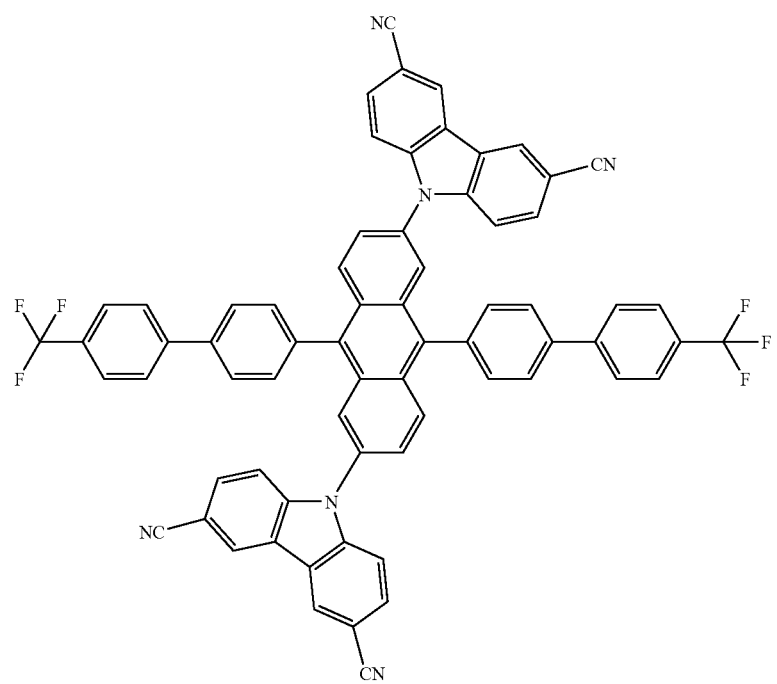
D-145

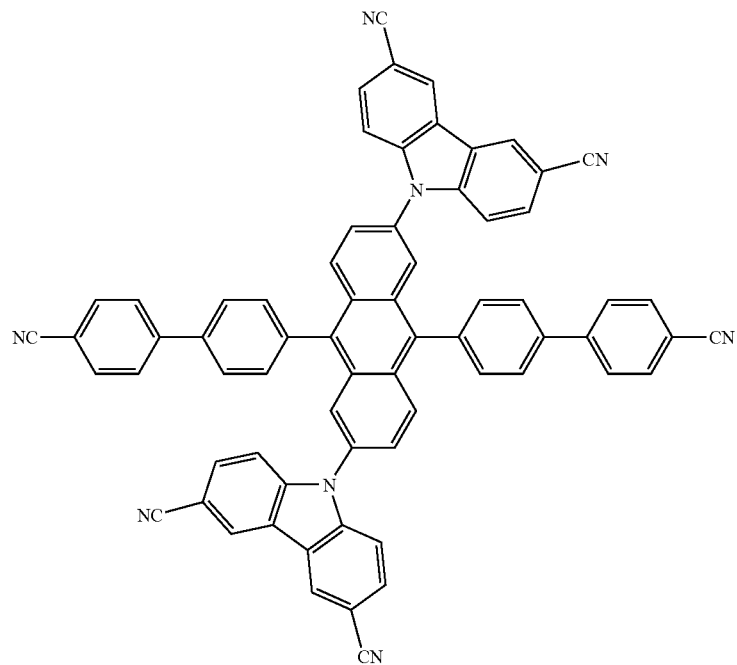
D-146
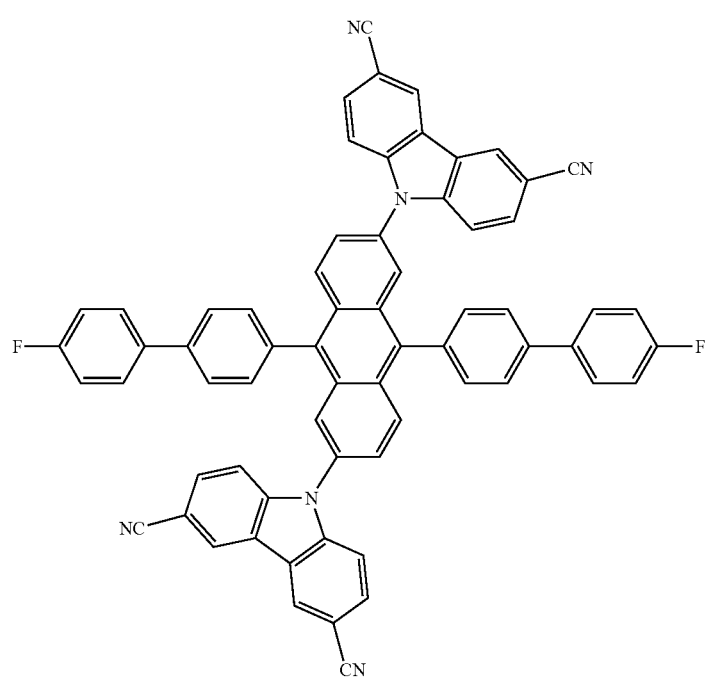
D-147

-continued
D-148
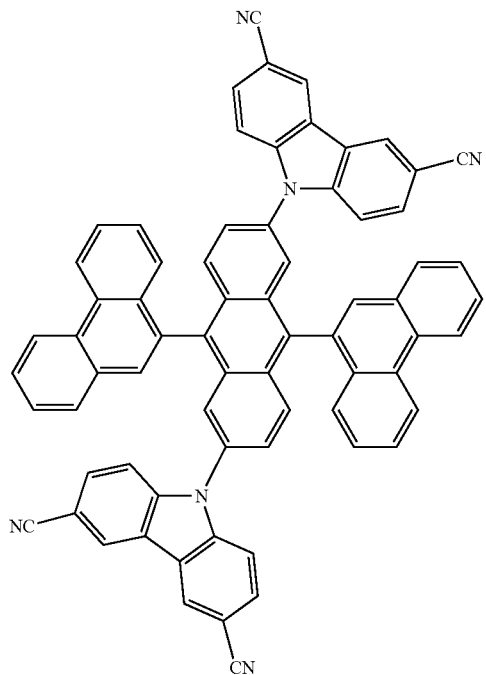
D-149
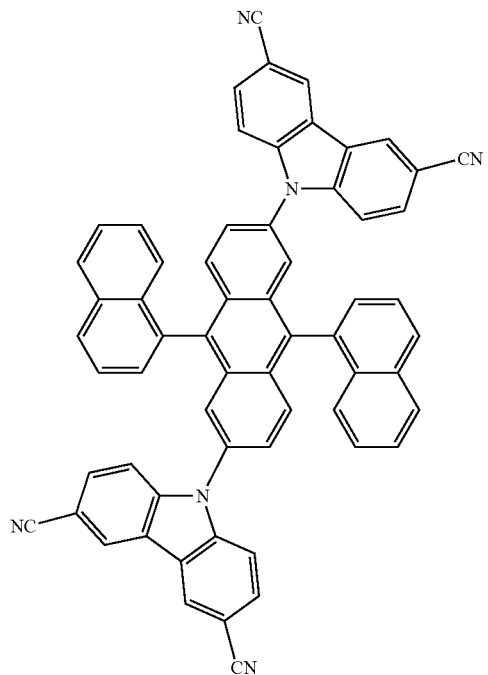
D-150
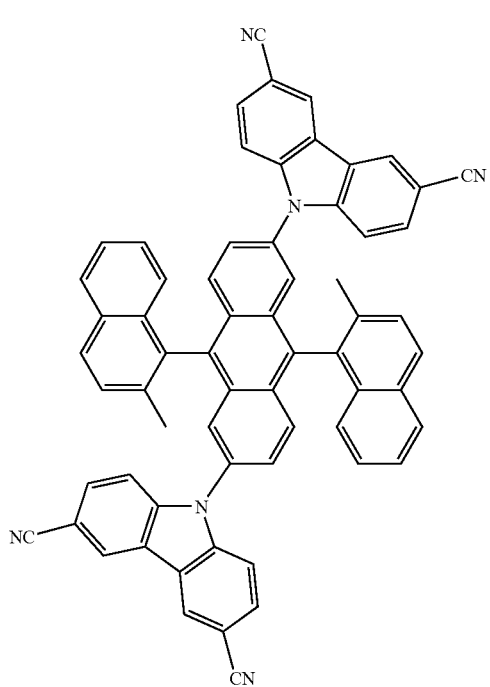
D-151
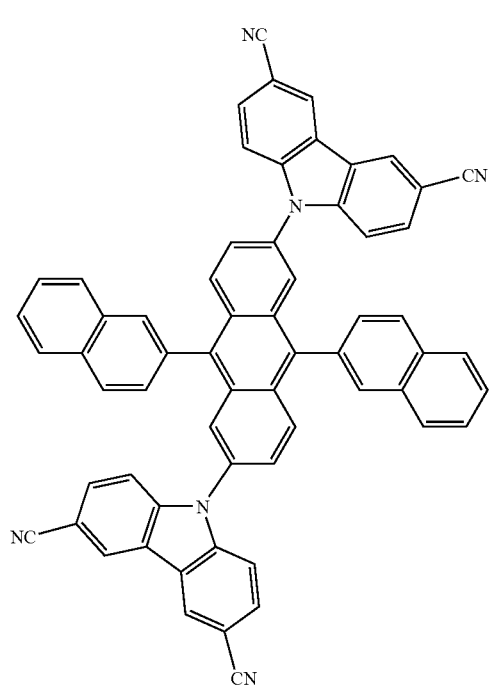

-continued
D-152
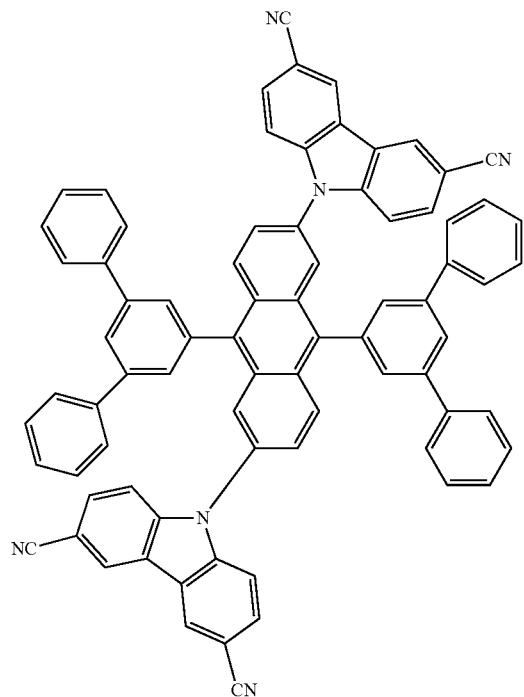
D-153
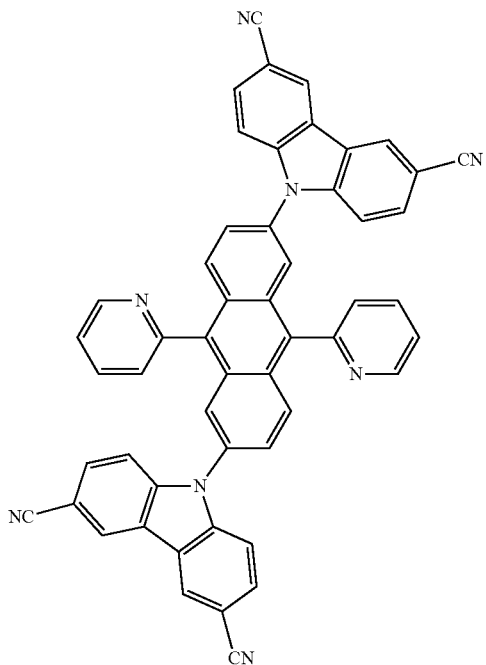
D-154
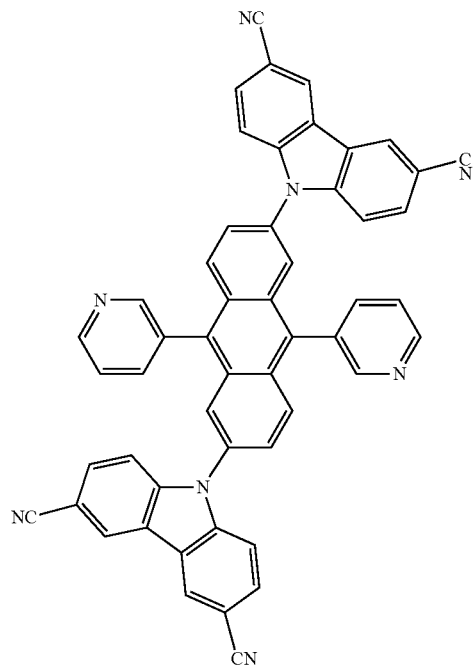
D-155
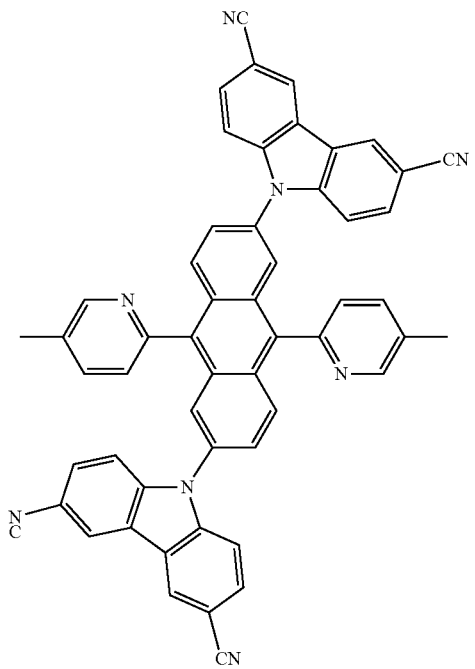

-continued
D-156
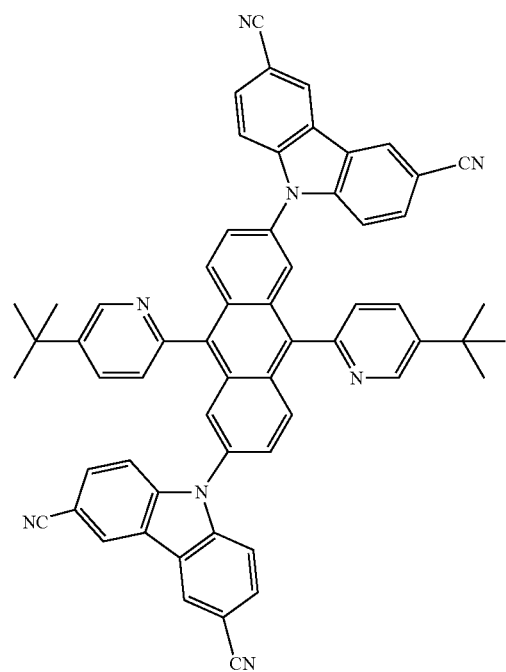
D-157
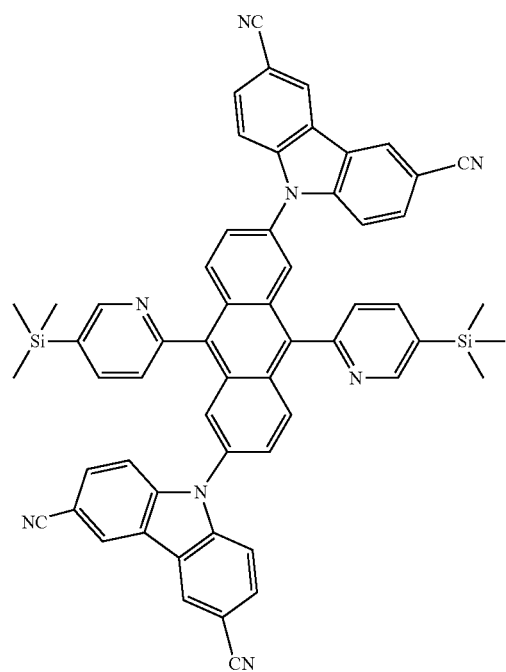
D-158
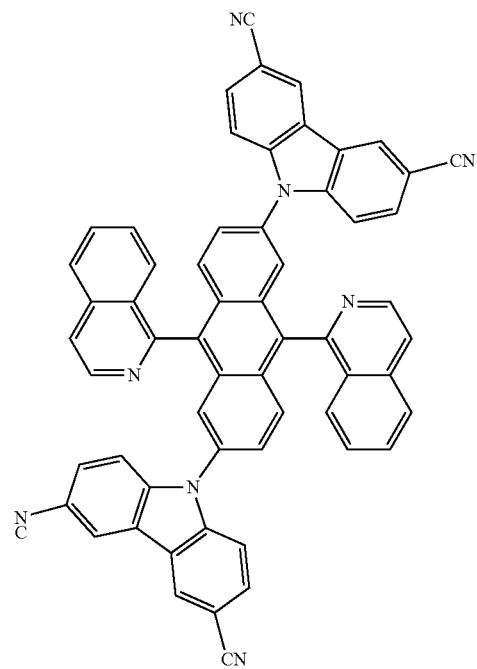
D-159
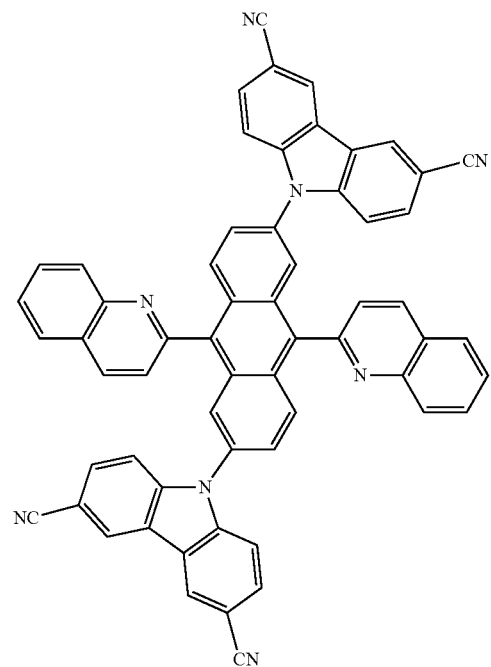

-continued
D-160
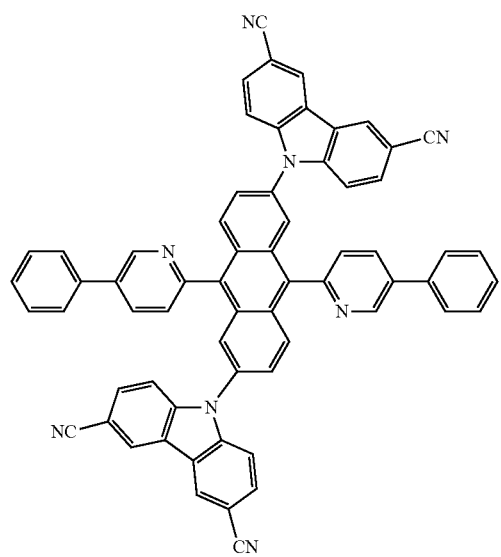
D-161
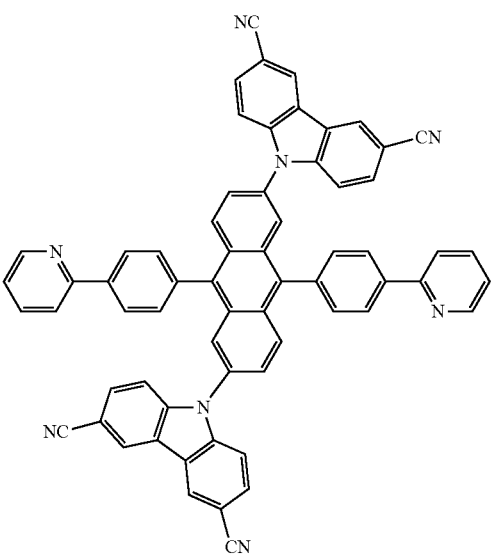
D-162
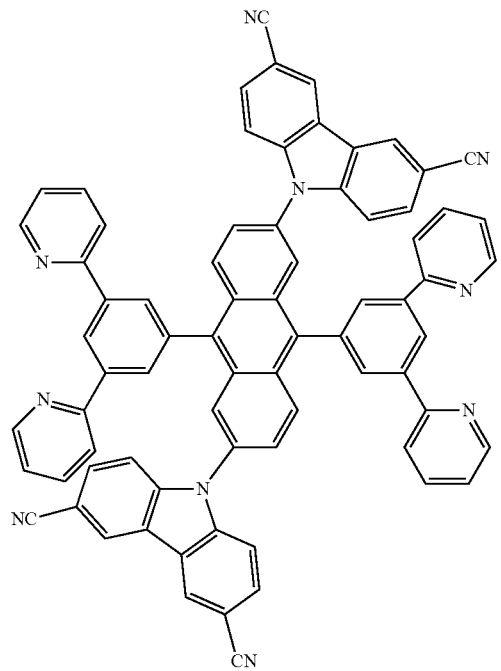
D-163
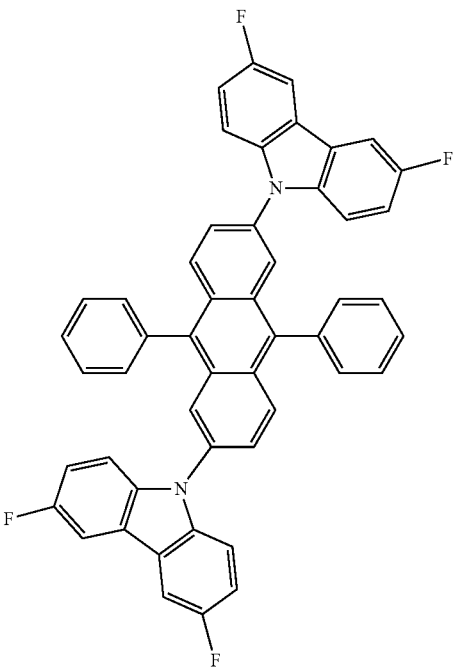

-continued
D-164
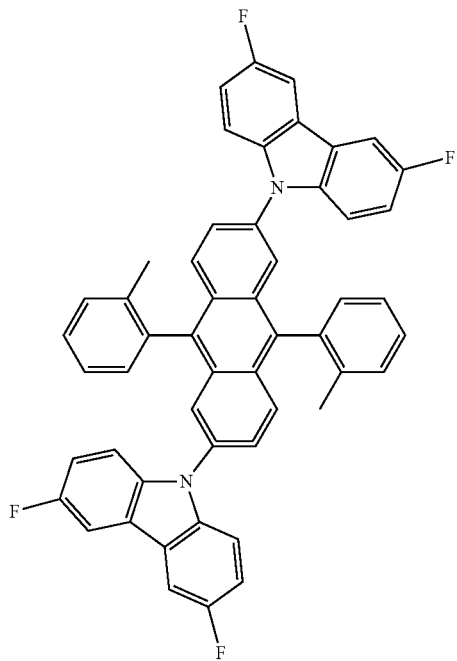
D-165
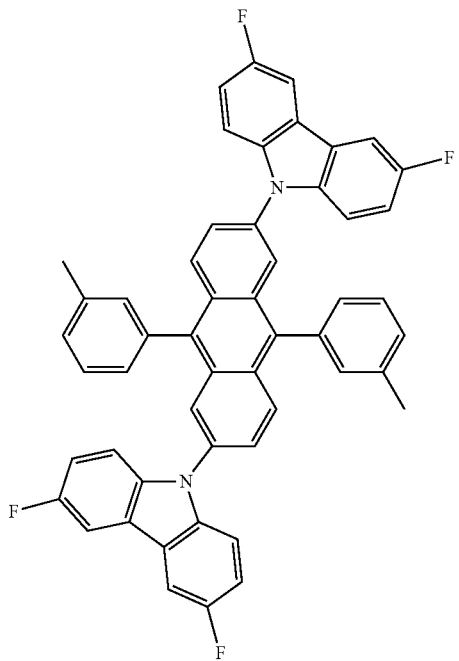
D-166
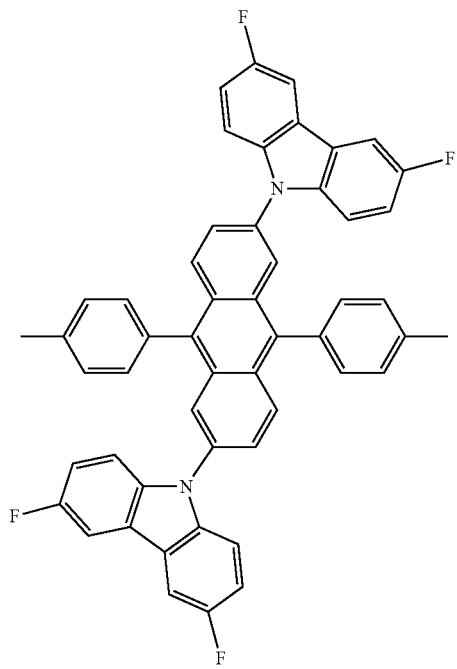
D-167
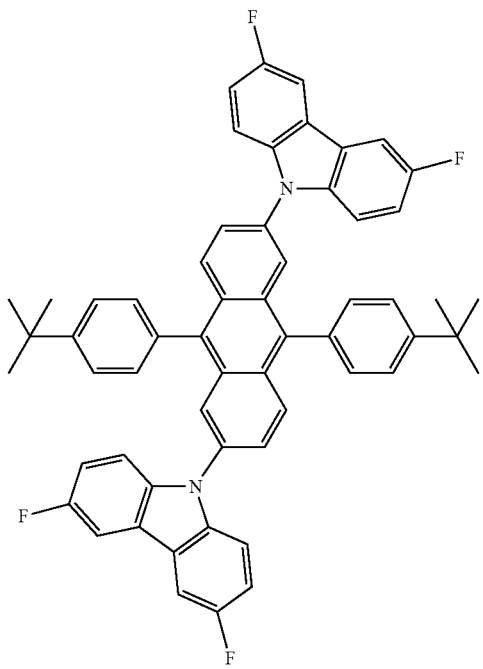

-continued
D-168
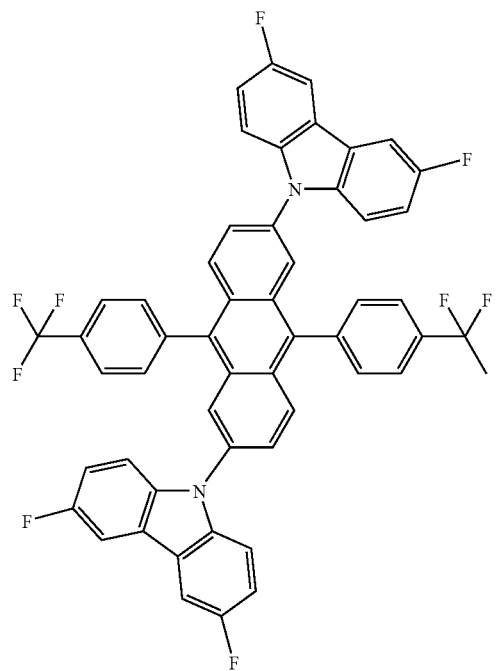
D-169
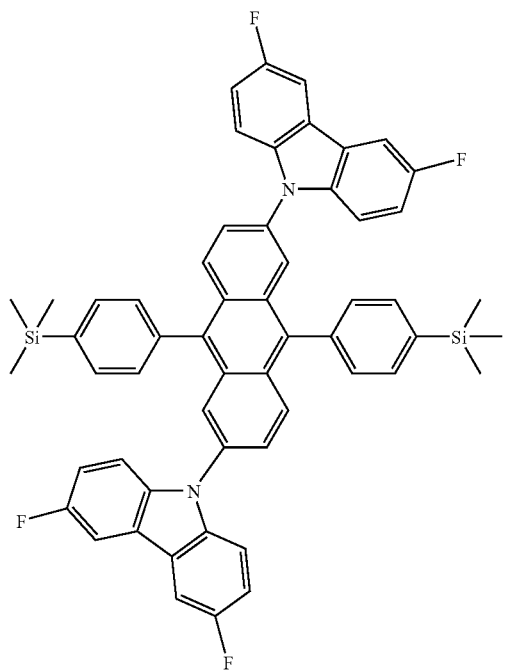
D-170
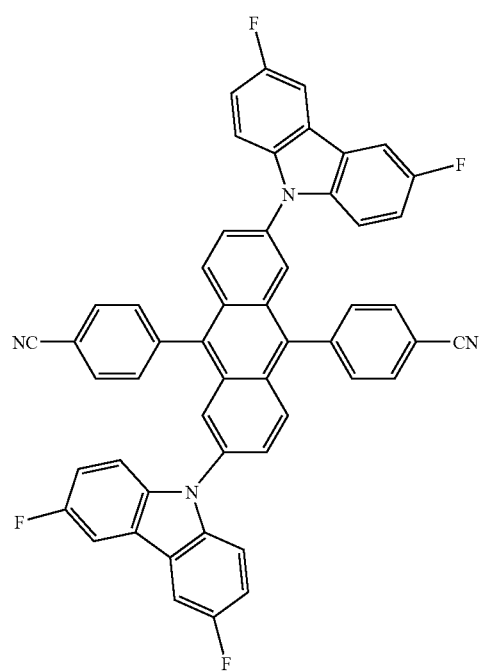
D-171
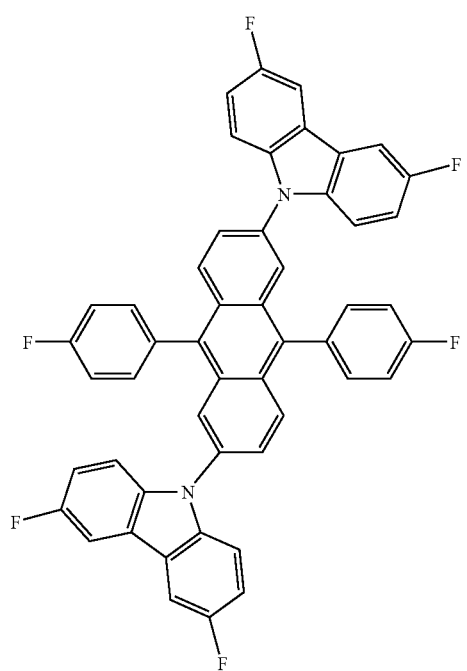

D-172
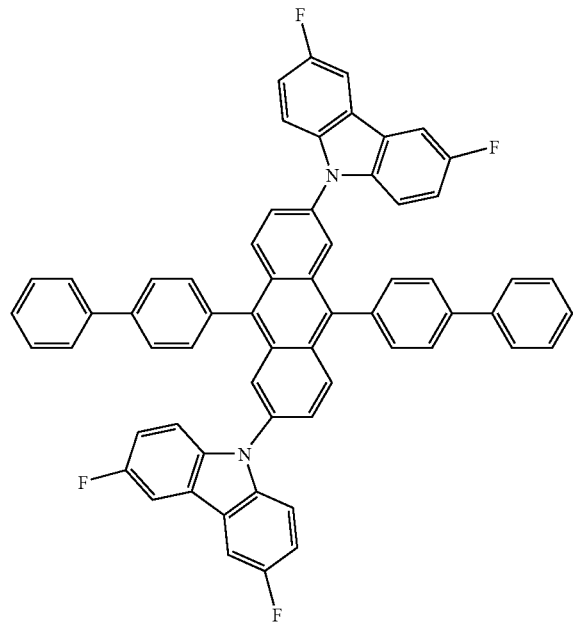
D-173
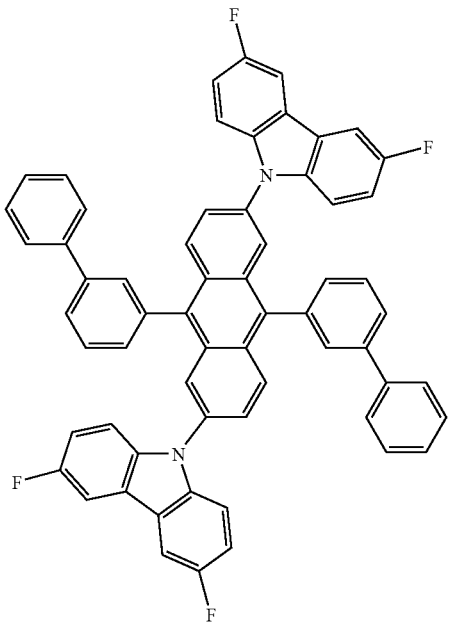
D-174
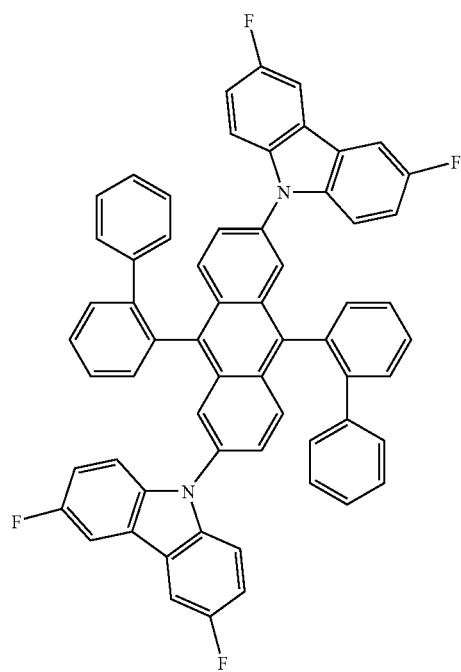

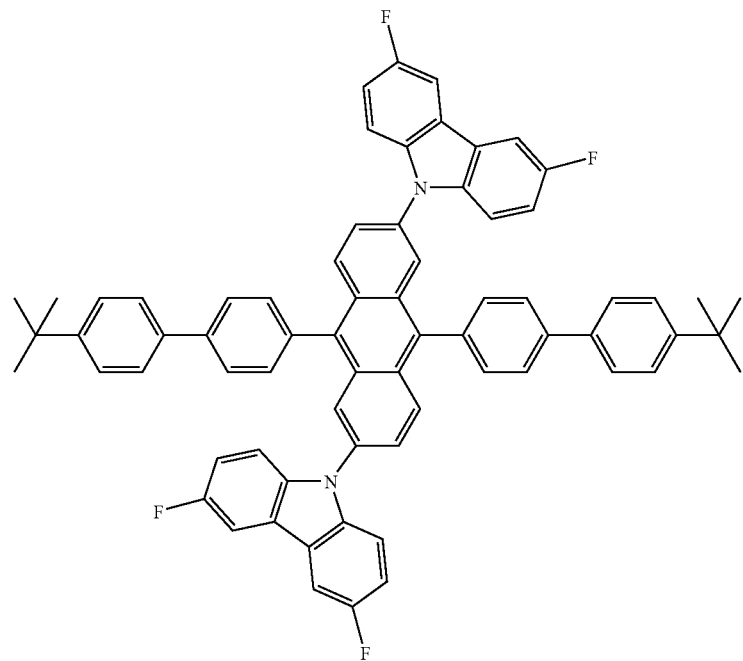
D-175
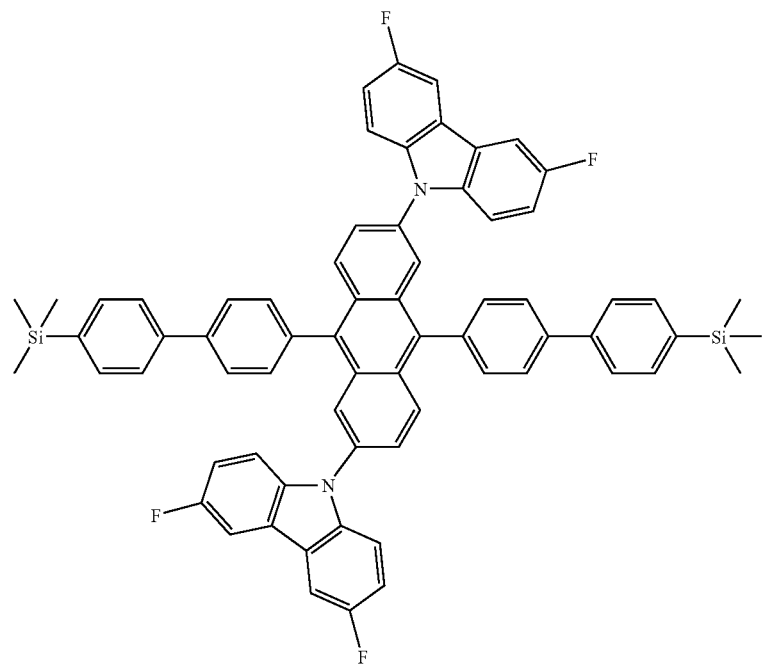
D-176

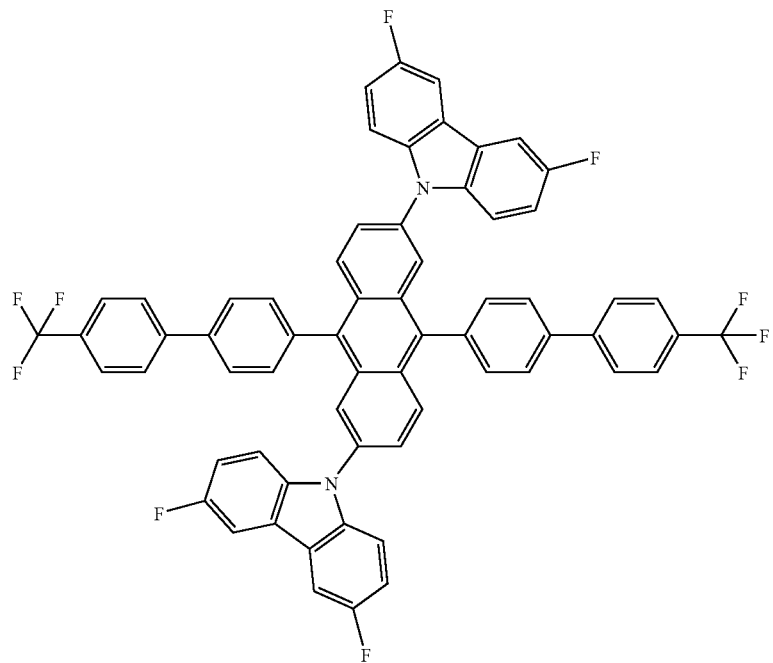
D-177
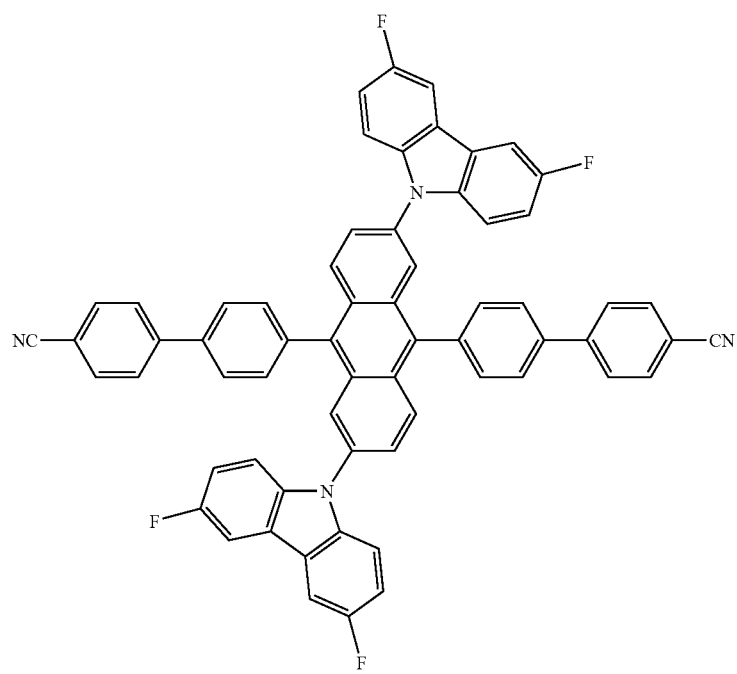
D-178

-continued
D-179
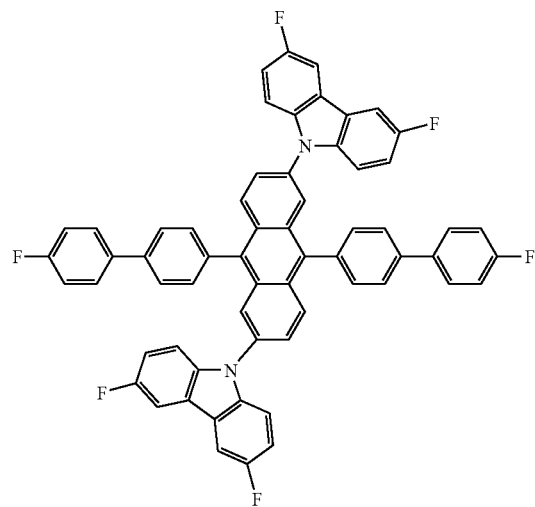
D-180
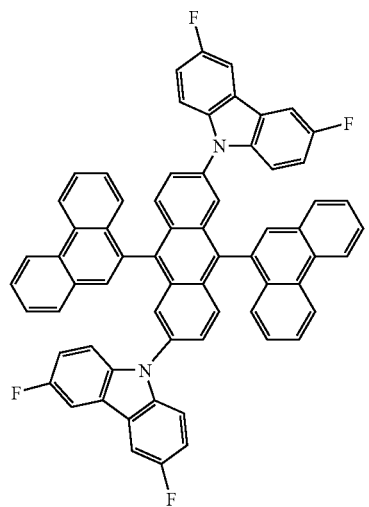
D-181
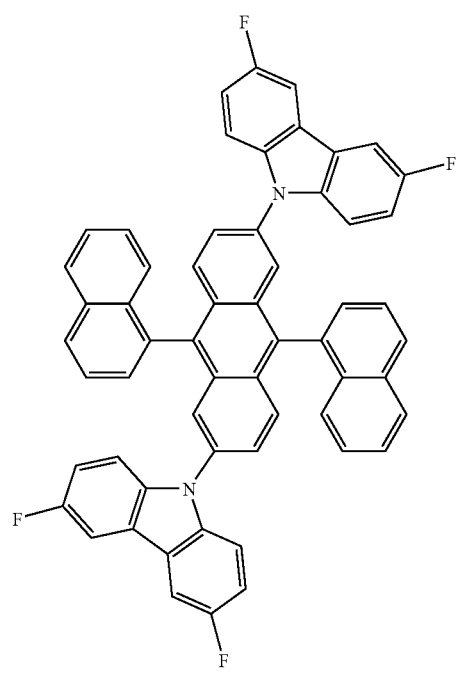
D-182
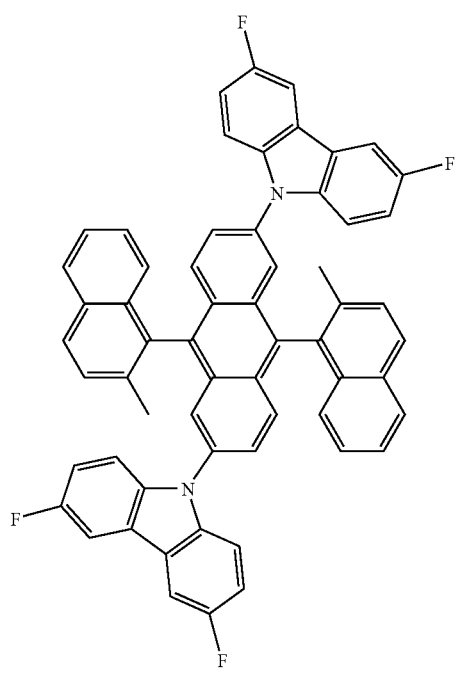

-continued
D-183
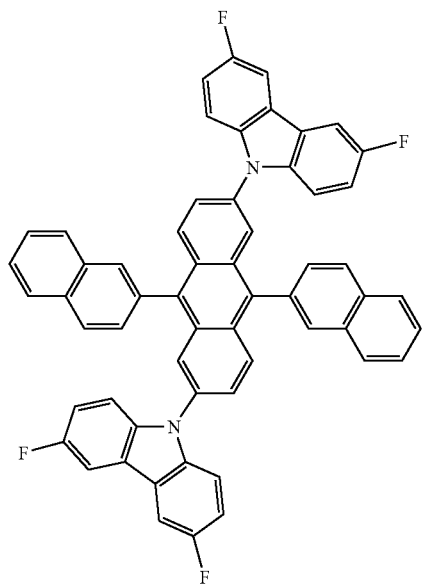
D-184
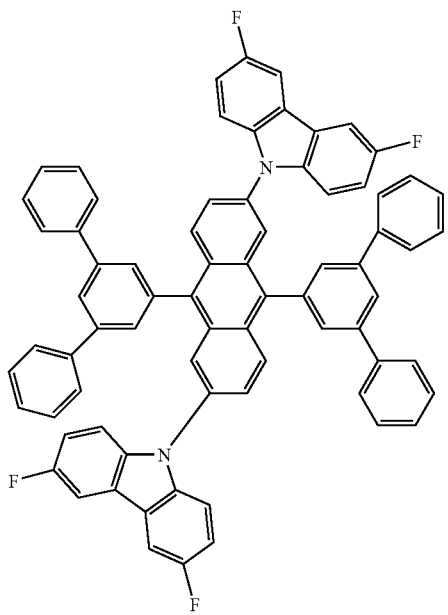
D-185
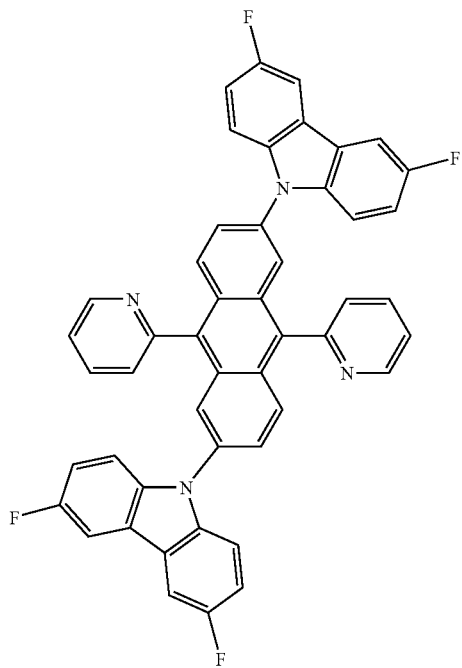
D-186
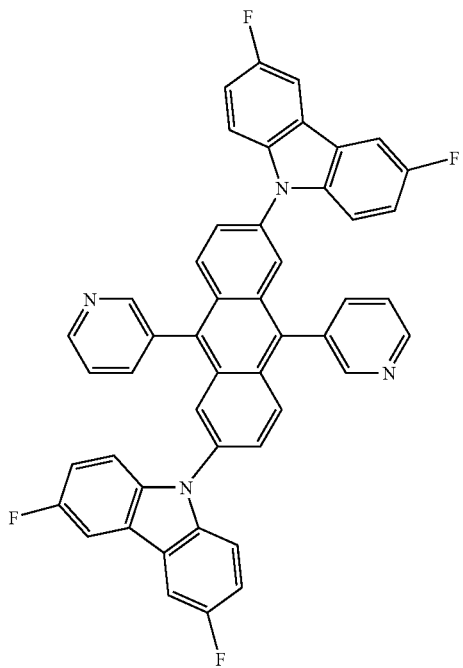

-continued
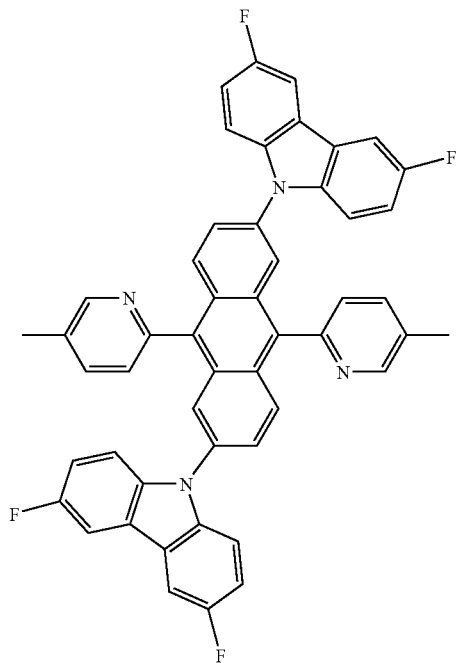
D-187
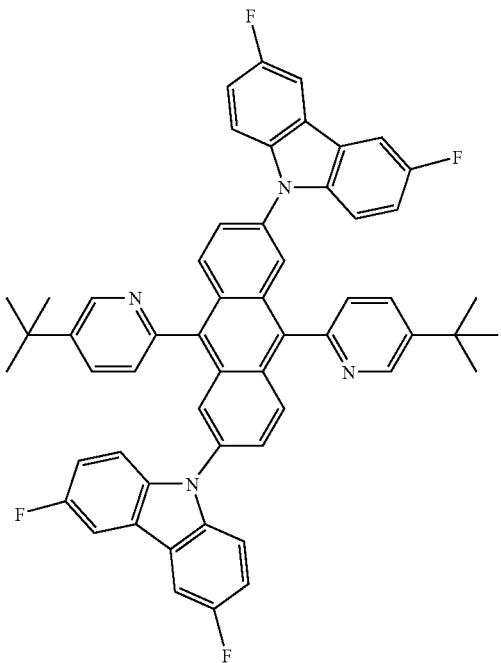
D-188
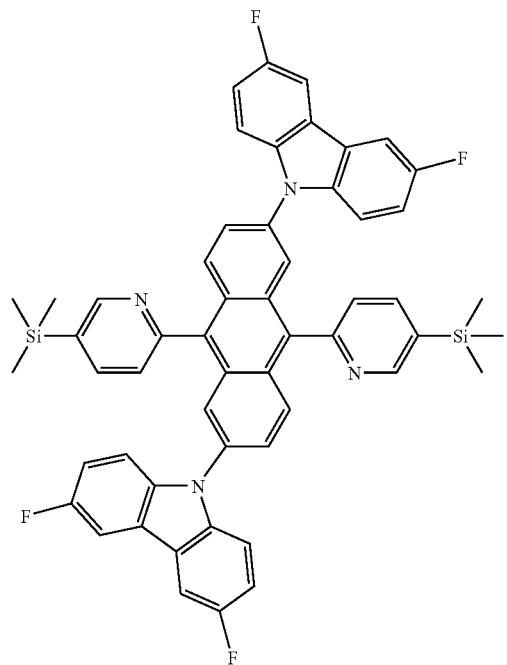
D-189
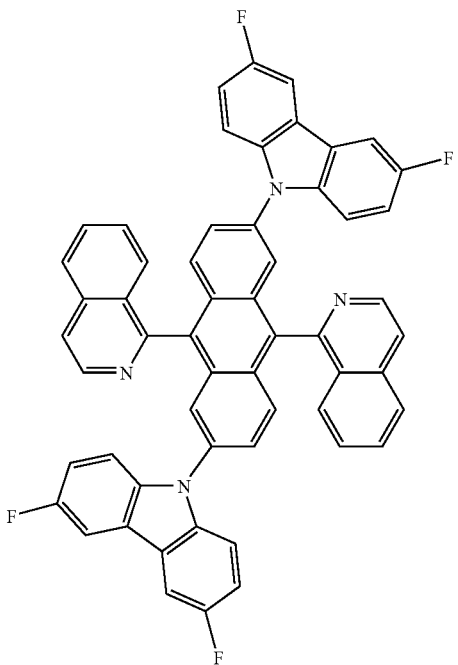
D-190

-continued

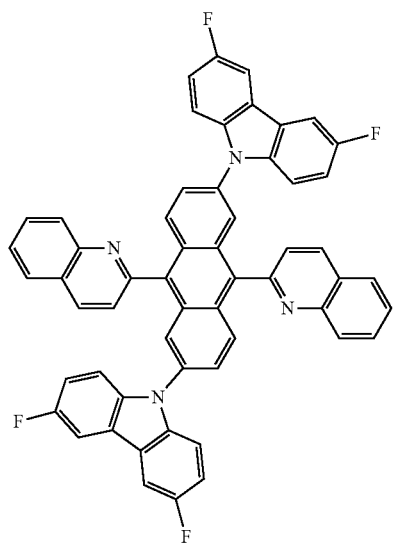
D-191

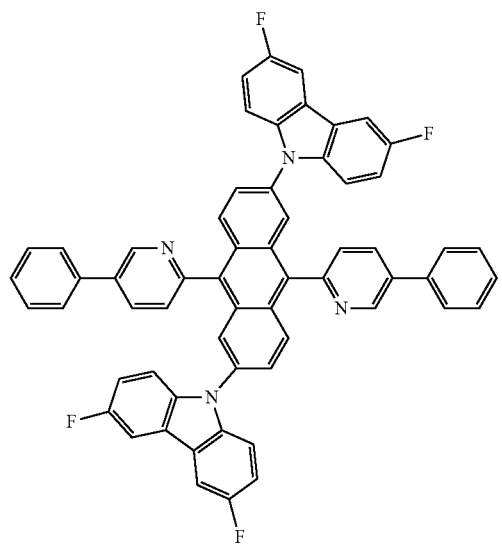
D-192

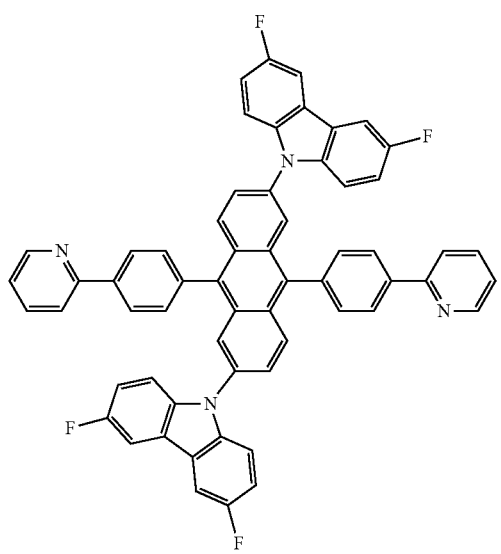
D-193

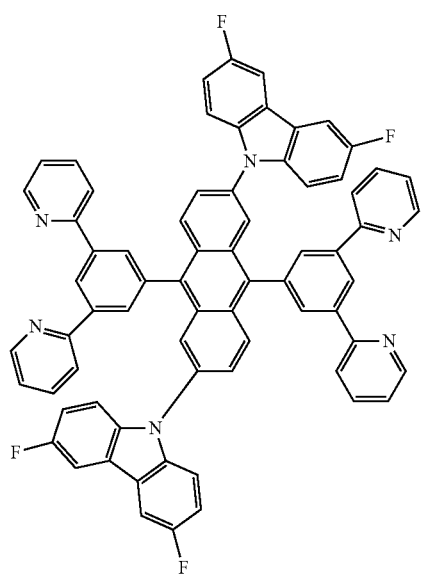
D-194

The doping concentration of the dopant may range from about 0.5 to about 10% by weight.

The hole transport layer 150 functions to smoothly transport holes. The hole transport layer 150 may be formed of at least one selected from the group consisting of Alq3(tris(8-hydroxyquinolino)aluminum, PBD, TAZ, spiro-PBD, BAlq, and SAlq, but is not limited thereto.

The hole transport layer 150 may also have a thickness of 1 to 50 nm. If the thickness of the hole transport layer 150 is 1 nm or greater, a reduction in a hole transport characteristic can be prevented. If the thickness of the hole transport layer 150 is 50 nm or less, an increase in the driving voltage, which is applied in order to increase movement of holes when the thickness of the hole transport layer 150 is too large, can be prevented.

The electron injection layer 160 functions to facilitate the injection of electrons. The electron injection layer 160 may be formed of Alq3(tris(8-hydroxyquinolino)aluminum), PBD, TAZ, spiro-PBD, BAlq or SAlq, but is not limited thereto.

The thickness of the hole injection layer 160 may range from about 1 to about 50 nm. If the thickness of the hole injection layer 160 is 1 nm or greater, a reduction in a hole injection characteristic can be prevented. If the thickness of the hole injection layer 160 is 50 nm or less, an increase in driving voltage, which is applied in order to increase the movement of holes when the thickness of the hole injection layer 160 is too large, can be prevented.

The cathode 170 is an electron injection electrode which is formed of magnesium (Mg), calcium (Ca), Aluminum (Al), and silver (Ag) having a low work function, or an alloy thereof. In case that the organic light emitting diode device has a top emission or dual emission structure, the cathode 170 may be thin enough to transmit light. In case that the organic light emitting diode device has a bottom emission structure, the cathode 170 may be thick enough to reflect light.

Hereinafter, the blue light emitting compound and the organic light emitting diode device comprising this compound according to the present invention will be described in detail in the following Synthesis Examples and Examples. However, it should be noted that the following examples are merely illustrative of the present invention, and the present invention is not limited thereto.

SYNTHESIS EXAMPLES

1) Synthesis of 2,6-dibromoanthraquinone

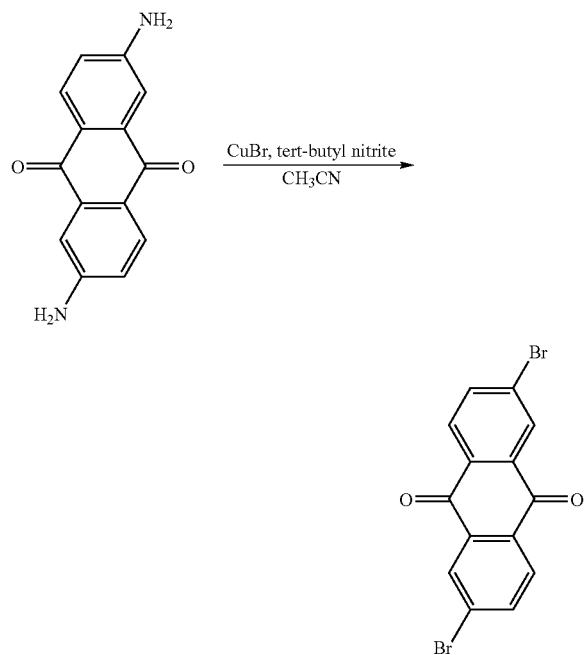

In a 2-neck round flask, copper (II) bromide (24 g, 0.1 mol) and tert-butyl nitrite (10.8 g, 0.1 mol) were added to 200 mL of acetonitrile and stirred, the mixture was warned to −65° C., and then 2,6-diaminoanthraquinone (10 g, 0.04 mol) was gradually added dropwise thereto for 10 minutes. The reaction was monitored with TLC, the reaction mixture was cooled down to room temperature, and then 200 mL of aq. 2N HC1 was added thereto. The resulting solid was filtered and washed with diluted water and methanol, thereby obtaining 2,6-dibromoanthraquinone (9.2 g, yield: 60%).

2) Synthesis of 2,6-dibromo-9,10-di-o-tolylanthracene

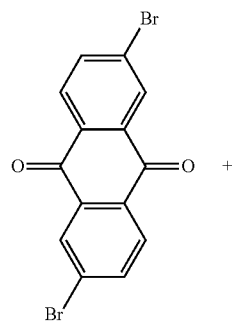 +

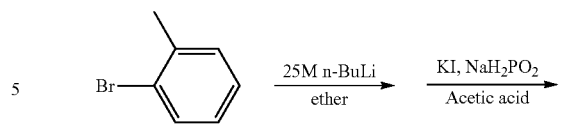

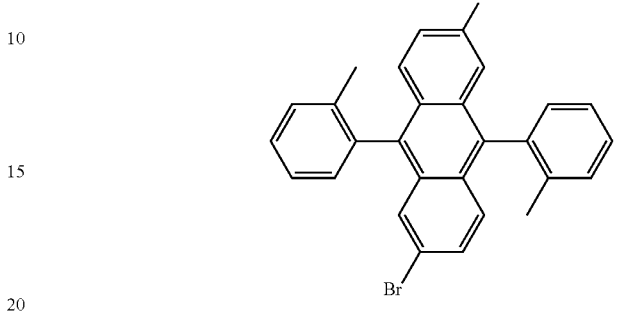

In a 2-neck round flask, 2-bromo-o-toluene (5 g, 31.3 mmol) was added to 50 mL of ether and stirred, the mixture was cooled down to −75° C., and then 2.5M n-BuLi (12.5 mL, 31.3 mmol) was gradually added dropwise thereto and stirred for 1 hour. The mixture was cooled down again to −78°, and then 2,6-dibromoanthraquinone (5 g, 14.9 mmol) was added thereto and stirred for 4 hours at room temperature. Then, the reaction mixture was quenched with 1N HC1 aq. solution, extracted with methylene chloride, evaporated with a solvent, and purified through silica gel column chromatography, thereby obtaining 2,6-dibromo-9,10-di-o-tolylanthraquinone. To the resulting mixture, potassium iodide (12.4 g, 0.07 mol), sodium hypophosphite (13 g, 0.15 mol), and 50 mL of acetic acid were added and stirred for 6 hours at 100□. Then, the reaction mixture was cooled down to room temperature, and 100 mL of aq. 2N HC1 was added thereto. The resulting solid was filtered and washed with diluted water and methanol, thereby obtaining 2,6-dibromo-9,10-di-o-tolylanthracene (5.4 g, yield: 70%).

3) Synthesis of 2,6-dicarbazolyl-9,10-di-o-tolyanthracene

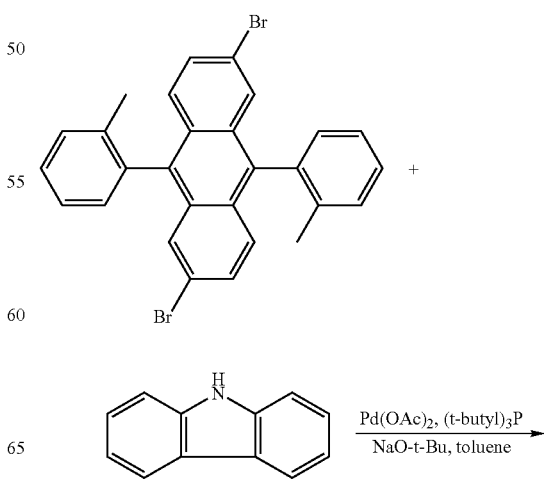

-continued

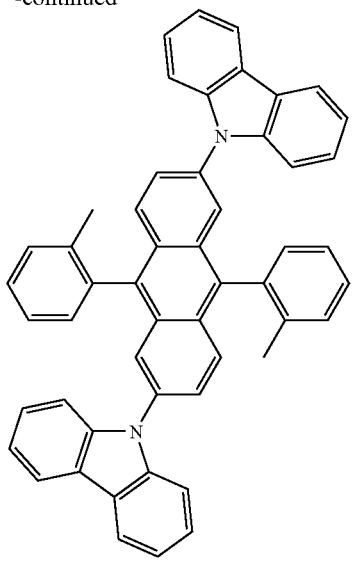

In a 2-neck round flask, 2,6-dibromo-9,10-di-o-tolyanthracene (2 g, 3.9 mmol), carbazole (1.4 g, 8.8 mmol), palladium acetate (0.03 g, 11.6 mmol %), tri(tert-butyl)phosphine (0.03 g, 15.5 mmol %), and sodium tert-butoxide (1.1 g, 11.6 mmol) were added to 30 mL of toluene and refluxed for 12 hours at 130□. Then, the reaction was monitored with TLC, and the reaction mixture was cooled down to room temperature and quenched with 50 mL of methanol. The resulting solid was filtered and purified through silica gel column chromatography, thereby obtaining 2,6-dicarbazolyl-9,10-di-o-tolyanthracene (2.1 g, yield: 80%).

EXAMPLES

Hereinafter, there are disclosed examples in which an organic light emitting diode device is manufactured by using the aforementioned blue light emitting compound of the present invention represented by D-1 or D-194.

Example 1

An ITO glass was patterned to have a luminescence area of 3 mm×3 mm, and then washed. Then, the substrate was mounted to a vacuum chamber, the base pressure was set to 1×10$^{-6}$ Torr, and then CuPc as a hole injection layer was deposited on the ITO (anode) at a thickness of 650 Å, NPD used as a hole transport layer was deposited at a thickness of 400 Å, and DPBVi (200 Å) as a host and a compound (50 Å) as a dopant represented by D-01 were deposited as an emission layer at a doping concentration of 1% by weight. Then, Alq3 as an electron transport layer was deposited at a thickness of 350 Å, LiF as an electron injection layer was deposited at a thickness of 5 Å, and Al as a cathode was deposited at a thickness of 1000 Å, thereby preparing an organic light emitting diode device.

Example 2

An organic light emitting diode device was prepared under the same condition as the above Example 1 except that the dopant is a compound represented by D-02.

Example 3

An organic light emitting diode device was prepared under the same condition as the above Example 1 except that the dopant is a compound represented by D-07.

Example 4

An organic light emitting diode device was prepared under the same condition as the above Example 1 except that the dopant is a compound represented by D-19.

Example 5

An organic light emitting diode device was prepared under the same condition as the above Example 1 except that the dopant is a compound represented by D-22.

Comparative Example

An organic light emitting diode device was prepared under the same condition as the above Example 1 except that the dopant is a compound having a distyryl which is represented by the following BD-1.

BD-1

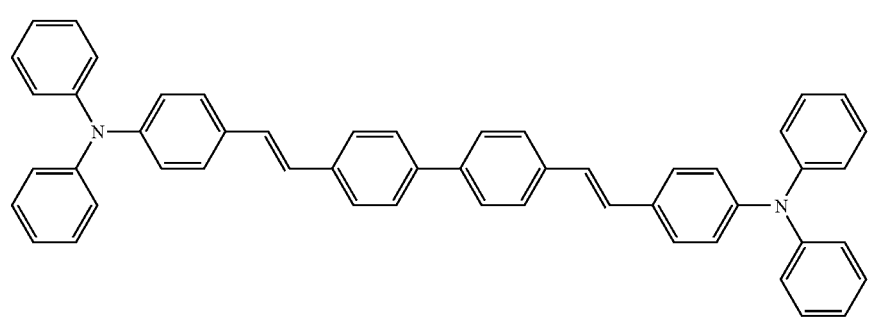

The voltages, currents, luminance, current efficiencies, power efficiencies, and color coordinates of the organic light emitting diode devices of Examples 1 to 5 and Comparative Example 1 were measured and shown in the following Table 1.

TABLE 1

|  | Voltage (v) | Current (mA) | Luminance (cd/m$^2$) | Current efficiency (cd/A) | Power efficiency (lm/W) | Color coordinates CIE (X) | CIE (Y) |
|---|---|---|---|---|---|---|---|
| Example 1 | 5.2 | 0.9 | 779 | 7.8 | 4.74 | 0.137 | 0.177 |
| Example 2 | 5.3 | 0.9 | 730 | 7.3 | 4.32 | 0.129 | 0.163 |
| Example 3 | 5.7 | 0.9 | 848 | 8.5 | 4.67 | 0.137 | 0.187 |
| Example 4 | 5.7 | 0.9 | 896 | 8.9 | 4.93 | 0.138 | 0.193 |
| Example 5 | 5.7 | 0.9 | 778 | 7.8 | 4.28 | 0.136 | 0.195 |
| Comparative Example 1 | 6.7 | 0.9 | 526 | 5.26 | 2.47 | 0.136 | 0.188 |

As shown in the above Table 1, it can be seen that the organic light emitting diode devices according to the present Examples 1 to 5 show color coordinates equivalent to those of Comparative Example and have better voltages, luminance, current efficiencies, and power efficiencies, compared to Comparative Example.

Accordingly, the blue light emitting compound and the organic light emitting diode display according to one exemplary embodiment of the present invention can have better voltage, luminance, current efficiency, and power efficiency compared to the conventional organic light emitting diode device.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures. Moreover, unless the term "means" is explicitly recited in a limitation of the claims, such limitation is not intended to be interpreted under 35 USC 112(6).

What is claimed is:

1. A blue light emitting compound represented by the following Chemical Formula 1:

[Chemical Formula 1]

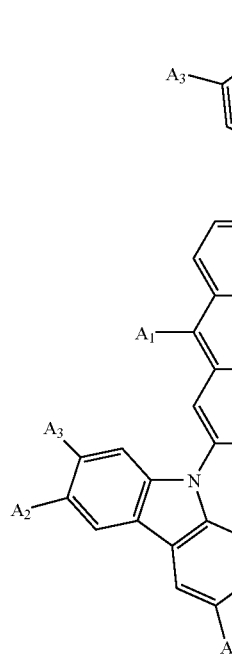

wherein $A_1$ is resented by one of the following Chemical Formulae 2, and $A_2$ and $A_3$ are represented by one of the following Chemical Formulae 3:

[Chemical Formulae 2]

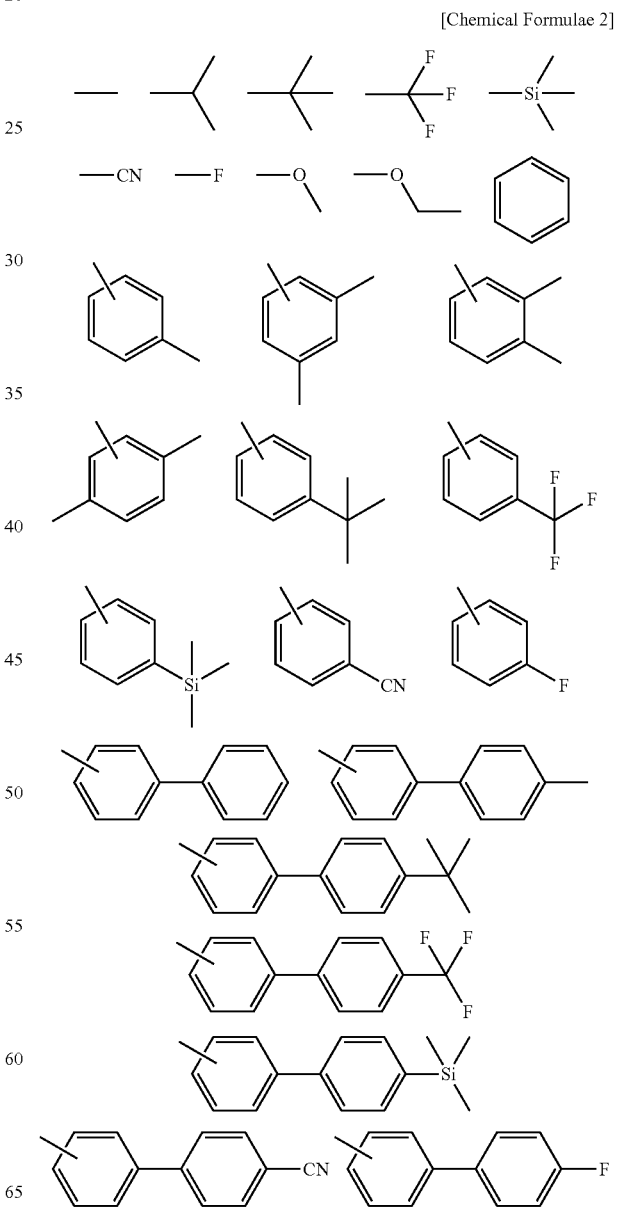

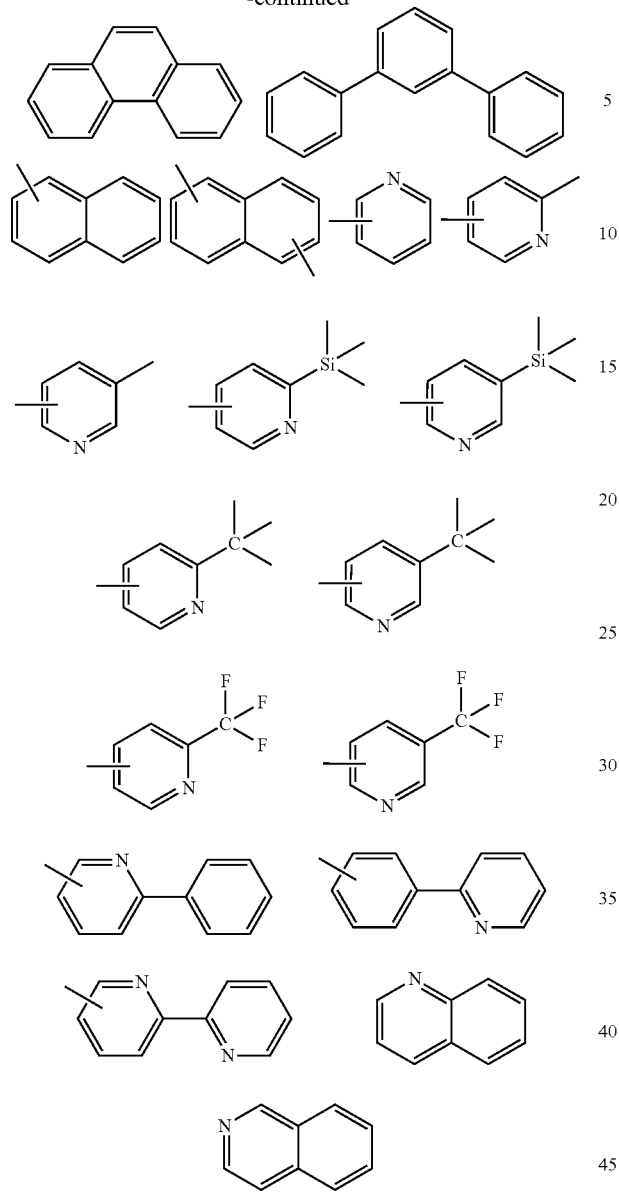

[Chemical Formulae 3]

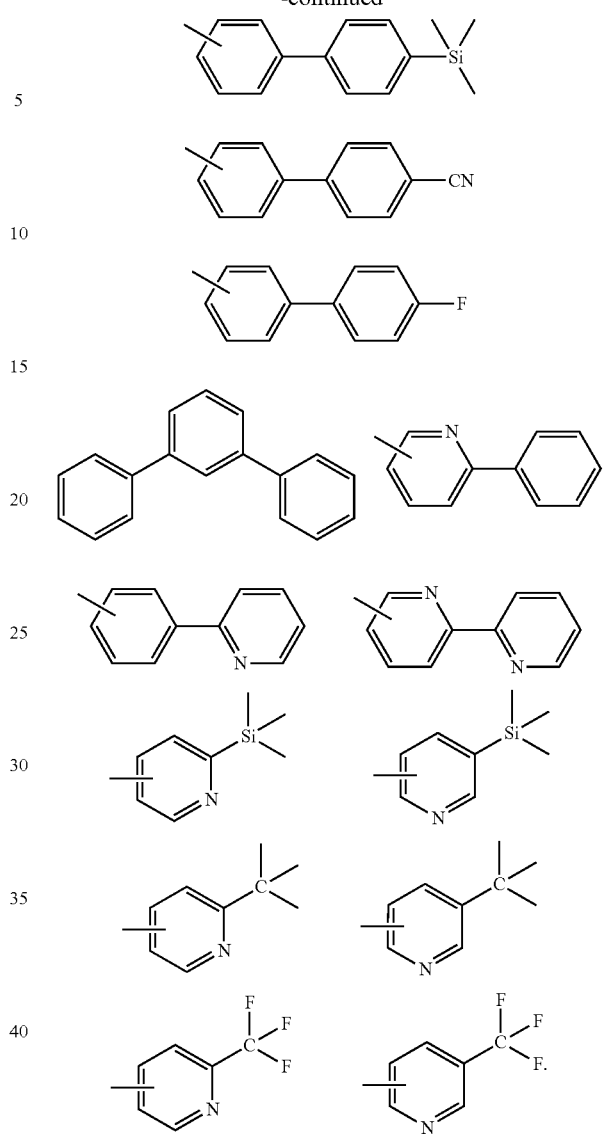

2. The blue light emitting compound of claim 1, wherein the $A_1$ is terphenyl, and the $A_2$ and the $A_3$ are each independently selected from the group consisting of phenyl, biphenyl, naphthyl, phenanthrenyl, terphenyl, pyridyl, bipyridyl, phenylpyridyl, pyridylphenyl, quinolinyl, isoquinolinyl, methyl, isopropyl, tert-butyl, trimethylsilyl, trifluoromethyl, cyano, fluoro, methoxy, and ethoxy.

3. An organic light emitting diode device comprising:
   an anode,
   a hole injection layer,
   a hole transport layer,
   an emission layer,
   an electron transport layer,
   an electron injection layer,
   a cathode, and
   a blue light emitting compound represented by the following Chemical Formula 1 as a dopant of the emission layer:

[Chemical Formula 1]
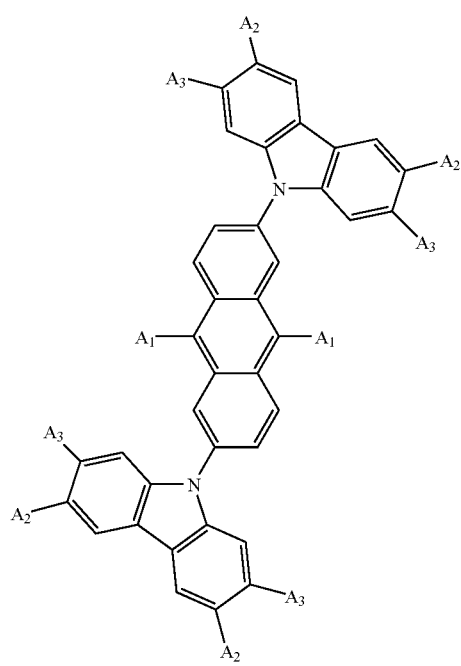
wherein $A_1$ is resented by one of the following Chemical Formulae 2, and $A_2$ and $A_3$ are represented by one of the following Chemical Formulae 3:
[Chemical Formulae 2]
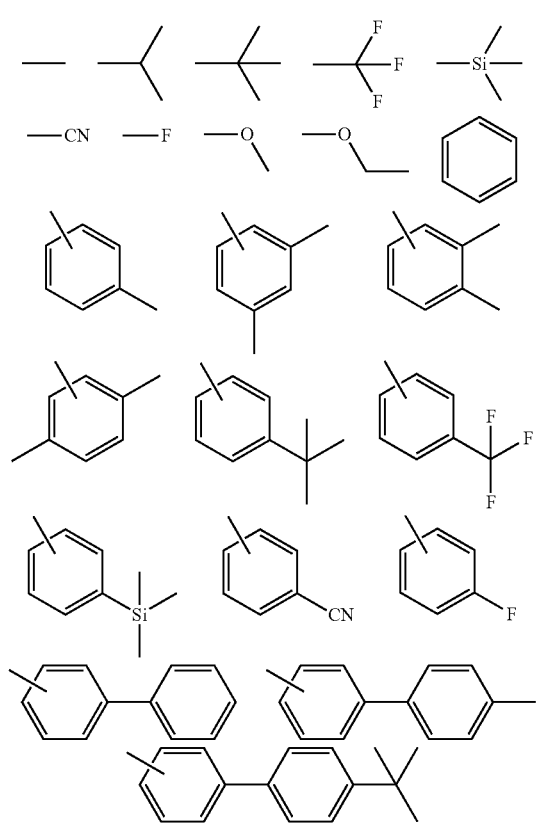
[Chemical Formulae 3]
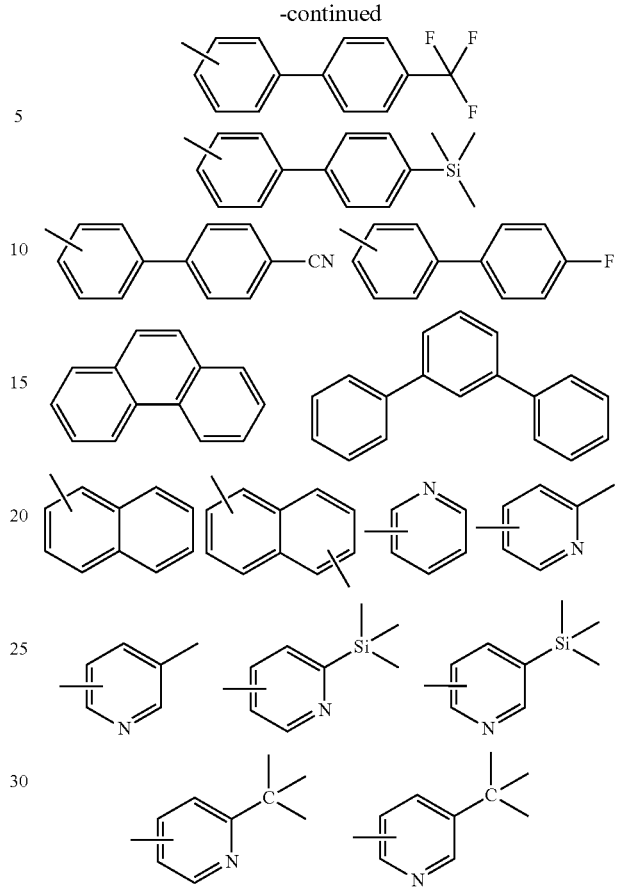
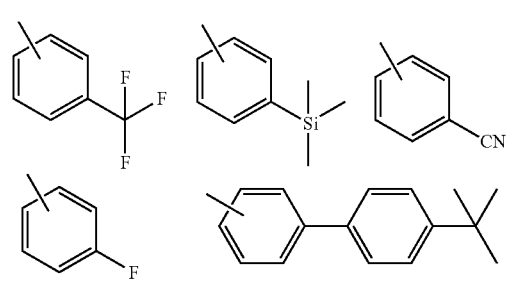

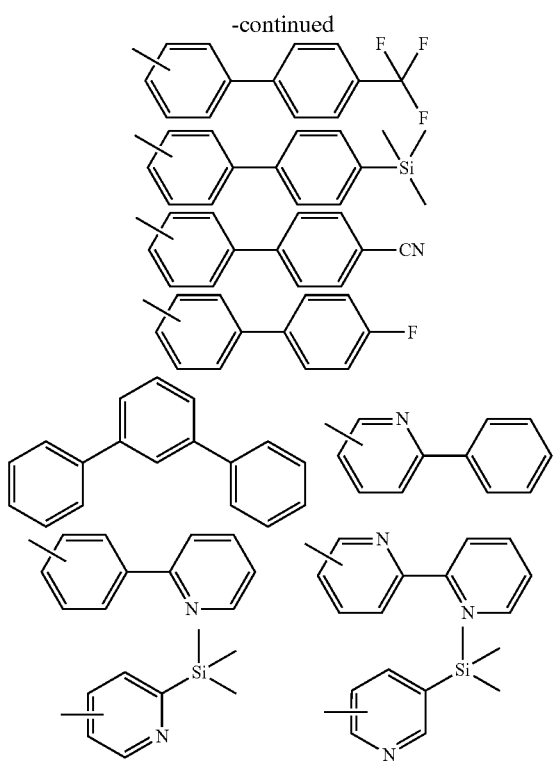

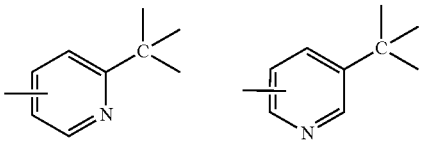

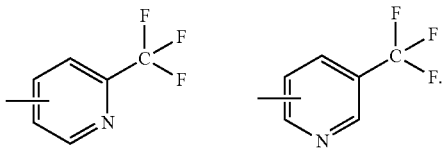

4. The organic light emitting diode device of claim 3, wherein the $A_1$ is terphenyl, and the $A_2$ and the $A_3$ are each independently selected from the group consisting of phenyl, biphenyl, naphthyl, phenanthrenyl, terphenyl, pyridyl, bipyridyl, phenylpyridyl, pyridyiphenyl, quinolinyl, isoquinolinyl, methyl, isopropyl, tert-butyl, trimethylsilyl, trifluoromethyl, cyano, fluoro, methoxy, and ethoxy.

5. The organic light emitting diode device of claim 3, wherein a doping concentration of the dopant ranges from about 0.5 to about 10% by weight.

* * * * *